United States Patent
Liedtke

(10) Patent No.: US 11,564,911 B2
(45) Date of Patent: Jan. 31, 2023

(54) SMALL MOLECULE DUAL-INHIBITORS OF TRPV4 AND TRPA1 FOR SANITIZING AND ANESTHETIZING

(71) Applicant: Duke University, Durham, NC (US)

(72) Inventor: Wolfgang Liedtke, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 16/091,960

(22) PCT Filed: Apr. 7, 2017

(86) PCT No.: PCT/US2017/026714
§ 371 (c)(1),
(2) Date: Oct. 5, 2018

(87) PCT Pub. No.: WO2017/177200
PCT Pub. Date: Oct. 12, 2017

(65) Prior Publication Data
US 2019/0091206 A1 Mar. 28, 2019

Related U.S. Application Data

(60) Provisional application No. 62/337,701, filed on May 17, 2016, provisional application No. 62/331,951, filed on May 4, 2016, provisional application No. 62/319,684, filed on Apr. 7, 2016.

(51) Int. Cl.
| | | |
|---|---|---|
| A61K 31/426 | (2006.01) | |
| A61K 33/18 | (2006.01) | |
| A61K 31/4439 | (2006.01) | |
| A61K 45/06 | (2006.01) | |
| A61P 29/02 | (2006.01) | |

(52) U.S. Cl.
CPC ........ *A61K 31/426* (2013.01); *A61K 31/4439* (2013.01); *A61K 33/18* (2013.01); *A61K 45/06* (2013.01); *A61P 29/02* (2018.01)

(58) Field of Classification Search
CPC .. A61K 31/426; A61K 45/06; A61K 31/4439; A61K 33/18; A61P 29/02
See application file for complete search history.

(56) References Cited

U.S. PATENT DOCUMENTS

| | | | |
|---|---|---|---|
| 4,921,333 | A | 5/1990 | Brody et al. |
| 7,459,450 | B2 | 12/2008 | Zhu et al. |
| 7,639,365 | B2 | 12/2009 | Herring |
| 8,178,542 | B2 | 5/2012 | Moran et al. |
| 9,290,489 | B2 | 3/2016 | Liedtke et al. |
| 9,701,675 | B2 | 7/2017 | Liedtke et al. |
| 10,329,265 | B2 | 6/2019 | Liedtke et al. |
| 2004/0198649 | A1 | 10/2004 | Davis et al. |
| 2006/0089351 | A1 | 4/2006 | Zhu et al. |
| 2007/0161560 | A1 | 7/2007 | Davis et al. |
| 2007/0259856 | A1 | 11/2007 | Kumar et al. |
| 2008/0039466 | A1 | 2/2008 | Moussy et al. |
| 2011/0009430 | A1 | 1/2011 | Moran et al. |
| 2011/0130400 | A1 | 6/2011 | Bury et al. |
| 2013/0310345 | A1* | 11/2013 | Moran ................. A61K 9/0014 514/154 |
| 2015/0105406 | A1 | 4/2015 | Gullapalli et al. |
| 2016/0194312 | A1 | 7/2016 | Liedtke et al. |
| 2016/0199363 | A1 | 7/2016 | Liedtke et al. |
| 2019/0112301 | A1 | 4/2019 | Liedtke et al. |
| 2019/0315700 | A1 | 10/2019 | Liedtke et al. |

FOREIGN PATENT DOCUMENTS

| | | |
|---|---|---|
| CN | 101747330 | 6/2010 |
| WO | WO 93/12227 | 6/1993 |
| WO | WO 00/45635 | 8/2000 |
| WO | WO 2005/000298 | 1/2005 |
| WO | WO 2005/073225 | 8/2005 |
| WO | WO 2005/111031 | 11/2005 |
| WO | WO 2006/122011 | 11/2006 |
| WO | WO 2006/122156 | 11/2006 |
| WO | WO 2007/026251 | 3/2007 |
| WO | WO 2007/095124 | 8/2007 |
| WO | WO 2007/118137 | 10/2007 |
| WO | WO 2009/002534 | 12/2008 |
| WO | WO 2009/010529 | 1/2009 |
| WO | WO 2010/109334 | 9/2010 |
| WO | WO 2012/084870 | 6/2012 |

(Continued)

OTHER PUBLICATIONS

United States Patent Office Notice of Allowance for U.S. Appl. No. 15/505,898 dated Jan. 22, 2019 (7 pages).
United States Patent Office Action for U.S. Appl. No. 14/993,010 dated Sep. 20, 2019 (6 pages).
United States Patent Office Action for U.S. Appl. No. 16/391,047 dated Sep. 9, 2019 (11 pages).
European Patent Office Extended Search Report for Application No. 17779954.1 dated Feb. 10, 2020 (12 pages).
United States Patent Office Action for U.S. Appl. No. 16/391,047 dated Feb. 3, 2020 (7 pages).
European Patent Office Partial Supplementary Search Report for Application No. 17779954.1 dated Oct. 31, 2019 (14 pages).
United States Patent Office Action for U.S. Appl. No. 16/217,948 dated Dec. 31, 2019 (7 pages).

(Continued)

*Primary Examiner* — Robert A Wax
*Assistant Examiner* — Quanglong N Truong
(74) *Attorney, Agent, or Firm* — Michael Best & Friedrich LLP

(57) ABSTRACT

Provided are methods of sanitizing a subject, and methods of anesthetizing a subject. Further provided are methods of treating and/or preventing dermatological disorders, reducing skin inflammation, reducing pain, and/or reducing itch in a subject in need thereof. The methods may include administering to the subject an effective amount of a TRPA1 and/or TRPV4 inhibitor. Further provided are compositions including a TRPA1 and/or TRPV4 inhibitor compound in combination with a carrier, vehicle, or diluent that is suitable for topical application.

25 Claims, 76 Drawing Sheets
Specification includes a Sequence Listing.

(56) References Cited

FOREIGN PATENT DOCUMENTS

| WO | WO 2014/008477 | 1/2014 |
| WO | WO 2016/028325 | 2/2016 |

OTHER PUBLICATIONS

United States Patent Office Action for U.S. Appl. No. 16/217,948 dated Jun. 3, 2019 (16 pages).
Adapala et al., "Activation of mechanosensitive ion channel TRPV4 normalizes tumor vasculature and improves cancer therapy," Oncogene, 2016. 35(3): p. 314-22.
Ahn, G.Y., Butt, K.I., Jindo, T., Yaguchi, H., Tsuboi, R., and Ogawa, H. (1998). The expression of endothelin-1 and its binding sites in mouse skin increased after ultraviolet B irradiation or local injection of tumor necrosis factor alpha. J Dermatol 25, 78-84.
Albers, K.M., and Davis, B.M. (2007). The skin as a neurotrophic organ. Neuroscientist 13, 371-382.
Albert et al., "TRPV4 channels mediate the infrared laser-evoked response in sensory neurons," J Neurophysiol, 2012. 107(12): p. 3227-34.
Alenmyr L, Hogestatt ED, Zygmunt PM, & Greiff L (2009) TRPV1-mediated itch in seasonal allergic rhinitis. Allergy 64(5):807-810.
Alessandri-Haber et al., "Hypotonicity induces TRPV4-mediated nociception in rat," Neuron, 2003. 39(3): p. 497-511.
Alessandri-Haber, N., Dina, O. A., Yeh, J. J., Parada, C. A., Reichling, D. B., and Levine, J. D. (2004) Transient receptor potential vanilloid 4 is essential in chemotherapy-induced neuropathic pain in the rat, J Neurosci 24, 4444-4452.
Alessandri-Haber, N., Joseph, E., Dina, O. A., Liedtke, W., and Levine, J.D. (2005). TRPV4 mediates pain-related behavior induced by mild hypertonic stimuli in the presence of inflammatory mediator. Pain 118, 70-79.
Alptekin, N. O., Ari, H., Ataoglu, T., Haliloglu, S., Alptekin, T., and Serpek, B. (2005). Neutrophil elastase levels in periapical exudates of symptomatic and asymptomatic teeth. Journal of endodontics 31, 350-353.
Andoh, T., T. Yoshida, J.B. Lee, and Y. Kuraishi, Cathepsin E induces itch-related response through the production of endothelin-1 in mice. Eur J Pharmacol, 2012. 686(1-3): p. 16-21.
Andrade et al., "TRPV4 channel is involved in the coupling of fluid viscosity changes to epithelial ciliary activity," J Cell Biol, 2005. 168(6): p. 869-74.
Andrews et al., "Keloids: The paradigm of Skin Fibrosis—Pathomechanisms and treatment," Matrix Biology, 2016, 51: 37-46.
Atoyan, R., D. Shander, and N.V. Botchkareva, Non-neuronal expression of transient receptor potential type A1 (TRPA1) in human skin. J Invest Dermatol, 2009. 129(9): p. 2312-5.
Aycock, R. et al., "Development of UV-induced Squamous Cell Carcinomas is Suppressed in the Absence of SPARC," Journal of Investigative Dermatology, 2004, vol. 123, No. 3, pp. 562-569.
Balonov, K., Khodorova, A., and Strichartz, G.R. (2006). Tactile allodynia initiated by local subcutaneous endothelin-1 is prolonged by activation of TRPV-1 receptors. Exp Biol Med (Maywood) 231, 1165-1170.
Baum et al. Antimicrobial Agents and Chemotherapy 2006, 50(1), 230-236.
Bellono NW, Kammel LG, Zimmerman AL, & Oancea E (2013) UV light phototransduction activates transient receptor potential A1 ion channels in human melanocytes. Proc Natl Acad Sci U S A 110(6):2383-2388.
Benemei et al., "TRPA1 and other TRP channels in migraine," J Headache Pain, 2013. 14: p. 71.
Benfenati et al., "An aquaporin-4/transient receptor potential vanilloid 4 (AQP4/TRPV4) complex is essential for cell-volume control in astrocytes," Proc Natl Acad Sci U S A, 2011. 108(6): p. 2563-8.
Benfenati et al., "Expression and functional characterization of transient receptor potential vanilloid-related channel 4 (TRPV4) in rat cortical astrocytes," Neuroscience, 2007. 148(4): p. 876-92.

Bernard JJ, et al. (2012) Ultraviolet radiation damages self noncoding RNA and is detected by TLR3. Nature medicine.
Bersinger, N.A., Gunthert, A.R., McKinnon, B., Johann, S., and Mueller, M.D. (2011). Dose-response effect of interleukin (IL)-1beta, tumour necrosis factor (TNF)-alpha, and interferon-gamma on the in vitro production of epithelial neutrophil activating peptide-78 (ENA-78), IL-8, and IL-6 by human endometrial stromal cells. Arch Gynecol Obstet 283, 1291-1296.
Bessac et al., "TRPA1 is a major oxidant sensor in murine airway sensory neurons," J Clin Invest, 2008. 118(5): p. 1899-910.
Bishop, T., Hewson, D. W., Yip, P.K., Fahey, M.S., Dawbarn, D., Young, A.R., and McMahon, S.B. (2007). Characterisation of ultraviolet-B-induced inflammation as a model of hyperalgesia in the rat. Pain 131, 70-82.
Bonvini et al., "Targeting TRP channels for chronic cough: from bench to bedside," Naunyn Schmiedebergs Arch Pharmacol, 2015. 388(4): p. 401-20.
Bonvini et al., "Transient receptor potential cation channel, subfamily V, member 4 and airway sensory afferent activation: Role of adenosine triphosphate," J Allergy Clin Immunol, 2016.
Bosch, U., "Arthrofibrosis," Orthopade, 2002. 31(8): p. 785-90.
Boulais, N., and Misery, L. (2008). The epidermis: a sensory tissue. Eur J Dermatol 18, 119-127.
Brandli, P., B.M. Loffler, V. Breu, R. Osterwalder, J.P. Maire, and M. Clozel, Role of endothelin in mediating neurogenic plasma extravasation in rat dura mater. Pain, 1996. 64(2): p. 315-22.
Brierley et al., "Selective role for TRPV4 ion channels in visceral sensory pathways," Gastroenterology, 2008. 134(7): p. 2059-69.
Brierley et al., "The ion channel TRPA1 is required for normal mechanosensation and is modulated by algesic stimuli," Gastroenterology, 2009. 137(6): p. 2084-2095 e3.
Burkhart, C.G. and H.R. Burkhart, Contact irritant dermatitis and anti-pruritic agents: the need to address the itch. J Drugs Dermatol, 2003. 2(2): p. 143-6.
Butenko et al., "The increased activity of TRPV1 channel in the astrocytes of the adult rat hippocampus after cerebral hypoxia/ischemia," PLoS One, 2012. 7(6): p. e39959.
Buzzi et al., "Peripheral and central activation of trigeminal pain pathways in migraine: data from experimental animal models," Cephalalgia, 2003. 23 Suppl 1: p. 1-4.
Cai X (2008) A new tr(i)p to sense pain: TRPA1 channel as a target for novel analgesics. Expert review of neurotherapeutics 8(11):1675-1681.
Cao, D.S., Yu, S.Q., and Premkumar, L.S. (2009). Modulation of transient receptor potential Vanilloid 4-mediated membrane currents and synaptic transmission by protein kinase C. Molecular pain 5, 5.
Cattaruzza et al., "Transient receptor potential ankyrin1 mediates chronic pancreatitis pain in mice," Am J Physiol Gastrointest Liver Physiol, 2013. 304(11): p. G1002-12.
Cenac et al., "Transient receptor potential vanilloid-4 has a major role in visceral hypersensitivity symptoms," Gastroenterology, 2008. 135(3): p. 937-46, 946 e1-2.
Ceppa et al., "Transient receptor potential ion channels V4 and A1 contribute to pancreatitis pain in mice," Am J Physiol Gastrointest Liver Physiol, 2010. 299(3): p. G556- 71.
Chang CY, et al. (2013) NFIB is a governor of epithelial-melanocyte stem cell behaviour in a shared niche. Nature 495(7439):98-102.
Chang, M. S., Mcninch, J., Basu, R., and Simonet, S. (1994). Cloning and characterization of the human neutrophil-activating peptide (ENA-78) gene. J Biol Chem 269, 25277-25282.
Charrua, et al. "Co-administration of TRPV4 and TRPV1 antagonists potentiate the effect of each drug in a rat model of cystitis," BJU Int, 2014.
Chen et al., "Marked attenuation of inflammatory mediator-induced C-fiber sensitization for mechanical and hypotonic stimuli in TRPV4-/-mice," Mol Pain, 2007. 3: p. 31.
Chen et al., "Selective blockade of TRPA1 channel attenuates pathological pain without altering noxious cold sensation or body temperature regulation," Pain, 2011. 152(5): p. 1165-72.
Chen et al., "The modulation of voltage-gated potassium channels by anisotonicity in trigeminal ganglion neurons," Neuroscience, 2008. 154(2): p. 482-95.

(56) References Cited

OTHER PUBLICATIONS

Chen et al., "TRPV4 is necessary for trigeminal irritant pain and functions as a cellular formalin receptor," Pain, 2014, 2662-2672.
Chen Y, et al. (2013) Temporomandibular joint pain: A critical role for Trpv4 in the trigeminal ganglion. Pain.
Chen, Y., Willcockson, H.H., and Valtschanoff, J.G. (2009). Vanilloid receptor TRPV1-mediated phosphorylation of ERK in murine adjuvant arthritis. Osteoarthritis Cartilage 17, 244-251.
Cheng, X., Jin, J., Hu, L., Shen, D., Dong, X. P., Sarnie, M. A., Knoff, J., Eisinger, B., Liu, M. L., Huang, S. M., et al. (2010). TRP channel regulates EGFR signaling in hair morphogenesis and skin barrier formation. Cell 141, 331-343.
Chung et al., "Role of TRP channels in pain sensation," Advances in experimental medicine and biology, 2011. 704: p. 615-36.
Chung, M.K., Lee, H., and Caterina, M.J. (2003). Warm temperatures activate TRPV4 in mouse 308 keratinocytes. The Journal of biological chemistry 278, 32037-32046.
Clay et al., "Ozone-Induced Hypertussive Responses in Rabbits and Guinea Pigs," J Pharmacol Exp Ther, 2016. 357(1): p. 73-83.
D'Aldebert et al., "Transient receptor potential vanilloid 4 activated inflammatory signals by intestinal epithelial cells and colitis in mice," Gastroenterology, 2011. 140(1): p. 275-85.
Davar, G., Endothelin-1 and metastatic cancer pain. Pain Med, 2001. 2(1): p. 24-7.
Dawes, J.M., Calvo, M., Perkins, J.R., Paterson, K.J., Kiesewetter, H., Hobbs, C., Kaan, T.K., Orengo, C., Bennett, D.L., and McMahon, S.B. (2011). CXCL5 mediates UVB irradiation-induced pain. Sci Transl Med 3, 90ra60.
De Jongh, R.F., Vissers, K.C., Meert, T.F., Booij, L.H., De Deyne, C.S., and Heylen, R.J. (2003). The role of interleukin-6 in nociception and pain. Anesth Analg 96, 1096-1103, table of contents.
Del Rosso, J., "Update on Rosacea Pathogenesis And Correlation With Medical Therapeutic Agents," Cutis, 2006, vol. 78, pp. 97-100.
Demehri, S., M. Morimoto, M.J. Holtzman, and R. Kopan, Skin-derived TSLP triggers progression from epidermal-barrier defects to asthma. PLoS Biol, 2009. 7(5): p. e1000067.
Denda, M., Sokabe, T., Fukumi-Tominaga, T., and Tominaga, M. (2007). Effects of skin surface temperature on epidermal permeability barrier homeostasis. The Journal of investigative dermatology 127, 654-659.
Dhand, A. and M.J. Aminoff, The neurology of itch. Brain, 2014. 137(Pt 2): p. 313-22.
Ding et al., "Involvement of TRPV4-NO-cGMP-PKG pathways in the development of thermal hyperalgesia following chronic compression of the dorsal root ganglion in rats," Behav Brain Res, 2010. 208(1): p. 194-201.
Domon et al., "Mass spectrometry and protein analysis," Science, 2006, 312(5771):212-7.
Dunn et al., "TRPV4 channels stimulate Ca2+-induced Ca2+ release in astrocytic endfeet and amplify neurovascular coupling responses," Proc Natl Acad Sci U S A, 2013. 110(15): p. 6157-62.
Dussor et al., "Targeting TRP channels for novel migraine therapeutics," ACS Chem Neurosci, 2014. 5(11): p. 1085-96.
Dussor, G., Zylka, M.J., Anderson, D.J., and McCleskey, E.W. (2008). Cutaneous sensory neurons expressing the Mrgprd receptor sense extracellular ATP and are putative nociceptors. Journal of neurophysiology 99, 1581-1589.
Dymecki, S.M. (1996). Flp recombinase promotes site-specific DNA recombination in embryonic stem cells and transgenic mice. Proc Natl Acad Sci U S A 93, 6191-6196.
Edelmayer et al., "Activation of TRPA1 on dural afferents: a potential mechanism of headache pain," Pain, 2012. 153(9): p. 1949-58.
Edwards RR, et al. (2008) Association of catastrophizing with interleukin-6 responses to acute pain. Pain 140(1):135-144.
Eid, S.R., "Therapeutic targeting of TRP channels—the TR(i)P to pain relief," Curr Top Med Chem, 2011. 11(17): p. 2118-30.
Elias, P.M., and Steinhoff, M. (2008). "Outside-to-inside" (and now back to "outside") pathogenic mechanisms in atopic dermatitis. The Journal of investigative dermatology 128, 1067-1070.
Elmariah, S.B. and E.A. Lerner, The missing link between itch and inflammation in atopic dermatitis. Cell, 2013. 155(2): p. 267-9.
Engel et al., "TRPA1 and substance P mediate colitis in mice," Gastroenterology, 2011. 141(4): p. 1346-58.
Eriksson, E., "Arthrofibrosis," Knee Surg Sports Traumatol Arthrosc, 1996. 4(4): p. 193.
European Patent Office Extended Search Report for Application No. 13813477.0 dated Aug. 25, 2016 (10 pages).
European Patent Office Search Report for Application No. 13813477.0 dated Apr. 18, 2016 (8 pages).
Everaerts et al., "Inhibition of the cation channel TRPV4 improves bladder function in mice and rats with cyclophosphamide-induced cystitis," Proc Natl Acad Sci U S A, 2010. 107(44): p. 19084-9.
Feetham et al., "The depressor response to intracerebroventricular hypotonic saline is sensitive to TRPV4 antagonist RN1734," Front Pharmacol, 2015. 6: p. 83.
Feldmeyer, L., Keller, M., Niklaus, G., Hohl, D., Werner, S., and Beer, H.D. (2007). The inflammasome mediates UVB-induced activation and secretion of interleukin-1beta by keratinocytes. Curr Biol 17, 1140-1145.
Fernandes et al., "IP3 sensitizes TRPV4 channel to the mechano- and osmotransducing messenger 5'-6'-epoxyeicosatrienoic acid," J Cell Biol, 2008. 181(1): p. 143-55.
Fichna et al., "Transient receptor potential vanilloid 4 blockade protects against experimental colitis in mice: a new strategy for inflammatory bowel diseases treatment?" Neurogastroenterol Motil, 2012. 24(11): p. e557-60.
Filosa et al., "Astrocyte regulation of cerebral vascular tone," Am J Physiol Heart Circ Physiol, 2013. 305(5): p. H609-19.
Forsmark et al., "The challenging task of treating painful chronic pancreatitis," Gastroenterology, 2012. 143(3): p. 533-5.
Franzen, L., C. Mathes, S. Hansen, and M. Windbergs, Advanced chemical imaging and comparison of human and porcine hair follicles for drug delivery by confocal Raman microscopy. J Biomed Opt, 2013. 18(6): p. 061210.
Fuchs, E. (2009). Finding one's niche in the skin. Cell stem cell 4, 499-502.
Geppetti et al., "Cough: The Emerging Role of the TRPA1 Channel," Lung, 2010. 188 Suppl 1: p. S63-8.
Gilchrest, B. A., Park, H. Y., Eller, M. S., and Yaar, M. (1996). Mechanisms of ultraviolet light-induced pigmentation. Photochemistry and photobiology 63, 1-10.
Gomes, L.O., D.B. Hara, and G.A. Rae, Endothelin-1 induces itch and pain in the mouse cheek model. Life Sci, 2012. 91(13-14): p. 628-33.
Gonczi, M., Szentandrassy, N., Fulop, L., Telek, A., Szigeti, G.P., Magyar, J., Biro, T., Nanasi, P.P., and Csemoch, L. (2007). Hypotonic stress influence the membrane potential and alter the proliferation of keratinocytes in vitro. Exp Dermatol 16, 302-310.
Grant et al., "Protease-activated receptor 2 sensitizes the transient receptor potential vanilloid 4 ion channel to cause mechanical hyperalgesia in mice," J Physiol, 2007. 578(Pt 3): p. 715-33.
Gunthorpe MJ & Chizh BA (2009) Clinical development of TRPV1 antagonists: targeting a pivotal point in the pain pathway. Drug discovery today 14(1-2):56-67.
Haeberle H, Bryan LA, Vadakkan TJ, Dickinson ME, & Lumpkin EA (2008) Swelling-activated Ca2+ channels trigger Ca2+ signals in Merkel cells. PLoS One 3(3):e1750.
Hargreaves, K., Dubner, R., Brown, F., Flores, C., and Joris, J. (1988). A new and sensitive method for measuring thermal nociception in cutaneous hyperalgesia. Pain 32, 77-88.
Harrison, G.I., Young, A.R., and McMahon, S.B. (2004). Ultraviolet radiation-induced inflammation as a model for cutaneous hyperalgesia. J Invest Dermatol 122, 183-189.
Hartmannsgruber et al., "Arterial response to shear stress critically depends on endothelial TRPV4 expression," PLoS One, 2007. 2(9): p. e827.
Heagerty et al., "Time-dependent ROC curves for censored survival data and a diagnostic marker," Biometrics, 2000, 56, 337-44.
Hill K & Schaefer M (2009) Ultraviolet light and photosensitising agents activate TRPA1 via generation of oxidative stress. Cell calcium 45(2): 155-164.

(56) References Cited

OTHER PUBLICATIONS

Hurd et al., "A mutation in TRPV4 results in altered chondrocyte calcium signaling in severe metatropic dysplasia," Am J Med Genet A, 2015. 167A(10): p. 2286-93.
Imamachi N, et al. (2009) TRPV1-expressing primary afferents generate behavioral responses to pruritogens via multiple mechanisms. Proc Natl Acad Sci U S A 106(27):11330-11335.
Joachim, R. A., Handjiski, B., Blois, S. M., Hagen, E., Paus, R., and Arck, P. C. (2008). Stress-induced neurogenic inflammation in murine skin skews dendritic cells towards maturation and migration: key role of intercellular adhesion molecule-1/leukocyte function-associated antigen interactions. Am J Pathol 173, 1379-1388.
Kanju et al., "Small molecule dual-inhibitors of TRPV4 and TRPA1 for attenuation of inflammation and pain," Nature Scientific Reports, 2016, 1-12.
Katugampola R, Church MK, Clough GF. The neurogenic vasodilator response to endothelin-1: a study in human skin in vivo. Exp Physiol. Nov. 2000;85(6):839-46.
Keller, M., Ruegg, A., Werner, S., and Beer, H. D. (2008). Active caspase-1 is a regulator of unconventional protein secretion. Cell 132, 818-831.
Kennedy Crispin M, et al. (2013) Gene profiling of narrowband UVB-induced skin injury defines cellular and molecular innate immune responses. J Invest Dermatol 133(3):692-701.
Khan et al., "Animal models of orofacial pain," Methods Mol Biol, 2010. 617: p. 93-104.
Khodorova, A., Montmayeur, J.P., and Strichartz, G. (2009). Endothelin receptors and pain. J Pain 10, 4-28.
Kim et al., "Astrocyte contributions to flow/pressure-evoked parenchymal arteriole vasoconstriction," J Neurosci, 2015. 35(21): p. 8245-57.
Kim SJ, et al. (2011) Analysis of cellular and behavioral responses to imiquimod reveals a unique itch pathway in transient receptor potential vanilloid 1 (TRPV1)-expressing neurons. Proc Natl Acad Sci U S A 108(8):3371-3376.
Kimball et al., "Stimulation of neuronal receptors, neuropeptides and cytokines during experimental oil of mustard colitis," Neurogastroenterol Motil, 2007. 19(5): p. 390-400.
King Jr. et al., "Idiopathic Pulmonary Fibrosis", 2011, Lancet, vol. 378, pp. 1949-1961.
Kligman LH & Murphy GF (1996) Ultraviolet B radiation increases hairless mouse mast cells in a dose-dependent manner and alters distribution of UV-induced mast cell growth factor. Photochemistry and photobiology 63(1): 123-127.
Knock, G.A., Terenghi, G., Bunker, C.B., Bull, H.A., Dowd, P.M., and Polak, J.M. (1993). Characterization of endothelin-binding sites in human skin and their regulation in primary Raynaud's phenomenon and systemic sclerosis. J Invest Dermatol 101, 73-78.
Knowlton WM & McKemy DD (2011) TRPM8: from cold to cancer, peppermint to pain. Current pharmaceutical biotechnology 12(1):68-77.
Köhler et al., "Continuous cultures of fused cells secreting antibody of predefined specificity," Nature 1975, 256, 495.
Kohler et al., "Evidence for a functional role of endothelial transient receptor potential V4 in shear stress-induced vasodilatation," Arterioscler Thromb Vasc Biol, 2006. 26(7): p. 1495-502.
Koivisto et al., "TRPA1: a transducer and amplifier of pain and inflammation," Basic Clin Pharmacol Toxicol, 2014. 114(1): p. 50-5.
Koltzenburg, M. (2004). The role of TRP channels in sensory neurons. Novartis Foundation symposium 260, 206-213; discussion 213-220, 277-279.
Kou et al., "Periostin levels correlate with disease severity and chronicity in patients with atopic dermatitis," Br J Dermatol, 2014. 171(2): p. 283-91.
Kowal et al., "ATP release, generation and hydrolysis in exocrine pancreatic duct cells," Purinergic Signal, 2015. 11(4): p. 533-50.
Krause et al., "Transient receptor potential ion channels as targets for the discovery of pain therapeutics," Curr Opin Investig Drugs, 2005. 6(1): p. 48-57.
Kunkler et al., " TRPA1 receptors mediate environmental irritant-induced meningeal vasodilatation," Pain, 2011. 152(1): p. 38-44.
Kupper TS & Groves RW (1995) The interleukin-1 axis and cutaneous inflammation. J Invest Dermatol 105(1 Suppl):62S-66S.
Kupper, T.S., Lee, F., Birchall, N., Clark, S., and Dower, S. (1988). Interleukin 1 binds to specific receptors on human keratinocytes and induces granulocyte macrophage colony-stimulating factor mRNA and protein. A potential autocrine role for interleukin 1 in epidermis. J Clin Invest 82, 1787-1792.
Lanciotti et al., "Megalencephalic leukoencephalopathy with subcortical cysts protein 1 functionally cooperates with the TRPV4 cation channel to activate the response of astrocytes to osmotic stress: dysregulationby pathological mutations," Hum Mol Genet, 2012. 21(10): p. 2166-80.
Lapointe TK & Altier C (2011) The role of TRPA1 in visceral inflammation and pain. Channels (Austin) 5(6):525-529.
Lazar J, Gharat L, Khairathkar-Joshi N, Blumberg PM, & Szallasi A (2009) Screening TRPV1 antagonists for the treatment of pain lessons learned over a decade. Expert opinion on drug discovery 4(2): 159-180.
Lechner, S.G., Markworth, S., Poole, K., Smith, E.S., Lapatsina, L., Frahm, S., May, M., Pischke, S., Suzuki, M., Ibanez-Tallon, I., et al. (2010). The molecular and cellular identity of peripheral osmoreceptors. Neuron 69, 332-344.
Lee, H., and Caterina, M. J. (2005). TRPV channels as thermosensory receptors in epithelial cells. Pflugers Arch 451, 160-167.
Lee, K.T., M.J. Byun, K.S. Kang, E.W. Park, S.H. Lee, S. Cho, H. Kim, K.W. Kim, T. Lee, J.E. Park, W. Park, D. Shin, H.S. Park, J.T. Jeon, B.H. Choi, G.W. Jang, S.H. Choi, D.W. Kim, D. Lim, H.S. Park, M.R. Park, J. Ott, L.B. Schook, T.H. Kim, and H. Kim, Neuronal genes for subcutaneous fat thickness in human and pig are identified by local genomic sequencing and combined SNP association study. PLoS One, 2011. 6(2): p. e16356.
Leung, D.Y., Atopic dermatitis: new insights and opportunities for therapeutic intervention. J Allergy Clin Immunol, 2000. 105(5): p. 860-76.
Levine et al., "TRP channels: Targets for the relief of pain," Biochim Biophys Acta, 2007, 989-1003.
Li, J., Ghio, A.J., Cho, S.H., Brinckerhoff, C.E., Simon, S.A., and Liedtke, W. (2009). Diesel exhaust particles activate the matrix-metalloproteinase-1 gene in human bronchial epithelia in a beta-arrestin-dependent manner via activation of RAS. Environ Health Perspect 117, 400-409.
Li, J., Kanju, P., Patterson, M., Chew, W.L., Cho, S.H., Gilmour, I., Oliver, T., Yasuda, R., Ghio, A., Simon, S.A., et al. (2011). TRPV4-mediated calcium influx into human bronchial epithelia upon exposure to diesel exhaust particles. Environ Health Perspect 119, 784-793.
Li, L., Liu, C., Chen, L., and Chen, L. (2010). Hypotonicity modulates tetrodotoxin-sensitive sodium current in trigeminal ganglion neurons. Molecular pain 7, 27.
Liang J, Ji Q, Ji W. Role of transient receptor potential ankyrin subfamily member 1 in pruritus induced by endothelin-1. Neurosci Lett. Apr. 4, 2011;492(3):175-8.
Liang J, Kawamata T, Ji W. Molecular signaling of pruritus induced by endothelin-1 in mice. Exp Biol Med (Maywood). Nov. 2010;235(11):1300-5.
Liddle et al., "Neurogenic inflammation and pancreatitis," Pancreatology, 2004. 4(6): p. 551-9; discussion 559-60.
Liddle, R.A., "Pancreatitis: the acid test," Gastroenterology, 2010. 139(5): p. 1457-60.
Liddle, R.A., "The role of Transient Receptor Potential Vanilloid 1 (TRPV1) channels in pancreatitis," Biochim Biophys Acta, 2007. 1772(8): p. 869-78.
Liedtke et al., "Functionality of the TRPV subfamily of TRP ion channels: add mechano-TRP and osmo-TRP to the lexicon!" Cell Mol Life Sci, 2005. 62(24): p. 2985-3001.
Liedtke et al., "Mammalian TRPV4 (VR-OAC) directs behavioral responses to osmotic and mechanical stimuli in Caenorhabditis elegans," Proc Natl Acad Sci U S A, 2003. 100: p. 14531-6.
Liedtke, W., "Molecular mechanisms of TRPV4-mediated neural signaling," Ann N Y Acad Sci, 2008. 1144: p. 42-52.

(56) References Cited

OTHER PUBLICATIONS

Liedtke, W., and Friedman, J.M. (2003). Abnormal osmotic regulation in trpv4-/- mice. Proc Natl Acad Sci U S A 100, 13698-13703.
Liedtke, W., Choe, Y., Marti-Renom, M.A., Bell, A.M., Denis, C.S., Sali, A., Hudspeth, A.J., Friedman, J.M., and Heller, S. (2000). Vanilloid receptor-related osmotically activated channel (VR-OAC), a candidate vertebrate osmoreceptor. Cell 103, 525-535.
Liu, B., J. Escalera, S. Balakrishna, L. Fan, A.I. Caceres, E. Robinson, A. Sui, M.C. McKay, M.A. McAlexander, C.A. Herrick, and S.E. Jordt, TRPA1 controls inflammation and pruritogen responses in allergic contact dermatitis. Faseb J, 2013. 27(9): p. 3549-63.
Liu, T., van Rooijen, N., and Tracey, D.J. (2000). Depletion of macrophages reduces axonal degeneration and hyperalgesia following nerve injury. Pain 86, 25-32.
Lu, C. P., Polak, L., Rocha, A. S., Pasolli, H. A., Chen, S. C., Sharma, N., Blanpain, C., and Fuchs, E. (2012). Identification of Stem Cell Populations in Sweat Glands and Ducts Reveals Roles in Homeostasis and Wound Repair. Cell 150, 136-150.
Luccarini et al., "Remind him to cut the existing cabinet covers to the size of our kitchen cabinets in the garage," J. Pain, 2006, 7(12):908-914.
Luck, J. V., "Traumatic arthrofibrosis; the fibroplastic response of joints to trauma," Bull Hosp Joint Dis, 1951. 12(2): p. 394-403.
Luvisetto et al., "Analgesic effects of botulinum neurotoxin type A in a model of allyl isothiocyanate- and capsaicin-induced pain in mice," Toxicon, 2015. 94: p. 23-8.
Magit et al., "Arthrofibrosis of the knee," J Am Acad Orthop Surg, 2007. 15(11): p. 682-94.
Maricich SM, et al. (2009) Merkel cells are essential for light-touch responses. Science 324(5934):1580-1582.
Maricich SM, Morrison KM, Mathes EL, & Brewer BM (2012) Rodents rely on Merkel cells for texture discrimination tasks. J Neurosci 32(10):3296-3300.
Martinez-Levasseur, L. M., Gendron, D., Knell, R. J., O'Toole, E. A., Singh, M., and Acevedo-Whitehouse, K. (2011). Acute sun damage and photoprotective responses in whales. Proc Royal Soc B 278, 1581-1586.
Masuoka et al., "Periostin promotes chronic allergic inflammation in response to Th2 cytokines," J Clin Invest, 2012. 122(7): p. 2590-600.
Matthews et al., "Ultra-rapid activation of TRPV4 ion channels by mechanical forces applied to cell surface beta1 integrins," Integr Biol (Camb), 2010. 2(9): p. 435-42.
McGrath, J.A., and Uitto, J. (2008). The filaggrin story: novel insights into skin-barrier function and disease. Trends in molecular medicine 14, 20-27.
McMahon SB & Wood JN (2006) Increasingly irritable and close to tears: TRPA1 in inflammatory pain. Cell 124(6):1123-1125.
McNulty et al., "TRPV4 as a therapeutic target for joint diseases," Naunyn Schmiedebergs Arch Pharmacol, 2015. 388(4): p. 437-50.
McQueen DS, Noble MA, Bond SM. Endothelin-1 activates ETA receptors to cause reflex scratching in BALB/c mice. Br J Pharmacol. May 2007;151(2):278-84.
Merrill et al., "Intravesical TRPV4 blockade reduces repeated variate stress-induced bladder dysfunction by increasing bladder capacity and decreasing voiding frequency in male rats," Am J Physiol Regul Integr Comp Physiol, 2014. 307(4): p. R471-80.
Merrill et al., "Transcriptional and translational plasticity in rodent urinary bladder TRP channels with urinary bladder inflammation, bladder dysfunction, or postnatal maturation," J Mol Neurosci, 2012. 48(3): p. 744-56.
Mishra SK & Hoon MA (2010) Ablation of TrpV1 neurons reveals their selective role in thermal pain sensation. Molecular and cellular neurosciences 43(1): 157-163.
Mishra SK & Hoon MA (2013) The cells and circuitry for itch responses in mice. Science 340(6135):968-971.
Mishra SK, Tisel SM, Orestes P, Bhangoo SK, & Hoon MA (2011) TRPV1-lineage neurons are required for thermal sensation. The EMBO journal 30(3):582-593.

Modir, J.G., and Wallace, M.S. (2011). Human experimental pain models 1: the ultraviolet light UV-B pain model. Methods in molecular biology (Clifton, NJ 617, 159-164.
Mogil et al., "The necessity of animal models in pain research," Pain, 2010. 151(1): p. 12-7.
Mogil, J.S., "Animal models of pain: progress and challenges," Nat Rev Neurosci, 2009. 10(4): p. 283-94.
Moilanen et al., "Monosodium iodoacetate-induced inflammation and joint pain are reduced in TRPA1 deficient mice—potential role of TRPA1 in osteoarthritis," Osteoarthritis Cartilage, 2015. 23(11): p. 2017-26.
Moore, C., F. Cevikbas, H.A. Pasolli, Y. Chen, W. Kong, C. Kempkes, P. Parekh, S.H. Lee, N.A. Kontchou, I. Yeh, N.M. Jokerst, E. Fuchs, M. Steinhoff, and W.B. Liedtke, UVB radiation generates sunburn pain and affects skin by activating epidermal TRPV4 ion channels and triggering endothelin-1 signaling. Proc Natl Acad Sci U S A, 2013. 110(34): p. E3225-34.
Moqrich, A., Hwang, S. W., Earley, T. J., Petrus, M. J., Murray, A. N., Spencer, K. S., Andahazy, M., Story, G. M., and Patapoutian, A. (2005). Impaired thermosensation in mice lacking TRPV3, a heat and camphor sensor in the skin. Science 307, 1468-1472.
Moran, M. M., McAlexander, M. A., Biro, T., and Szallasi, A. (2011). Transient receptor potential channels as therapeutic targets. Nature reviews Drug discovery 10, 601-620.
Morita et al., "HTR7 Mediates Serotonergic Acute and Chronic Itch," Neuron, 2015. 87(1): p. 124-38.
Motta, E.M., Calixto, J.B., and Rae, G.A. (2006). Mechanical hyperalgesia induced by endothelin-1 in rats is mediated via phospholipase C, protein kinase C, and MAP kinases. Exp Biol Med (Maywood) 231, 1141-1145.
Mueller-Tribbensee et al., "Differential Contribution of TRPA1, TRPV4 and TRPMB to Colonic Nociception in Mice," PLoS One, 2015. 10(7): p. e0128242.
Mutai, H., and Heller, S. (2003). Vertebrate and invertebrate TRPV-like mechanoreceptors. Cell calcium 33, 471-478.
Muto et al., "Development and histologic characteristics of synovitis induced by trauma in the rat temporomandibular joint," Int J Oral Maxillofac Surg, 1998. 27(6): p. 470-5.
Nakatsuka et al., "Identification of molecular determinants for a potent mammalian TRPA1 antagonist by utilizing species differences," J Mol Neurosci, 2013. 51(3): p. 754-62.
Namer, B., Hilliges, M., Orstavik, K., Schmidt, R. Weidner, C., Torebjork, E., Handwerker, H., and Schmelz, M. (2008) Endothelin 1 activates and sensitizes human C-nociceptors. Pain 137, 41-49.
Nassini et al., "The 'headache tree' via umbellulone and TRPA1 activates the trigeminovascular system," Brain, 2012. 135(Pt 2): p. 376-90.
Nassini et al., "The TRPA1 channel in inflammatory and neuropathic pain and migraine," Rev Physiol Biochem Pharmacol, 2014. 167: p. 1-43.
Nemes, Z., and Steinert, P.M. (1999). Bricks and mortar of the epidermal barrier. Experimental & molecular medicine 31, 5-19.
Nilins, B., Vriens, J., Prenen, J., Droogmans, G., and Voets, T. (2004). TRPV4 calcium entry channel: a paradigm for gating diversity. American journal of physiology 286, C195-205.
Ning et al., "Functional interaction of TRPV4 channel protein with annexin A2 in DRG," Neurol Res, 2012. 34(7): p. 685-93.
Ning et al., "Role of colchicine-induced microtubule depolymerization in hyperalgesia via TRPV4 in rats with chronic compression of the dorsal root ganglion," Neurol Res, 2014. 36(1): p. 70-8.
Norris et al., "Periostin Regulates Collagen Fibrillogenesis and the Biomechanical Properties of Connective Tissues," Journal of Cellular Biochemistry, 2007, 101, 695-711.
O'Conor et al., "TRPV4-mediated mechanotransduction regulates the metabolic response of chondrocytes to dynamic loading," Proc Natl Acad Sci U S A, 2014. 111(4): p. 1316-21.
Okada et al., "TRPA1 is required for RGF-β signaling and its loss blocks inflammatory fribrosis in mouse corneal stroma," Laboratory Investigation, 2014, 94, 1030-1041.
O'Neil et al., "The mechanosensitive nature of TRPV channels," Pflugers Arch, 2005. 451(1): p. 193-203.

(56) References Cited

OTHER PUBLICATIONS

Ovaere, P., Lippens, S., Vandenabeele, P., and Declercq, W. (2009). The emerging roles of serine protease cascades in the epidermis. Trends in biochemical sciences 34, 453-463.
Pande et al. Acta Pharmaceutica Jugoslavica 1984, 34(2), 61-8.
Patapoutian, A. (2005). TRP Channels and Thermosensation. Chem Senses 30 Suppl 1, il93-il94.
Patel KN, Liu Q, Meeker S, Undem BJ, & Dong X (2011) Pirt, a TRPV1 modulator, is required for histamine-dependent and -independent itch. PLoS One 6(5):e20559.
Paus, R., Theoharides, T.C., and Arck, P.C. (2006). Neuroimmunoendocrine circuitry of the 'brain-skin connection'. Trends in immunology 27, 32-39.
Peier, A. M., Reeve, A. J., Andersson, D. A., Moqrich, A., Earley, T. J., Hergarden, A. C., Story, G. M., Colley, S., Hogenesch, J. B., McIntyre, P., et al. (2002). A Heat-Sensitive TRP Channel Expressed in Keratinocytes. Science 296, 2046-2049.
Phan, M.N., Leddy, H.A., Votta, B.J., Kumar, S., Levy, D.S., Lipshutz, D.B., Lee, S.H., Liedtke, W., and Guilak, F. (2009). Functional characterization of TRPV4 as an osmotically sensitive ion channel in porcine articular chondrocytes. Arthritis Rheum 60, 3028-3037.
Porro, C.A., and Cavazzuti, M. (1993). Spatial and temporal aspects of spinal cord and brainstem activation in the formalin pain model. Progress in neurobiology 41, 565-607.
Pradhan et al. Journal of Environmental Research and Development, 2006, 1(1), 16-21.
Rabbani P, et al. (2011) Coordinated activation of Wnt in epithelial and melanocyte stem cells initiates pigmented hair regeneration. Cell 145(6):941-955.
Rahaman et al. "Role of Cation Channel TRPV4 in Mechanosensing, Myofibroblast Differentiation, and Pulmonary Fibrosis." Annals of the American Thoracic Society, Mar. 1, 2015, vol. 12, supplement 1, pp. S74-S75.
Rahaman et al. "TRPV4 mediates myofibroblast differentiation and pulmonary fibrosis in mice." The Journal of Clinical Investigation, Dec. 2014, vol. 124, pp. 5225-5238.
Rahaman et al., "Trpv4 Channel Regulates Tgfbeta-Induced Myofibroblast Differentiation By Activation Of Pi3k/akt Pathway," Am J Respir Crit Care Med 187, 2013:A3838.
Rausch, L., E.C. Bisinger, Jr., A. Sharma, and R. Rose, Use of the domestic Swine as an alternative animal model for conducting dermal irritation/corrosion studies on fatty amine ethoxylates. Int J Toxicol, 2003. 22(4): p. 317-23.
Rauschmayr T, Groves RW, & Kupper TS (1997) Keratinocyte expression of the type 2 interleukin 1 receptor mediates local and specific inhibition of interleukin 1-mediated inflammation. Proc Natl Acad Sci U S A 94(11):5814-5819.
Ren, K., and Torres, R. (2009). Role of interleukin-1beta during pain and inflammation. Brain Res Rev 60, 57-64.
Riccio MM, Reynolds CJ, Hay DW, Proud D. Effects of intranasal administration of endothelin-1 to allergic and nonallergic individuals. Am J Respir Crit Care Med. Dec. 1995;152(6 Pt 1):1757-64.
Roosterman, D., Goerge, T., Schneider, S.W., Bunnett, N. W., and Steinhoff, M. (2006). Neuronal control of skin function: the skin as a neuroimmunoendocrine organ. Physiological reviews 86, 1309-1379.
Rustagi et al., "Antioxidant therapy for pain reduction in patients with chronic pancreatitis: a systematic review and meta-analysis," Pancreas, 2015. 44(5): p. 812-8.
Sacerdote P, Bianchi M, Ricciardi-Castagnoli P, & Panerai AE (1992) Tumor necrosis factor alpha and interleukin-1 alpha increase pain thresholds in the rat. Ann N Y Acad Sci 650:197-201.
Schwartz et al., "TRPV1 and TRPA1 antagonists prevent the transition of acute to chronic inflammation and pain in chronic pancreatitis," J Neurosci, 2013. 33(13): p. 5603-11.
Schweizer A, Feige U, Fontana A, Muller K, & Dinarello CA (1988) Interleukin-1 enhances pain reflexes. Mediation through increased prostaglandin E2 levels. Agents and actions 25(3-4):246-251.

ScienceDaily Article, UC SanDiego, "Researchers identify a new culprit behind fibrosis," 2015, <https://www.sciencedaily.com/releases/2015/10/151015114803.htm> accessed Oct. 1, 2018, 3 pages.
Shibasaki et al., "A novel subtype of astrocytes expressing TRPV4 regulates neuronal excitability via release of gliotransmitters," J Biol Chem, 2014, vol. 289, No. 21, pp. 14470-14480.
Shibasaki et al., "Effects of body temperature on neural activity in the hippocampus: regulation of resting membrane potentials by transient receptor potential vanilloid 4," J Neurosci, 2007. 27(7): p. 1566-75.
Shigetomi et al., "TRPA1 channels are regulators of astrocyte basal calcium levels and long-term potentiation via constitutive D-serine release," J Neurosci, 2013. 33(24): p. 10143-53.
Shigetomi et al., "TRPA1 channels regulate astrocyte resting calcium and inhibitory synapse efficacy through GAT-3," Nat Neurosci, 2012. 15(1): p. 70-80.
Shiraishi et al., "Periostin contributes to the pathogenesis of atopic dermatitis by inducing TSLP production from keratinocytes," Allergol Int, 2012. 61(4): p. 563-72.
Simon et al., "How irritating: the role of TRPA1 in sensing cigarette smoke and aerogenic oxidants in the airways," J Clin Invest, 2008. 118(7): p. 2383-6.
Sipe, W., Brierley, S. M., Martin, C. M., Phillis, B. D., Bautista Cruz, F., Grady, E. F., Liedtke, W., Cohen, D. M., Vanner, S. J., Blackshaw, L. A., et al. (2008). Transient Receptor potential Vanilloid 4 Mediates Protease Activated Receptor 2-Induced Sensitization of Colonic Afferent Nerves and Visceral Hyperalgesia. American Journal of Physiology 294, G1288-1298.
Situm, M. et al., "The Role of UV Radiation in the Development of Basal Cell Carcinoma," Coll. Antropol., 2008, vol. 32, Suppl. 2, pp. 167-170.
Sokabe, T., and Tominaga, M. (2011). The TRPV4 cation channel: A molecule linking skin temperature and barrier function. Communicative & integrative biology 3, 619-621.
Sokabe, T., Fukumi-Tominaga, T., Yonemura, S., Mizuno, A., and Tominaga, M. (2010). The TRPV4 channel contributes to intercellular junction formation in keratinocytes. The Journal of biological chemistry 285, 18749-18758.
Soter, N.A. (1990). Acute effects of ultraviolet radiation on the skin. Seminars in dermatology 9, 11-15.
Soya et al., "Plasma membrane stretch activates transient receptor potential vanilloid and ankyrin channels in Merkel cells from hamster buccal mucosa," Cell Calcium, 2014. 55(4): p. 208-18.
Stotz et al., "Citral sensing by Transient [corrected] receptor potential channels in dorsal root ganglion neurons," PLoS One, 2008. 3(5): p. e2082.
Strotmann et al., "OTRPC4, a nonselective cation channel that confers sensitivity to extracellular osmolarity," Nat Cell Biol, 2000. 2(10): p. 695-702.
Su et al., "TRPA1 and TRPV1 contribute to iodine antiseptics-associated pain and allergy," EMBO Reports, 2016, vol. 17, p. 1422-1430.
Sulk, M., Seeliger, S., Aubert, J., Schwab, V.D., Cevikbas, F., Rivier, M., Nowak, P., Voegel, J.J., Buddenkotte, J., and Steinhoff, M. (2012). Distribution and Expression of Non-Neuronal Transient Receptor Potential (TRPV) Ion Channels in Rosacea. The Journal of investigative dermatology, 132(4): 1253-1262.
Sullivan, T.P., W.H. Eaglstein, S.C. Davis, and P. Mertz, The pig as a model for human wound healing. Wound Repair Regen, 2001. 9(2): p. 66-76.
Svensson CI (2010) Interleukin-6: a local pain trigger? Arthritis Res Ther 12(5):145.
Tai C, Zhu S, & Zhou N (2008) TRPA1: the central molecule for chemical sensing in pain pathway? J Neurosci 28(5):1019-1021.
Taniguchi et al., "Periostin controls keratinocyte proliferation and differentiation by interacting with the paracrine IL-1alpha/IL-6 loop," J Invest Dermatol, 2014. 134(5): p. 1295-304.
Terada et al., "Roles of Cav3.2 and TRPA1 channels targeted by hydrogen sulfide in pancreatic nociceptive processing in mice with or without acute pancreatitis," J Neurosci Res, 2015. 93(2): p. 361-9.

(56) References Cited

OTHER PUBLICATIONS

Thodeti et al., "TRPV4 channels mediate cyclic strain-induced endothelial cell reorientation through integrin-to-integrin signaling," Circ Res, 2009. 104(9): p. 1123-30.
Tominaga, M., and Caterina, M. J. (2004). Thermosensation and pain. J Neurobiol 61, 3-12.
Trentin PG, Fernandes MB, D'Orleans-Juste P, Rae GA. Endothelin-1 causes pruritus in mice. Exp Biol Med (Maywood). Jun. 2006;231(6):1146-51.
Trevisan et al., "TRPA1 mediates trigeminal neuropathic pain in mice downstream of monocytes/macrophages and oxidative stress," Brain, 2016, 139:1361-1377.
Tsuboi, R., Sato, C., Oshita, Y., Hama, H., Sakurai, T., Goto, K., and Ogawa, H. (1995). Ultraviolet B irradiation increases endothelin-1 and endothelin receptor expression in cultured human keratinocytes. FEBS Lett 371, 188-190.
Turner, M.J. and B. Zhou, A new itch to scratch for TSLP. Trends Immunol, 2014. 35(2): p. 49-50.
Van Keymeulen A, et al. (2009) Epidermal progenitors give rise to Merkel cells during embryonic development and adult homeostasis. J Cell Biol 187(1):91-100.
Vasioukhin, V., Bauer, C., Degenstein, L., Wise, B., and Fuchs, E. (2001a). Hyperproliferation and defects in epithelial polarity upon conditional ablation of alpha-catenin in skin. Cell 104, 605-617.
Vasioukhin, V., Bowers, E., Bauer, C., Degenstein, L., and Fuchs, E. (2001b). Desmoplakin is essential in epidermal sheet formation. Nat Cell Biol 3, 1076-1085.
Vasioukhin, V., Degenstein, L., Wise, B., and Fuchs, E. (1999). The magical touch: genome targeting in epidermal stem cells induced by tamoxifen application to mouse skin. Proc Natl Acad Sci U S A 96, 8551-8556.
Vergnolle et al., "A role for transient receptor potential vanilloid 4 in tonicity-induced neurogenic inflammation," Br J Pharmacol, 2010. 159(5): p. 1161-73.
Vergnolle, N., "TRPV4: new therapeutic target for inflammatory bowel diseases," Biochem Pharmacol, 2014. 89(2): p. 157-61.
Verhoeven, E.W., S. de Klerk, F.W. Kraaimaat, P.C. van de Kerkhof, E.M. de Jong, and A.W. Evers, Biopsychosocial mechanisms of chronic itch in patients with skin diseases: a review. Acta Derm Venereol, 2008. 88(3): p. 211-8.
Vincent et al., "Identification and characterization of novel TRPV4 modulators," Biochem Biophys Res Commun, 2009. 389(3): p. 490-4.
Vincent, F., and Duncton, M.A. (2011). TRPV4 agonists and antagonists. Current topics in medicinal chemistry 11, 2216-2226.
Von Banchet et al., "Neuronal IL-17 receptor upregulates TRPV4 but not TRPV1 receptors in DRG neurons and mediates mechanical but not thermal hyperalgesia," Mol Cell Neurosci, 2013. 52: p. 152-60.
Walker SL & Young AR (1997) Sunscreens offer the same UVB protection factors for inflammation and immunosuppression in the mouse. J Invest Dermatol 108(2):133-138.
Wang, X., Zinkel, S., Polonsky, K., and Fuchs, E. (1997). Transgenic studies with a keratin promoter-driven growth hormone transgene: prospects for gene therapy. Proc Natl Acad Sci U S A 94, 219-226.
Wegierski, T., Lewandrowski, U, Muller, B., Sickmann, A., and Walz, G. (2009). Tyrosine phosphorylation modulates the activity of TRPV4 in response to defined stimuli. The Journal of biological chemistry 284, 2923-2933.
Wei et al., "Activation of TRPV4 on dural afferents produces headache-related behavior in a preclinical rat model," Cephalalgia, 2011. 31(16): p. 1595-600.
Wenzel RR, Zbinden S, Noll G, Meier B, Lüscher TF. Endothelin-1 induces vasodilation in human skin by nociceptor fibres and release of nitric oxide. Br J Clin Pharmacol. May 1998;45(5):441-6.
Willis WD, Jr. (2009) The role of TRPV1 receptors in pain evoked by noxious thermal and chemical stimuli. Exp Brain Res 196(1):5-11.
Wilson et al., "The ion channel TRPA1 is required for chronic itch," J Neurosci, 2013. 33(22): p. 9283-94.
Wilson, S.R., L. The, L.M. Batia, K. Beattie, G.E. Katibah, S.P. McClain, M. Pellegrino, D.M. Estandian, and D.M. Bautista, The epithelial cell-derived atopic dermatitis cytokine TSLP activates neurons to induce itch Cell, 2013. 155(2): p. 285-95.
Wolf G, Gabay E, Tai M, Yirmiya R, & Shavit Y (2006) Genetic impairment of interleukin-1 signaling attenuates neuropathic pain, autotomy, and spontaneous ectopic neuronal activity, following nerve injury in mice. Pain 120(3):315-324.
Wolf G, Livshits D, Beilin B, Yirmiya R, & Shavit Y (2008) Interleukin-1 signaling is required for induction and maintenance of postoperative incisional pain: genetic and pharmacological studies in mice. Brain, behavior, and immunity 22(7):1072-1077.
Woo SH, Stumpfova M, Jensen UB, Lumpkin EA, & Owens DM (2010) Identification of epidermal progenitors for the Merkel cell lineage. Development 137(23):3965-3971.
Yamaguchi, Y., "Periostin in skin tissue and skin-related diseases," Allergol Int, 2014. 63(2): p. 161-70.
Yang et al., "Histamine contributes to tissue remodeling via periostin expression," J Invest Dermatol, 2014. 134(8): p. 2105-13.
Yang et al., "OP0230 Periostin, a novel matricellular protein, is required for cutaneous sclerosis in a mouse model of scleroderma," Annals of the Rheumatic Diseases, 2013, 71:133-134.
Yang et al., "Transient receptor potential ankyrin-1 participates in visceral hyperalgesia following experimental colitis," Neurosci Lett, 2008. 440(3): p. 237-41.
Ye, L., S. Kleiner, J. Wu, R. Sah, R.K. Gupta, A.S. Banks, P. Cohen, M.J. Khandekar, P. Bostrom, R.J. Mepani, D. Laznik, T.M. Kamenecka, X. Song, W. Liedtke, V.K. Mootha, P. Puigserver, P.R. Griffin, D.E. Clapham, and B.M. Spiegelman, TRPV4 is a regulator of adipose oxidative metabolism, inflammation, and energy homeostasis. Cell, 2012. 151(1): p. 96-110.
Yeo M, Berglund K, Augustine G, & Liedtke W (2009) Novel repression of Kcc2 transcription by REST-RE-1 controls developmental switch in neuronal chloride. J Neurosci 29(46):14652-14662.
Ying et al., "The transient receptor potential vanilloid 4 channel modulates uterine tone during pregnancy," Sci Transl Med, 2015. 7(319): p. 319ra204.
Yohn JJ, et al. (1993) Cultured human keratinocytes synthesize and secrete endothelin-1. J Invest Dermatol 100(1):23-26.
Yuspa, S.H., Kilkenny, A.E., Steinert, P.M., and Roop, D.R. (1989). Expression of murine epidermal differentiation markers is tightly regulated by restricted extracellular calcium concentrations in vitro. J Cell Biol 109, 1207-1217.
Zarpelon, A.C., T.M. Cunha, J.C. Alves-Filho, L.G. Pinto, S.H. Ferreira, I.B. McInnes, D. Xu, F.Y. Liew, F.Q. Cunha, and W.A. Verri, Jr., IL-33/ST2 signalling contributes to carrageenin-induced innate inflammation and inflammatory pain: role of cytokines, endothelin-1 and prostaglandin E2. Br J Pharmacol, 2013. 169(1): p. 90-101.
Zeichen et al., "Immunohistochemical localization of collagen VI in arthrofibrosis," Arch Orthop Trauma Surg, 1999. 119(5-6): p. 315-8.
Zhan et al., "The role of TRPV4 in fibrosis," Gene, 2018, 642: 1-8.
Zhang et al., "Alcohol and high fat induced chronic pancreatitis: TRPV4 antagonist reduces hypersensitivity," Neuroscience, 2015. 311: p. 166-79.
Zhang et al., "Next-Gen Sequencing-Based Mapping and Identification of Ethyl Methanesulfonate-Induced Mutations in *Arabidopsis thaliana*," Current Protocols in Molecular Biology, 2014, 108:7. 18:7.18.1-7.18.16.
Zhang et al., "Overview of Peptide and protein analysis by mass spectrometry," Curr Protoc Mol Biol, 2014. 108: p. 10 21 1-10 21 30.
Zhang et al., "Prolonged high fat/alcohol exposure increases TRPV4 and its functional responses in pancreatic stellate cells," Am J Physiol Regul Integr Comp Physiol, 2013. 304(9): p. R702-11.
Zhang, Y., Wang, Y.H., Ge, H.Y., Arendt-Nielsen, L., Wang, R., and Yue, S.W. (2008). A transient receptor potential vanilloid 4 contributes to mechanical allodynia following chronic compression of dorsal root ganglion in rats. Neuroscience letters 432, 222-227.

(56) References Cited

OTHER PUBLICATIONS

Zhao et al., "Cathepsin S causes inflammatory pain via biased agonism of PAR2 and TRPV4," J Biol Chem, 2014. 289(39): p. 27215-34.
Zhao et al., "Neutrophil elastase activates PAR2 and TRPV4 to cause inflammation and pain," J Biol Chem, 2015, vol. 290, No. 22, pp. 13875-13887.
Zhou et al., "Spatiotemporal expression of periostin during skin development and incisional wound healing: lessons for human fibrotic scar formation," J Cell Commun Signal, 2010. 4(2): p. 99-107.
International Search Report and Written Opinion for Application No. PCT/US13/49457 dated Feb. 24, 2014 (13 pages).
International Search Report and Written Opinion for Application No. PCT/US14/52394 dated Feb. 24, 2015 (21 pages).
International Search Report and Written Opinion for Application No. PCT/US2017/026714 dated Jul. 21, 2017 (10 pages).
European Patent Office Action for Application No. 13813477.0 dated Aug. 29, 2018 (5 pages).
United States Patent Office Action for U.S. Appl. No. 14/993,010 dated Mar. 13, 2017 (11 pages).
United States Patent Office Action for U.S. Appl. No. 15/018,595 dated Aug. 18, 2016 (15 pages).
United States Patent Office Action for U.S. Appl. No. 15/505,898 dated Oct. 16, 2017 (13 pages).
United States Patent Office Notice of Allowance for U.S. Appl. No. 14/413,172 dated Nov. 9, 2015 (9 pages).
United States Patent Office Notice of Allowance for U.S. Appl. No. 15/018,595 dated Mar. 7, 2017 (6 pages).
United States Patent Office Action for U.S. Appl. No. 14/993,010 dated Jan. 10, 2018 (15 pages).
United States Patent Office Action for U.S. Appl. No. 14/993,010 dated Nov. 5, 2018 (16 pages).
United States Patent Office Action for U.S. Appl. No. 15/624,508 dated Jan. 16, 2018 (15 pages).
United States Patent Office Action for U.S. Appl. No. 15/505,898 dated Jun. 12, 2018 (6 pages).
United States Patent Office Action for U.S. Appl. No. 15/624,508 dated Aug. 24, 2018 (7 pages).
Zhao, "Discovery and Mechanism Study of the Irritating Effects of Iodine and Lead Ions and Targets," CMFD of Kunming University of Science and Technology, Jan. 2016, 85 pages.
Chinese Patent Office Action for Application No. 201780029193.5 dated Jul. 28, 2020 (18 pages, English translation included).
United States Patent Office Action for U.S. Appl. No. 14/993,010 dated Sep. 8, 2020 (5 pages).
United States Patent Office Action for U.S. Appl. No. 14/993,010 dated May 1, 2020 (8 pages).
United States Patent Office Action for U.S. Appl. No. 16/217,948 dated Jul. 27, 2020 (6 pages).
United States Patent Office Notice of Allowance for U.S. Appl. No. 16/391,047 dated Jul. 29, 2020 (7 pages).
United States Patent Office Notice of Allowance for U.S. Appl. No. 14/993,010 dated Sep. 9, 2021 (9 pages).
Japanese Patent Office Action for Application No. 2018-552815 dated Apr. 22, 2021 (3 pages, statement of relevance included).
Hypojin Disinfectant Solution 10% <https://www.info.pmda.go.jp/go/pack/2612701Q3385_1_3/?view=frame&style=SGML&lang=ja> 2009.
Nilius et al., "The transient receptor potential family of ion channels," Genome Biology, 2011, 12:218.
Abels et al., "Introduction to Extracellular Vesicles: Biogenesis, RNA Cargo Selection, Content, Release, and Uptake," Cell. Mol. Neurobiol., 2016, 36: 301-312.
Abu-Hayyeh et al., "Prognostic and mechanistic potential of progesterone sulfates in intrahepatic cholestasis of pregnancy and pruritus gravidarum," Hepatology, 2016, 63: 1287-1298.
Agarwal et al., "Analysis of exosome release as a cellular response to MAPK pathway inhibition," Langmuir, 2015, 31: 5440-5448.

Agarwal et al., "Conditional gene deletion in primary nociceptive neurons of trigeminal ganglia and dorsal root ganglia," Genesis, 2004, 38: 122-129.
Akiyama et al., "Involvement of TRPV4 in Serotonin-Evoked Scratching," J. Invest. Dermatol., 2016, 136: 154-160.
Alemi et al., "The TGR5 receptor mediates bile acid-induced itch and analgesia," J. Clin. Invest., 2013, 123: 1513-1530.
Andersson et al., "Modulation of the cold-activated channel TRPM8 by lysophospholipids and polyunsaturated fatty acids," J. Neurosci., 2007, 27: 3347-3355.
Banerjee et al., "MicroRNAs in skin and wound healing," Physiol. Genomics, 2011, 43: 543-556.
Barabas et al., "TRPA1 is functionally expressed primarily by IB4-binding, non-peptidergic mouse and rat sensory neurons," PLoS One, 2012, 7: e47988.
Bartel, "MicroRNAs: genomics, biogenesis, mechanism, and function," Cell, 2004, 116: 281-297.
Bautista et al., "Why we scratch an itch: the molecules, cells and circuits of itch," Nat. Neurosci., 2014, 17: 175-182.
Berdyshev et al., "Lipid abnormalities in atopic skin are driven by type 2 cytokines," JCI Insight, 2018, 3: e98006.
Chen et al., "Characterization of microRNAs in serum: a novel class of biomarkers for diagnosis of cancer and other diseases," Cell Res., 2008, 18: 997-1006.
Chen et al., "Epithelia-Sensory Neuron Cross Talk Underlies Cholestatic Itch Induced by Lysophosphatidylcholine," Gastroenterology, 2021, 161: 301-317.
Chen et al., "Phosphorylation of connexin 43 induced by traumatic brain injury promotes exosome release," J. Neurophysiol., 2018, 119: 305-311.
Chen et al., "Transient Receptor Potential Vanilloid 4 Ion Channel Functions as a Pruriceptor in Epidermal Keratinocytes to Evoke Histaminergic Itch," J. Biol. Chem., 2016, 291: 10252-10262.
Colombo et al., "Biogenesis, secretion, and intercellular interactions of exosomes and other extracellular vesicles," Annu. Rev. Cell Dev. Biol., 2014, 30: 255-289.
Dai et al., "TRPV4-pathy, a novel channelopathy affecting diverse systems," J. Human Genet., 2010, 55: 400-402.
Dankort et al., "Braf(V600E) cooperates with Pten loss to induce metastatic melanoma," Nat. Genet., 2009, 41:544-552.
Datta et al., "High-throughput screening identified selective inhibitors of exosome biogenesis and secretion: A drug repurposing strategy for advanced cancer," Sci. Rep., 2018, 8: 8161.
Datta et al., "Manumycin A suppresses exosome biogenesis and secretion via targeted inhibition of Ras/Raf/ERK1/2 signaling and hnRNP H1 in castration-resistant prostate cancer cells," Cancer letters, 2017, 408: 73-81.
Deng et al., "Cryo-EM and X-ray structures of TRPV4 reveal insight into ion permeation and gating mechanisms," Nat. Struct. Mol. Biol., 2018, 25: 252-260.
Dull et al., "Treatment of Pruritus Secondary to Liver Disease," Curr. Gastroenterol. Rep., 2019, 21:48.
Field et al., "Pruritus Reduction with Systemic Anti-lymphoma Treatments in Patients with Cutaneous T Cell Lymphoma: A Narrative Review," Dermatol Ther (Heidelb), 2016, 6: 579-595.
Flemming et al., "Sensing of lysophospholipids by TRPC5 calcium channel," J. Biol. Chem., 2006, 281:4977-4982.
Friesner et al., "Glide: a new approach for rapid, accurate docking and scoring. 1. Method and assessment of docking accuracy," J. Med. Chem., 2004, 47: 1739-1749.
Fukasawa et al., "Qualitative and quantitative comparison of cyclic phosphatidic acid and its related lipid species in rat serum using hydrophilic interaction liquid chromatography with tandem-mass spectrometry," J. Chromatogr. A, 2018, 1567: 177-184.
Garcia-Elias et al., "Phosphatidylinositol-4,5-biphosphate-dependent rearrangement of TRPV4 cytosolic tails enables channel activation by physiological stimuli," Proc. Natl. Acad. Sci. U. S. A., 2013, 110: 9553-9558.
Grove et al., "Diabetic nephropathy induces alterations in the glomerular and tubule lipid profiles," J. Lipid Res., 2014, 55: 1375-1385.

(56) References Cited

OTHER PUBLICATIONS

Gupta et al., "HSP60 trafficking in adult cardiac myocytes: role of the exosomal pathway," Am. J. Physiol. Heart Circ. Physiol., 2007, 292: H3052-H3056.
Hamill et al., "Improved patch-clamp techniques for high-resolution current recording from cells and cell-free membrane patches," Pflugers Arch., 1981, 391: 85-100.
Han et al., "miRNA-711 Binds and Activates TRPA1 Extracellularly to Evoke Acute and Chronic Pruritus," Neuron, 2018, 99: 449-463.e446.
Harder et al., "OPLS3: A Force Field Providing Broad Coverage of Drug-like Small Molecules and Proteins," J. Chem. Theory Comput., 2016, 12: 281-296.
Hayakawa et al., "Lysophosphatidic acids and their substrate lysophospholipids in cerebrospinal fluid as objective biomarkers for evaluating the severity of lumbar spinal stenosis," Sci. Rep., 2019, 9: 9144.
Heagerty et al., "Time-Dependent ROC Curves for Censored Survival Data and Diagnostic Marker," Biometrics, 2000, 56: 337-44.
Hidding et al., "Sensory Qualities Point to Different Structural and Functional Skin Patterns in Chronic Pruritus Patients. A Translational Explorative Study," Acta Derm. Venereol., 2019, 99: 668-674.
Hirschfield et al., "EASL Clinical Practice Guidelines: The diagnosis and management of patients with primary biliary cholangitis," J. Hepatol., 2017, 67: 145-172.
Hosogaya et al., "Measurement of plasma lysophosphatidic acid concentration in healthy subjects: strong correlation with lysophospholipase D activity," Ann. Clin. Biochem., 2008, 45: 364-368.
Hsieh et al., "Protein engineering: single or multiple site-directed mutagenesis," Methods Mol. Biol., 2013, 978: 173-186.
Inoue et al., "Lysophosphatidylcholine induces neuropathic pain through an action of autotaxin to generate lysophosphatidic acid," Neuroscience, 2008, 152: 296-298.
Jacoby et al., "Development, validation, and evaluation of the PBC-40, a disease specific health related quality of life measure for primary biliary cirrhosis," Gut, 2005, 54: 1622-1629.
Kim et al., "Central terminal sensitization of TRPV1 by descending serotonergic facilitation modulates chronic pain," Neuron, 2014, 81: 873-887.
Kim et al., "Facilitation of TRPV4 by TRPV1 is required for itch transmission in some sensory neuron populations," Sci Signal, 2016, 9: ra71.
Kishimoto et al., "A novel colorimetric assay for the determination of lysophosphatidic acid in plasma using an enzymatic cycling method," Clin. Chim. Acta, 2003, 333: 59-67.
Kishimoto et al., "An enzymatic assay for lysophosphatidylcholine concentration in human serum and plasma," Clinical Biochemistry, 2002, 35: 411-416.
Kittaka et al., "Lysophosphatidic acid-induced itch is mediated by signalling of LPA5 receptor, phospholipase D and TRPA1/TRPV1," J. Physiol., 2017, 595: 2681-2698.
Kittaka et al., "The molecular and cellular mechanisms of itch and the involvement of TRP channels in the peripheral sensory nervous system and skin," Allergol Int, 2017, 66: 22-30.
Knuplez et al., "Lysophosphatidylcholines inhibit human eosinophil activation and suppress eosinophil migration in vivo," Biochim Biophys Acta Mol Cell Biol Lipids, 2020, 1865: 158686.
Kozina et al.,"Oleoyl-lysophosphatidylcholine limits endothelial nitric oxide bioavailability by induction of reactive oxygen species," PLoS One, 2014, 9: e113443.
Kremer et al., "Lysophosphatidic acid is a potential mediator of cholestatic pruritus," Gastroenterology, 2010, 139: 1008-1018.
Kurano et al., "Possible involvement of minor lysophospholipids in the increase in plasma lysophosphatidic acid in acute coronary syndrome," Arterioscler. Thromb. Vasc. Biol., 2015, 35: 463-470.
Kyte et al., "A Simple Method for Displaying the Hydropathic Character of a Protein," J. Mol. Biol., 1982, 157: 105-132.
Labonté et al., "Postprandial lysophospholipid suppresses hepatic fatty acid oxidation: the molecular link between group 1B phospholipase A2 and diet-induced obesity," FASEB J., 2010, 24: 2516-2524.
Leader et al., "Pruritus epidemiology and quality of life," Handb. Exp. Pharmacol., 2015, 226: 15-38.
Lee et al.."Distinct functions of opioid-related peptides and gastrin-releasing peptide in regulating itch and pain in the spinal cord of primates," Sci. Rep., 2015, 5: 11676.
Lieu et al., "The bile acid receptor TGR5 activates the TRPA1 channel to induce itch in mice," Gastroenterology, 2014, 147: 1417-1428.
Lorenzo et al., "TRPV4 channel participates in receptor-operated calcium entry and ciliary beat frequency regulation in mouse airway epithelial cells," Proc. Natl. Acad. Sci. U. S. A., 2008, 105: 12611-12616.
Luo et al., "Transient receptor potential vanilloid 4-expressing macrophages and keratinocytes contribute differentially to allergic and nonallergic chronic itch," J. Allergy Clin. Immunol., 2018, 141:608-619.
Malik et al., "Cardiac Myocyte Exosome Isolation," Methods Mol. Biol., 2016, 1448: 237-248.
Meixiong et al., "Identification of a bilirubin receptor that may mediate a component of cholestatic itch," Elife, 2019, 8: e44116.
Meixiong et al., "MRGPRX4 is a G protein-coupled receptor activated by bile acids that may contribute to cholestatic pruritus," Proc. Natl. Acad. Sci. U. S. A., 2019, 116: 10525-10530.
Mettang et al., "Uremic pruritus," Kidney Int., 2015, 87: 685-691.
Middleton Jr. et al., "Release of histamine activity in human skin by lysolecithin," J. Lab. Clin. Med., 1964, 64: 889-894.
Mihara et al., "Transient receptor potential vanilloid 4 (TRPV4)-dependent calcium influx and ATP release in mouse oesophageal keratinocytes," J. Physiol., 2011, 589: 3471-3482.
Moehring et al., "Keratinocytes mediate innocuous and noxious touch via ATP-P2X4 signaling," Elife, 2018, 7: e31684.
Moolenaar et al., "Insights into autotaxin: howto produce and present a lipid mediator," Nat. Rev. Mol. Cell Biol., 2011, 12: 674-679.
Moore et al., "Regulation of Pain and Itch by TRP Channels," Neurosci. Bull., 2018, 34: 120-142.
Morales-Lazaro et al., "Inhibition of TRPV1 channels by a naturally occurring omega-9 fatty acid reduces pain and itch," Nat Commun, 2016, 7: 13092.
Nieto-Posadas et al., "Lysophosphatidic acid directly activates TRPV1 through a C-terminal binding site," Nat Chem Biol, 2011, 8: 78-85.
Noguchi et al., "Lysophosphatidic acid (LPA) and its receptors," Curr. Opin. Pharmacol., 2009, 9: 15-23.
Pankey et al., "Analysis of responses to the TRPV4 agonist GSK1016790A in the pulmonary vascular bed of the intact-chest rat," Am. J. Physiol. Heart Circ. Physiol., 2014, 306: H33-H40.
Park et al., "Extracellular microRNAs activate nociceptor neurons to elicit pain via TLR7 and TRPA1," Neuron, 2014, 82: 47-54.
Patel et al., "Cholestatic pruritus: Emerging mechanisms and therapeutics," J. Am. Acad. Dermatol., 2019, 81: 1371-1378.
Raszeja-Wyszomirska et al., "Assessment of health related quality of life in polish patients with primary biliary cirrhosis," Clin. Res. Hepatol. Gastroenterol., 2016, 40: 471-479.
Rebane et al., "MicroRNA-146a alleviates chronic skin inflammation in atopic dermatitis through suppression of innate immune responses in keratinocytes," J. Allergy Clin. Immunol., 2014, 134: 836-847.
Rosenbaum et al., "Dissecting intersubunit contacts in cyclic nucleotide-gated ion channels," Neuron, 2002, 33: 703-713.
Ryborg et al., "Increased lysophosphatidylcholine content in lesional psoriatic skin," Br. J. Dermatol., 1995, 133: 398-402.
Ryborg et al., "Intracutaneous injection of lysophosphatidylcholine induces skin inflammation and accumulation of leukocytes," Acta Derm. Venereol., 2000, 80: 242-246.
Sadler et al., "Keratinocytes contribute to normal cold and heat sensation," Elife, 2020, 9: e58625.
Salazar et al., "Structural determinants of gating in the TRPV1 channel," Nat. Struct. Mol. Biol., 2009, 16: 704-710.

(56) References Cited

OTHER PUBLICATIONS

Schneider et al., "Bioactive lipids, LPC and LPA, are novel prometastatic factors and their tissue levels increase in response to radio/chemotherapy," Mol. Cancer Res., 2014, 12: 1560-1573.
Schwarzenbach et al., "Data Normalization Strategies for MicroRNA Quantification," Clin. Chem., 2015, 61: 1333-1342.
Sharif et al., "Differential Coding of Itch and Pain by a Subpopulation of Primary Afferent Neurons," Neuron, 2020, 106: 940-951.e944.
Shimada et al., "Behavioral differentiation between itch and pain in mouse," Pain, 2008, 139: 681-687.
Sigworth et al., "Data transformations for improved display and fitting of single-channel dwell time histograms," Biophys. J., 1987, 52: 1047-1054.
Sonkoly et al., "MicroRNAs: novel regulators in skin inflammation," Clin. Exp. Dermatol., 2008, 33: 312-315.
Takahashi et al., "TRPV4 channel activity is modulated by direct interaction of the ankyrin domain to PI(4,5)P(2)," Nat Commun, 2014, 5: 4994.
Tanaka et al., "ANIT-induced intrahepatic cholestasis alters hepatobiliary transporter expression via Nrf2-dependent and independent signaling," Toxicol. Sci., 2009, 108: 247-257.
Thorneloe et al., "N-((1S)-1-{[4-((2S)-2-{[(2,4-dichlorophenyl)sulfonyl]amino}-3-hydroxypropanoyl)-1-piperazinyl]carbonyl}-3-methylbutyl)-1-benzothiophene-2-carboxamide (GSK1016790A), a novel and potent transient receptor potential vanilloid 4 channel agonist induces urinary bladder contraction and hyperactivity: Part I," J. Pharmacol. Exp. Ther., 2008, 326: 432-442.
Tokumura et al., "Elevated serum levels of arachidonoyl-lysophosphatidic acid and sphingosine 1-phosphate in systemic sclerosis," Int. J. Med. Sci., 2009, 6: 168-176.
Uranbileg et al., "Alteration of the lysophosphatidic acid and its precursor lysophosphatidylcholine levels in spinal cord stenosis: A study using a rat cauda equina compression model," Sci. Rep., 2019, 9: 16578.
Van Keymeulen et al., "Distinct stem cells contribute to mammary gland development and maintenance," Nature, 2011, 479: 189-193.
Wang et al., "Activation of Different Heterodimers of TLR2 Distinctly Mediates Pain and Itch," Neuroscience, 2020, 429: 245-255.
Wu et al., "UPLC-QTOF MS-Based Serum Metabolomic Profiling Analysis Reveals the Molecular Perturbations Underlying Uremic Pruritus," Biomed. Res. Int., 2018, 4351674.
Yan et al., "MicroRNA146a as a potential regulator involved in the pathogenesis of atopic dermatitis," Mol. Med. Rep., 2019, 20(5): 4645-4653.
Yu et al., "MRGPRX4 is a bile acid receptor for human cholestatic itch," Elife, 2019, 8: e48431.
Zeng et al., "Lipidomics profiling reveals the role of glycerophospholipid metabolism in psoriasis," Gigascience, 2017, 6: 1-11.
Zhao et al., "PAR2 Mediates Itch via TRPV3 Signaling in Keratinocytes," J. Invest. Dermatol., 2020, 140: 1524-1532.
Zou et al., "Exosome Release Is Regulated by mTORC1," Adv Sci (Weinh), 2019, 6: 1801313.
International Search Report and Written Opinion for Application No. PCT/US2021/055288 dated Jan. 28, 2022 (17 pages).
European Patent Office Action for Application No. 13813477.0 dated Jun. 8, 2022 (6 pages).
Vanhoutte et al. Contact Dermatitis 2019, 81, 17-23.
Raudonis et al. Advances in Skin & Wound Care 2019, 32, 558-562.
European Patent Office Action for Application No. 17779954.1 dated Aug. 11, 2022 (4 pages).

* cited by examiner

Trpv4 wildtype
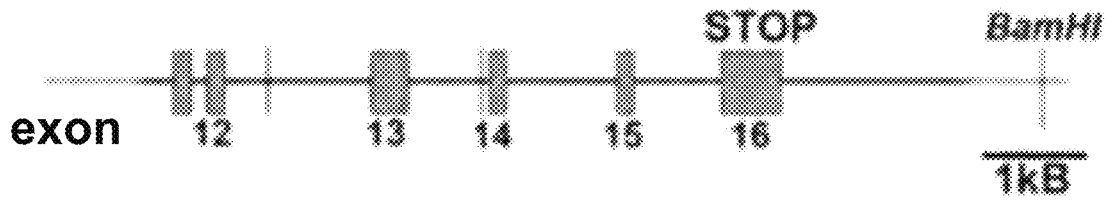
insertion loxP, frt-neo, PacI
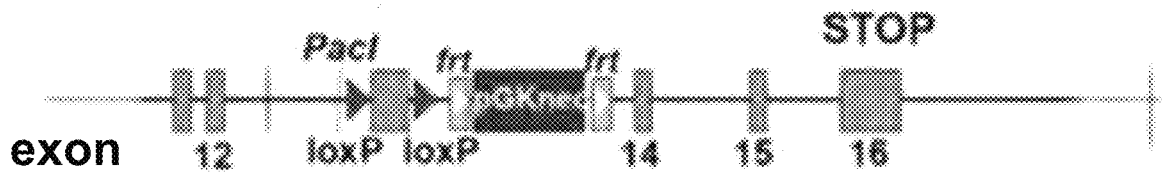
excision frt-neo using FLPe (ES cells)
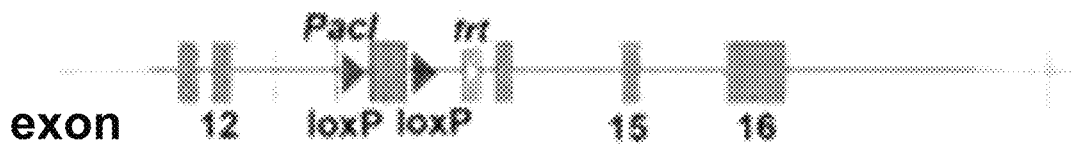
excision exon13 by CRE in KC in-vivo
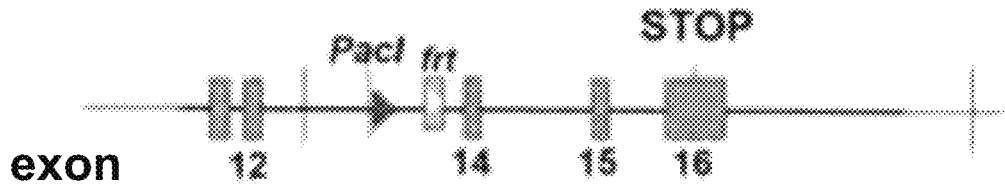
FIG. 1A

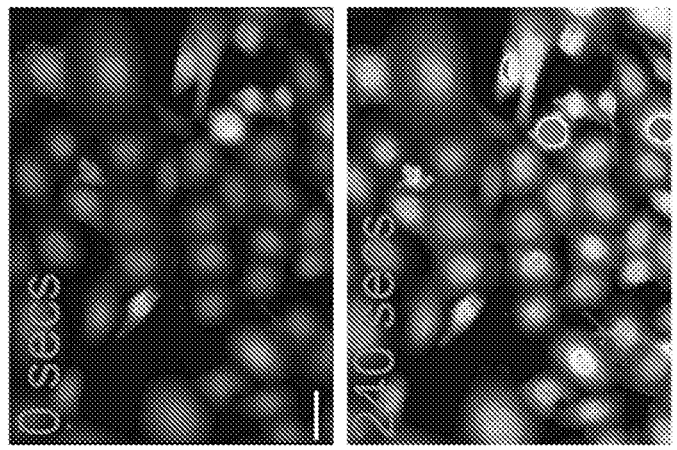
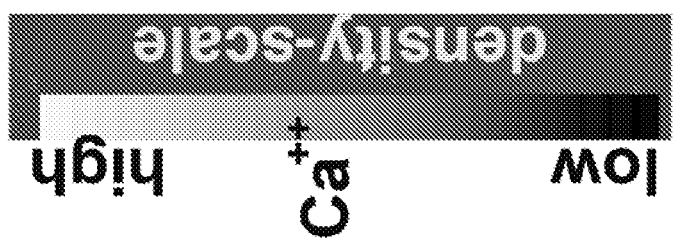
FIG. 6B
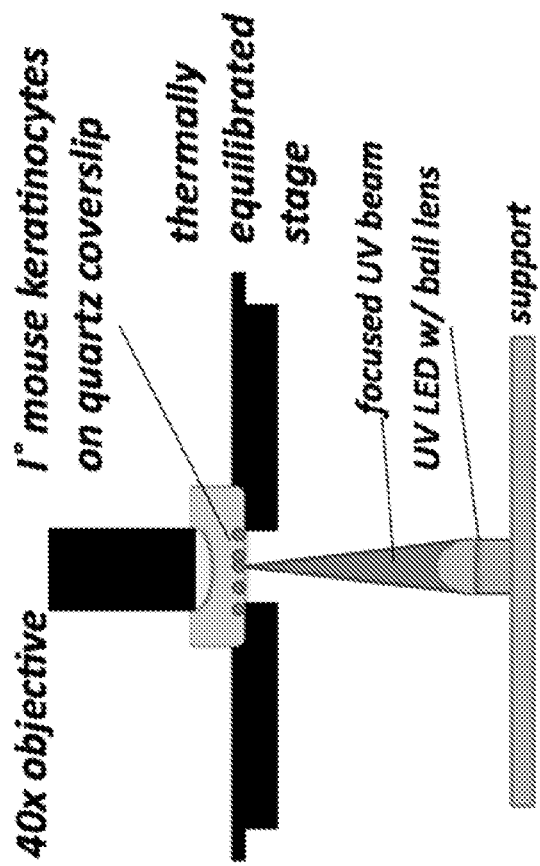
FIG. 6A

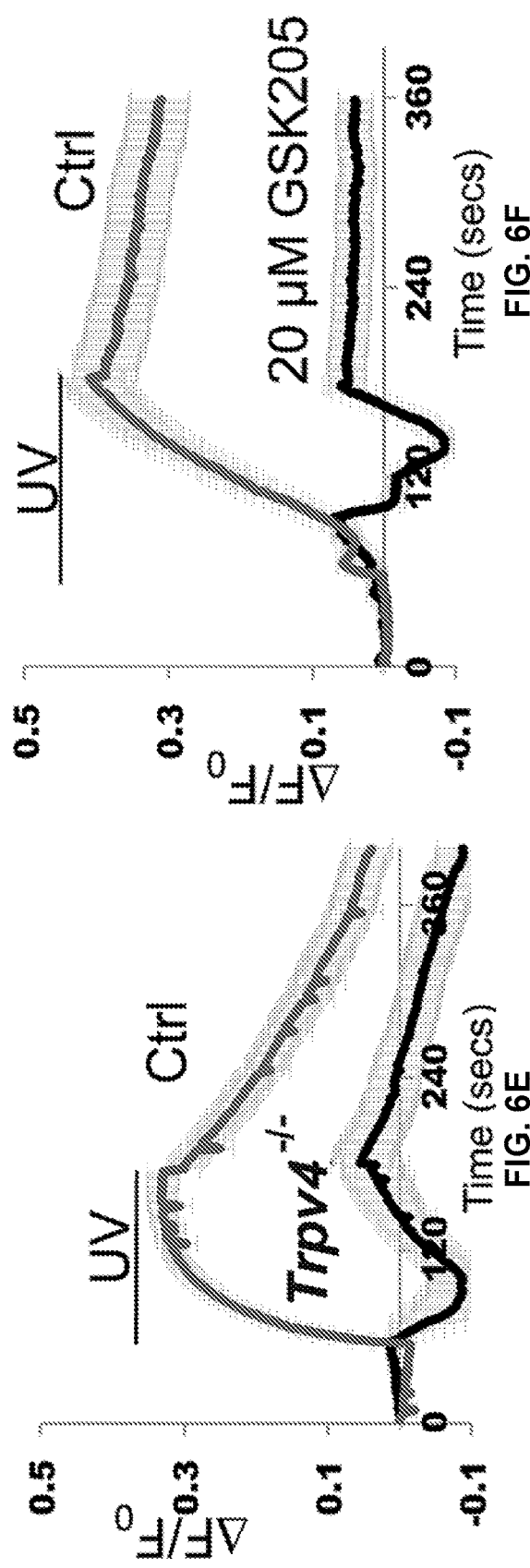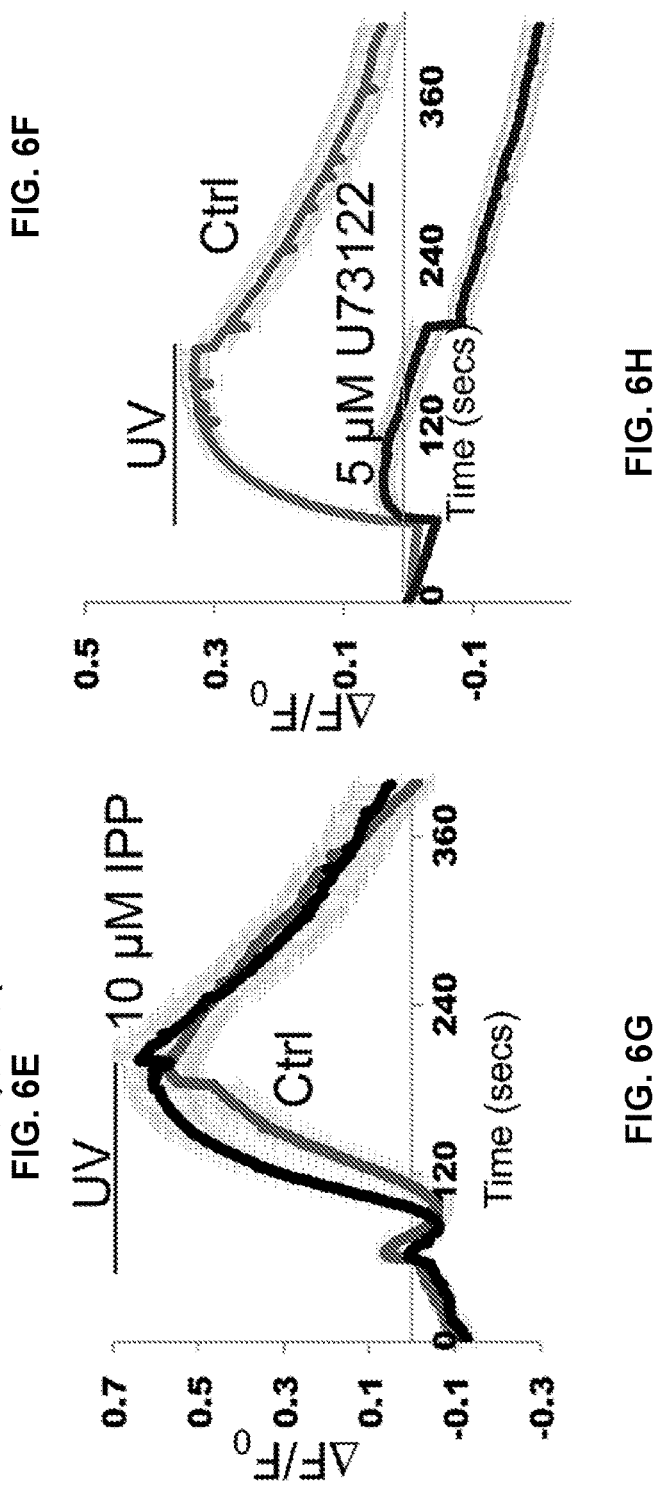
FIG. 6E
FIG. 6F
FIG. 6G
FIG. 6H

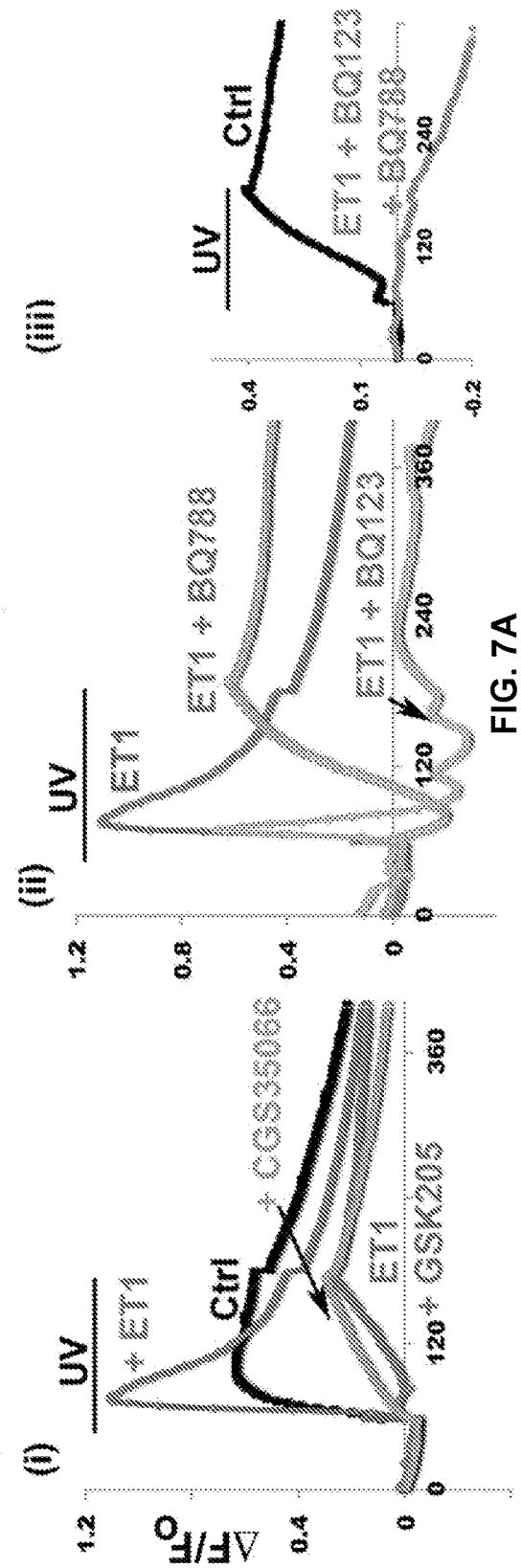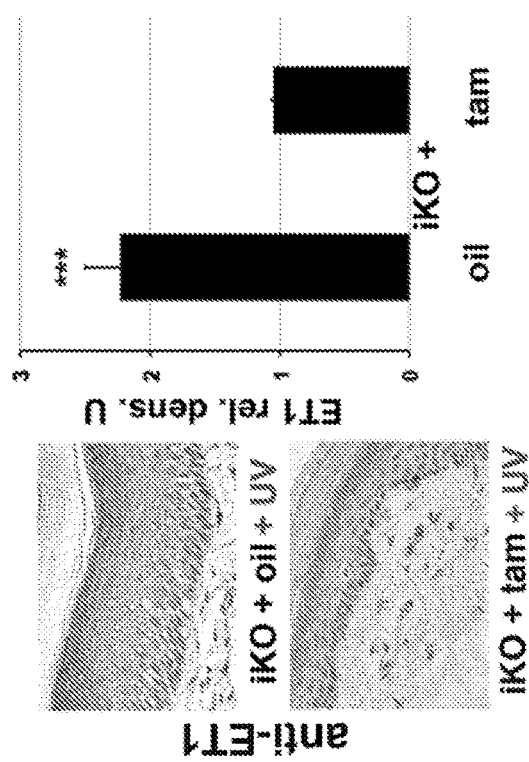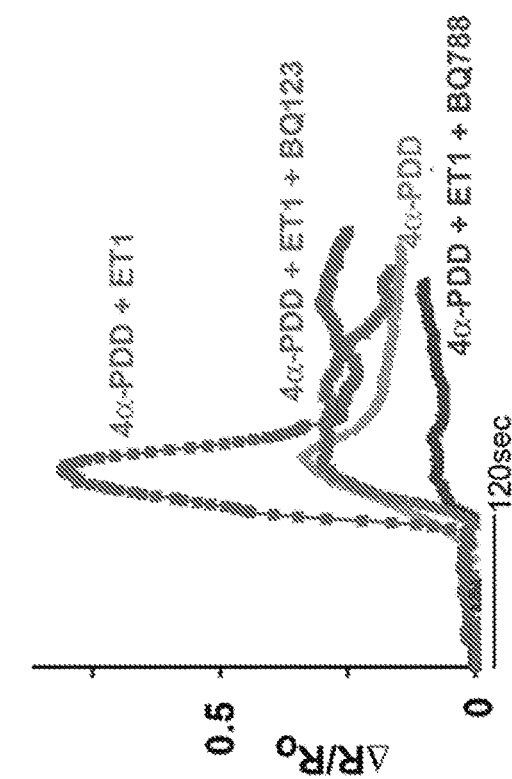
FIG. 7A
FIG. 7B
FIG. 7C

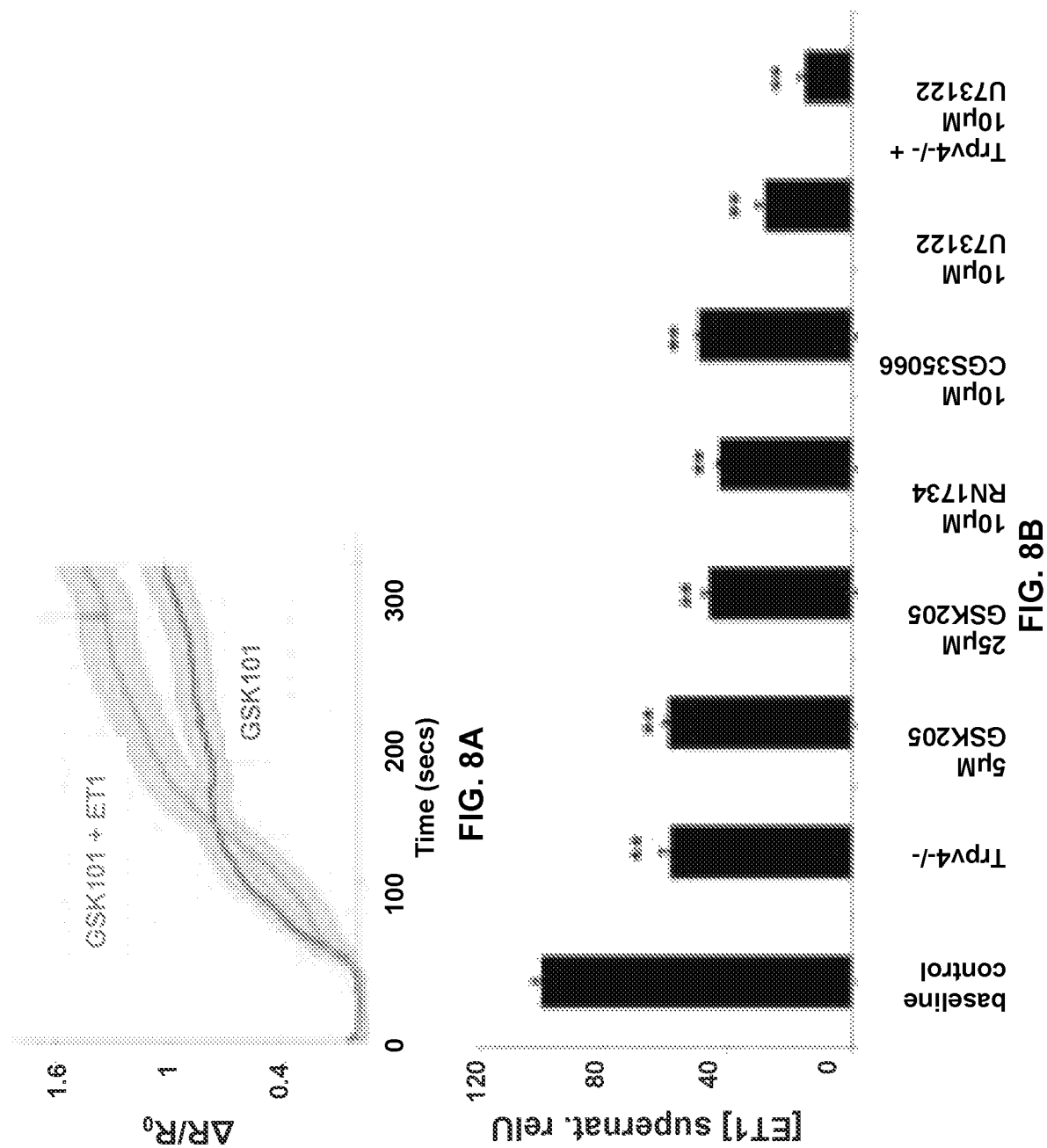

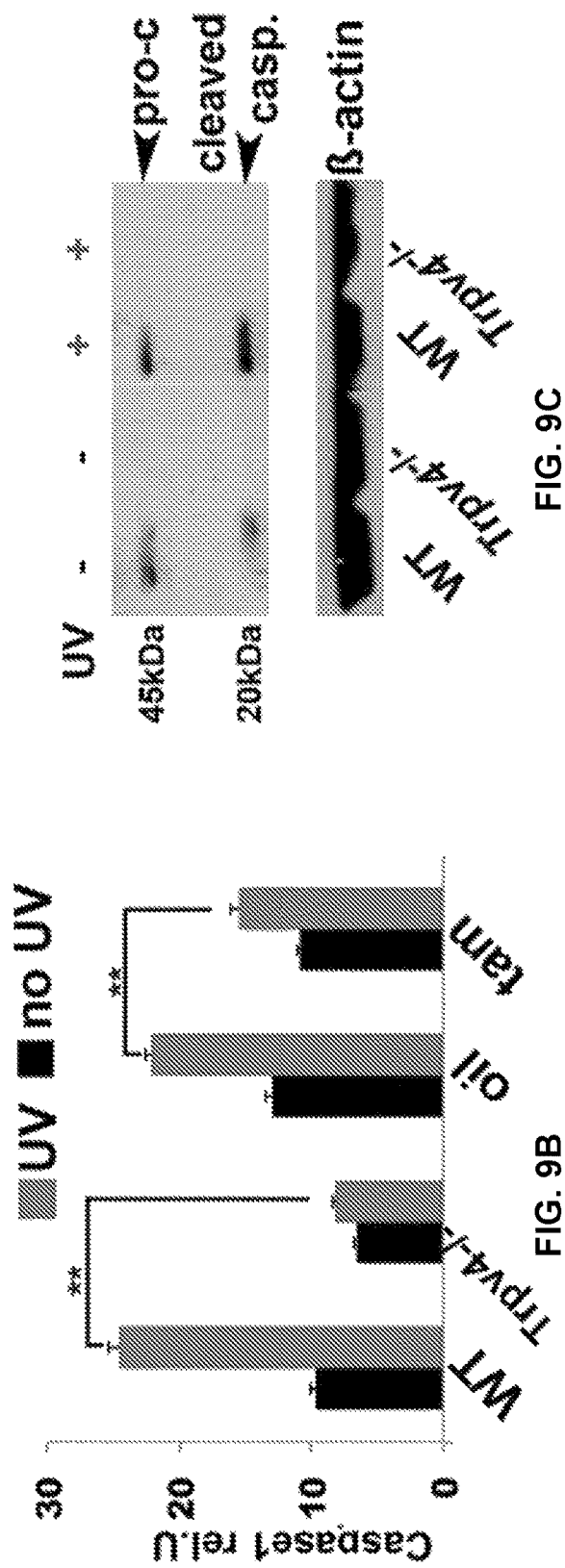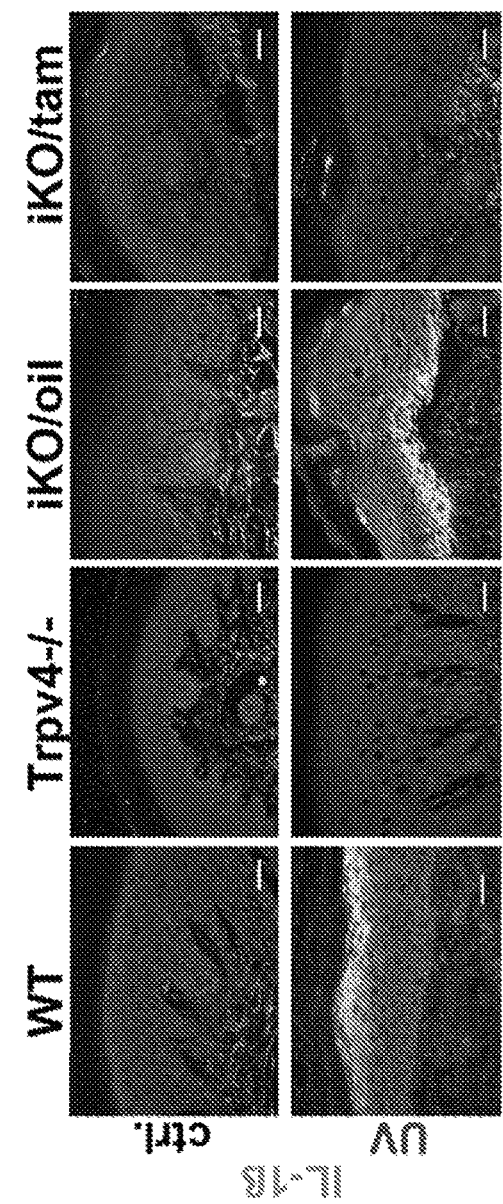
FIG. 9B
FIG. 9C
FIG. 9D

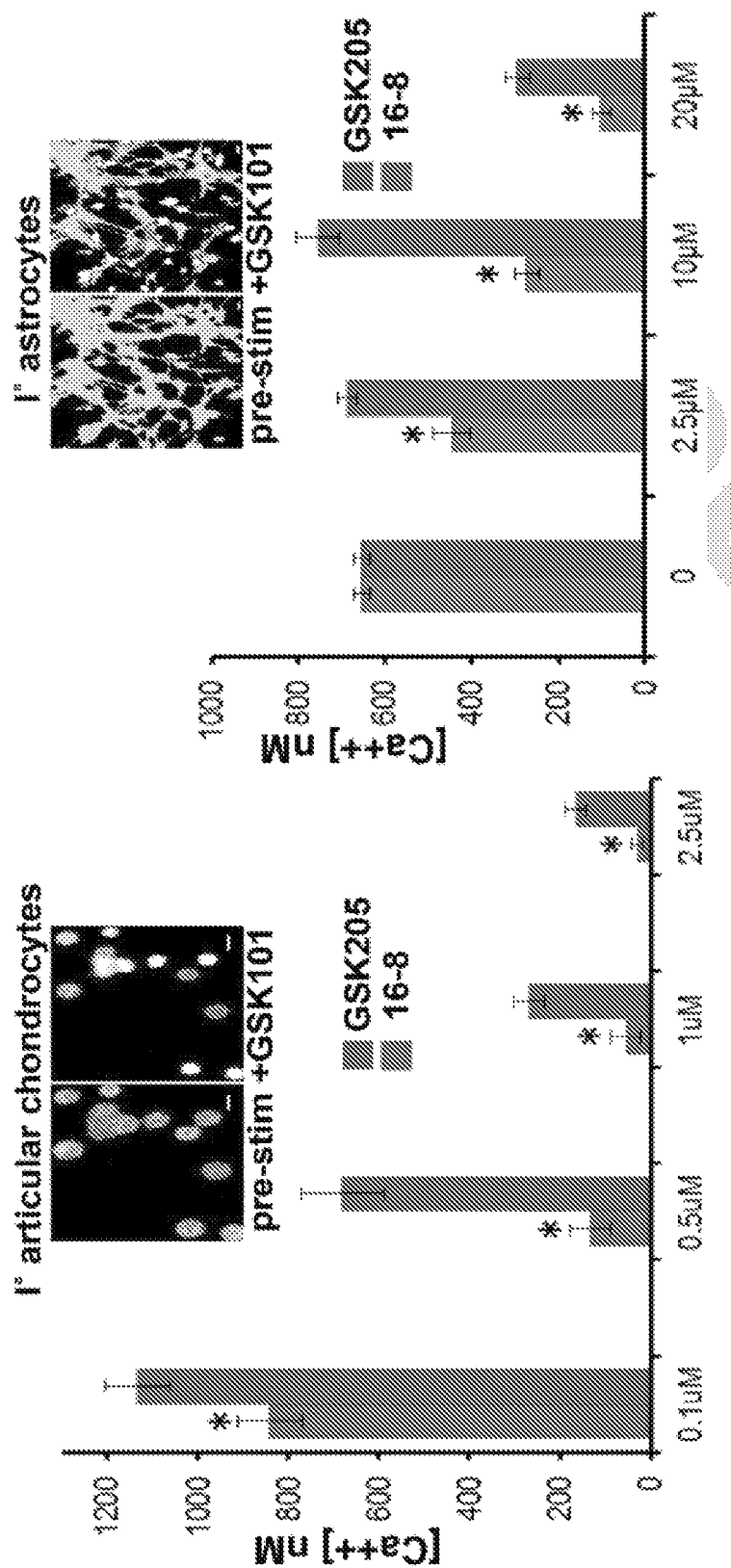

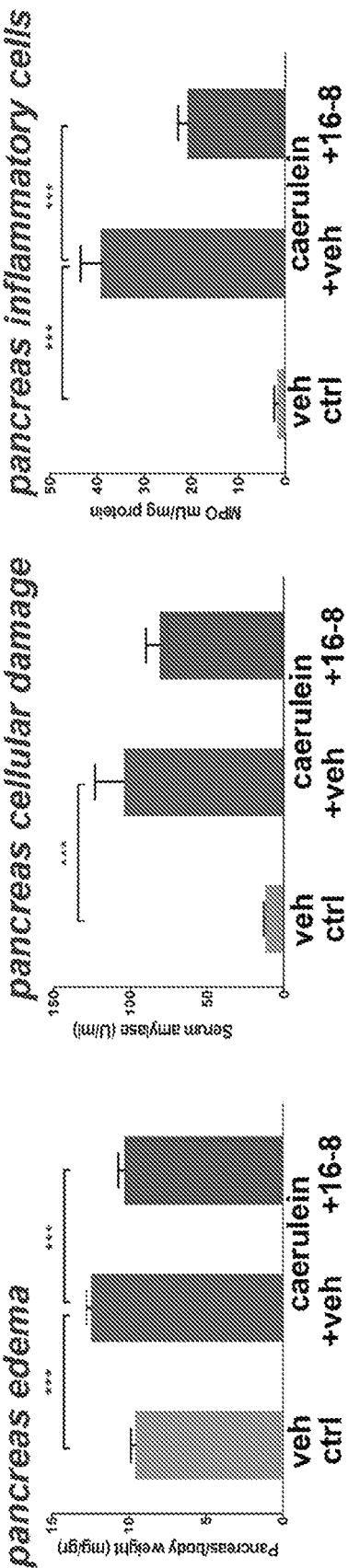

SEQUENCE LISTING

<160> NUMBER OF SEQ ID NOS: 2

<210> SEQ ID NO 1
<211> LENGTH: 20
<212> TYPE: DNA
<213> ORGANISM: Artificial sequence
<220> FEATURE:
<223> OTHER INFORMATION: Synthetic

<400> SEQUENCE: 1
cctgctggtc acctacatca                                    20

<210> SEQ ID NO 2
<211> LENGTH: 20
<212> TYPE: DNA
<213> ORGANISM: Artificial sequence
<220> FEATURE:
<223> OTHER INFORMATION: Synthetic

<400> SEQUENCE: 2
ctcaggaaca cagggaagga                                    20

SMALL MOLECULE DUAL-INHIBITORS OF TRPV4 AND TRPA1 FOR SANITIZING AND ANESTHETIZING

CROSS-REFERENCE TO RELATED APPLICATIONS

This application is the U.S. national stage entry, under 35 U.S.C. 371, of international application number PCT/US2017/026714, filed Apr. 7, 2017, which claims priority to U.S. Provisional Patent Application No. 62/319,684, filed Apr. 7, 2016, U.S. Provisional Patent Application No. 62/331,951, filed May 4, 2016, and U.S. Provisional Patent Application No. 62/337,701, filed May 17, 2016, each of which is incorporated herein by reference in its entirety.

STATEMENT REGARDING FEDERALLY SPONSORED RESEARCH

This invention was made with government support under grant numbers DE018549 and DE01852951 awarded by the National Institutes of Health/National Institute of Dental and Craniofacial Research (NIH/NIDCR), and grant numbers AR059402, AR31737, and AR050452 awarded by the National Institutes of Health/National Institute of Arthritis and Musculoskeletal and Skin Diseases (NIH/NIAMS). The government has certain rights in the invention.

SEQUENCE LISTING

The sequence listing is filed with the application in electronic format only and is incorporated by reference herein. The sequence listing text file "028193-9128-US12_As_filed_Sequence_Listing" was created on Oct. 4, 2018 and is 776 bytes in size.

FIELD

This disclosure relates to methods and compositions for sanitizing a surface, anesthetizing a subject, and treating inflammation, pain, itch, cancer, autoimmune diseases, fibrotic diseases, skin pigmentation, and/or other dermatological disorders.

INTRODUCTION

The skin is the largest organ in many vertebrates, including humans. It provides barrier protection against the potentially harmful external environment. The skin also represents the site of first interaction of the ambient environment to immunologically competent and sentient structures of the organism. Cells endowed with sensory transduction capacity for warmth, cold, mechanical cues, pain, and itch are sensory neurons in the dorsal root and trigeminal ganglia with their peripheral axons directly interfacing with skin. However, successfully targeting the skin for treatment of inflammation, pain, itch, cancer, autoimmune diseases, fibrotic diseases, skin pigmentation, and other dermatological disorders has remained elusive.

Biochemical pathways in the skin include those relating to the transient receptor potential (TRP) superfamily of ion channels. One ion channel in this family is TRPV4. TRPV4 is a multimodally-activated non-selective cation channel permeable to calcium (i.e., Ca++). The TRPV4 ion channel is expressed robustly in epidermal keratinocytes of mammalian skin. However, TRPV4 is also expressed in skin-innervating sensory neurons. In Trpv4–/– mice, an epidermal phenotype of impaired barrier function between epidermis and dermis has been shown. In regards to pain signaling, TRPV4 has been found critical for physiological withdrawal responses to noxious osmotic and mechanical, but not thermal, cues and has also been found relevant for inflammation or nerve-damage-induced sensitization of nociception. While it is understood that TRPV4 is expressed in epidermal keratinocytes and skin-innervating sensory neurons, an in vivo role of TRPV4 in pathological pain evoked by UVB exposure has not been demonstrated. Moreover, a direct role of TRPV4 in itch transmission has not been demonstrated as of yet.

TRPA1 is another TRP ion channel located on the plasma membrane. TRPA1 acts as sensor for environmental irritants, pain, cold, and stretch. Although TRPV4 and TRPA1 function in the skin, it is not known whether targeting TRPV4 and/or TRPA1 would be useful in the treatment of inflammation, pain, itch, cancer, autoimmune diseases, fibrotic diseases, skin pigmentation, and other dermatological disorders. Furthermore, specific TRPV4 and TRPA1 inhibitors are not presently known. New and successful treatments for dermatological disorders, as well as and methods for sanitizing and anesthetizing are needed.

SUMMARY

In an aspect, the disclosure relates to a composition comprising an inhibitor and iodine, wherein the inhibitor inhibits TRPV4, TRPA1, or a combination thereof.

In an aspect, the disclosure relates to composition comprising an inhibitor and an anesthetic, wherein the inhibitor inhibits TRPV4, TRPA1, or a combination thereof.

In an aspect, the disclosure relates to an inhibitor that inhibits TRPV4, TRPA1, or a combination thereof.

In some embodiments, the inhibitor does not inhibit TRPV1, TRPV2, or TRPV3. In some embodiments, the inhibitor comprises a compound according to Formula I:

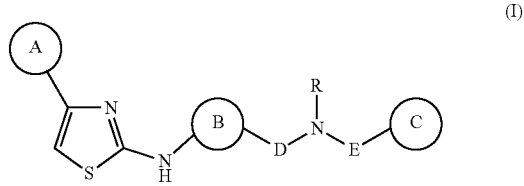

wherein A, B, and C are independently selected from the group consisting of aromatic, heteroaromatic, cycloalkenyl, and heterocycloalkenyl groups; D is $C_1$-$C_3$ alkylene; E is a bond, or $C_1$-$C_2$ alkylene; and R is selected from the group consisting of hydrogen, hydroxyl, amino, alkyl, alkenyl, heteroalkyl, aromatic ring, or heteroaromatic ring. In some embodiments, the inhibitor comprises a compound selected from the following:

16-18

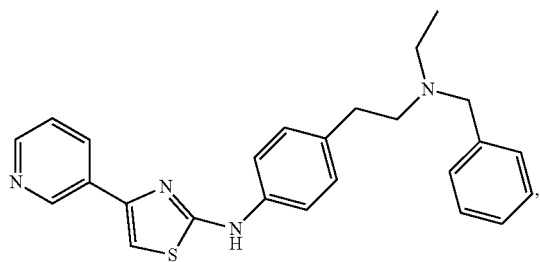

16-8

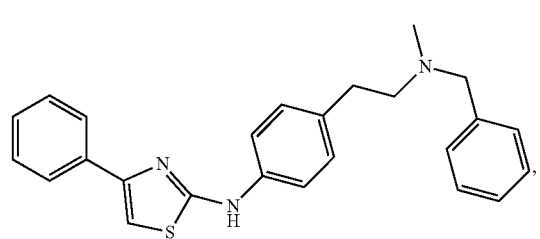

16-12c

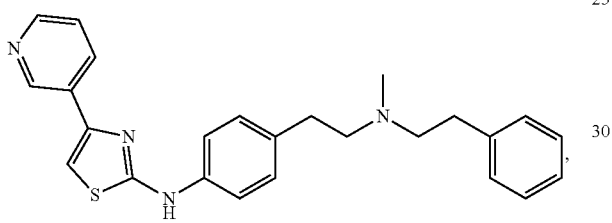

16-13

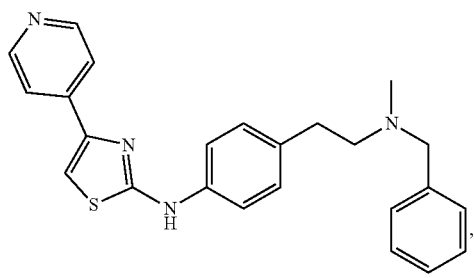

16-14

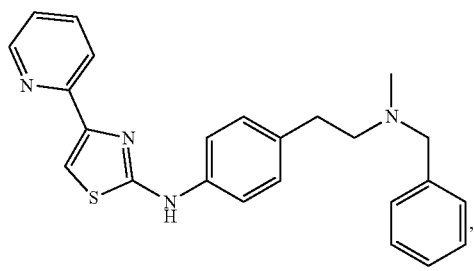

16-16

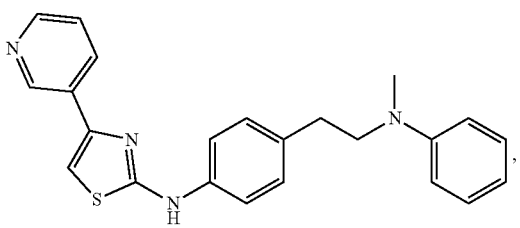

16-19 (16-8/18hy)

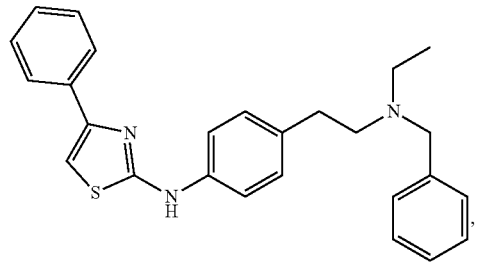

15-43

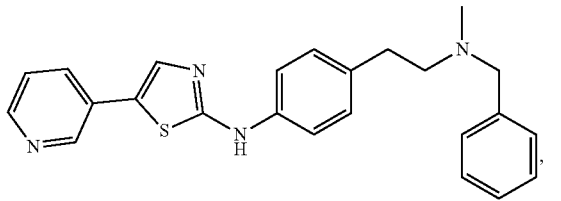

16-12

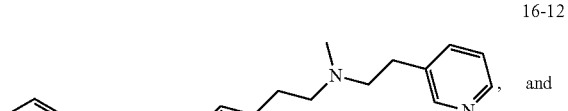

and

GSK-205

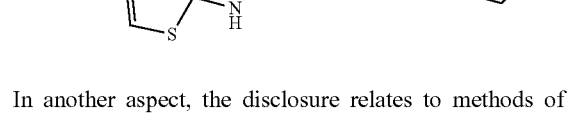

In another aspect, the disclosure relates to methods of sanitizing a subject. In some embodiments, the method includes contacting the subject with the composition as detailed herein. In some embodiments, the subject is contacted with the composition for a period of time sufficient to cause a reduction in the population of microorganisms on the subject. In some embodiments, the composition is administered to a surface of the subject, wherein the surface is selected from the group consisting of a skin area, a wound, and an ulcer. In some embodiments, the composition disinfects the subject. In some embodiments, the composition sterilizes the subject. In some embodiments, the composition has antibacterial activity.

In another aspect, the disclosure relates to methods of anesthetizing a subject. In some embodiments, the method includes administering to the subject the composition as detailed herein. In some embodiments, the method includes co-administering an anesthetic and an inhibitor to the subject, wherein the inhibitor inhibits TRPV4, TRPA1, or a combination thereof. In some embodiments, the composition sanitizes and reduces pain.

In another aspect, the disclosure relates to methods of treating and/or preventing a dermatological disorder in a subject in need thereof, the method comprising administering to the subject an effective amount of a TRPV4 and/or TRPA1 inhibitor. In some embodiments, the dermatological disorder is selected from the group consisting of pancreatitis, epilepsy, arthritis, osteoarthritis, multiple sclerosis, stroke, CNS autoimmune condition, traumatic brain injury, spinal cord injury, brain edema, CNS infection, neuropsychiatric disorder, skeletal degenerative-inflammatory disorder, trigeminal pain, colitis, and sclerosis. In some embodiments, the trigeminal pain comprises headache.

In some embodiments, the TRPV4 and/or TRPV4 inhibitor comprises a compound according to Formula I:

(I)

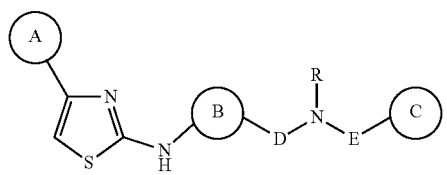

wherein A, B, and C are independently selected from the group consisting of aromatic, heteroaromatic, cycloalkenyl, and heterocycloalkenyl groups; D is $C_1$-$C_3$ alkylene; E is a bond, or $C_1$-$C_2$ alkylene; and R is selected from the group consisting of hydrogen, hydroxyl, amino, alkyl, alkenyl, heteroalkyl, aromatic ring, or heteroaromatic ring. In some embodiments, TRPV4 and/or TRPA1 inhibitor comprises a compound selected from the following:

16-18

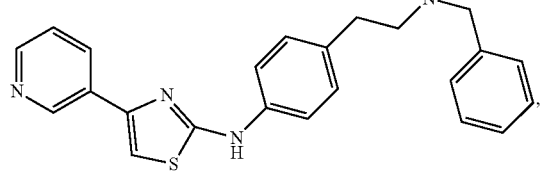

16-8

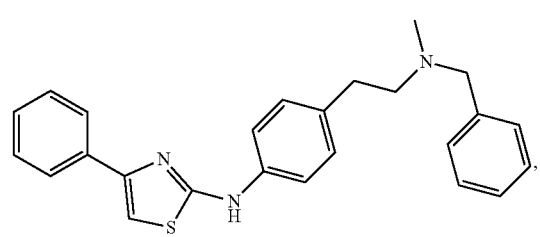

16-12c

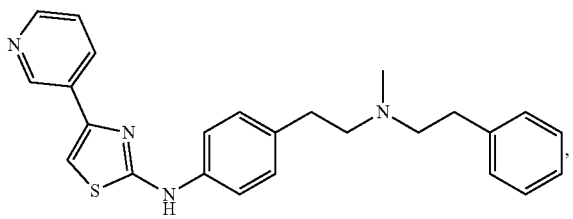

-continued 16-13

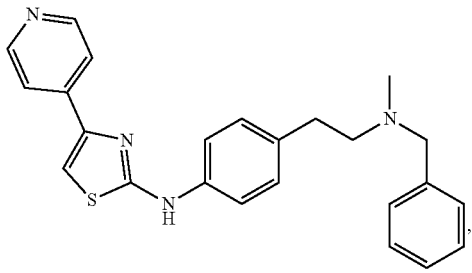

16-14

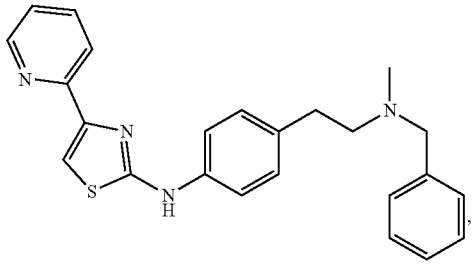

16-16

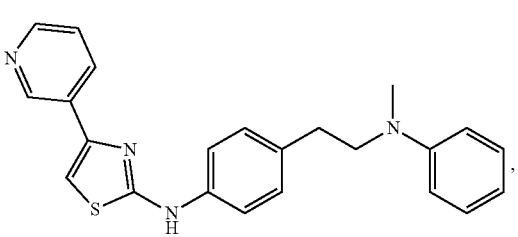

16-19

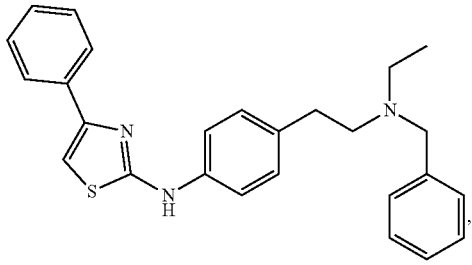

15-43

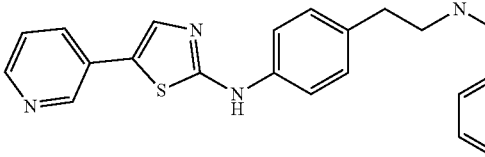

16-12

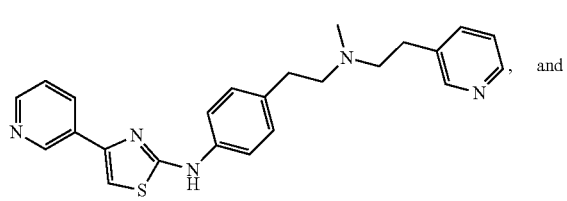

and

-continued

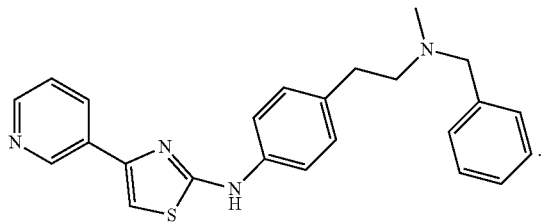
GSK-205

In some embodiments, the compound inhibits TRPV4 and TRPA1. In some embodiments, the compound does not inhibit TRPV1, TRPV2, or TRPV3.

The disclosure provides for other aspects and embodiments that will be apparent in light of the following detailed description and accompanying Figures.

BRIEF DESCRIPTION OF THE DRAWINGS

FIGS. 1A-1G: Keratinocyte-specific and inducible Trpv4 null mouse and its UVB response. (FIG. 1A) Gene-targeting of Trpv4 and genetic manipulation underlying generation of keratinocyte-specific and inducible Trpv4 knockout mice. Shown are sequential steps of mouse Trpv4 targeting, starting with flanking Trvp4 exon13 with loxP elements and insertion of a selection cassette, flanked by frt sites, in mouse embryonic stem cells. After generation of chimeric mice and stable transmission of the engineered mutation, the selection cassette was removed by breeding to FLPe mice. Resulting mice were homozygosed and crossed with K14-CRE-ER$^{tam}$ mice, which then permitted keratinocyte-specific and inducible Trpv4 knockout/knockdown. (FIG. 1B) DNA genotyping. Shown are PCR products of WT, heterozygote and homozygous Trpv4$^{lox/lox}$ mice. Note that the PCR products needed to be digested with PacI, and that all mice were pre-screened to be CRE+ by another genotyping PCR. (FIG. 1C) Co-labeling of mouse skin for keratin-1 and keratin-14 indicate the established pattern for vehicle-induced control mice (upper panel), and a similar pattern for specific TRPV4 knockdown in keratinocytes (lower panel). However, in these animals note a slightly increased expression of K14 in the stratum spinosum, reflecting attenuated TRPV4 expression and thus reduced Ca$^{++}$ influx. K14 is normally down-regulated at the basal-to-suprabasal transition, concomitant with the rise in Ca$^{++}$-signaling and induction of terminal differentiation. (FIG. 1D) TRPV4 protein expression in L5 DRG neurons not different between genotypes. Densitometry of TRPV4 immunohistochemistry in L5 (=foot-pad innervating) DRG neurons (upper panel micrographs), the bar-diagram illustrates the lack of a difference in terms of TRPV4 protein abundance in oil- vs. tam-treated mice, for both base-line and 48 hours after UV exposure, confirming the specificity of TRPV4 knockdown in skin when using K14 as CRE driver. Note the characteristic morphology of decorated cells identifying them as DRG sensory neurons. Note also the different levels of TRPV4 expression in these neurons, as noted previously; n=3 mice/group, 50 neurons/mouse. (FIG. 1E) Lack of TRPV4 expression in Merkel cells in foot-pad epidermis. A confocal triple-fluorescent micrograph panel is shown, depicting representative images of immuno-labeled paw-pads from iKO control vs. tamoxifen-induced mice. Note complete knockdown of TRPV4 in this example (red channel). For Merkel cells (green channel), an anti-cytokeratin 8 antibody was used. Note lack of TRPV4 co-labeling in Merkel cells. Blue channel=DAPI. (FIG. 1F) Lack of effect of tamoxifen application in K14-CRE-ER$^{tam}$ mice on UVB behavioral sensitization. Note very similar withdrawal thresholds in (K14-CRE-ER$^{tam}$ X Trpv4$^{lox/+}$) mice (=Trpv4 heterozygotes in keratinocytes when induced with tamoxifen) for noxious mechanical (upper diagram) and thermal (lower diagram) stimulation; n=7 mice per group. Also note the time-course with peak sensitivity at time-point 48 hours. (FIG. 1G) Size distribution of pERK-expressing L5 DRG neurons in oil-treated iKO mice, exposed to UVB. The bar diagram illustrates size prevalence of small and medium-size sensory neurons that express pERK 48 hours after UVB exposure, note absence of larger neurons (>1200 µm$^2$), n=22 neurons.

(FIG. 2A) UV spectrum emitted by the LEDs, overlapped with the spectrum of quartz (red trace), which is almost fully permeable to UVB, and glass (blue trace), which has a very low UVB permeability. (FIG. 2B) Focusing properties of the ball lens. (FIG. 2C) Focal geometry of the combination of UV-LED and ball lens. (FIG. 2D) Absence of thermal effects of the UV-LEDs; measurement of temperature in the focal point over time. (FIG. 2E) TRPV3 activation experiment. Induction of a Ca++ transient by camphor, which can be blocked effectively by 10 µM IPP, suggesting TRPV3-mediated signaling. (FIG. 2F) TRPV4 selective activator GSK101-related findings. Ca++ transient in 1° MK in response to 5 nM GSK101, which can be completely blocked by 20 µM GSK205, suggesting it is specifically mediated by TRPV4. The GSK101-response can also be eliminated by absence of external Ca++, in keeping with TRPV4 signaling. (FIG. 2G) TRPV4 is sufficient for the UVB-Ca++ response—HEK293T cell heterologous transfection. Directed expression of TRPV4 in HEK293T cells leads to a Ca++-transient in response to UVB radiation, which is greatly reduced in control-transfected cells. Preexposure to 20 µM GSK205 virtually eliminates the Ca++-signal in TRPV4-transfected cells, and eliminates the moderate signal of control-transfected cells.

(FIG. 3A) Epidermal TRPV4 expression and its loss upon keratinocyte-specific ablation of Trpv4 in tam-induced iKO mice. (i) TRPV4 immunofluorescence. Note TRPV4 in epidermis of vehicle (oil) treated control, but not tam-induced iKO mice. Bar=10 µm. (ii) Western blot of epidermal lysates from paw-pad skin. Note knockdown and more complete loss of TRPV4 following induced Trpv4-ablation (β-actin used for normalization). (iii) qRT-PCR for Trpv4 mRNA from paw-pad skin is shown, indicating significant Trpv4 knockdown in response to tam-treatment vs. carrier (oil). P<0.0001, t-test. (iv) Immunofluorescence for epidermal lineage markers. In WT skin, basal epidermal marker keratin-14 is downregulated and suprabasal marker keratin-1 is induced upon commitment to terminal differentiation. Upon knockdown of TRPV4, this balance appears perturbed, with some spinous layer cells showing co-labeling. Bar=10 µm. (FIG. 3B) Nocifensive behavior in response to UVB exposure. Time-course (in hours) for nocifensive behavior elicited by either a noxious mechanical stimulus (automatic von Frey hair assay, left) or thermally-evoked nocifensive behavior (Hargreaves' assay, right). Note significantly less sensitization in Trpv4$^{-/-}$ and in tam-treated iKO mice, relative to oil-treated (vehicle) iKO and WT mice. n≥10 animals per group; p<0.01 ANOVA. (FIG. 3C) Correlation between nocifensive behavior and level of Trpv4 knockdown. n=12 animals are shown for which both parameters were available and Trpv4 mRNA levels <0.45. Note the four vehicle-induced animals (green symbols) vs. their tamoxifen-induced counterparts (red symbols). (FIG. 3D) Loss of epidermal TRPV4 shows no significant effect on nocifensive behaviors caused by formalin injection. Bars depict average cumulative nocifensive behavior within the first 10 minutes (phase I), and 10-45 minutes (phase II) post-injection. n=4 per group. (FIG. 3E) Phosphorylated ERK in L5 DRG neurons. pERK immunofluorescence of L5 DRG sections are shown for oil- and tam-treated iKO animals±exposure to UVB. Note that only UVB-exposed control mice show pERK expression in the paw-pad-innervating L5 DRG. Quantifications are shown at right. n=3 animals per group, 6 sections per DRG per animal, p<0.01 ANOVA.

(FIG. 4A) 1 µm toluidine-blue semi-thin sections. Micrographs show representative findings of skin in response to UVB, sampled 48 hours after UVB exposure. Note that upon UVB stimulation, oil-(TRPV+) but not tam-treated (TRPV−) iKO mice exhibit separations at the epidermal-dermal boundary and robust signs of tissue injury; note granulocytes (Gr, neutrophil). Note also that just beneath the stratum corneum (SC), the upper epidermis shows extensive structural damage which could also be seen in skin of tam-treated iKO mice where Trpv4 knockdown was incomplete, but not in those animals where it was more complete (see FIG. S2A). Bars=20 µm. Der=dermis; Epi=epidermis. (FIG. 4B) Ultrastructural findings by EM. Selected areas from 1 µm semithin sections of paw skin were examined by transmission electron microscopy. (A-A') and (C-C') show normal epidermal (Epi) structure for both, oil- and tam-treated iKO mice, in the absence of UVB stimulation. (A) and (C) show and intact epidermis. Basal (BL) and spinous (Sp) layers are magnified A' and C' displaying a normal organization with no evidence of epidermal damage. (B,B'B"), (D-D') and (E-E') show representative findings of skin in response to UVB, sampled 48 h after UVB exposure. (B) Disrupted epidermis in oil treated iKO mice. An area equivalent to the boxed area is magnified in (B'), where granulocyte infiltration of epidermis is evident (Gr) and blistering with detachment of the epidermis from the dermis (double arrows). (B") Upper part of epidermis in contact with stratum corneum (SC), showing extensive vacuolization and deposits of fibrin inside the vacuoles (asterisks). (D) Tamoxifen treated iKO mice with incomplete knockdown of trvp4 show similar skin phenotype to oil treated iKO mice, with robust signs of tissue damage to basal and spinous layer, fibrin deposits (asterisks) and intercellular spaces (arrowheads in D'). (E) Intact epidermis in iKO with complete knockdown of trvp4, with normal basal and spinous layers in (E'). Der, dermis. Dotted lines indicate the dermo-epidermal boundary. Bars=20 µm for A, B, C and D; 10 µm for B' and E' and 2 µm for the other micrographs. (FIG. 4C) IL-6 upregulation in keratinocytes as marker of epidermal activation. IL-6 immunofluorescence reveals a reduced ability of TRPV4-deficient mice to elevate keratinocyte IL-6 expression in response to UVB exposure. Quantifications for protein is shown next to micrograph. Densitometries are for n≥3 mice per group, showing significant upregulation for oil-treated iKO mice, lack thereof for tam-treated. Right-hand bar diagram shows Il-6 mRNA quantification and time-course. Il-6 mRNA was determined by qPCR after isolation of total RNA from paw-pad epidermis. Note the early and robust increase, albeit with variation, at the 2 hour time-point, in WT control epidermis, in contrast the very moderate increase in Trpv4$^{-/-}$ epidermis. Note also the sustained robust upregulation at 24 hours, again moderately upregulated in Trpv4$^{-/-}$ epidermis. Quantifications are for n=8-12 mice/group. * denotes statistically significant (p=0.011, t-test); scale-bar=20 µm. (FIG. 4D) Recruitment of macrophages in UVB-exposed skin. Note that the numbers of dermal CD68+ macrophages induced by UVB-exposure in control mice is significantly reduced when Trpv4 is ablated in the epidermis. Quantifications are shown at right (n=3 mice/group; *p<0.05 t-test); scale-bar=20 µm. (FIG. 4E) Recruitment of elastase-expressing neutrophils to UVB-exposed skin. Shown are representative immunofluorescence micrographs and respective quantifications. Note a strong increase in abundance of elastase-expressing neutrophils in control mice, and a lack thereof in tam-treated iKO mice. (n=4 mice/group, *p<0.05 t-test); scale-bar=40 µm.

(FIG. 5A) Trpv4 knockdown level of samples shown in FIGS. 4A-4E. This bar diagram shows relative level of knockdown of Trpv4 in comparison with WT, of UVB-exposed skin samples shown in FIG. 4. An adjacent sample of hindpaw skin was RNA-extracted at 48 h post-exposure and subjected to Trpv4 qRT-PCR; pooled WT mRNA values from 10 mice were set as 100%. (FIG. 5B) Light microscopic analyses of 1 µm semithin sections findings from Trpv4−/− and WT control mice. Normal skin is shown in the upper row for both genotypes in the unstimulated state, presence of epidermal and dermal inflammation in WT control vs. absence thereof in Trpv4−/− when exposing the skin to UVB, sampling conducted at 48 hours. Note inflammatory changes similar to those of oil-treated iKO mice, as shown in FIG. 4. (FIG. 5C) Ultrastructural analyses of Trpv4−/− and WT control mice. (A-A') and (B-B') WT and Trpv4−/− mice show normal skin morphology with intact epidermis (Epi) in the absence of UVB stimulation. A' and B' show higher magnification of basal layer (BL) cells. (C-C') Damaged epidermis with vacuolization (inset in C) and granulocyte (neutrophil) (granulocyte—Gr) infiltrate (C'). (D-D') Normal epidermal and dermal ultrastructure in Trpv4−/− mice exposed to UVB. Der-dermis; NT, nerve terminals. Dotted lines indicate the dermo-epidermal boundary. Bars=10 µm for A, B, C, C' and D and 2 µm for the other micrographs. (FIG. 5D) IL-6 upregulation in epidermal keratinocytes in response to UVB depends on Trpv4; findings from Trpv4−/− and WT control mice. Fluorescent micrographs from Trpv4−/− and WT control skin, unexposed and exposed to UVB are shown. Note strong IL-6 signal in WT, exposed to UVB, and low signal in Trpv4−/− for both non-exposed and UVB-exposed states. Also note IL-6-expressing innervating peripheral nerve endings in the dermis. (FIG. 5E) No difference in mast cell abundance in UVB-photodermatitis in iKO mice. Left-hand micrograph shows mast-cells within sub-epidermal inflammatory tissue, stained with toluidine-blue, in an iKO mouse induced with tamoxifen, right micrograph its counterpart in an oil-treated iKO mouse. Mast-cells are indicated by white arrow-heads. Bar=20 µm. Right-hand bar diagram indicates quantification of mast-cell count per 63× visual field (5 fields per mouse, 3 mice per group).

FIGS. 6A-6H: Ca++ influx into keratinocytes in response to UVB depends on TRPV4. (FIG. 6A) Custom-built UVB cell illumination apparatus. See also FIG. 2. (FIG. 6B) Fluo-4 Ca++ imaging in 1° MKs. Fluorescent micrographs of 1° MKs after loading with Ca++-sensitive dye, fluo-4, before (upper) and at the end of UVB exposure (lower). Bar=10 μm. C—H UVB-evoked Ca++ signaling profiles. Fluo-4 imaging was used to detect Ca++ transients in 1° MKs following UVB exposure. y-axis indicates the increase in fluorescence, ΔF, normalized for prestimulation signal, F0 (ΔF/F0). The signal shown is that averaged from ≥50 cells. (FIG. 6C) Ca++ signaling is dependent upon UVB, and is strikingly reduced when quartz coverslips are replaced by glass ones, which prevent UVB permeation (see FIG. 2A). Note that this particular Ca++ signal in WT 1° MKs persisted after UVB, as is sometimes observed. (FIG. 6D) UVB-evoked Ca++ signaling is dependent on external [Ca++]. (FIG. 6E) UVB-evoked Ca++ signaling is not seen in Trpv4−/− 1° MKs, revealing the importance of the TRPV4 ion channel. (FIG. 6F) UVB-evoked Ca++ signaling is strongly down-regulated in the presence of TRPV4-selective inhibitor, GSK205 (20 μM). (FIG. 6G) The UVB-evoked Ca++ signal is not inhibited by the TRPV3-selective inhibitor, IPP. For validation of IPP's activity, see FIG. 2E. (FIG. 6H) The UVB-evoked Ca++ signal can be strongly reduced with specific PLC inhibitor, U73122.

FIGS. 7A-7D: Central role for keratinocyte TRPV4 in UVB-evoked Ca++ signaling and nocifensive behavior—effects of ET1. (FIG. 7A) Effects of ET1 on UVB-evoked Ca++ signaling in 1° MKs. Panel (i) shows averaged Ca++ transients in 1° MK in response to UVB, their augmentation by co-exposure to ET1 peptide, and their significant attenuation by either GSK205, which inhibits TRPV4, or ET-convertase inhibitor CGS35066, which blocks ET1 proteolytic processing. Panel (ii) shows ET-augmented, UVB-induced Ca++ transients as in (i), but in this case where they are attenuated by selective antagonism of ET(R)-A (BQ123) and ET(R)-B (BQ788). Panel (iii) illustrates the complete elimination of the ET1-augmented Ca++ transients when both subtypes of ET(R) are blocked. (FIG. 7B) 4α-PDD-evoked Ca++ signaling in 1° MKs—ET1-related findings. Left-hand panel shows Ca++ transients (as per fura-2 ratiometric imaging) in response to the selective TRPV4 activator 4α-PDD. A significant increase in the response can be observed by co-application of ET1, and this is partially dependent on ET(R)-A and completely dependent on ET(R)-B. (FIG. 7C) Upregulation of ET1 in mouse paw in response to UVB. Immunohistochemistry reveals a significantly stronger ET1 signal in UVB-exposed skin of oil-vehicle-treated (TRPV4+) rather than tamtreated iKO mice. Quantifications are for n=3 mice/group. * denotes statistically significant (p<0.001, t-test). (FIG. 7D) Nocifensive behavior in response to ET1 footpad injection depends on epidermal TRPV4. Bar diagram summarizes behavioral findings for Trpv4−/− vs. WT and for oil-treated vs. tam-treated iKO mice. Note that in WT and oil-treated iKO mice, footpad injection of ET1 leads to significant levels of mechanical allodynia. Trpv4−/− and tam-treated iKO mice fail to respond; n≥7 mice/group, p<0.01, ANOVA.

FIGS. 8A-8D: Central role for KC TRPV4 in UVB-evoked $Ca^{++}$ signaling and nocifensive behavior—ET1-related supplementary findings. (FIG. 8A) Augmentation of GSK101-evoked $Ca^{++}$ signaling by ET1. Shown are averaged $Ca^{++}$ measurements (fura-2) in response to 5 nM GSK101. Note the increase in signal in response to co-exposure to ET1. (FIG. 8B) ET1 secretion by non-stimulated 1° MK depends on TRPV4 and PLC. Shown are relative ET1 concentrations (determined by ELISA, pg/mL; vehicle-treated and WT control normalized to 100) in supernatant of non-stimulated 1° MK. Note the clear dependence on TRPV4, as indicated by a 50% reduction in Trpv4$^{-/-}$ 1° MK. Moreover, there is a significant down-regulation by specific inhibition of TRPV4, which is dose-dependent (two doses of GSK205) and can be mediated by two different compounds (GSK205, RN1734). There is also down-regulation of ET1 secretion by a specific inhibitor of PLC (U73122), and by an ET-convertase inhibitor, CGS35066, which served as a control compound. In addition, PLC-inhibitor robustly affects ET1 secretion in WT and Trpv4$^{-/-}$ 1° MK. (FIG. 8C) ET1 expression by UVB-exposed 1° MK depends on TRPV4 and PLC—immunocytochemistry. Shown is specific ET1 immunolabeling in 1° MK, exposed to UVB using the UVB-LEDs, as for $Ca^{++}$ imaging. Use of the UVB-LED device precluded application of a ET1 ELISA, only irradiated cells could be examined. Note the significant down-regulation of ET1 immunoreactivity by specific inhibition of TRPV4 (two different compounds, GSK205, RN1734), by PLC inhibition (U73122), also by inhibition of ET-convertase (CGS35066). (FIG. 8D) ET1 expression by UVB-exposed 1° MK depends on TRPV4 and PLC—quantification of immunocytochemistry. Densitometric measurements of n≥25 cells per condition, background subtracted, are shown, indicating a significant upregulation of ET1 in response to UVB (*p<0.05 ANOVA), and significant down-regulation vs. control-treated and UVB-exposed cells for treatments with selective TRPV4 antagonists (GSK205, RN1734), PLC-inhibitor U73122 and ET-convertase inhibitor CGS35066; *p<0.05, t-test; #p<0.05 ANOVA.

FIGS. 9A-9H: UVB-evoked inflammasome activation in keratinocytes depends on TRPV4. (FIG. 9A) Caspase-1 immunolabeling in footpad skin in response to UVB. Representative images are from sections of skins before stimulation (control) or 48 hours post-UVB exposure. Bars=20 μm. (FIG. 9B) Quantifications of caspase-1 immunolabeling. Bar diagrams show densitometry, n≥3 animals/group. Comparisons: UVB exposed WT vs. Trpv4−/− and iKO+oil vs. iKO+tam. p<0.01 ANOVA. (FIG. 9C) Western blotting for caspase-1 from 1° MK±UVB-exposure. Note that caspase-1 levels, in particular cleaved caspase-1 (lower band), are elevated in UVB-exposed WT cells, but there is a complete absence of both procaspase-1 and cleaved caspase-1 in 1° MK from Trpv4−/− mice. (FIG. 9D) IL-1β is induced upon UVB-exposure and is dependent on TRPV4. Anti-IL-1β immunofluorescence, otherwise as in panel A. (FIG. 9E) Quantifications of IL-1β immunolabeling, n≥3 animals/group. Comparisons: UVB exposed WT vs. Trpv4−/− and iKO+oil vs. iKO+tam, p<0.01 ANOVA. (FIG. 9F) IL-1β concentrations in interstitial fluid of UVB-exposed footpad. IL-1β levels (ELISA) are shown in lavaged interstitial fluid. Note strong up-regulation in WT and oil-treated iKO mice after UVB, in contrast significant attenuation in Trpv4−/− and tam-treated iKO mice. n≥5 mice/group, p<0.01 ANOVA. (FIG. 9G) CXCL5 is induced upon UVB-exposure and is dependent upon TRPV4. Anti-CXCL5 immunolabeling, otherwise as in panel A. (FIG. 9H) Quantifications of CXCL5 immunolabeling, n≥3 animals/group. Comparisons: UVB exposed WT vs. Trpv4−/− and iKO+oil vs. iKO+tam, p<0.01 ANOVA.

(FIG. 10A) Representative micrographs of TRPV4, ET1 and IL-1β distribution in the epidermis of acute photodermatitis, as compared to healthy human skin. Immunostaining for each antigen is increased in acute photodermatitis vs. healthy skin. Scale-bars=50 μm (left), 100 μm (middle), 50 μm (right). (FIG. 10B) Morphometric analysis for immunoreactive TRPV4, ET1 and IL-1β. Findings reveal significantly increased immunolabeling for all three proteins in acute photodermatitis as compared to healthy human skin (n=3 subjects for normal, healthy skin, and 3 patients for acute UV photodermatitis).

(FIG. 12A) UVB-induced nocifensive behavior. Pain behavior is attenuated by topical application of GSK205. The left-hand diagram shows withdrawal thresholds after UVB-exposure in response to noxious thermal cues (Hargreaves' test), and their modulation by two doses of topically applied GSK205 (1 mM and 5 mM; applied 60' and 10' pre-exposure). The higher dose led to a significant attenuation of thermal allodynia at 48 hours post-UVB; n=6 mice/group; p<0.01 ANOVA. The right-hand diagram shows development of moderate thermal allodynia in Trpv4−/− mice, and similar sensitization for vehicle-treated vs. 5 mM GSK205-treated mice, indicating lack of off-target effects of the compound at 5 mM; n=5 mice/group. (FIG. 12B) GSK205-treatment attenuates keratinocyte expression of IL-1β in UVB-exposed footpad—representative micrographs. Bars=20 μm. (FIG. 12C) GSK205-treatment attenuates keratinocyte expression of IL-1β in UVB-exposed footpad quantifications. Bar diagrams show densitometry results from n=3 mice/group, p<0.01 ANOVA. (FIG. 12D) GSK205-treatment attenuates secretion of IL-1β by UVB-exposed 1° MK. IL-1β concentrations in supernatant (ELISA), are shown in response to UVB. Cells were cultured+/−5 μM GSK205. Note prevention of increase in IL-1β secretion in response to UVB upon treatment with GSK205. **P<0.01 ANOVA.

(FIG. 13A) GSK205-treatment attenuates keratinocyte expression of CXCL5 in UVB-exposed footpad—micrographs and quantitation. As in FIG. 12B, specific immunolabeling for CXCL5, which is selectively upregulated in footpad keratinocytes in response to UVB, note attenuation with GSK205 treatment. Bar diagrams show densitometry of CXCL5 immunolabeling, n=3 animals per group, sections analyzed per animal. Note significant differences for vehicle-treated mice between UVB-exposed and non-exposed, no such difference for mice treated topically with 5 mM GSK205. Comparison UVBexposed between vehicle and GSK205-treated, p<0.01 ANOVA. Bar=20 μm. (FIG. 13B) GSK205-treatment attenuates keratinocyte expression of IL-6 in UVB-exposed footpad—micrographs and quantification. As in FIG. 12B and FIG. 13A, specific immunolabeling for IL-6, demonstrates similar regulation of IL-6 as for CXCL5 and IL-1β. Comparison UVB-exposed between vehicle and GSK205-treated, p<0.01 ANOVA. Bar=20 μm.

FIGS. 14A-14O: External-topical application of a selective TRPV4 inhibitor attenuates UVB-evoked nocifensive behavior and inflammation. (FIG. 14A) UVB-photodermatitis is attenuated in mice treated with GSK205. Representative H&E micrographs of paw-pad skin are shown, bars=20 μm. Treatment of UVB-exposed skin with GSK205 improved the skin architecture in mice as compared to vehicle-treated mice after 24 hours. (i) and (iii) Representative skin sections of UVB-induced photodermatitis after GSK205 treatment showed markedly reduced inflammatory infiltrate, less spongiosis and dermal-epidermal blisters with remaining epidermal thickening. (ii) and (iv) Vehicle-treated mice after UVB-induced photodermatitis were characterized by signs of severe acute photodermatitis such as spongiosis, epidermal hyperkeratosis, disrupted dermal-epidermal border (blister), and a marked inflammatory infiltrate with dilated blood vessels and dermal edema (arrows). Also note the erythrocyte accumulation in blood vessels indicative of dermatitis.

(FIG. 16A) Experimental set-up for testing of skin permeability to UVB. (FIG. 16B) Results from FIG. 16A. Note that intensity is 70% within 500 μm radius to the center of the UV beam.

(FIG. 26A) Ca++ imaging screening of all compounds in N2A cells with directed expression of TRPV4 (rat). The cells were stimulated with TRPV4-selective activator compound, GSK101 (5 nM) in the presence of 5 µM of the respective inhibitor. The number on each bar corresponds to average peak ΔCa++ concentrations in ≈100 cells. Inset: micrographs of pseudo-colored cells before and after activation with 5 nM GSK101, in addition note the corresponding time course of the averaged Ca++ signal (fura-2 Ca++ imaging). Except for compound 16-430, the difference to vehicle control reach the level of statistical significance p<0.01 (one-way ANOVA). (FIG. 26B) Dose-response of the most potent, "winner" compounds in TRPV4-expressing N2a cells. The $IC_{50}$ were; 0.45±0.05 µM (16-8), 0.59±0.12 µM (16-18), 0.81±0.1 µM (16-19), 4.19±0.71 µM (GSK205). Plot generated from averaged peak ΔCa++ concentration of 75 cells per data-point.

(FIG. 27A) Current-voltage relationship of TRPV4-mediated currents after activation with 5 nM GSK101. Recordings were performed in TRPV4-GFP+N2a cells. The representative traces represent an average of ≈12 sweeps. In all experiments, cells were preincubated with the respective compound (5 µM) for 5 minutes. (FIG. 27B) Average current densities at −100 mV/+100 mV were significantly diminished by inhibitors (*p<0.05; one-way ANOVA; n≥5 cells/group).

FIGS. 28A-28B: Compound 16-8 inhibits TRPV4 in 1° cells more potently than GSK205. (FIG. 28A) 1° (primary) articular chondrocytes (pig); dose-response comparison between the most potent compound, 16-8, and GSK205 in response to stimulation with 5 nM GSK101. Inset: Chondrocytes responding to activation with GSK101, fura-2 Ca++ imaging; right-hand image taken at 5 sec after GSK101 application. 16-8 was significantly more potent than GSK205 (mean±SEM, n=6 independent expts, n≥25 cells/expt; *p<0.05, t-test). Ordinate shows average peak ΔCa++ concentrations. (FIG. 28B) 1° (primary) astrocytes (rat); dose-response comparison between 16-8 and GSK205 in response to 5 nM GSK101. Inset: Astrocytes responding to activation with GSK101; right-hand image taken at 5 sec after GSK101 application (mean±SEM, n=5 independent expts, 200 cells/expt; *p<0.05, t-test). Ordinate shows average peak ΔCa++ concentrations.

(FIG. 29A) Specificity vs TRPV1-3. Both 16-8 and 16-19 (5 µM each) compounds did not inhibit TRPV1, -2 or -3 channels (all mouse isoforms), directed over-expression in N2a cells and subsequent Ca++ imaging. Mean±SEM is shown, ≥100 cells per condition. (FIG. 29B) Dose-dependent inhibition of TRPA1 (mouse, directed expression in N2a cells) by GSK 205, 16-8 and 16-19, activation with 100 µM mustard oil, resulting in $IC_{50}$ of 5.56±0.4 µM (GSK205), 0.41±0.37 µM (16-19), 0.43±0.3 µM (16-8). Plot generated from averaged peak ΔCa++ concentration of 75 cells per data-point.

(FIG. 30A) Time course of cell viability in the presence of various concentrations of 16-8. Note clear reduction at 40 and 80 µM. (FIG. 30B) As in (FIG. 30A), for compound 16-19, with similar outcome. Representative result of 2 independent experiments.

(FIG. 31A) Time-course of nocifensive behavior in WT mice following whisker-pad injection of 4% formalin. The mice were pre-injected (i.p., 10 mg/kg; 15 min before formalin) with GSK205, 16-8 or 16-19. Note effective reduction of nocifensive behavior in the late "neural" phase by compounds 16-8, 16-19, not by GSK205. (FIG. 31B) Cumulative response binned into 3 phases: acute phase (0-5 min), interphase (5-15 min), and late "neural" phase (15-45 min). Note significant reduction of nocifensive behavior in the late phase by 16-8, 16-19, not GSK205 (*P<0.01 vs vehicle and GSK205, one-way ANOVA). (FIG. 31C) As in (FIG. 31A), but also including Trpv4$^{-/-}$ mice. Compounds were applied i.p. 15 min before formalin challenge, at 10 mg/kg except established TRPA1 blocker, A967079 (25 mg/kg). Previously-established attenuated nocifensive behavior in early and late phase in Trpv4$^{-/-}$ mice was recapped, which was reduced further by TRPA1 blocker, A967079. (FIG. 31D) As in (FIG. 31B), plus inclusion of Trpv4$^{-/-}$ mice. Robust effects of TRPA1-blocker, A967079, were mimicked equipotently by 16-8 and 16-19 for early phase, and by 16-8 for late phase, partially by 16-19 for late phase. (FIG. 31A, FIG. 31C) show averaged behavioral metrics per time-point, bars in (FIG. 31B, FIG. 31D) represent mean±SEM; for (D) *p<0.05; #P<0.005, one-way ANOVA; for all panels n=5-8 mice/group.

FIGS. 32A-32F: Compound 16-8 attenuates acute pancreatitis and improves pain behavior. (FIG. 32A) Caerulein-evoked acute pancreatitis causes pancreatic edema, which is eliminated by compound 16-8 (10 mg/kg, applied at 30 min before first exposure to caerulein). (FIG. 32B) Caerulein-evoked acute pancreatitis strongly elevates cellular toxicity marker amylase in serum. Amylase is reduced, but not significantly, in 16-8 treated animals. (FIG. 32C) caerulein-evoked acute pancreatitis causes elevated myelo-peroxidase (MPO) activity in serum, a marker for infiltration of inflammatory cells into the pancreas. MPO activity is significantly reduced in 16-8 treated mice. (FIG. 32D) caerulein-evoked acute pancreatitis can be readily demonstrated histologically, exemplified in the micrograph panels shown. Note increased pancreas inflammation in the middle-panel vs non-inflamed pancreas in vehicle-control challenged mice, and its attenuation by treatment with compound 16-8. (FIG. 32E) Bar diagram shows quantitation of inflammatory histologic parameters as shown in (FIG. 32D). Note significant increase of inflammation-index in caerulein acute pancreatitis mice, and its significant reduction upon treatment with compound 16-8. (FIG. 32F) Caerulein-evoked acute pancreatitis causes pain behavior, significantly reduced by compound 16-8. Note greatly reduced activity over the 6 h test period in caerulein-induced acute pancreatitis. This nocifensive behavior is greatly improved in response to systemic application of compound 16-8. Results are expressed as mean±SEM; n=6 mice/group; *P<0.05 (one-way ANOVA).

(FIG. 33A) Concentrations of compounds 16-8, 16-19 and GSK205 (10 mg/kg) in several murine tissues/organs 1 h post-i.p. injection. (FIG. 33B) Compound 16-19 time-course at 6 h and 24 h in several organs. 16-19 was selected because of its elevated levels at the 1 h time-point, and based on the estimate that 16-19 is more lipophilic than 16-8 and GSK205. Note that metrics at 6 h are invariably higher than at 24 h. All values are appreciably higher than at 1 h. (FIG. 33C) Concentrations of 16-8, 16-19 and GSK205 in fat and pancreas after one hour. Note lower concentration of 16-8 vs. 16-19 and GSK205, yet above its IC50. (FIG. 33D) Concentrations of 16-8 in the pancreas at 1 h and 24 h time-points. (FIG. 33E) Structural stability of compound 16-19 in plasma as suggested by stable concentration after 4 h/37° C. Results are expressed as means±SEM, n=6 mice/experimental group for all experiments.

(FIG. 34A) Heart rate time-course after i.p. injection (10 mg/kg) of compounds. There was no significant difference in heart rates between vehicle and compounds. (FIG. 34B) Serum creatinin was not significantly elevated in animals treated with 16-19 and 16-8 vs vehicle control. (FIG. 34C) Serum alanin-amino-transferase (ALT) levels were not significantly elevated in animals treated with 16-19 and 16-8 vs vehicle control. n=6 mice/group for all experiments.

DETAILED DESCRIPTION

Figure 1B:
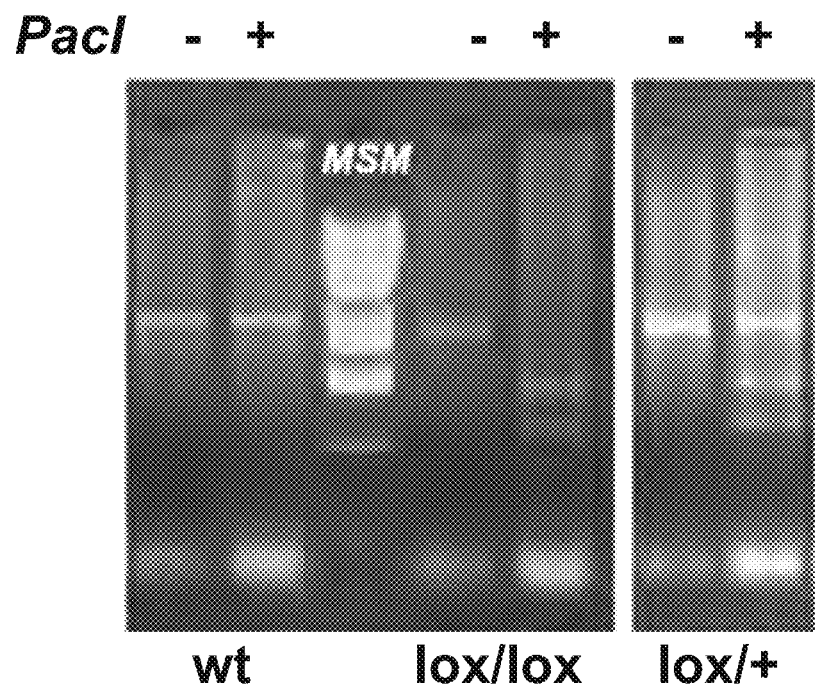

The disclosure relates to treating a subject's skin or wounds in order to sanitize them and remove any contaminating and possibly harmful bacteria or other microorganisms. The disclosure also relates to diminishing pain, inflammation, and/or irritation that may be caused by iodine or a local anesthetic. Described herein are compositions and methods for sanitizing a subject, anesthetizing a subject, and treating and/or preventing a dermatological disorder. The skin functions as an essential barrier between the external environment and the vertebrate organism. Keratinocytes in the skin absorb UV-light, leading to skin inflammation, pain, and itch after over-exposure, which subsequently leads to skin pigmentation. The inventors have identified that the skin, in particular its epidermal epithelia, is substantially involved in sensory transduction. A mouse model of sunburn is described herein and used to induce a state of lowered sensory thresholds evoked by a limited, self-resolving inflammation in response to UV spectrum of light. UV-evoked lowering of sensory thresholds shares major hallmarks of pathological pain, which is a valuable feature of this model.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Definitions of specific functional groups and chemical terms are described in more detail herein. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "acyl" or "carbonyl" refers to the group —C(O)R wherein R is selected from the group consisting of hydrogen, alkyl, alkenyl, alkynyl, aryl, cycloalkyl, heterocyclyl, heteroaryl, arylalkyl, cycloalkylalkyl, heteroarylalkyl and heterocyclylalkyl, any of which may be optionally substituted, e.g., with one or more substituents. For example, when R is alkyl, such a group may be referred to as an alkylcarbonyl group. The term "acyl" or "carbonyl" includes, for example, an alkylcarbonyl, cycloalkylcarbonyl, heterocyclylcarbonyl, arylcarbonyl, or heteroarylcarbonyl substituent, any of which may be further substituted (e.g., with one or more substituents).

The term "alkyl" refers to a straight or branched hydrocarbon chain, containing the indicated number of carbon atoms. For example, $C_1$-$C_{12}$ alkyl indicates that the alkyl group may have from 1 to 12 (inclusive) carbon atoms, and $C_1$-$C_4$ alkyl indicates that the alkyl group may have from 1 to 4 (inclusive) carbon atoms. An alkyl group may be optionally substituted. Examples of $C_1$-$C_4$ alkyl groups include methyl, ethyl, n-propyl, isopropyl, n-butyl, sec-butyl and tert-butyl.

The term "alkylene" refers to divalent hydrocarbon groups having 1 to 6 carbon atoms such as methylene, ethylene, propylene, and butylene. Alkylene groups include $C_1$-$C_2$ alkylene, or $C_1$-$C_3$ alkylene, or $C_1$-$C_4$ alkylene.

The term "alkenyl" refers to a straight or branched hydrocarbon chain having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. An alkenyl group may be optionally substituted.

The term "alkynyl" refers to a straight or branched hydrocarbon chain having one or more triple bonds. Examples of alkynyl groups include, but are not limited to, ethynyl, propargyl, and 3-hexynyl. One of the triple bond carbons may optionally be the point of attachment of the alkynyl substituent. An alkynyl group may be optionally substituted.

The term "aryl" or "aromatic" refers to an aromatic monocyclic, bicyclic, or tricyclic hydrocarbon ring system, wherein any ring atom capable of substitution can be substituted (e.g., with one or more substituents). Examples of aryl moieties include, but are not limited to, phenyl, naphthyl, and anthracenyl. An aromatic amine is an aryl group substituted with one or more amino groups. An aromatic alcohol is an aryl group substituted with one or more hydroxyl groups. Both aromatic amines and aromatic alcohols may be further substituted with other substitutents.

The term "arylalkyl" refers to an alkyl moiety in which an alkyl hydrogen atom is replaced with an aryl group. Arylalkyl includes groups in which more than one hydrogen atom has been replaced with an aryl group. Examples of arylalkyl groups include benzyl, 2-phenylethyl, 3-phenylpropyl, 9-fluorenyl, benzhydryl, and trityl groups.

The term "carboxyl" refers to the group —C(=O)OR, wherein R is selected from the group consisting of hydrogen, alkyl, alkenyl, alkynyl, aryl, cycloalkyl, heterocyclyl, heteroaryl, arylalkyl, cycloalkylalkyl, heteroarylalkyl, and heterocyclylalkyl any of which may be optionally substituted, e.g., with one or more substituents.

The term "carbonylamino" or "amido" refers to the group —C(O)NR'R" wherein R' and R" are independently selected from the group consisting of hydrogen, alkyl, alkenyl, alkynyl, aryl, cycloalkyl, heterocyclyl, heteroaryl, arylalkyl, cycloalkylalkyl, heteroarylalkyl, and heterocyclylalkyl, or R' and R", together with the nitrogen to which they are attached, may form a ring. The groups R' and R" may be optionally substituted, e.g., with one or more substituents, or when R' and R" together with the nitrogen to which they are attached form a ring, the ring may be optionally substituted, e.g., with one or more substituents.

The term "cycloalkyl" as used herein refers to nonaromatic, saturated or partially unsaturated cyclic, bicyclic, tricyclic, or polycyclic hydrocarbon groups having 3 to 12 carbons (e.g., 3, 4, 5, 6, or 7 carbon atoms). Any ring atom can be substituted (e.g., with one or more substituents). Cycloalkyl groups can contain fused rings. Fused rings are rings that share one or more common carbon atoms. Examples of cycloalkyl groups include, but are not limited to, cyclopropyl, cyclobutyl, cyclopentyl, cyclohexyl, cyclohexenyl, cyclohexadienyl, methylcyclohexyl, adamantyl, norbornyl, and norbornenyl. The term "cycloalkenyl" refers to cyclic alkenyl groups of from 4 to 8 carbon atoms having a single cyclic ring and at least one point of internal unsaturation. Any ring atom can be substituted (e.g., with one or more substituents).

The term "halo" or "halogen" as used herein refers to any radical of fluorine, chlorine, bromine, or iodine.

The term "haloalkyl" as used herein refers to an alkyl in which one or more hydrogen atoms are replaced with a halogen, and includes alkyl moieties in which all hydrogens have been replaced with halogens (e.g., perfluoroalkyl such as $CF_3$).

The term "heteroaryl" or "heteroaromatic" as used herein refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, S, P, and Si (e.g., carbon atoms and 1-3, 1-6, or 1-9 heteroatoms independently selected from O, N, S, P, and Si if monocyclic, bicyclic, or tricyclic, respectively). Any ring atom can be substituted (e.g., with one or more substituents). Heteroaryl groups can contain fused rings, which are rings that share one or more common atoms. Examples of heteroaryl groups include, but are not limited to, radicals of pyridine, pyrimidine, pyrazine, pyridazine, pyrrole, imidazole, pyrazole, oxazole, isoxazole, furan, thiazole, isothiazole, thiophene, quinoline, isoquinoline, quinoxaline, quinazoline, cinnoline, indole, isoindole, indolizine, indazole, benzimidazole, phthalazine, pteridine, carbazole, carboline, phenanthridine, acridine, phenanthroline, phenazine, naphthyridines, and purines.

The term "heterocyclyl" as used herein refers to a non-aromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si, and P (e.g., carbon atoms and 1-3, 1-6, or 1-9 heteroatoms of O, N, S, Si and P if monocyclic, bicyclic, or tricyclic, respectively). Any ring atom can be substituted (e.g., with one or more substituents). Heterocyclyl groups can contain fused rings, which are rings that share one or more common atoms. Heterocyclyl groups can include heterocycloalkenyl groups. Examples of heterocyclyl groups include, but are not limited to, radicals of tetrahydrofuran, tetrahydrothiophene, tetrahydropyran, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like.

The term heteroalkyl refers to a alkyl-, a alkenyl- or a alkynyl group, wherein one or more (preferably 1, 2, or 3) carbon atoms are replaced by one or more heteroatoms, said heteroatoms selected from O, N, S, Si, and P. Heteralkyl groups include, for example, an alkyloxy group, as for example methoxy or ethoxy, or a methoxymethyl-, nitrile-, methylcarboxyalkylester- or 2,3-dioxyethyl-group. The term heteroalkyl refers furthermore to a carboxylic acid or a group derived from a carboxylic acid as for example acyl, acyloxy, carboxyalkyl, carboxyalkylester, such as for example methylcarboxyalkylester, carboxyalkylamide, alkoxycarbonyl, or alkoxycarbonyloxy.

The term "hydroxy" or "hydroxyl" refers to an —OH radical. The term "alkoxy" refers to the group —O—R wherein R is alkyl, alkenyl, alkynyl, cycloalkyl or heterocyclyl, any of which may be optionally substituted, e.g., with one or more substituents. The term "aryloxy" refers to an —O-aryl radical. The term "haloalkoxy" refers to an —O-haloalkyl radical.

The term "substituent" refers to a group "substituted" on an alkyl, alkenyl, alkynyl, cycloalkyl, heterocyclyl, aryl, arylalkyl, or heteroaryl group at any atom of that group. Suitable substituents include, without limitation: acyl, acylamido, acyloxy, alkoxy, alkyl, alkenyl, alkynyl, amido, amino, carboxy, cyano, ester, halo, hydroxy, imino, nitro, oxo (e.g., C=O), phosphonate, sulfinyl, sulfonyl, sulfonate, sulfonamino, sulfonamido, thioamido, thiol, thioxo (e.g., C=S), and ureido. In embodiments, substituents on a group are independently any one single, or any combination of the aforementioned substituents. In embodiments, a substituent may itself be substituted with any one of the above substituents.

The above substituents may be abbreviated herein, for example, the abbreviations Me, Et, and Ph represent methyl, ethyl and phenyl, respectively. A more comprehensive list of the abbreviations used by organic chemists appears in the first issue of each volume of the Journal of Organic Chemistry; this list is typically presented in a table entitled Standard List of Abbreviations. The abbreviations contained in said list, and all abbreviations used by organic chemists of ordinary skill in the art, are hereby incorporated by reference.

For compounds, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —CH$_2$O— optionally also recites —OCH$_2$—.

In accordance with a convention used in the art, the group:

is used in structural formulas herein to depict the bond that is the point of attachment of the moiety or substituent to the core or backbone structure.

The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration" or "administering" refers to delivery of a compound or composition by any appropriate route to achieve the desired effect. Administration may include any convenient route of administration, whether systemically/peripherally or at the site of desired action, including but not limited to, oral (e.g. by ingestion); topical (including e.g. transdermal, intranasal, ocular, buccal, and sublingual); pulmonary; respiratory (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly. In certain embodiments, administration may be topical. "Co-administered" refers to simultaneous or sequential administration. A compound or composition may be administered before, concurrently with, or after administration of another compound or composition. One skilled in the art can select an appropriate dosage and route of administration depending on the patient, the particular disease, disorder, or condition being treated, the duration of the treatment, concurrent therapies, etc. In certain embodiments, a dosage is selected that balances the effectiveness with the potential side effects, considering the severity of the disease, disorder, or condition (e.g., skin inflammation, pain, or itch).

The terms "control," "reference level," and "reference" are used herein interchangeably. The reference level may be a predetermined value or range, which is employed as a benchmark against which to assess the measured result. "Control group" as used herein refers to a group of control subjects or cells. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, Tex.; SAS Institute Inc., Cary, N.C.). The healthy or normal levels or ranges for a target or for a protein activity may be defined in accordance with standard practice. A control may be a subject, or a sample therefrom, whose disease state is known. A control may include cells, referred to as "control cells." The subject, or sample therefrom, may be healthy, diseased, diseased prior to treatment, diseased during treatment, or diseased after treatment, or a combination thereof.

"Effective amount" refers to a dosage of a compound or composition effective for eliciting a desired effect, commensurate with a reasonable benefit/risk ratio. This term as used herein may also refer to an amount effective at bringing about a desired in vivo effect in an animal, preferably, a human, such as reduction in skin inflammation, reduction in pain, or reduction in itch.

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including uracil, adenine, thymine, cytosine, guanine, inosine, xanthine hypoxanthine, isocytosine, and isoguanine. Polynucleotides can be obtained by chemical synthesis methods or by recombinant methods.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide", "protein," and "peptide" are used interchangeably herein. "Primary structure" refers to the amino acid sequence of a particular peptide. "Secondary structure" refers to locally ordered, three dimensional structures within a polypeptide. Secondary structure may include beta-sheet and alpha-helices. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units. A "motif" is a portion of a polypeptide sequence and includes at least two amino acids. A motif may be 2 to 20, 2 to 15, or 2 to 10 amino acids in length. In some embodiments, a motif includes 3, 4, 5, 6, or 7 sequential amino acids.

"Subject" as used herein can mean a mammal that wants or is in need of the herein described methods or compositions. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant. As used herein, a "subject in need of treatment" refers to a subject in need of the compositions and methods detailed herein. The subject may have a surface in need of sanitizing. The subject may be in need of anesthetization. The subject may have been diagnosed with a dermatological disease or disorder associated with skin inflammation, pain, itch, or a combination thereof. In embodiments a subject can include human and non-human animals. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.). Accordingly, embodiments of the methods described herein relate to treatment of a cell or tissue, a cell or tissue from a subject, or a subject that may be a eukaryote, an animal, a vertebrate animal, a mammal, a rodent (e.g., a guinea pig, a hamster, a rat, a mouse), murine (e.g., a mouse), canine (e.g., a dog), feline (e.g., a cat), equine (e.g., a horse), a primate, simian (e.g., a monkey or ape), a monkey (e.g., marmoset, baboon), an ape (e.g., gorilla, chimpanzee, orangutan, gibbon), or a human.

"Pharmaceutically acceptable" means suitable for use in a human or other mammal. The terms "pharmaceutically acceptable carriers" and "pharmaceutically acceptable excipients" are used interchangeably and refer to substances that are useful for the preparation of a pharmaceutically acceptable composition. In certain embodiments, pharmaceutically acceptable carriers are generally compatible with the other ingredients of the composition, not deleterious to the recipient, and/or neither biologically nor otherwise undesirable. The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. In some embodiments, a carrier includes a solution at neutral pH. In some embodiments, a carrier includes a salt. In some embodiments, a carrier includes a buffered solution.

"Sample" or "test sample" as used herein can mean any sample in which the presence and/or level of a target is to be detected or determined, or a portion from a subject or portion of a composition as detailed herein. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises cells. In some embodiments, the sample comprises an aliquot. In other embodiments, the sample comprises a biological fluid. Samples can be obtained by any means known in the art. The sample can be used directly as obtained from a patient or can be pretreated, such as by filtration, distillation, extraction, concentration, centrifugation, inactivation of interfering components, addition of reagents, and the like, to modify the character of the sample in some manner as discussed herein or otherwise as is known in the art.

"Treatment" or "treating," when referring to disease in a subject, means suppressing, repressing, reducing, ameliorating, or completely eliminating the disease. Suppressing the disease involves administering a composition to a subject after induction of the disease but before its clinical appearance. Repressing or reducing or ameliorating the disease involves administering a composition to a subject after clinical appearance of the disease. "Preventing" the disease involves administering a composition to a subject prior to onset of the disease.

2. INHIBITION OF TRPV4 AND/OR TRPA1

Provided herein are compositions and methods for inhibiting TRPV4 and/or TRPA1. Detailed herein are inhibitors of TRPV4 and/or TRPA1, as well as compositions comprising the inhibitors. The inhibitors may be used in a variety of methods including sanitizing a surface of a subject, anesthetizing a subject, and treating various disorders and diseases.

a. TRP Channels

The compositions and methods disclosed herein relate to the discovery that epidermal keratinocytes function prominently to orchestrate UVB-mediated inflammation and sensitization of peripheral nerve endings in the skin. In that respect, epidermal keratinocytes have a role similar to a co-sensory cell. Keratinocytes abundantly express TRPV4. As described herein, TRPV4, expressed in epidermal keratinocytes, plays a role in UV-induced inflammation and pain. The TRPV4 channel exerts its role as a master regulator of UVB-evoked skin inflammation and nociception through Ca++ influx into keratinocytes. This UVB-evoked, TRPV4-mediated Ca++ influx re-programs the keratinocyte to function in a pro-inflammatory and pro-algesic (pro-pain) manner, via TRPV4-dependent secretion of endothelin-1 (ET-1), which may lead to sensation of itch and skin pigmentation. TRPV4 is activated contemporaneously with UVB exposure, which leads to activation of pro-algesic pathways via secreted factors previously demonstrated to have relevance in human pain. As described in further detail herein, mice with inducible Trpv4 deletions targeted to keratinocytes were induced for TRPV4 deletion, subsequently UVB-exposed, and found to be less sensitive to noxious thermal and mechanical stimulation than control mice. Based on these studies, epidermal TRPV4 was identified as a protein involved in the orchestration of UVB-mediated skin inflammation. In mouse skin, UVB-evoked inflammasome activation and increased expression of pro-algesic/algogenic mediators, such as IL1-β, CXCL5, ET-1, and IL-6, were TRPV4-dependent. ET-1 has been shown in humans to not only elicit painful sensations, but to also elicit itch, when injected into the skin. Also, ET-1 has been identified as a melanogen, that is, to increase skin pigmentation by signaling to melanocytes. In primary murine keratinocytes, UVB caused a direct, TRPV4-dependent $Ca^{++}$-response. Moreover, in mice, topical application of a TRPV4-selective inhibitor reduced UVB-evoked epidermal inflammation and pain behavior. Additionally, it was found that epidermal expression of TRPV4, ET1, and IL-1β were increased in acute human UV-photodermatitis. The term photodermatitis is used in this application referring to skin inflammation in response to UV radiation/light. This tissue response can include pain, irritation, itch, influx of inflammatory and pain-enhancing cells and tissue injury. The compounds as detailed herein may inhibit TRPV4. The compounds as detailed herein may inhibit TRPA1. The compounds as detailed herein may inhibit TRPV4 and TRPA1. The compounds as disclosed herein may not inhibit TRPV1, TRPV2, or TRPV3. The inhibitor may specific for TRPV4 and TRPA1.

b. TRPA1 and/or TRPV4 Inhibitor

As TRPV4 is a $Ca^{2+}$-permeable, nonselective cation channel, some embodiments provide for a TRPA1 and/or TRPV4 inhibitor that can inhibit the biological function of TRPA1 and/or TRPV4 (e.g., inhibit cation channel activity, inhibit Ca++ transport and/or availability). Other embodiments provide for a TRPA1 and/or TRPV4 inhibitor that may inhibit the expression of mRNA encoding TRPA1 or TRPV4. Some embodiments provide a TRPA1 and/or TRPV4 inhibitor that may inhibit the translation of mRNA encoding TRPA1 or TRPV4 to protein. Thus, a TRPA1 and/or TRPV4 inhibitor may indirectly or directly bind and inhibit the activity of TRPA1 and/or TRPV4 (e.g., binding activity or enzymatic activity), reduce the expression of TRPA1 and/or TRPV4, prevent expression of TRPA1 and/or TRPV4, or inhibit the production of TRPA1 and/or TRPV4 in a cell. Inhibit or inhibiting relates to any measurable reduction or attenuation of amounts or activity, e.g., amounts or activity of TRPA1 and/or TRPV4, such as those disclosed herein. "Amounts" and "levels" of protein or expression may be used herein interchangeably.

The inhibitors as detailed herein may inhibit TRPA1. The inhibitors as detailed herein may inhibit TRPV4. The inhibitors as detailed herein may inhibit TRPV4 and TRPA1. The inhibitors as disclosed herein may not inhibit TRPV1, TRPV2, or TRPV3. The inhibitor may specific for TRPV4 and TRPA1.

In some embodiments, a TRPA1 and/or TRPV4 inhibitor can increase the amount of, or the biological activity of, a protein that can reduce the activity of TRPA1 and/or TRPV4. Inhibitors capable of increasing the level of such a protein may include any inhibitor capable of increasing protein or mRNA levels or increasing the expression of the protein that inhibits TRPV4 and/or TRPA1. In one embodiment, a TRPA1 and/or TRPV4 inhibitor may comprise the protein itself. For example, a TRPA1 and/or TRPV4 inhibitor may include exogenously expressed and isolated protein capable of being delivered to the cells. The protein may be delivered to cells by a variety of methods, including fusion to Tat or VP16 or via a delivery vehicle, such as a liposome, all of which allow delivery of protein-based inhibitors across the cellular membrane. Those of skill in the art will appreciate that other delivery mechanisms for proteins may be used. Alternatively, mRNA expression may be enhanced relative to control cells by contact with a TRPA1 and/or TRPV4 inhibitor. For example, an inhibitor capable of increasing the level of a natively expressed protein that inhibits TRPV4 and/or TRPA1 may include a gene expression activator or de-repressor. As another example, a TRPA1 and/or TRPV4 inhibitor capable of decreasing the level of natively expressed TRPV4 and/or TRPA1 protein may include a gene expression repressor. An inhibitor capable of increasing the level of a protein that inhibits TRPV4 and/or TRPA1 may also include inhibitors that bind to directly or indirectly and increase the effective level of the protein, for example, by enhancing the binding or other activity of the protein. An inhibitor capable of decreasing the level of TRPV4 and/or TRPA1 protein may also include compounds or compositions that bind to directly or indirectly and decrease the effective level of TRPV4 and/or TRPA1 protein, for example, by inhibiting or reducing the binding or other activity of the TRPV4 and/or TRPA1 protein.

The amount or level of expression of a biomolecule (e.g., mRNA or protein) in a cell may be evaluated by any variety of techniques that are known in the art. For example, the inhibition of the level of protein expression (e.g., TRPV4 and/or TRPA1) may be evaluated at the protein or mRNA level using techniques including, but not limited to, Western blot, ELISA, Northern blot, real time PCR, immunofluorescence, or FACS analysis. For example, the expression level of a protein may be evaluated by immunofluorescence by visualizing cells stained with a fluorescently-labeled protein-specific antibody, Western blot analysis of protein expression, and RT-PCR of protein transcripts. The expression level of TRPA1 and/or TRPV4 may be compared to a control. The comparison may be made to the level of expression in a control cell, such as a non-disease cell or other normal cell. Alternatively the control may include an average range of the level of expression from a population of normal cells. Alternatively, a standard value developed by analyzing the results of a population of cells with known responses to therapies or agents may be used. Those skilled in the art will appreciate that any of a variety of controls may be used.

A TRPA1 and/or TRPV4 inhibitor may include one or more compounds and compositions. In some embodiments, a TRPA1 and/or TRPV4 inhibitor comprises a compound. In some embodiments, a TRPA1 and/or TRPV4 inhibitor is a compound. In some embodiments, a TRPA1 and/or TRPV4 inhibitor comprises a small molecule. In some embodiments, a TRPA1 and/or TRPV4 inhibitor is a small molecule. A TRPA1 and/or TRPV4 inhibitor may comprise a biological molecule, including nucleic acid molecules, such as a polynucleotide having RNAi activity against TRPA1 and/or TRPV4 or a substrate thereof. In some embodiments, the nucleic acid molecules include RNAs, dsRNAs, miRNAs, siRNAs, nucleic acid aptamers, antisense nucleic acid molecules, and enzymatic nucleic acid molecules that comprise a sequence that is sufficient to allow for binding to an encoding nucleic acid sequence and inhibit activity thereof (i.e., are complementary to such encoding nucleic acid sequences). Suitably, an RNAi molecule comprises a sequence that is complementary to at least a portion of a target sequence such that the RNAi can hybridize to the target sequence under physiological or artificially defined (e.g., reaction) conditions. In some embodiments an RNAi molecule comprises a sequence that is complementary such that the molecule can hybridize to a target sequence under moderate or high stringency conditions, which are well known and can be determined by one of skill in the art. In some embodiments an RNAi molecule has complete (100%) complementarity over its entire length to a target sequence. A variety of RNAi molecules are known in the art, and can include chemical modifications, such as modifications to the sugar-phosphate backbone or nucleobase that are known in the art. The modifications may be selected by one of skill in the art to alter activity, binding, immune response, or other properties. In some embodiments, the RNAi can comprise an siRNA having a length from about 18 to about 24 nucleotides, about 5 to about 50 nucleotides, about 5 to about 30 nucleotides, or about 10 to about 20 nucleotides.

In some embodiments, the inhibitory nucleic acid molecule can bind to a target nucleic acid sequence under stringent binding conditions. The terms "stringent conditions" or "stringent hybridization conditions" includes reference to conditions under which a polynucleotide will hybridize to its target sequence, to a detectably greater degree than other sequences (e.g., at least 2-fold over background). An example of stringent conditions include those in which hybridization in 50% formamide, 1 M NaCl, 1% SDS at 37° C., and a wash in 0.1×SSC at 60 to 65° C. is performed. Amino acid and polynucleotide identity, homology and/or similarity can be determined using the ClustalW algorithm, MEGALIGN™ (Lasergene, Wis.). Given a target polynucleotide sequence, for example of TRPA1 and/or TRPV4 or biological substrate thereof, an inhibitory nucleic acid molecule can be designed using motifs and targeted to a region that is anticipated to be effective for inhibitory activity, such as is known in the art.

In other embodiments, a TRPA1 and/or TRPV4 inhibitor comprises an antibody that can specifically bind to a protein such as TRPA1 and/or TRPV4 or a fragment thereof. Embodiments also provide for an antibody that inhibits TRPA1 and/or TRPV4 through specific binding to a TRPA1 and/or TRPV4 substrate molecule. The antibodies can be produced by any method known in the art, such as by immunization with a full-length protein such as TRPA1 and/or TRPV4, or fragments thereof. The antibodies can be polyclonal or monoclonal, and/or may be recombinant antibodies. In embodiments, antibodies that are human antibodies can be prepared, for example, by immunization of transgenic animals capable of producing a human antibody (see, for example, International Patent Application Publication No. WO 93/12227). Monoclonal antibodies (mAbs) can be produced by a variety of techniques, including conventional monoclonal antibody methodology, e.g., the standard somatic cell hybridization technique of Kohler and Milstein, and other techniques, e.g., viral or oncogenic transformation of B-lymphocytes. Animal systems for preparing hybridomas include mouse. Hybridoma production in the mouse is very well established, and immunization protocols and techniques for isolation of immunized splenocytes for fusion are well known in the art. Fusion partners (e.g., murine myeloma cells) and fusion procedures are also known.

Any suitable methods can be used to evaluate a candidate active compound or composition for inhibitory activity toward TRPA1 and/or TRPV4. Such methods can include, for example, in vitro assays, in vitro cell-based assays, ex vivo assays, and in vivo methods. The methods can evaluate binding activity, or an activity downstream of the enzyme of interest. Ex vivo assays may involve treatment of cells with an inhibitor of the invention, followed by detection of changes in transcription levels of certain genes, such as TRPA1 and/or TRPV4 through collection of cellular RNA, conversion to cDNA, and quantification by quantitative real time polymerase chain reaction (RT-QPCR). Additionally, the cell viability or inflammation may be determined after treatment with an inhibitor.

i. Compounds of Formula I

In certain embodiments, the TRPA1 and/or TRPV4 inhibitor is a compound according to Formula I:

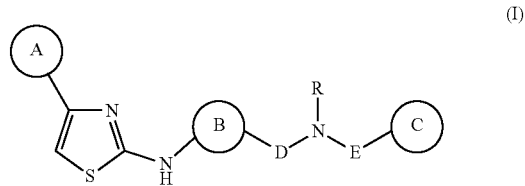

wherein A, B, and C are independently selected from the group consisting of aromatic, heteroaromatic, cycloalkenyl, and heterocycloalkenyl groups;

D is $C_1$-$C_3$ alkylene;

E is a bond, or $C_1$-$C_2$ alkylene; and

R is selected from the group consisting of hydrogen, hydroxyl, amino, alkyl, alkenyl, heteroalkyl, aromatic ring, or heteroaromatic ring. In some embodiments, B and C are independently a phenyl group. In some embodiments, A is phenyl or heteroaryl. In some embodiments, A is pyridnyl. In some embodiments, R is C1-C4 alkyl. In some embodiments, A is heteroaryl, B and C are phenyl, D is ethylene, E is methylene, and R is methyl. In some embodiments, R is ethyl.

In certain embodiments, the TRPA1 and/or TRPV4 inhibitor is the following compound:

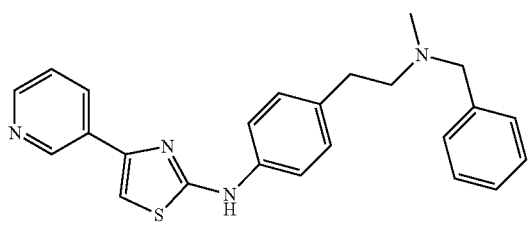

In certain embodiments, the TRPA1 and/or TRPV4 inhibitor excludes the following compound:

In certain embodiments, the TRPA1 and/or TRPV4 inhibitor is the following compound:

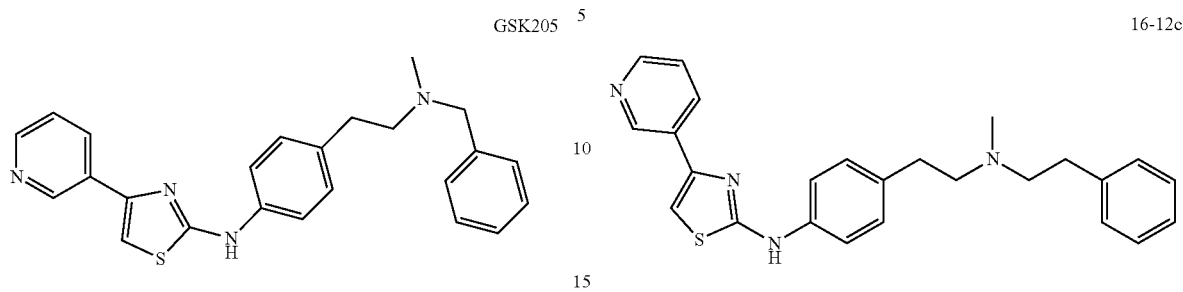

In certain embodiments, the TRPA1 and/or TRPV4 inhibitor is the following compound:

In certain embodiments, the TRPA1 and/or TRPV4 inhibitor is the following compound:

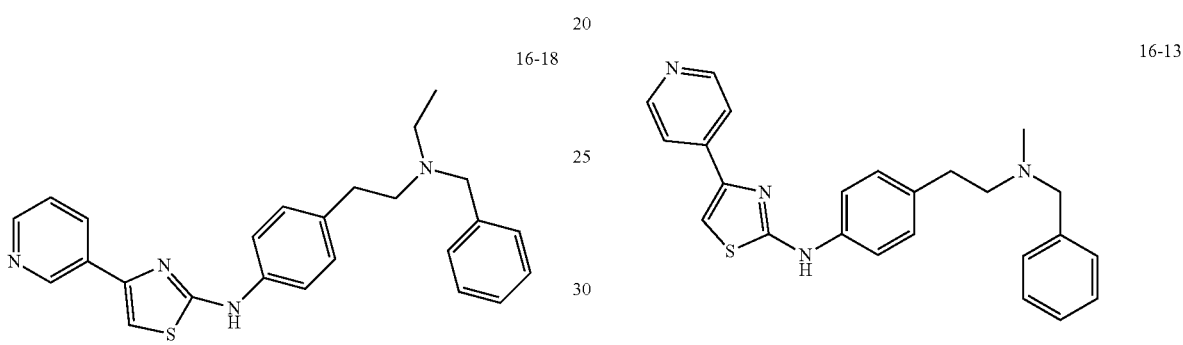

In certain embodiments, the TRPA1 and/or TRPV4 inhibitor is the following compound:

In certain embodiments, the TRPA1 and/or TRPV4 inhibitor is the following compound:

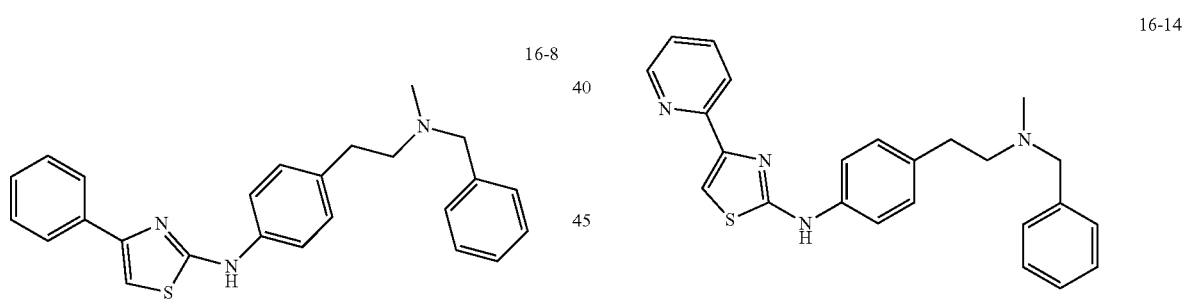

In certain embodiments, the TRPA1 and/or TRPV4 inhibitor is the following compound:

In certain embodiments, the TRPA1 and/or TRPV4 inhibitor is the following compound:

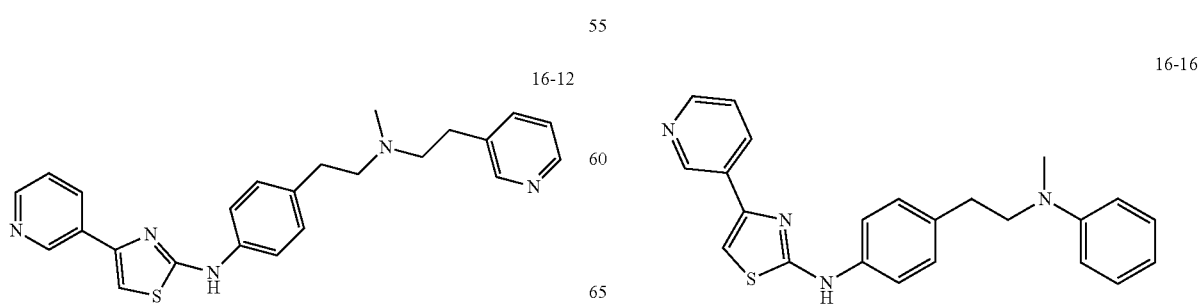

In certain embodiments, the TRPA1 and/or TRPV4 inhibitor is the following compound:

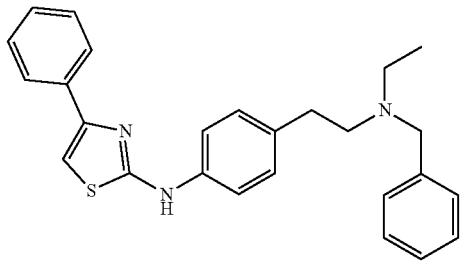

16-19

In certain embodiments, the TRPA1 and/or TRPV4 inhibitor comprises the following compound:

15-43

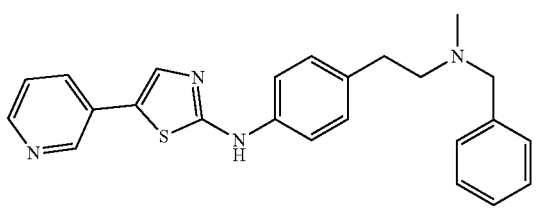

ii. Synthesis of Compounds

Figure 35:
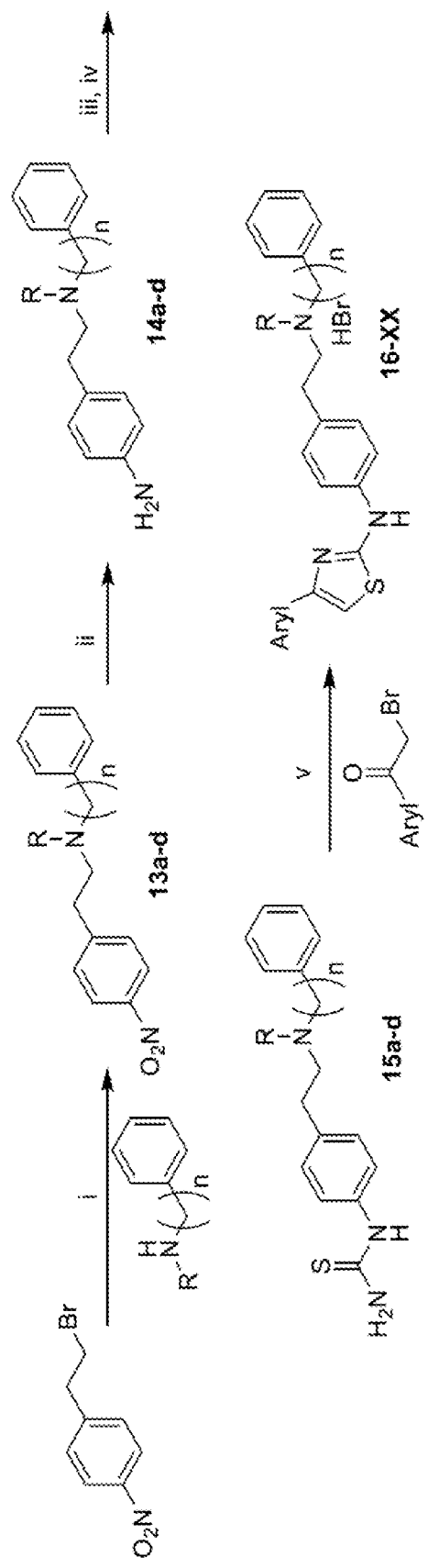
FIG. 35: General synthetic scheme for compounds 16-08 to 16-19. Reagents and conditions: (i) $K_2CO_3$, $CH_3CN$. (ii) Zn, MeOH, 12M HCl. (iii) 1,1'-Thiocarbonyldiimidazole. (iv) 7M $NH_3$ in MeOH. (v) EtOH, reflux.

Compounds of Formula I may be synthesized by a variety of means known in the art. An exemplary synthesis is detailed in the Examples and FIG. 35.

General Procedure for the $S_N2$ Displacement of 4-Nitrophenethyl Bromide:

Powdered, oven-dried $K_2CO_3$ (1.5 eq.) and the amine (1.5 eq.) may be sequentially to a room temperature solution of the bromide (0.33 M) in anhydrous $CH_3CN$. The reaction mixture may be heated to 80° C. (oil bath temp) until analysis of the reaction mixture by LCMS indicated complete consumption of the bromide (~6-18 h). The mixture may be cooled to room temperature and diluted with brine (two volume equivalents). The resulting emulsion may be extracted with EtOAc (2× one volume equivalent). The combined extracts may be added to silica gel (mass of silica gel=2× mass of starting bromide) and the mixture may be concentrated to dryness under reduced pressure. Flash column chromatography (RediSepRf $SiO_2$, 100% $CH_2Cl_2 \rightarrow 5\%$ MeOH in $CH_2Cl_2$) may confirm the product as a brown to amber oil.

General Procedure for the Nitro to Aniline Reduction:

A solution of the nitro compound (0.5 M in MeOH) may be cooled in an ice-NaCl bath. Zinc dust (4.5 eq.) may be added in one portion followed by drop wise addition of 12M HCl (4.5 eq.) over 2-3 minutes. After 1 h, the cooling bath may be removed and the reaction mixture may be allowed to stir over night at room temperature. The following morning, the mixture may be cooled in an ice-NaCl bath once again and 30% aqueous NaOH may be added drop wise until pH 14 (universal indicating pH paper) was reached. The mixture may be diluted with $CH_2Cl_2$ (five volume equivalents) and stirred for 5 minutes. After this time, insolubles may be removed at the vacuum and the filter cake may be washed with $CH_2Cl_2$ (2×25 mL). The organic phase of the filtrate may be separated, washed with brine (100 mL) and dried ($MgSO_4$).

The drying agent may be removed by filtration. Silica gel (~5 g) may be added and the filtrate may be concentrated to dryness under reduced pressure. Flash column chromatography (RediSepRf $SiO_2$, 100% $CH_2Cl_2 \rightarrow 5\%$ MeOH in $CH_2Cl_2$) may confirm the product as a clear, amber oil.

General Procedure for Thiourea Formation:

A solution of the aniline (0.22 M) in anhydrous $CH_2Cl_2$ may be s added drop wise over 2-5 minutes to an ice-NaCl bath cooled solution of 1,1-thiocarbonyldiimidazole (2 eq., 0.15 M) in anhydrous $CH_2Cl_2$. After 15 minutes, the cooling bath may be removed and the reaction mixture may be stirred at room temperature until analysis by TLC (5% MeOH in $CH_2Cl_2$) indicates complete consumption of the starting aniline. The mixture may be cooled once again in an ice bath and 7M $NH_3$ in MeOH (10.5 eq.) may be added drop wise over 2-5 minutes. The bath may be removed and the mixture may be stirred over night at room temperature. Silica gel (mass of silica gel=2× mass of starting aniline) may be added and the mixture was concentrated to dryness under reduce pressure. Flash column chromatography (RediSepRf $SiO_2$, 100% $CH_2Cl_2 \rightarrow 10\%$ MeOH in $CH_2Cl_2$) may confirm the pure thiourea.

General Procedure for Thiazole Formation:

A mixture of the thiourea (0.1 M) in EtOH and the α-bromoacetophenone derivative (1.1 eq.) may be heated to 75° C. (oil bath temperature) until analysis by TLC (5% MeOH in $CH_2Cl_2$) indicates complete consumption of the thiourea. Silica gel (mass of silica gel=2× mass of starting thiourea) may be added and the mixture may be concentrated to dryness under reduce pressure. Flash column chromatography (RediSepRf $SiO_2$, 100% $CH_2Cl_2 \rightarrow 10\%$ MeOH in $CH_2Cl_2$) may confirm the pure thiazole hydrobromide.

c. Compositions

In other aspects, the disclosure provides compositions comprising one or more TRPA1 and/or TRPV4 inhibitor. The compositions may be used to treat a subject's skin or wounds in order to sanitize them, or to remove or reduce contaminating and possibly harmful bacteria or other microorganisms. While doing so, the compositions may also reduce pain, inflammation, irritation, or a combination thereof, that may be caused by or result from a local anesthetic.

In some embodiments, the composition comprises an inhibitor and iodine. Iodine may be present in the composition as elemental iodine, or as an iodine salt, or a combination thereof. Iodine salts may include, for example, potassium iodide and sodium iodide.

In some embodiments, the composition comprises an inhibitor and an anesthetic. In some embodiments, the anesthetic is a local anesthetic. In some embodiments, the anesthetic is not a general anesthetic. In some embodiments, the anesthetic numbs the skin of the subject. The composition comprising an inhibitor and an anesthetic may be used to efficiently clean a subject's skin. The composition comprising an inhibitor and an anesthetic may be applied to the subject prior to a medical procedure, surgery, or an incision. The composition comprising an inhibitor and an anesthetic may be applied to the subject's wound to promote healing.

Local anesthetics reduce or eliminate the tactile and pain sensations blocking transmission in pain fibers and allow a medical professional to manipulate anesthetized tissue without fear of causing the subject pain. Unlike general anesthesia, local anesthesia allows the subject to be awake and aware during the procedure, thus promoting subject confidence and well-being during the medical procedure. Additionally, local anesthesia avoids the some of the risks associated with general anesthesia, such as nausea, vomiting, and malignant hyperthermia. Many compounds are available for use as local anesthetics. Local anesthetics may be divided into two broad categories based on their chemical structure. Amide-containing anesthetics include, for example, articaine, bupivacaine, cinchocaine, etidocaine, levobupivacaine, lidocaine, mepivacaine, prilocaine, ropivacaine, and trimecaine. Another class of local anesthetics contains an ester chemical residue and includes, for example, benzocaine, chloroprocaine, cocaine, cyclomethycaine, dimethocaine, piperocaine, propoxycaine, procaine (novocaine), proparacaine, and tetracaine.

The composition may comprise the TRPA1 and/or TRPV4 inhibitor in combination with a carrier, vehicle, or diluent. Embodiments provide for pharmaceutically acceptable carriers including, but not limited to, substances useful for topical, intrathecal, ocular, parenteral, intravenous, intraperitoneal intramuscular, sublingual, nasal, and oral administration. Administration may be systemic. "Pharmaceutically acceptable carrier" also includes agents for preparation of aqueous dispersions and sterile powders for injection or dispersions. Examples of pharmaceutically acceptable carriers and excipients are discussed, e.g., in *Remington Pharmaceutical Science,* 16th Ed. Certain exemplary techniques and compositions for making dosage forms are described in the following references: *Modern Pharmaceutics,* Chapters 9 and 10, Banker & Rhodes, eds. (1979); Lieberman et al., *Pharmaceutical Dosage Forms: Tablets* (1981); and Ansel, *Introduction to Pharmaceutical Dosage Forms,* 2nd Ed., (1976). The carrier, vehicle, or diluent may be suitable for topical application. In some embodiments, the carrier comprises water. In some embodiments, the carrier comprises an alcohol such as methanol or ethanol.

In certain embodiments, compositions are formulated for injection. In certain embodiments, compositions are formulated for topical administration. For compositions suitable for topical administration, the composition may be combined with one or more carriers and used in the form of cosmetic formulations. Formulations may include a foam, cream, gel, lotion, ointment, or solution. For example, a TRPA1 and/or TRPV4 inhibitor may be suitably dissolved in the alcohol of skin disinfectant gel or in lotions, creams, or other formulations. In certain embodiments, a TRPA1 and/or TRPV4 inhibitor may be included in or added to a cosmetic formulation. In certain embodiments, a TRPA1 and/or TRPV4 inhibitor may be included in or added to sun protection topical formulations.

For oral therapeutic administration, the composition may be combined with one or more carriers and used in the form of ingestible tablets, buccal tablets, troches, capsules, elixirs, suspensions, syrups, wafers, chewing gums, foods, and the like. The percentage of the compositions and preparations may, of course, be varied and may conveniently be between about 0.1 to about 100% of the weight of a given unit dosage form. The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring. The above listing is merely representative and one skilled in the art could envision other binders, excipients, sweetening agents and the like. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like.

The amount of a TRPA1 and/or TRPV4 inhibitor in such therapeutically useful compositions is such that an effective dosage level will be obtained. The selected dosage level will depend upon a variety of factors including the activity of the particular compound employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

In general, the daily dose contains from about 0.1 mg to about 2000 mg of the active ingredient, or about 0.5 to about 60 mg of the active ingredient. This dosage form permits the full daily dosage to be administered in one or two oral doses. More than once daily or twice daily administrations, e.g., 3, 4, 5, or 6 administrations per day, are also contemplated herein.

In some embodiments, as noted above, administering relates to providing an amount effective at bringing about a desired in vivo effect such as inhibition of TRPA1 and/or TRPV4 in an animal, such as a human.

d. Mouse Model

In other aspects, the disclosure provides a transgenic mouse whose genome comprises deletions of the Trpv4 gene in keratinocytes of the epidermis. The transgenic mouse may be a knockout for the Trpv4 gene in keratinocytes of the epidermis following keratinocyte-specific activation and expression of a site-specific recombination enzyme. Knockout of the Trpv4 gene may be carried out by any suitable means known in the art. For example, the transgenic mouse may be generated by Keratin-14 promoter expression of a site-specific recombination enzyme. Site-specific recombination enzymes may include CRE recombinase. The site-specific recombination enzyme may be fused to a mutated estrogen receptor. An anti-estrogen may have increased affinity to the mutated estrogen receptor relative to wild-type estrogen. The anti-estrogen may comprise tamoxifen. In some embodiments, addition of the anti-estrogen to the transgenic mouse drives the site-specific recombination enzyme to the nucleus and results in knockdown of expression of the Trpv4 gene. As such, the keratinocyte-specific deletion of the Trpv4 gene may be induced by applying an anti-estrogen. In some embodiments, deletion of the Trpv4 gene can be specifically and conditionally induced in keratinocytes of the epidermis. In some embodiments, deletion of the Trpv4 gene may be achieved by expression of a constitutively active or inducible recombination enzyme in keratinocytes of the epidermis. In some embodiments, the transgenic mouse may exhibit reduced expression relative to a control of at least one of IL6, ET1, caspase1, IL1β, and CXCL5, or a combination thereof, in response to UVB exposure.

e. Methods i. Methods of Sanitizing a Subject

Provided herein are methods of sanitizing a subject, or a surface or portion of the subject. The methods may include contacting the subject with a composition comprising an inhibitor and iodine, wherein the inhibitor inhibits TRPV4, TRPA1, or a combination thereof. In some embodiments, the inhibitor does not inhibit TRPV1, TRPV2, or TRPV3. In some embodiments, the inhibitor comprises a compound according to Formula I as detailed herein. In some embodiments, the subject is contacted with the composition for a period of time sufficient to cause a reduction in the population of microorganisms on the surface. The surface of the subject, or a portion thereof, contacted with the composition may be selected from the group consisting of a skin area, a wound, sore, and ulcer. In some embodiments, the composition is applied to a medical dressing or bandage, which is then applied to the subject.

In some embodiments, the composition is administered to the subject to treat the subject's skin or wounds in order to sanitize them and reduce or remove any contaminating and possibly harmful bacteria or other microorganisms. In some embodiments, the composition disinfects the subject or a surface thereof. In some embodiments, the composition sterilizes the subject or surface thereof. In some embodiments, the composition has antibacterial activity. In some embodiments, the composition promotes healing of the skin, wound, sore, or ulcer. In some embodiments, the composition also diminishes pain, inflammation, irritation, or a combination thereof, that may be caused by or result from the iodine. In some embodiments, the inhibitor reduces or attenuates pain induced by the iodine. In some embodiments, the composition provides local inhibition of pain. In some embodiments, the composition is applied to the subject prior to a medical procedure such as surgery or an incision. In such embodiments, the composition may sanitize an area of the subject, prevent a microbial infection, reduce a microbial infection, treat a microbial infection, or a combination thereof. The composition may be administered prior to, during, or after surgery or other medical procedure.

ii. Methods of Anesthetizing a Subject

Provided herein is a method of anesthetizing a subject. The method may include administering to the subject a composition comprising an inhibitor and an anesthetic, wherein the inhibitor inhibits TRPV4, TRPA1, or a combination thereof. The methods may include co-administering an anesthetic and an inhibitor to the subject, wherein the inhibitor inhibits TRPV4, TRPA1, or a combination thereof. In some embodiments, the inhibitor does not inhibit TRPV1, TRPV2, or TRPV3. In some embodiments, the inhibitor comprises a compound according to Formula I as detailed herein. In some embodiments, the anesthetic is a local anesthetic. In some embodiments, the composition diminishes pain, inflammation, irritation, or a combination thereof, that may be caused by or result from the local anesthetic. In some embodiments, the composition provides local inhibition of pain. In some embodiments, the inhibitor reduces or attenuates pain and/or burning induced by the anesthetic. In some embodiments, the subject has acute pulpitis or an inflamed "hot" tooth. In some embodiments, the subject has a purulent infection of the skin or soft tissue. In some embodiments, the composition is administered to the acute pulpitis, inflamed "hot" tooth, or purulent infection of the skin or soft tissue of the subject. In some embodiments, the composition is applied to the subject prior to a medical procedure such as surgery or an incision. The composition may be administered prior to, during, or after surgery, oral surgery, or other dental or medical procedure.

iii. Methods of Treating a Disease or Disorder

The compositions and methods may be used to treat a variety of diseases and disorders, including dermatological disorders. Provided herein are methods of treating a disease or disorder. The methods may include administering to the subject an effective amount of a TRPV4 and/or TRPA1 inhibitor as detailed herein.

In some embodiments, the disease or disorder that may be treated by the compositions and methods disclosed herein may include pancreatitis (for example, according to a model of pancreatitis induced by caerulein), epilepsy, arthritis, osteoarthritis, multiple sclerosis, stroke, CNS autoimmune conditions, traumatic brain/spinal cord injury, brain edema, CNS infections, neuro-psychiatric disorders, skeletal degenerative-inflammatory disorders, trigeminal pain such as headaches, colitis, and sclerosis.

In other aspects, the disclosure provides methods of preventing dermatological diseases or disorders such as irritation, pain, itch, pruritus, autoimmune diseases, skin cancer (including melanoma, for example, with topical treatment of TRPA1 and/or TRPV4 inhibitor-based UV protection), autoimmune diseases, fibrotic disorders, pigmentation disorders, and others as described above. In some embodiments, the disclosure provides methods of preventing the development and/or exacerbation of Xeroderma pigmentosum, Cockayne syndrome, Bloom syndrome, Rothmund-Thomson syndrome, and Hartnup syndrome.

The dermatological disorder may be associated with the TRPA1 or TRPV4 pathway. Dermatological disorders include, but are not limited to, photo-induced inflammation, pain in diseases involving skin pain, itch, cancer, autoimmune diseases, fibrotic diseases, other acneiform or inflammatory skin diseases, and pigmentation disorders. For example, dermatological disorders may include, but are not limited to, sunburn; photoallergic reaction; phototoxic reaction; phytophotodermatitis (Berloque dermatitis); acute and chronic actinic dermatitis; atopic dermatitis exacerbation; all subtypes of rosacea including trigeminal-pain associated rosacea; all lupus erythematosus subtypes (systemic, discoid, subacute); atopic dermatitis; actinic prurigo; prurigo nodularis; prurigo subacuta; prurigo pigmentosa; Lichen simplex (also called neurodermatitis); diabetic pruritus; uremic pruritus; pruritus induced by metabolic (liver) diseases; pruritus induced by malignancies like lymphoma; pruritus induced by polycythemia vera; pruritus induced by scabies; pruritus induced by bullous pemphigoid; pruritus induced by urticaria (especially but not exclusively actinic urticaria); pruritus induced by insect/arachnoid vector bite; pruritus induced by parasitosis; melanoma; non-melanoma skin cancer (BCC, SCC); actinic keratosis and other premalignant skin cancers; mycosis fungoides; Sézary syndrome; Xeroderma pigmentosum; Cockayne syndrome; all lupus erythematosus subtypes (systemic, discoid, subacute); dermatomyositis; erythema multiforme; lichen planus; fibrotic diseases induced by UV-exposure (Rhinophyma, chronic actinic dermatitis, actinic reticuloid, photoaging, hyalinosis cutis et mucosae; polymorph light eruption; Acne aestivalis; all porphyria subforms with implications on photo-induced skin changes (erythropoetic porphyria, erythropoetic protoporphyria, Porphyria variegate); photo-induced Herpes simplex infection (Herpes labialis); morbus Darier; disseminated superficial actinic porokeratosis; pityriasis rubra pilaris; Bloom syndrome; Rothmund-Thomson syndrome; Hartnup syndrome photoaging; wrinkles; photo-induced inflammation; pigmentation; and pigmentation disorders.

In some embodiments, the disclosure provides a method of treating a subject wherein the method comprises administering an inhibitor of TRPA1 and/or TRPV4 in a pharmaceutically acceptable composition.

iv. Methods of Reducing Skin Inflammation

In an aspect, the disclosure provides methods of reducing skin inflammation in a subject in need thereof. The methods may comprise administering to the subject an effective amount of a TRPA1 and/or TRPV4 inhibitor. The skin inflammation may be related to UVB exposure.

Skin inflammation may be associated with conditions including, but not limited to, sunburn (acute photodermatitis), photoallergic reaction, phototoxic reaction, phytophotodermatitis (Berloque dermatitis), acute and chronic actinic dermatitis, atopic dermatitis exacerbation, and rosacea.

v. Pain Management

In other aspects, the disclosure provides methods of pain management. The methods may comprise administering to at least a portion of the skin of a subject in need thereof an effective amount of a TRPA1 and/or TRPV4 inhibitor. The pain may be related to UVB exposure.

Pain may be chronic or acute. Pain may be associated with or result from conditions including, but not limited to, all subtypes of rosacea including trigeminal-pain associated rosacea, reflex sympathetic dystrophy (RSD), and all lupus erythematosus subtypes (systemic, discoid, subacute).

vi. Methods of Reducing Itch

In other aspects, the disclosure provides methods of reducing itch in a subject in need thereof. ET-1 has been shown to elicit itch, and as shown in the Examples, increased expression of ET-1 was TRPV4-dependent. The methods may comprise administering to the subject an effective amount of a TRPA1 and/or TRPV4 inhibitor.

Itch may be chronic or acute. Itch may be associated with or result from conditions including, but not limited to, rosacea, atopic dermatitis, actinic prurigo, prurigo nodularis, prurigo subacuta, prurigo pigmentosa, Lichen simplex (also called neurodermatitis), diabetic pruritus, and uremic pruritus. Itch or pruritus may be associated with or result from conditions including metabolic (liver) diseases, malignancies like lymphoma, polycythemia vera, scabies, bullous pemphigoid, urticaria (especially but not exclusively actinic urticaria), insect/arachnoid vector bite, and parasitosis.

vii. Method of Treating Cancer

In other aspects, the disclosure provides methods of treating cancer in a subject in need thereof. The methods may comprise administering to the subject an effective amount of a TRPA1 and/or TRPV4 inhibitor.

The cancer and related conditions may include, but are not limited to, melanoma, non-melanoma skin cancer (BCC, SCC), actinic keratosis and other premalignant skin cancers, mycosis fungoides, Sézary syndrome, and Xeroderma pigmentosum.

viii. Methods of Treating an Autoimmune Disease

In other aspects, the disclosure provides methods of treating an autoimmune disease in a subject in need thereof. The methods may comprise administering to the subject an effective amount of a TRPA1 and/or TRPV4 inhibitor.

Autoimmune diseases may include, but are not limited to, all lupus erythematosus subtypes (systemic, discoid, subacute), dermatomyositis, erythema multiforme, and lichen planus.

ix. Methods of Treating a Fibrotic Disease

In other aspects, the disclosure provides methods of treating a fibrotic disease in a subject in need thereof. The methods may comprise administering to the subject an effective amount of a TRPA1 and/or TRPV4 inhibitor.

Fibrotic diseases may include conditions induced by UV-exposure, such as, for example, Rhinophyma, chronic actinic dermatitis, actinic reticuloid, photoaging, and hyalinosis cutis et mucosae.

x. Methods of Treating Other Acneiform or Inflammatory Skin Disease

In other aspects, the disclosure provides methods of treating other acneiform or inflammatory skin disease in a subject in need thereof. The methods may comprise administering to the subject an effective amount of a TRPA1 and/or TRPV4 inhibitor.

Acneiform or inflammatory skin diseases may include, but are not limited to, polymorph light eruption, Acne aestivalis, photo-induced Herpes simplex infection (Herpes labialis), morbus Darier, disseminated superficial actinic porokeratosis, Pityriasis rubra pilaris, and all porphyria subforms with implications on photo-induced skin changes such as, for example, erythropoetic porphyria, erythropoetic protoporphyria, and Porphyria variegate.

xi. Methods of Reducing Skin Pigmentation

In other aspects, the disclosure provides methods of reducing skin pigmentation in a subject in need thereof. ET-1 has been shown to signal to skin melanocytes and function as a major melanogen (=enhancing skin pigmentation), and as shown in the Examples, increased expression of ET-1 was TRPV4-dependent. The methods may comprise administering to the subject an effective amount of a TRPA1 and/or TRPV4 inhibitor.

Skin inflammation, pain, itch, and/or pigmentation may also be associated with disorders including, but not limited to, Cockayne syndrome, non-UV skin burn less than $3^{rd}$ degree, disturbed wound healing, exposure and pathological response to poison ivy, and pain of bone fractures directly adjacent to the skin such as fractures of the tibia, digits, or skull. For example, one or more of these disorders may be symptomatic of reflex sympathetic dystrophy (RSD).

xii. Methods of Treating or Preventing Cosmetic Conditions

In other aspects, the disclosure provides methods of treating or preventing cosmetic conditions. For example, the disclosure provides methods of treating or preventing photoaging, wrinkles, photo-induced inflammation, pigmentation, and pigmentation disorders. The methods may comprise administering to the subject an effective amount of a TRPA1 and/or TRPV4 inhibitor.

xiii. Methods for Identifying a Selective Inhibitor of TRPA1 and/or TRPV4

In a further aspect, the disclosure provides methods for identifying a selective inhibitor of TRPA1 and/or TRPV4. The methods may include (a) contacting a mouse with a test compound; (b) determining a biological activity of TRPA1 and/or TRPV4 after contacting with the test compound; and (c) determining a control level of biological activity of TRPA1 and/or TRPV4 in the absence of the test compound; (d) comparing the biological activity of TRPA1 and/or TRPV4 from step (b) with the biological activity of TRPA1 and/or TRPV4 from a model of TRPV4 deletion, wherein the model of TRPV4 deletion includes the transgenic mouse as disclosed herein or a pan-null Trpv4−/− mouse; and (e) identifying the test compound as a selective inhibitor of TRPA1 and/or TRPV4 when at least one of (i) the TRPA1 and/or TRPV4 biological activity is lower in the presence of the test compound than the TRPA1 and/or TRPV4 biological activity in the absence of the test compound; (ii) the TRPA1 and/or TRPV4 biological activity in the presence of the test compound is about the same as, or lower than, the TRPA1 and/or TRPV4 biological activity in the model of TRPV4 deletion; or (iii) any combination of (i) and (ii).

3. EXAMPLES

Example 1: Materials and Methods

Animals. The Trpv4 genomic locus was engineered so that loxP sites surrounded exon13 which encodes TM5-6. This mutation was propagated in mice which were crossed to K14-CRE-ERtam mice, so that ((Trpv4lox/lox)×(K14-CRE-ERtam))-mice could be induced by tamoxifen administration via oral gavage for 5 consecutive days at 6 mg/day in 0.3 mL cornoil, at age 2-4 months of age, plus a one-time booster two weeks after the last application. Male and female mice were induced equally. Efficiency of knockdown was verified by qRT-PCR for Trpv4 using primers sense 5'-CCTGCTGGTCACCTACATCA (SEQ ID NO: 1) and antisense 5'-CTCAGGAACACAGGGAAGGA (SEQ ID NO: 2), with the former primer located in exon 13. All animal experimentation described here was conducted in full compliance with NIH and Duke University internal guidelines, and under a valid IACUC protocol.

Using the same genomic clone that was used for generating the Trpv4−/− pan-null mouse, the Trpv4 targeting construct was electroporated into mouse ES cells (C57BL6 background), and orthotopic integration was verified by PCR and Southern blot. The engineered mutation was introduced into the germline by mating of chimeric mice with C57BL6 WT mice. The selection marker was deleted by FLPemediated excision of the frt-pGK-neo-frt cassette in FLPe deleter mice. Genotyping was accomplished by PCR and subsequent PacI digest (FIG. 1B).

8-12 week old mice were used throughout the experiments. Trpv4−/− mice[3] have been outcrossed to WT (C57BL/6J) background and genotyped by PCR[3,15]. Animals were housed in climate-controlled rooms on a 12/12 h light/dark cycle with water and standardized rodent diet that was available ad libitum. All experiments were conducted in compliance and accordance with the guidelines of the NIH and the Institutional Animals' Care and Use Committee (IACUC) of Duke University, and under a valid IACUC protocol of the Duke University IACUC. All animal methods described in this publication were approved by the Duke University IACUC.

Behavioral Assessment of Withdrawal Thresholds.

Behavioral tests were performed to evaluate the decrease in withdrawal thresholds in response to mechanical von Frey hair or thermal stimuli applied to hind paws. Tests were conducted. These withdrawal thresholds were ascertained before and after UV exposure. Mice were exposed using a Bio Rad Gel Doc 2000 UV transilluminator (302 nm) for 5 minutes with an exposure of 600 mJ/cm$^2$, 3-5 days after the last application of tamoxifen/oil.

Paw Interstitial Fluid Analysis.

48 hours after UV exposure, each animal received an intraplantar injection of 10 µL PBS directly posteuthanasia. The interstitial fluid was immediately collected and analyzed by ELISA (Biorad) for presence of IL-1l1.

In-Vivo Topical Interventions.

ET1 injections: After determining base-line withdrawal thresholds, each animal received an intraplantar injection of 10 µL 100 nM ET-1 plus contralateral vehicle. Thresholds were again evaluated 1 hour after injection.

GSK205 topical treatment: A viscous solution of 68% EtOH/5% glycerol plus 1 mM or 5 mM GSK205 (none for control) was applied to hindpaws by rubbing in 20 µL, applied at time-points 1 hour and again 10 min before UV exposure.

Formalin-induced nocifensive behavior: 4% formalin was injected into the right hindpaw. Mice were then videotaped for 50 mins and behavior analyzed by blinded observers.

Mouse Tissue Processing for 1 µm Semithin Sections and EM.

Samples were processed and subjected to EM.

Mouse and Human Tissue Processing for Immunohistochemistry.

Routine procedures were followed, and human tissue was processed under institutional review-board approval (UCSF).

Primary Mouse Keratinocyte Cell Culture.

Primary mouse keratinocytes were derived from back skin of newborn mice.

Analysis of IL-1β Secreted by Cultured Keratinocytes after UV Exposure.

Before UV irradiation, culture media was replaced with PBS. The cells were then irradiated at a dose of 50 mJ/cm$^2$ with UVB. 24 hours later, supernatants were assayed using IL-1β ELISA (R&D Systems, Minneapolis, Minn.).

Ca++ Imaging of Cultured Keratinocytes.

Ca++ imaging of 1° MK was conducted following routine procedures. For UVB stimulation, a customized device was built. The system comprised a printed circuit board for electrical interconnects and mechanical support and an ultraviolet light-emitting diode (UV LED). Customized provisions at the cellular end included a quartz coverslip as the bottom of the cell culture dish plus a thermal equilibration stage (HW-101 Dagan Corporation), fitted to an Olympus BX61 upright microscope. The UV LED was a III-nitride-based type (UVTOP-295 BL; Sensor Electronic Technology).

Figure 2A:
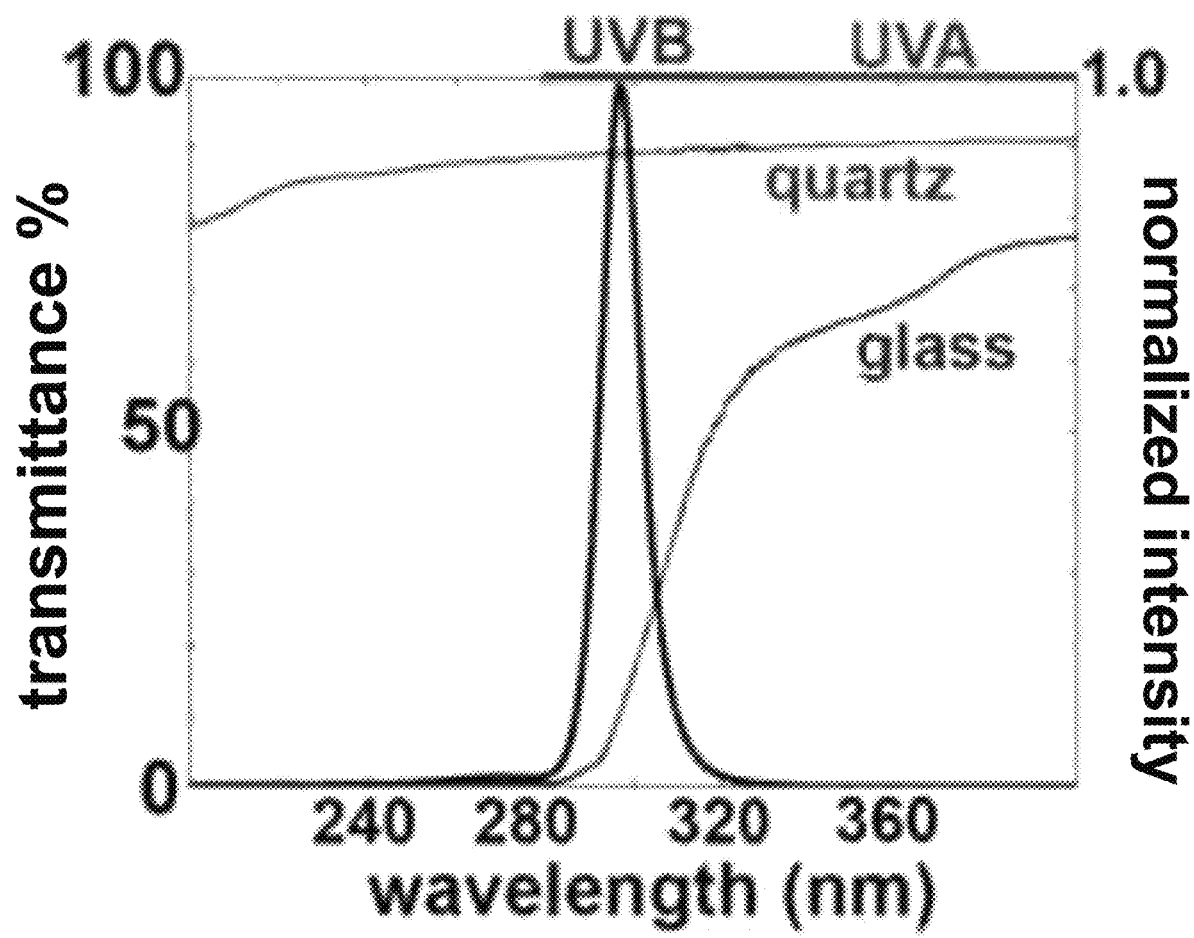
FIGS. 2A-2G: UVB stimulation device and UVB keratinocyte control experiments.
Figure 2B:
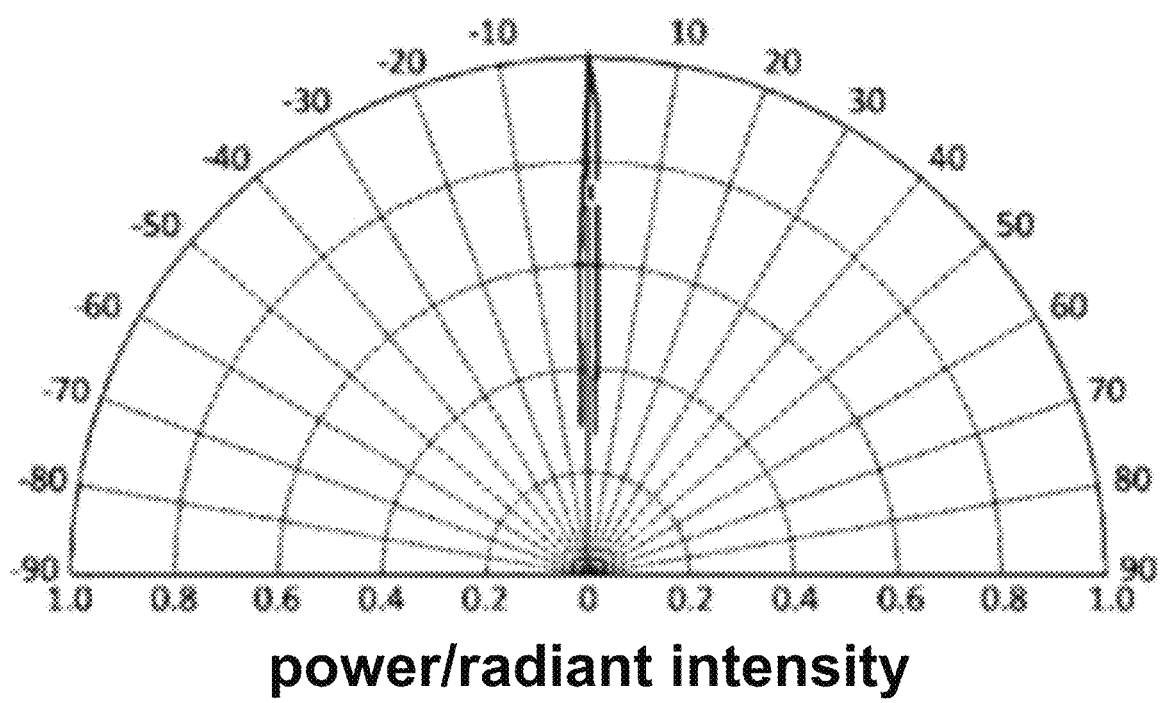
Figure 2C:
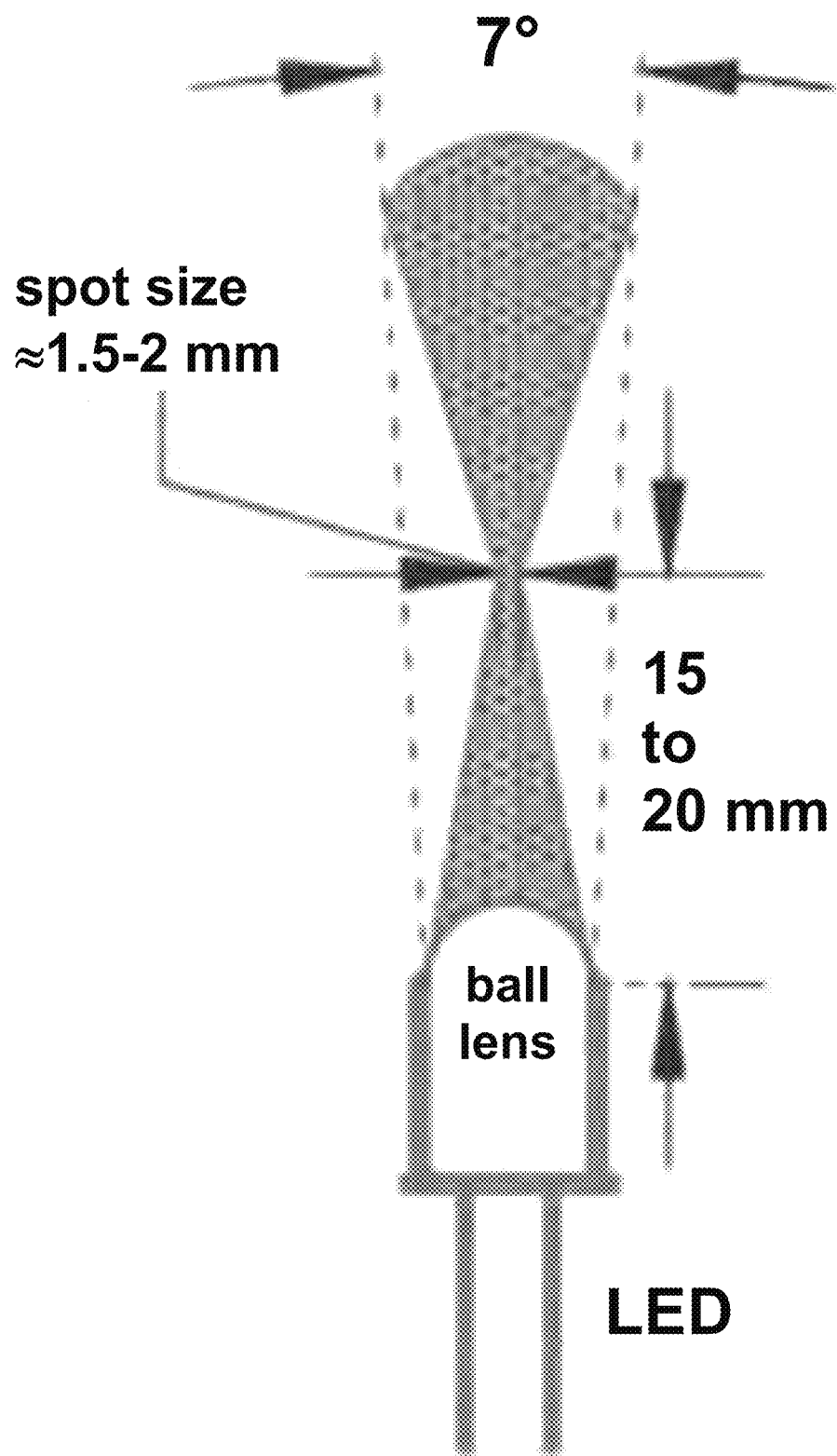

The operating wavelength was 295 nm (FIG. 2A), with a full-width half-max of 12 nm. The optical power was 500 mW. The focal point was aimed at the plane of the upper surface of the quartz coverslip, which was used to minimize UV absorption along the optical path towards the cells (FIG. 2A-C). The optical intensity at the focal point was estimated to be 150 mW/mm$^2$.

Keratinocyte UV Irradiation Using 295 nm LED and Immunocytochemistry.

1° MK were exposed to UVB using the UV optical system (295 nm LED). 24 hours later the cells were fixed and fluorescently immunolabeled for ET1. Digital images were captured and subjected to morphometry.

Statistical Analysis.

Data are expressed as mean±SEM. Numeric signals or values were averaged for their respective groups, and the statistical mean+/−standard error of the mean were compared between groups by using a fixed-effect one-way ANOVA and post-hoc Scheffe test, or Student's t-test, or two-tail t-tests, or one-way ANOVA followed by Tukey post-hoc test at a significance level of $p<0.05$.

Chemicals/Biological.

The following biologicals and compounds were used: Endothelin1; BQ123 and BQ788 (ET(R) blockers for ET(R)-A and ET(R)-B; Sigma, St. Louis, Mo.), U73122 (PLC inhibitor; Tocris, Ellisville, Mo.), 4α-phorbol 12,13 didecanoate (4α-PDD; TRPV4 activator; Tocris), GSK205 (TRPV4 inhibitor (Li et al., 2011; Phan et al., 2009; Vincent and Duncton, 2011)), RN-1734 (TRPV4 inhibitor; Tocris), CGS35066 (endothelin-converting enzyme inhibitor, Tocris), isopentenyl pyrophosphate, IPP (TRPV3 inhibitor; Sigma); and Camphor (TRPV3 activator; Whole Foods).

Behavioral Assessment of Withdrawal Thresholds and Nocifensive Behavior.

Behavioral tests were performed to evaluate the decrease in withdrawal thresholds in response to mechanical or thermal stimuli applied to hind paws. These withdrawal thresholds were ascertained before and after UVB exposure.

Mice were confined by plexi-glass enclosures on top of 25×26 cm Bio Rad Gel Doc 2000 UV transilluminator (302 nm), and otherwise allowed to openly explore this environment. UV-exposure lasted for 5 minutes with an exposure of 600 mJ/cm². Careful observations upon initiation of this method demonstrated that hindpaws were exposed to UV throughout this period.

Automated Von Frey Hair Testing.

Hindpaw mechanical withdrawal thresholds were determined by the automated von Frey hair method, using a 0.5 mm diameter stainless steel filament, part of an automated plantar touch stimulator (Ugo Basile, Modena, Italy). Relevant detail included pre-test acclimatization in a quiet room for 30 min, conducting the test at the same time of day and blinded observers. The stimulus was delivered to the hindpaw, automatically discontinued upon withdrawal, and its intensity recorded automatically. 6-8 trials per animal were conducted, with equal exposure of both hindpaws, leading to an average withdrawal threshold. Results are reported as Δ-threshold, which was calculated by subtracting post-treatment from pre-treatment measurements, expressed as % or relative to 1.0.

Hargreaves' Test.

Hindpaw thermal (hot) withdrawal thresholds were determined by the well-established Hargreaves' method, using an infra-red thermal stimulation device that delivers the stimulus from underneath the hindpaw combined with automatic shut-off upon withdrawal (Ugo Basile). Stimulation and measurements were conducted as described for von Frey hair testing. A cutoff of 20 sec was set to prevent tissue damage.

Formalin-Induced Nocifensive Behavior.

Videos were read by blinded observers for the total amount of time each mouse spent flinching or licking the injected hindpaw.

Mouse Tissue Processing for 1 μm Semithin Sections and Electron Microscopy.

Samples were fixed in 2% glutaraldehyde, 4% PFA, and 2 mM $CaCl_2$ in 0.05 M sodium cacodylate buffer, pH 7.2, at room temperature for >1 h, dehydrated, postfixed in 1% osmium tetroxide, and processed for Epon embedding. Semi-thin sections (1 μm) were stained with toluidine blue and photographed with an Axioplan 2 microscope (Zeiss). For EM analysis, ultrathin sections (60-70 nm) were counterstained with uranyl acetate and lead citrate. EM images were taken with a transmission electron microscope (Tecnai G2-12; FEI) equipped with a digital camera (model XR60; Advanced Microscopy Techniques, Corp.).

Mouse Tissue Processing for Immunohistochemistry.

Routine procedures were followed as described previously (Chen et al., 2009). Mice were perfused transcardially with 30 mL PBS, followed by 30 mL 4% paraformaldehyde. Tissues, including the L5 DRGs (bilateral), and footpad preparations, were dissected and post-fixed in 4% paraformaldehyde. Tissue blocks were further cryoprotected in 30% sucrose in PBS for 24-48 hours. For mouse TRPV4, keratin-specific antibodies, phospho-ERK, IL-6, IL-1β, CXCL5 and caspase-1, tissue was prepared as frozen blocks and subsequently sectioned on a cryostat. For CD68, CD15 (neutrophil elastase) and CD3, mouse skin was prepared by 2% PFA perfusion. Footpad and DRG sections (both at 6-10 μm) were thaw-mounted, blocked with 5% normal goat serum (NGS; Jackson), then incubated overnight at 4° C. with the following primary antibodies: rabbit anti-TRPV4 (1:300; Abcam), mouse anti-keratin 14 (1:300; Abcam against C-terminal peptide beyond residue 850); rabbit anti-keratin 14 (1:1000; Fuchs-Lab), rabbit anti-phosph-ERK1/2 (1:500; Cell signaling technologies), goat anti-IL-1β (1:800; Abcam), goat anti-IL-6 (1:200; Santa Cruz Biotechnology Inc); rabbit anti-caspase-1 (1:200; Biovision Research Products, CA); goat anti-mouse LIX/CXCL5 (1:200; R&D Systems Inc), anti-CD68, anti-CD25, and anti-CD3 (AbDSerotec). Immunodetection was accomplished with appropriate fluorescently-labeled secondary antibodies (AlexaFluor595, AlexaFluor488-conjugated antibodies at 1:600; Invitrogen; for CD15 biotinylated secondary antibody from donkey, 1:400 followed by rhodamine-streptavidine 1:250), or with peroxidase-linked detection reagents (for CD68) for 2 hours at room-temperature. Sections were rinsed, mounted, and cover-slipped with fluoromount (Sigma). Digital micrographs were obtained using a BX61 Olympus upright microscope, also with a Zeiss LSM510 confocal, both equipped with high-res CCD camera, and acquired with constant exposure settings, using ISEE or Zeiss Zen software. Morphometric analysis was conducted using ImageJ freeware (v1.45) with tailored regions-of-interest that spared the nuclear compartment. ImageJ was also used for determination of DRG surface area.

Human Tissue Specimens Immunolabeling.

Human tissue was deparaffinized with xylene and ethanol series, then washed in PBS, and incubated at 80° C. for 20 min in Antigen Retrieval buffer (Biogenex). Subsequently, specimens were washed in PBS. Endogenous peroxidase was blocked with 0.3% $H_2O_2$+0.01% sodium azide in PBS for 10 min at room temperature, followed by washing steps in PBS. Blocking was performed in 5% normal horse serum+0.3% Triton-X-100 in PBS for 1 hour at room temperature. Primary antibodies (anti-TRPV4, Abcam, same as for mouse, 1:8,000; anti-ET1; anti-IL-1b as for mouse tissue) were incubated overnight at 4° C. in Ventana Antibody dilution buffer (Fisher). After washing in PBS, specimens were incubated with biotinylated donkey-anti-rabbit secondary (Vector, BA-1000), in diluted blocking buffer for 30 min. After washing with PBS, Avidin Biotin block was applied (Vector, PK4000) for 30 min at room temperature, and the positive immunoreactivity was visualized with DAB (Fisher, NC 9567138). After washing in water, hematoxylin was used to counterstain nuclei. Tissues were washed, dehydrated, and then mounted in Permount (Fisher). For morphometric quantificaton of TRPV4, IL-1β, and ET1, five sections from each patient and healthy volunteers (n=3/group) were examined at a magnification of ×20 and photographed. The entire section was digitalized using Leica software, and analyzed using ImageJ. For quantification, DAB and HE staining in 3 randomly selected epidermal regions (3.5×1.25 inches) of each image were separated using the IsoData thresholding method in the Color Threshold Plugin. Relative signal intensities were calculated from background-corrected measurements. Values are expressed as mean of averages determined from five sections per patient. Quantification of human skin tissue for TRPV4, ET1, and IL-1β was performed from acute photodermatitis as compared to healthy skin (n=3 per group). Quantification of various subforms of chronic photodermatitis as compared to acute photodermatitis and healthy skin is currently under active study. More final results await availability and proper staining of at least 3 cases per subgroup of human chronic photodermatitis.

Primary Mouse Keratinocyte Cell Culture.

The epidermis was separated from the dermis by a 1-hour dispase (BD Biosciences) treatment. Then the keratinocytes were dissociated from the epidermis using trypsin. Keratinocytes were plated on collagen coated dishes or glass or quartz coverslips and grown in keratinocyte serum free media (Gibco) supplemented with bovine pituitary extract and epidermal growth factor (EGF) (R&D Systems), 100 pmol cholera toxin (Calbiochem, San Diego, Calif., USA) and 1× antibiotics/antimycotics (Gibco), in an incubator at 5% $CO_2$ and 37° C.

UVB-Stimulation of Cultured Keratinocytes; Calcium Imaging.

Figure 2D:
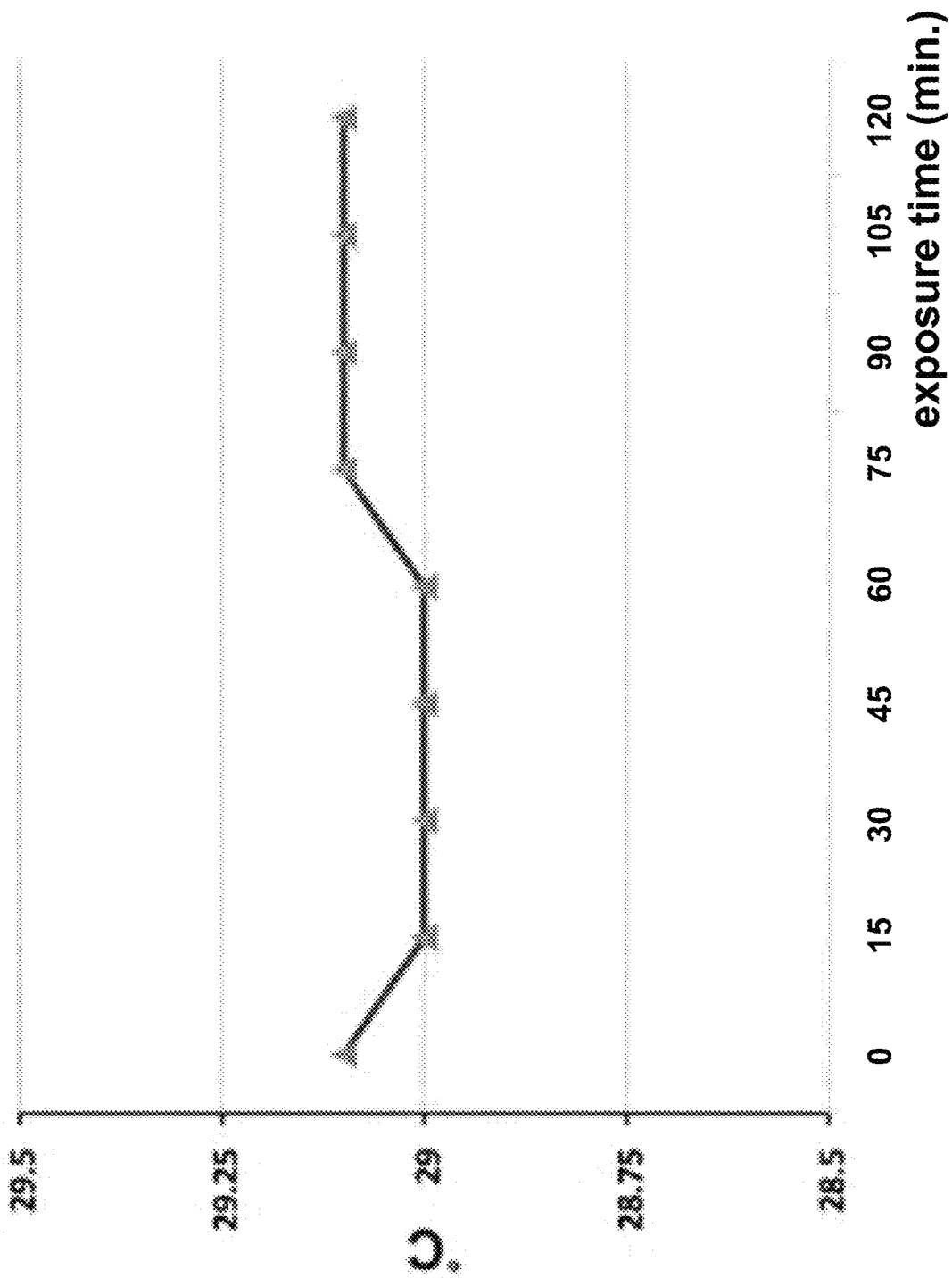

Ca++ imaging of mouse 1° MK in response to chemical activation of TRPV4 was conducted after loading with 2 µM fura2-AM, following a ratiometric Ca2+ imaging protocol with 340/380 nm blue light for dual excitation. Ratios of emissions were acquired at 0.5 Hz. ΔR/R0 was determined as the fraction of the increase of a given ratio over baseline ratio, divided by baseline ratio. For stimulation of cells with UVB, where fura-2 was not suitable because of the proximity of stimulation with 340/380 nm and 295 nm, 2 µM fluo4-AM was used instead. Ca++ imaging was carried out at 488 nm excitation, acquisition of emissions at 0.5 Hz, expressed as ΔF/F0. In the custom-built UV optical system, UV LEDs were capped with a ball lens, a transparent optical window in the shape of a hemispherical lens (FIG. 2B). The LED output optical beam focused at 15-20 mm from the lens, with a spot diameter of approximately 1.5-2.0 mm (FIG. 2C). The electrical power supply for the UV LEDs was a surface mount component on the printed circuit board, which had a steady state 20 mA current output that was controlled by an external switch. The thermal equilibration stage was set for physiological temperature. We confirmed the non-thermal nature of UVB stimulation using the customized 295 nm LED device in a dedicated experiment (FIG. 2D), thus confirming the specific modality of stimulation as UVB.

Keratinocyte UV Irradiation Using 295 nm LED and Immunocytochemistry.

Mouse keratinocytes were cultured on collagen coated quartz coverslips and then stimulated from the bottom using the previously mentioned UV optical system using the 295 nm LED. 24 hours later the cells were fixed in 4% formaldehyde in PBS for 20 minutes, permeabilized with 0.1% Triton X-100 in PBS for 10 minutes, washed, then blocked in 10% normal goat serum in PBS for 45 minutes. Coverslips were incubated overnight with primary antibody mouse anti-ET1 (1:200; Abcam), washed three times in PBS and incubated with secondary antibody for 2 hours at 25° C. Coverslips were washed three times in PBS, once with double-distilled $H_2O$. Digital images were captured using a 40× immersion lens on the BX61 Olympus upright microscope. Morphometric analysis was conducted using ImageJ freeware with tailored regions-of-interest.

Determining UVB Permeation of the Skin.

Figure 16A:
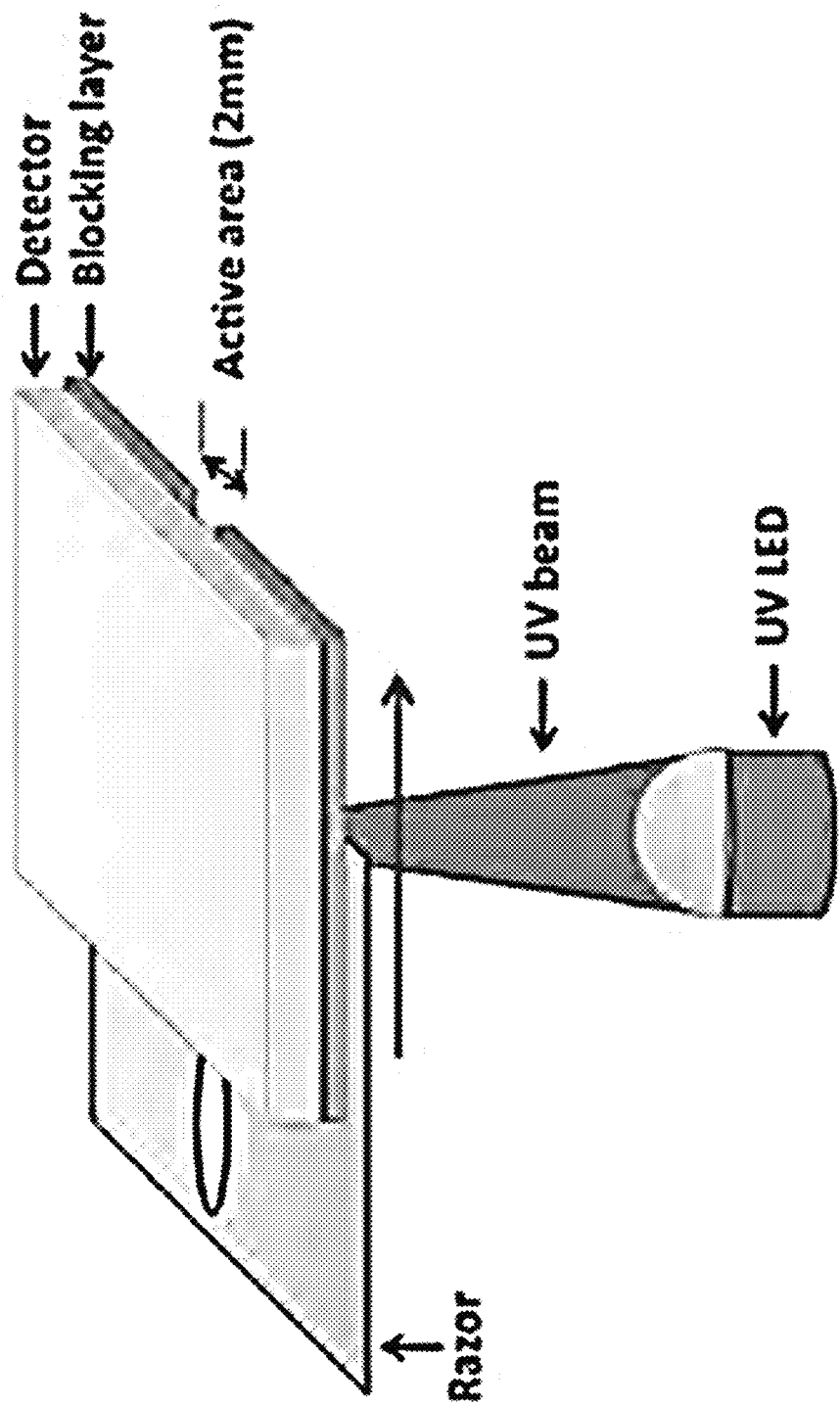
FIGS. 16A-16B: Skin UVB permeability testing.
Figure 16B:
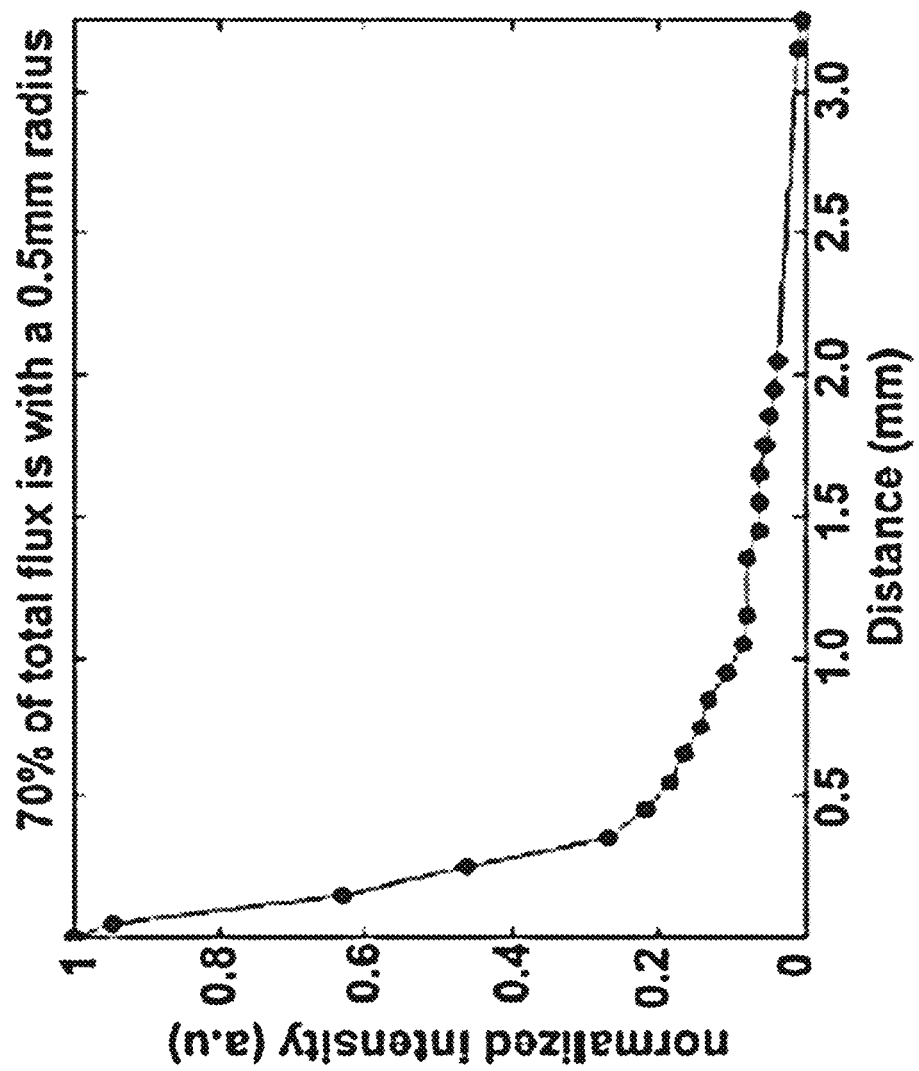

First, the spot size of the UV input optical beam from a LED (UVTOP-295 UV) was estimated, as shown in FIG. 16A, using the razor-edge optical spot occlusion method (results shown in FIG. 16B). The UV LED was powered with 20 mA of current, resulting in 500 µW of optical power in a circular focal spot 1.5 mm in diameter, with 70% of the total flux in a 0.5 mm beam radius. The UV optical power transmitted through the sample was detected by a Hamamatsu S127-66BR UV detector, and the output of the photodetector was measured using a Keithley 236 source measure unit. Next, the foot-pad epidermis of a mouse was measured for UV transmission by placing it on a quartz coverslip and exposure to the UV beam. The GSK205 was administered to the foot-pad skin in an alcohol and glycerol solution as for the experiments shown in FIG. 12A. The vehicle-control group was treated with the alcohol and glycerol solution only. Another control group consisted of a commercially-available SPF100 preparation sunscreen in form of a cream, which was applied similar to the vehicle-control. The data for the GSK205 and sunscreen was normalized to this control data.

Western Blotting.

Samples were separated by SDS-PAGE, and transferred to PVDF membranes (Bio-Rad). Membranes were blocked with dry milk, then probed with primary antibodies (rabbit anti-TRPV4 (immunogen=final C-terminal epitope of TRPV4 as for immunolabeling), Alomone; anti-caspase-1, Biovision; mouse anti-β-actin, (clone AC-5) Abcam; mouse anti-β-tubulin, Iowa Hybridoma bank), followed by horseradishperoxidase-conjugated secondary antibodies (Jackson Immunoresearch). Secondary antibodies were detected using Supersignal West Dura Extended Duration substrate (Amersham).

Acute Pancreatitis Mouse Model.

C57BL/6J male mice 8-10 weeks of age were subjected to acute pan-creatitis by intraperitoneal injections of supramaximal doses of caerulein (50 µg/kg) every hour for a total of 6 h, as previously described in[61]. Control animals received 25% DMSO-saline solution by intraperitoneal injection every hour for 6 h. Compound 16-8 was dissolved in this vehicle (10 mg/kg) and injected i.p. 30 min prior to the first injection of caerulein. Animals were sacrificed 1 h after the last injection. Blood was collected and pancreatic tissue was promptly isolated, weighed for determination of pancreas wet weight/body weight ratio. Samples of tis-sues were fixed overnight in 10% neutral-buffered formalin, paraffin embedded and H&E-stained, or pancreatic tissue was quickly frozen and assessed for myeloperoxidase (MPO) activity. Serum amylase, MPO and histologic evaluation were conducted as described previously[61].

Assessment of nocifensive behavior[8]: Mice were housed in individual cages and video-recorded during the entire experiment. Two mice at a time were observed. Linear movement was measured as one event when mice passed through the median plane of the cage. Analysis began immediately after the first caerulein/vehicle injec-tion and continued until the end of the experiment. Results were expressed as the sum of the movement events spanning the 6 h time-period following the first injection.

Cell Cultures.

N2a cells were used for directed expression of TRP ion channels as described previously[13]. TRPV4-eGFP from rat was used, previously found to respond to stimulation with GSK101 and hypotonicity in similar manner as native, non-fused TRPV4. All other channels were native channels from mouse, eGFP was co-transfected. Stimulation of overexpressed TRPV4 was conducted with GSK101 (5 nM), TRPV1 with capsaicin (10 µM), TRPV2 with hypotonicity (270 mosmol/L), TRPV3 with camphor (100 µM) and TRPA1 with mustard oil (100 µM). eGFP control-transfected N2a cells did not respond to these stimuli. Ca++ imaging was performed as described previously[13,14,34].

To visualize dose-response relationships, Hill plots were conducted using the Igor Pro software program, which derived the plots based on the following equation:

$$y = \text{Base} + (\text{Max} = \text{Base}) \Big/ \left\{ 1 + \left[\frac{x \text{ half}}{x}\right]^{rate} \right\}$$

Primary porcine chondrocytes derived from femoral condyles of skeletally mature pigs were cultured and subjected to Ca++ imaging as described previously[19,32,62,63].

Astrocyte cultures were conducted following established protocols[64-66]. Astrocytes were prepared from Sprague Dawley rat embryos (E18). Briefly, the isolated cortices were minced, and then incubated with trypsin and DNase. Dissociated cells were suspended in Dulbeccco's Modified Eagle's Medium (DMEM) supplemented with 10% fetal calf serum and penicillin/streptomycin (100 U/ml and 100 µg/ml, respectively). Thereafter, cell sus-pensions were plated in 75 cm$^2$ tissue culture flasks ($10 \times 10^6$ cells/flask) which were pre-coated with poly-L-lysine (10 µg/ml). The cells were maintained in a 10%002 incubator at 37° C. After 10-12 days, the media was removed and adherent cells were trypsinized (0.25%) and plated out onto coverslips for subsequent Ca++ imaging[34,67]. >95% of the cells were found to express astrocyte marker, glial fibrillary acidic protein (GFAP)[68].

Cell Viability in Culture.

N2a cells were cultured in 96 well plates for 24-48 h. Cell viability studies relied on metabolic capability monitored with the indicator dye resazurin. Its reduction to resorufin (indicated by color change dark blue to pink) was monitored over time. Changes in absorbance at $\lambda$=570 nm were recorded using a microplate reader (Molecular Devices). Metabolically active and viable cells shared the ability to reduce resazurin to resorufin whereas dead cells did not. Eight replicate cultures per experimental point were studied.

Assessment of Hepatic, Renal and Cardiac Function in Mice Treated with 16- . . . Compounds.

Mice were treated i.p. with compounds 16-8 and 16-19 (10 mg/kg). Hepatic and renal integrity were analyzed by alanine amino-transferase- and creatinine assays (Sigma), both relying on measurement of absorbance at $\lambda$=570 nm in 96-well micro-titerplates. 8 technical replicates per animal were performed.

For heart rate assessment in mice treated with 16-8 and 16-19, animals were fitted with two electrodes, one to the ear, via clip, one to the rib-cage, using firm adhesive. Heart rate was monitored and analyzed using axoscope and clampfit 9.2 software (Molecular Devices)

Liquid Chromatography—Tandem Mass Spectrometry (LC-MS/MS).

Mice were treated with 10 mg/kg i.p. of the respective inhibitor. Post-euthanasia harvested tissue was frozen in liquid nitrogen and stored at –80° C. for further analysis.

Frozen tissue samples were partially thawed and cut into 1 mm slices, 5-15 mg tissue, 2-fold excess water (mass/vol.), 6-fold excess acetonitrile (16- . . . compounds) or methanol (GSK205) containing appropriate amount of internal standard, and 2.5 mm zirconia/silica bead (Biospec Products Inc.) were added to 500-µL polypropyl-ene (PP) conical tube, homogenized in a Fast-Prep apparatus (Thermo-Savant) at speed "4" for 20 sec at room temp, and centrifuged at 13,600 g for 5 min at room temp. Depending on the expected concentration range of the measured compound, the supernatant was diluted 1/4-1/20 (in Mobile phase A, see below) and placed in autosampler for LC-MS/MS analysis.

The LC-MS/MS assay for 16- . . . compounds and GSK205 was developed on an Agilent 1200 series LC system interfaced with Applied Biosystems API 5500QTrap, a hybrid triple quadruple-linear trap MS/MS spectrometer. Analyst (version 1.6.1) software was used for mass parameters tuning, data acquisition, and quantification. LC column: 3×4 mm RP C18 (Phenomenex, AJ0-4287) was operated at 35° C. Mobile phase A: 0.1% formic acid, 2% acetonitrile, in LC/MS-grade water; mobile phase B: acetonitrile; flow rate: 1 mL/min, 1:1 MS/MS:waste split. Run time was 4 min. Diverter valve was used to send flow to MS/MS only between 1.2 and 2.5 min. The elution gradi-ent was: 0-0.5 min, 1% B; 0.5-1.2 min, 1-95% B; 1.2-1.5 min, 95% B; 1.5-1.6 min, 95-1% B. Autosampler was oper-ated at 4° C.; injection volume was kept at 10-50 µL. Electrospray ionization (ESI) source parameters were: positive ionization mode, curtain gas flow=30, ionization potential=5500 V, temperature=500° C., nebulizing gas 1 flow=30, nebulizing gas 2=30, declustering potential=20 V. 16- . . . compounds and GSK205 were individually infused as 100 nM solutions in 50% A/50% B at 10 µL/min flow rate and parameters optimized to provide maximal ion count for "parent" and collision-produced ("daughter") MS/MS ions. Parent/daughter quantifier [qualifier] ions utilized: GSK205 (401.1/280[370]), 16-8 (400.1/279.1[91.1], 16-16 (387.1/280[105]), 16-18 (415.2/280[370], 16-19 (414.1/279.2 [91.1]. Standard (analyte of interest)/internal standard pairs utilized: GSK205/16-16, 16-8/16-16, 16-18/GSK205, 16-19/16-8.

Calibration samples (n=6) were prepared by adding pure standard of the measured compound to tissue homogenate (tissue+2-fold excess water, mass/vol) in the appropriate range needed for the particular dosing regime. Organs studied were analyzed alongside the study samples. The following are typical ranges used (the lower value repre-senting also the LLOQ at 80% accuracy limit, all other calibrator levels at 85% accuracy limit): 0.38-6 nM (plasma), 6-100 nM (skin), 6-48 nM (heart), 7.5-120 nM (brain), 19-300 or 1500-24000 nM (liver), 56-900 or 1500-12000 nM (kidney), 500-8000 nM (fat). Peak integration, calibration, and quantification was performed within Analyst software. The response of the peak area standard/int. std. to nominal concentration was linear with r=0.999 or better.

Patch Clamp Recordings.

Heterologously transfected N2a cells were subjected to patch clamp electrophys-iological recordings. Briefly, 24 h after transfection cells were prewashed with extracellular fluid (ECF) which contained (in mM) 1 MgCl$_2$, 10 Glucose, 10 HEPES, 145 NaCl and 2 CaCl$_2$) (pH 7.4, 310 mOsM). Cells were then incubated with or without TRPV4 inhibitors in ECF for 5 min before whole cell recording. Cover slips were transferred to a recording chamber mounted on the stage of a Leica inverted microscope that was equipped with fluorescent filters. Transfected cells were identified before patching by their green florescent color. Cells were patched with a 2.5-3.0 M$\Omega$ glass electrode pulled from borosilicate glass capillaries using pipette puller (Sutter instruments). The intracellular solution contained (mM) 140 CsCl, 10 HEPES, 1 EGTA, 0.3 Na-GTP, 2 Na$_2$-ATP, and 2 MgCl$_2$ (pH 7.4, 295 mOsM). Whole cell currents were recorded using pclamp 9.2 software and Axopatch 200B amplifier (Molecular Devices). The cells were first clamped at –65 mV before applying a 1 s voltage ramp from –110 mV to +120 mV. The voltage ramp was applied every 2 seconds for 15 to 20 sweeps. Capacitance was monitored throughout the experi-mental recordings. Reported data was within ±3 pF.

Example 2: Generation of an Epidermal-Specific, Tamoxifen-Inducible Trpv4 Null Mouse To circumvent developmental issues that can arise in gene-targeted mice with ubiquitous deletions, we developed an inducible conditional system to assess the roles of TRPV4 in UVBmediated skin irritation, inflammation, and sensory sensitization. Using mouse ES cells, we first built Trpv4lox/lox mice so that the sizable exon coding for transmembrane domains 5, 6, and the interjacent pore loop was flanked by loxP elements. After crossing to FLPe mice to remove the selection marker, flanked by frt elements, these animals were mated with tamoxifen (tam)-inducible, Keratin-14 (K14)-CRE$^{EK}$ transgenic mice. The constructs and genotyping are summarized in FIG. 1A-B.

Figure 1C:
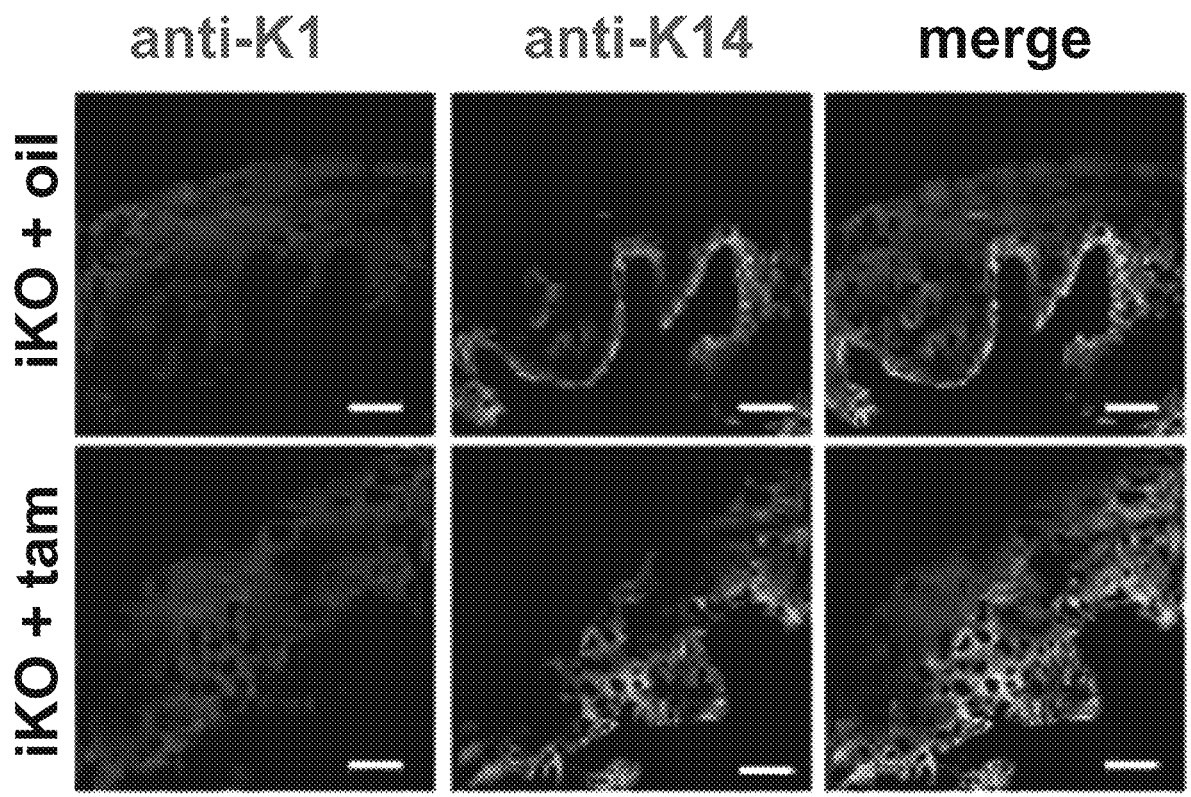
Figure 3A:
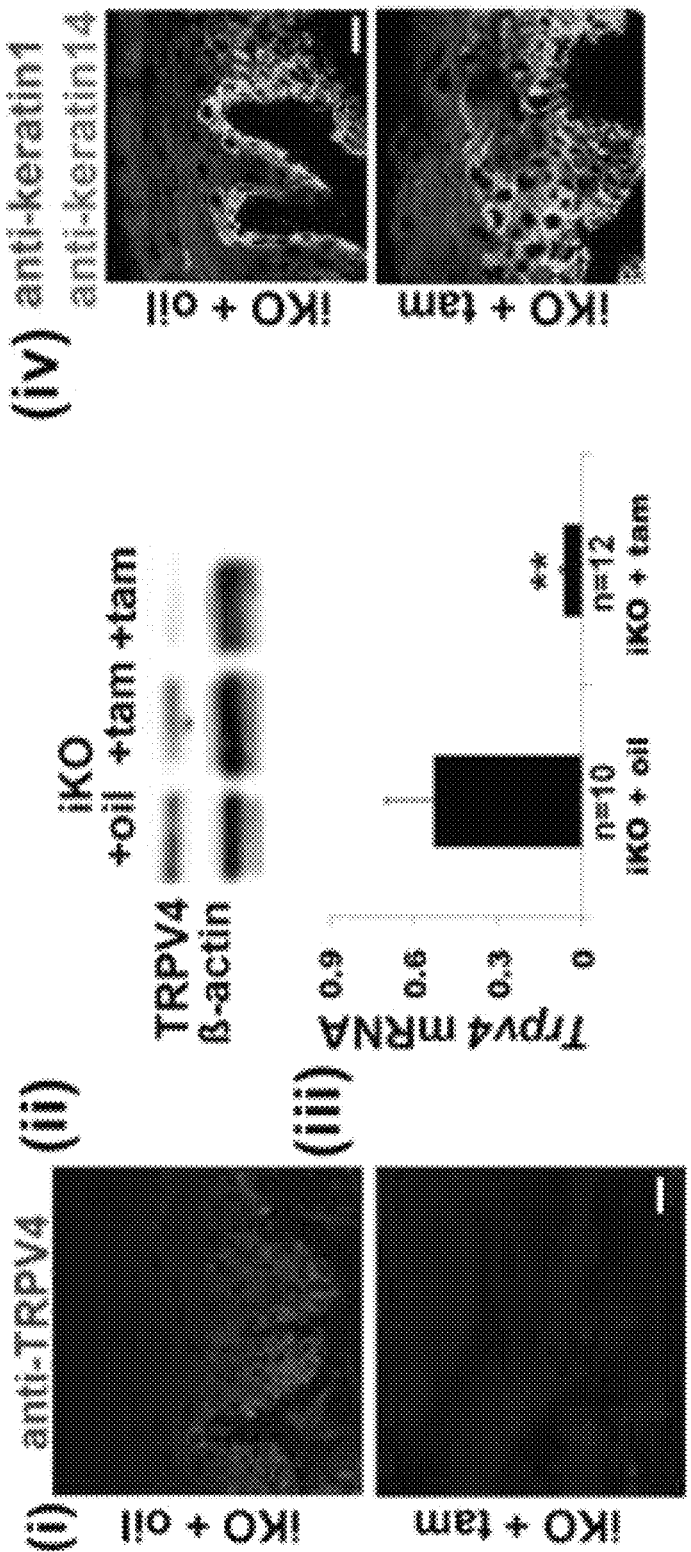
FIGS. 3A-3E: Keratinocyte-specific ablation of Trpv4 leads to alterations in nocifensive behavior in response to UVB.

We focused on adult (2 month) glandular mouse paw-pad skin for our analyses, as it more closely resembles human skin. Tamoxifen-induction resulted in efficient knockdown of Trpv4 expression in skin epidermis, as judged by anti-TRPV4 immunolabeling, qRT-PCR and Western blotting (FIG. 3A). However, the gross and microscopic appearance of the skin/epidermis in tam-treated inducible Trpv4 knockout (iKO) mice was normal. Given the established dependence of skin renewal on keratinocyte Ca++ signaling, we noted that, interestingly, Trpv4-knockdown resulted in no gross alterations in the skin/epidermis nor in the induction of the terminal differentiation-specific marker keratin-1 (K1), which is known to be governed by elevated Ca++ influx suprabasally (FIG. 3A and FIG. 1C). Closer analysis of Trpv4-deficient skin revealed that expression of K14 was sustained suprabasally. This keratin is normally down-regulated at the basal-to-suprabasal transition, concomitant with the rise in Ca++ signaling and induction of terminal differentiation.

Taken together, despite these more moderate abnormalities, inducing Trpv4 knockdown in keratinocytes at age 8 weeks does not lead to gross interference with cyto- and layer architecture of the epidermis.

Example 3: Nocifensive Behavior Elicited by UVB Exposure is Dependent on Epidermally-Expressed TRPV4

Figure 1D:
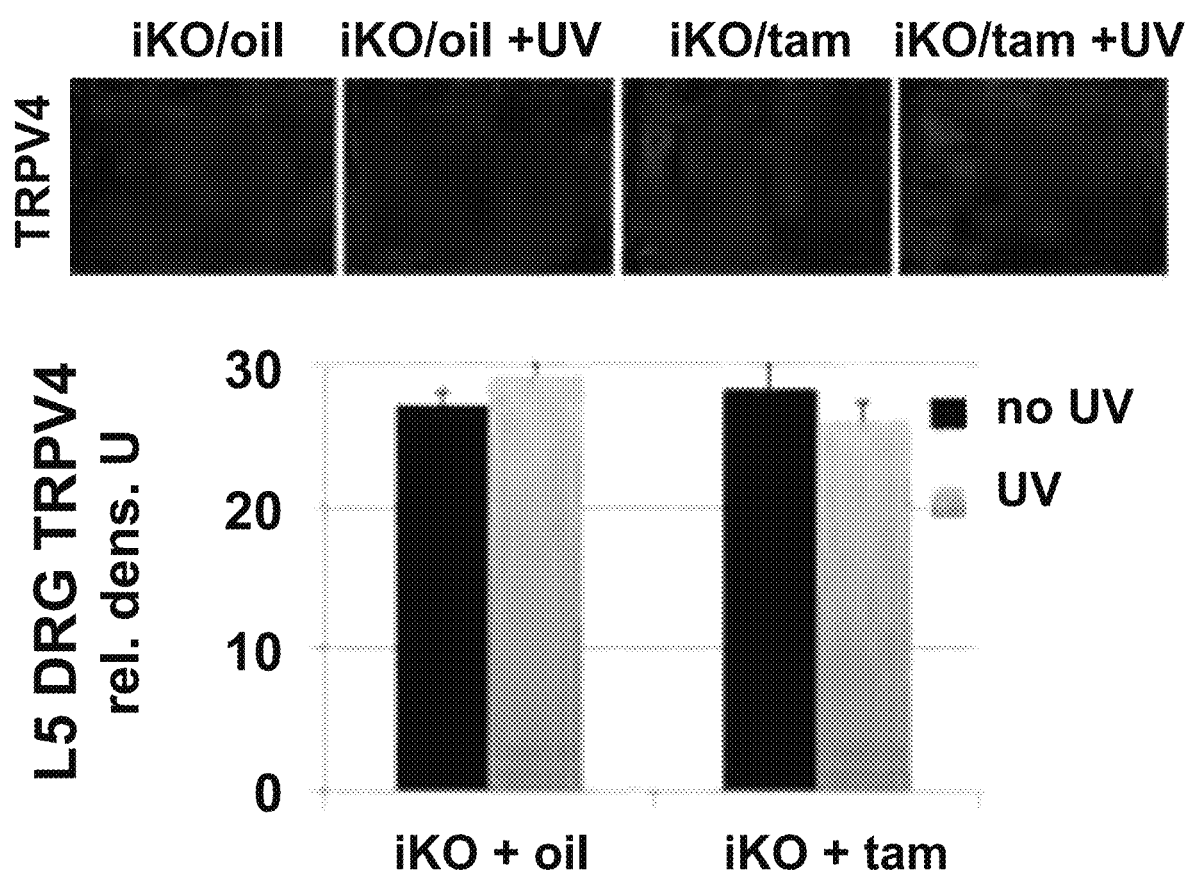
Figure 3B:
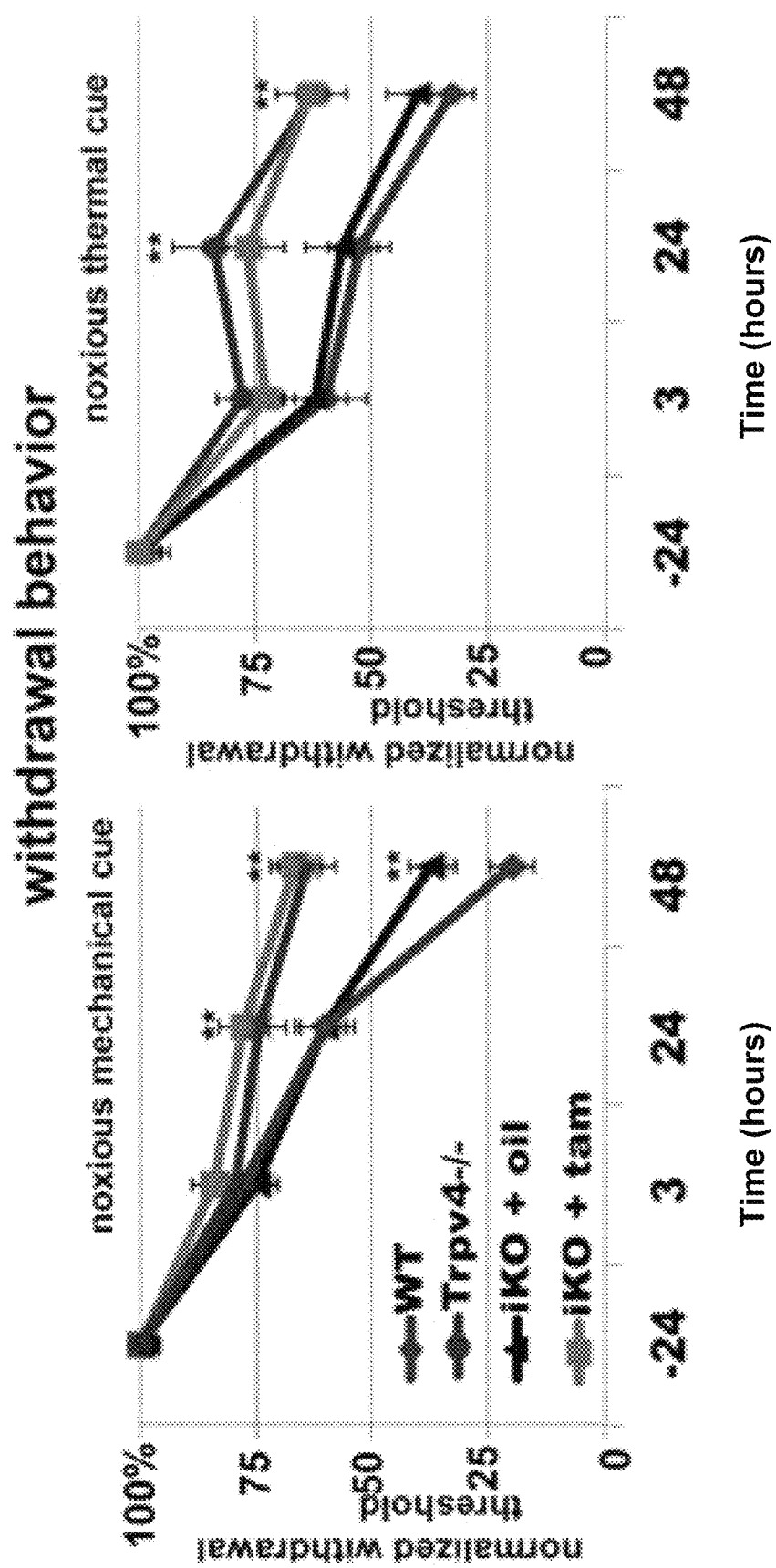

Underscoring the specificity of Trpv4 gene targeting, peripheral sensory neurons innervating the footpad still showed robust expression of TRPV4 (FIG. 1D). This enabled us to evaluate whether epidermal Trpv4-deficiency critically affects UVB-mediated nocifensive behaviors. For this purpose, we assayed two relevant submodalities—thermal and mechanical stimulation—and compared our iKO mice to pan-null Trpv4-/- and their wild-type (WT) controls (FIG. 3B). 48 hours after UV-exposure, both tamtreated iKO and Trpv4-/- mice displayed much lower sensitivity to noxious radiant heat (Hargreaves' test), also towards noxious mechanical stimulation (using automated von Frey hair testing), than their respective controls. We concluded that epidermal-specific TRPV4 deficiency is equivalent to global Trpv4 ablation in reducing UVB-induced behavioral sensitization to radiant heat and mechanical stimuli, that is, in attenuating thermal and mechanical allodynia.

Figure 3C:
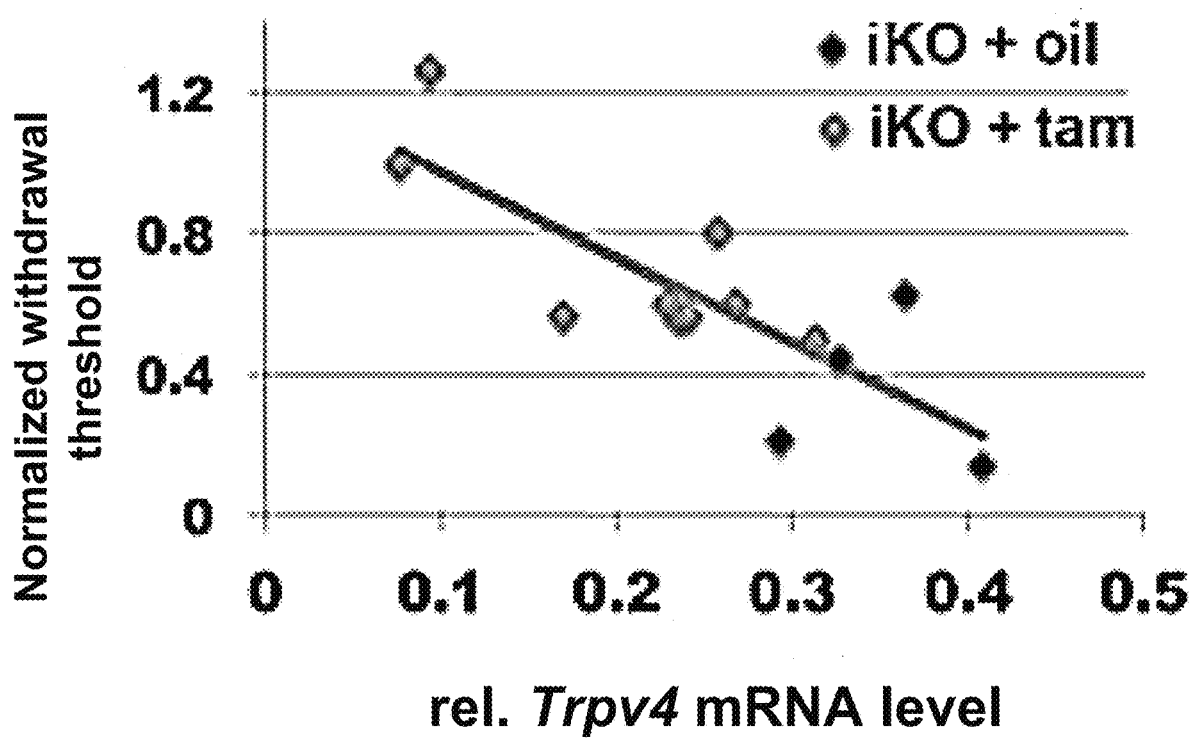

Further underscoring the importance of epidermal TRPV4 in regulating nocifensive behavior, a good correlation existed between UV-sensitivity to thermal stimuli and the level of Trpv4 gene knockdown, particularly at <0.45 the WT levels of Trpv4 mRNA (FIG. 3C). This indicated presence of a threshold for Trpv4 knockdown to influence nocifensive behavior. Although the dose-responsiveness was less obvious in our mechanical assay (not shown), we attributed this to the involvement of forced hind limb (foot) movement in the assay, which will confound the stimulus. By contrast, the Hargreaves' assay applies a purely thermal cue which becomes noxious without involving confounding stimuli.

Figure 3D:
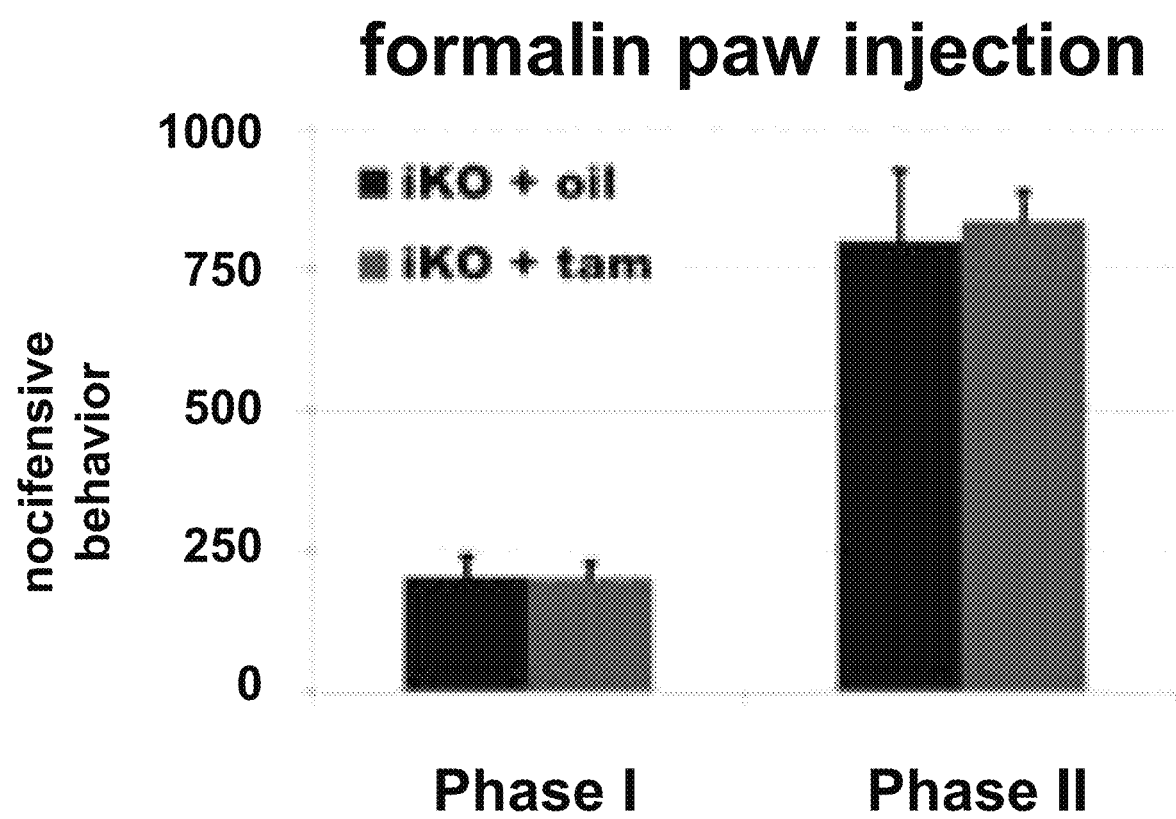

In order to assess the specificity of the injurious stimulus, we induced irritation with foot-pad injections of formalin, eliciting the well-established bi-phasic response. In this assay, conditional epidermal knockdown of TRPV4 had no effect on direct peripheral chemical irritation (phase I) or the early maladaptive neural response (phase II) (FIG. 3D). Taken together, these results suggested that the level of epidermal Trpv4 knockdown is the determining factor for the degree of attenuation of nocifensive behavior caused by UVB-irradiation. This is specific because chemical irritant-induced nocifensive behavior is not affected by epidermal Trpv4 knockdown.

Figure 1E:
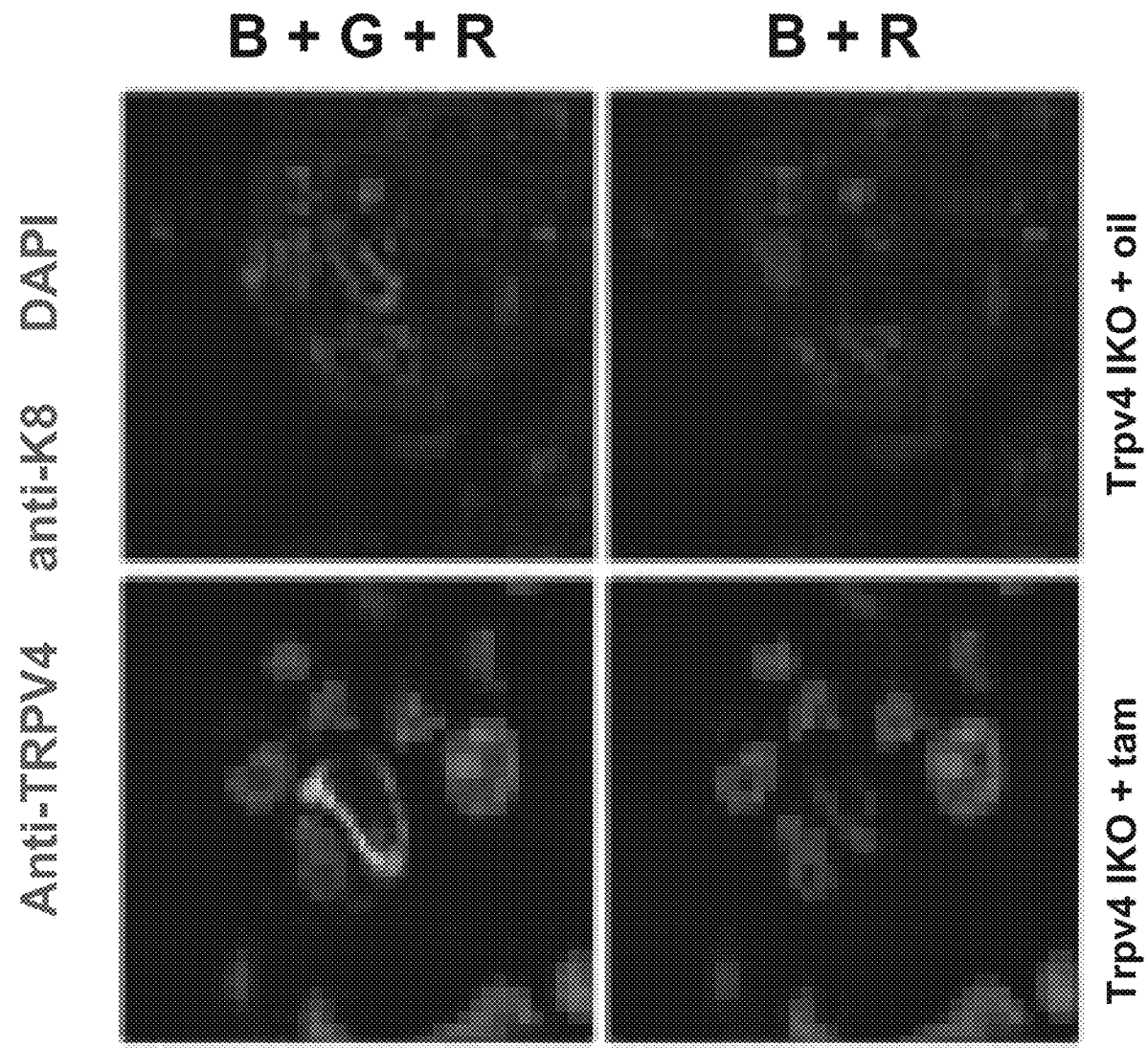

In additional control experiments, Trpv4lox/+ heterozygous mice had virtually identical behavioral sensitization (similar to WT) in response to UVB, irrespective of CRE-induction with tamoxifen or vehicle (FIG. 1E). These findings exclude a functional role for CRE$^{ER}$ on its own and reiterate the specificity of our approach in targeting Trpv4 ablation to keratinocytes. Also, Trpv4-/- skin was equally permeable to UVB as its WT counterpart.

Figure 1F:
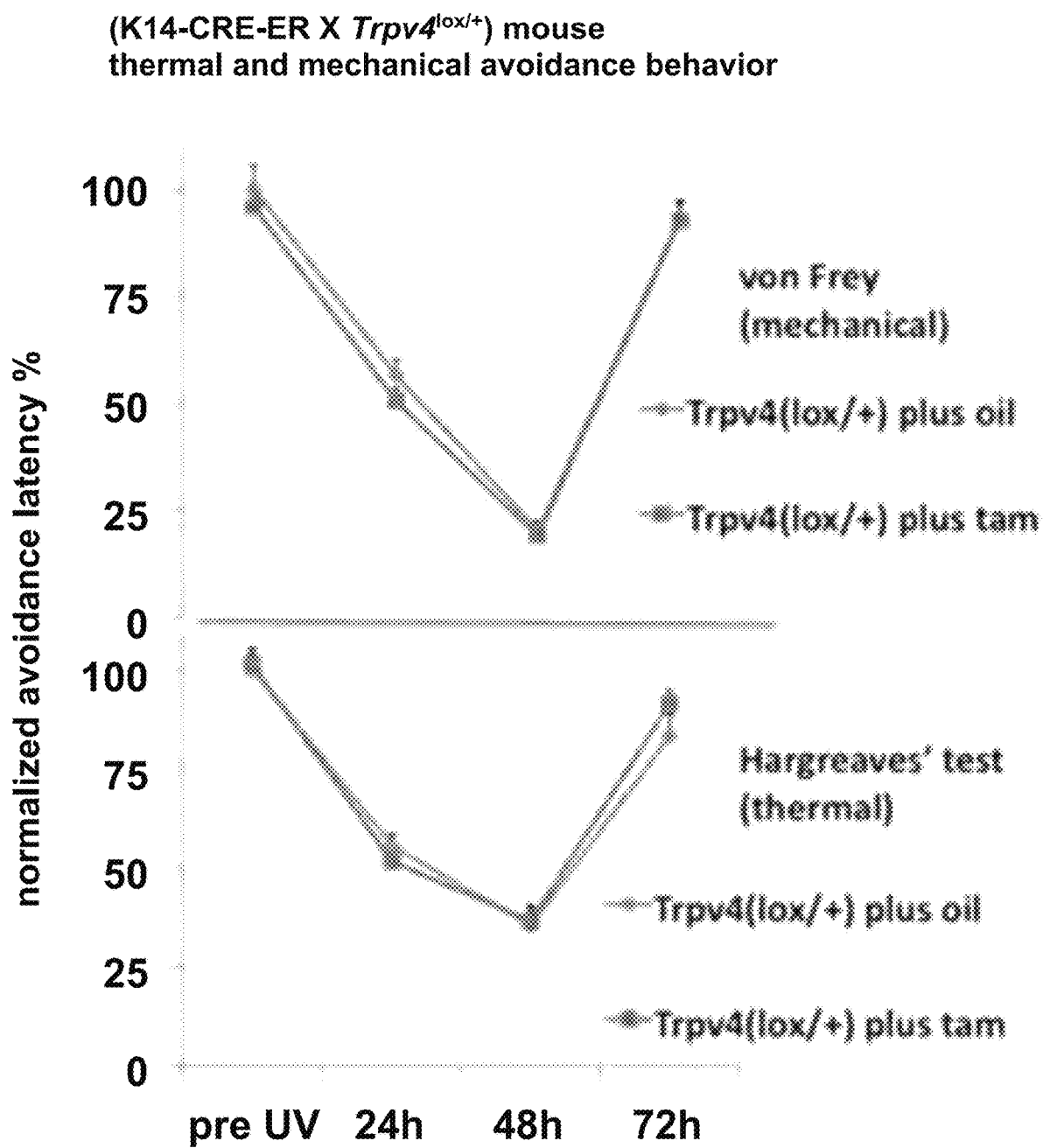
Figure 1G:
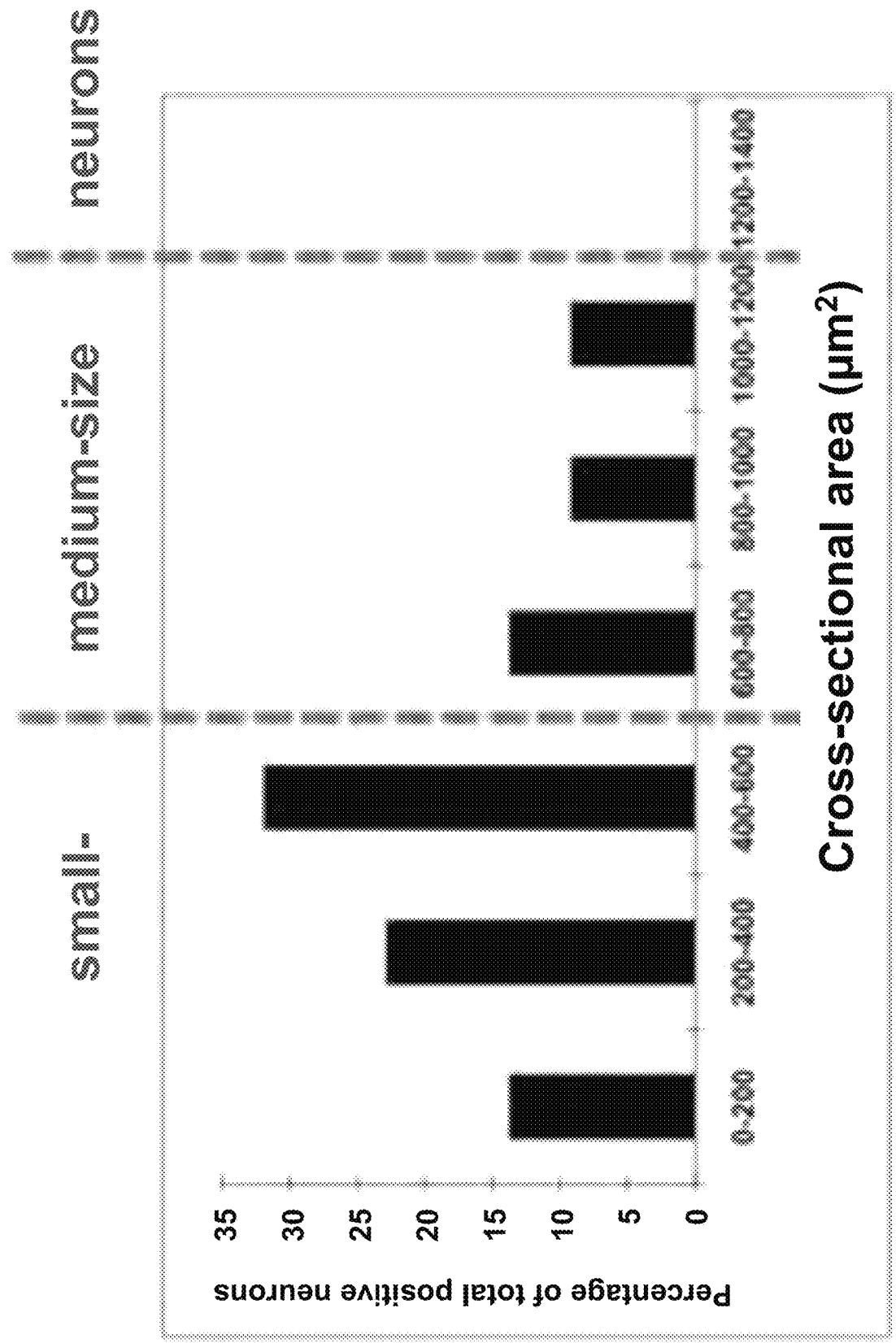
Figure 3E:
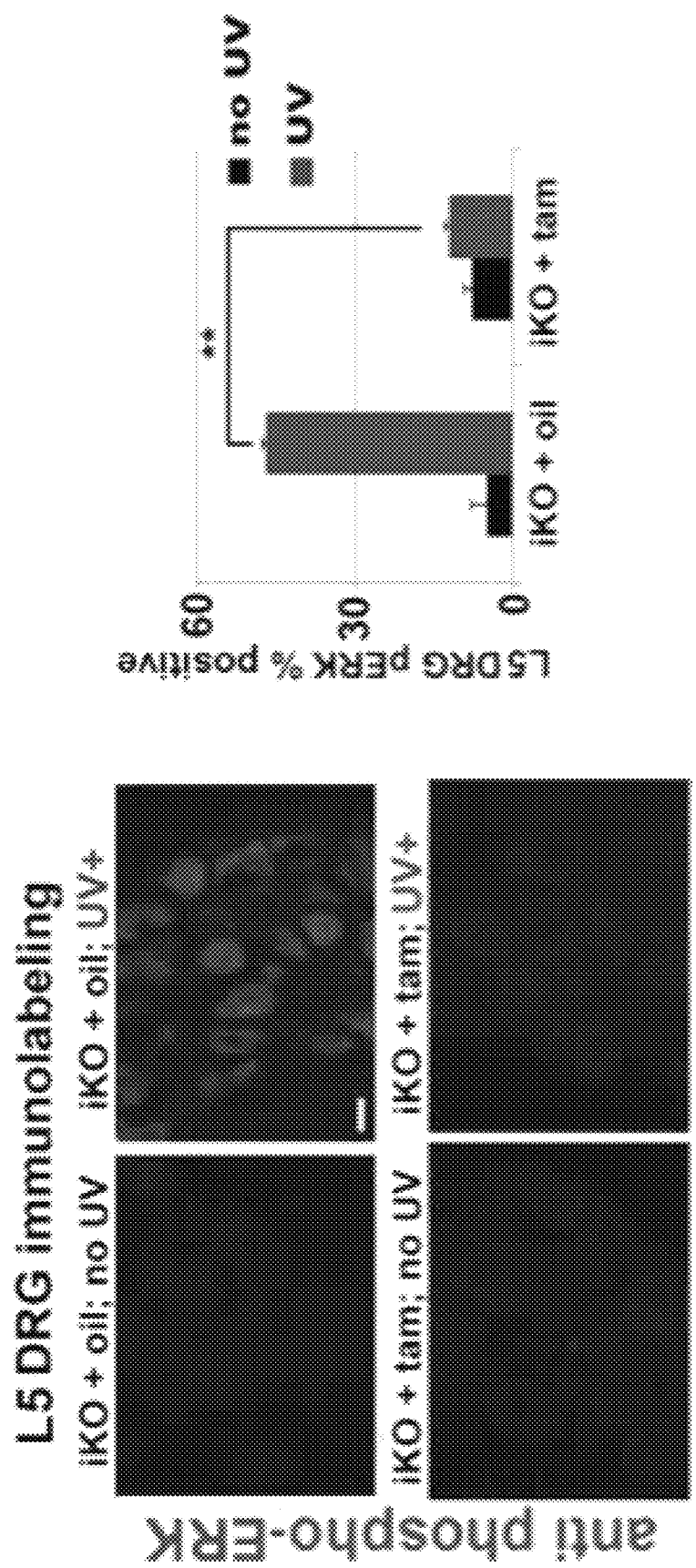

Example 4: Activation Markers of Skin-Innervating Peripheral Neurons Support Behavioral Findings In WT mice, the footpad is innervated by sensory neurons of the L5 DRG, which we examined by immunolabeling. TRPV4 expression was unchanged with foot-pad exposure to UVB, an irritant cue known to sensitize innervating neurons (FIG. 1D). Interestingly, while sensitization could be verified in control mice, it appeared to be absent in tam-treated iKO mice, as documented by labeling for phosphorylated ERK (pERK), a known marker of sensory neuron activation in response to inflammation and irritation (FIG. 3E). Furthermore, size-measurements of pERK-expressing L5 DRG neurons revealed them to be small-to-medium size, suggesting their possible involvement in relay of noxious stimuli (FIG. 1F). These results are in good agreement with the nocifensive behavior defects seen in our mice, and further underscore a role for epithelial-expressed TRPV4 in governing UVB-induced activation in skin-innervating DRG sensory neurons.

Example 5: UVB-Induced Skin Inflammation Depends Upon Epidermal Expression of TRPV4

To understand how loss of TRPV4 affects UVB-induced skin, we performed light microscopy and ultrastructural analyses (FIG. 4A and FIG. 5A-C). In response to UVB, robust signs of inflammation appeared within control skin, as evidenced by intra-epidermal infiltrates of granulocytes. With the epidermis, focal blistering occurred, accompanied by extensive vacuolization. In skin of tam-treated iKO mice with incomplete targeting, inflammatory changes were still observed and were perhaps moderately less severe. In striking contrast, however, in skin areas where conditional epidermal ablation of Trpv4 was complete, no signs of inflammation or blistering were seen. These data demonstrated convincingly that epidermal TRPV4 is necessary for skin to mount a pro-inflammatory response to UVB exposure. Moreover, since the inflammation involved immune cells and the conditional knockout was specific to epidermis, the data further highlight the importance of epidermal-inflammatory cell crosstalk in the response. Specifically, these data imply that in normal skin, the epidermal keratinocyte triggers inflammatory cell recruitment as part of a UVB response, and that this circuitry is interrupted when epidermal TRPV4 is knocked down.

Figure 4A:
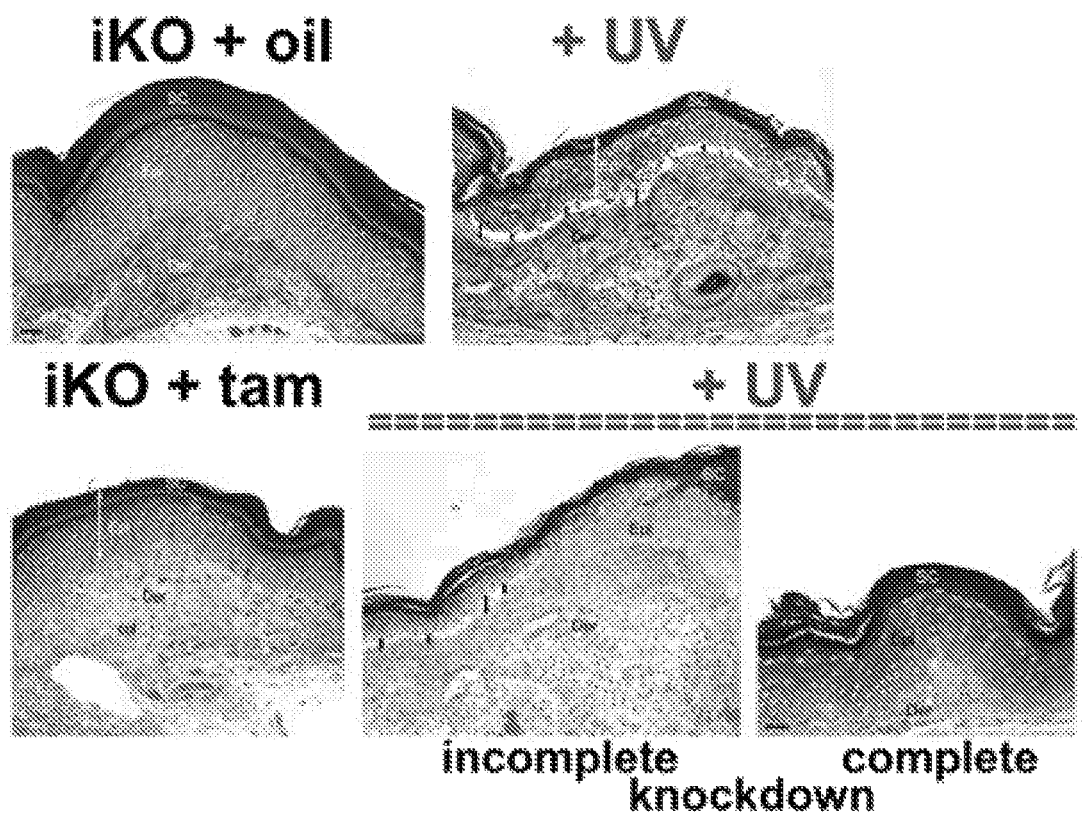
FIGS. 4A-4E: Structural and ultrastructural analyses showing that UVB-mediated skin tissue injury depends upon keratinocyte TRPV4, and Immuno-histochemical analysis demonstrates that UVB-mediated activation of keratinocytes and recruitment of macrophages and neutrophils depends upon keratinocyte TRPV4.
Figure 4B:
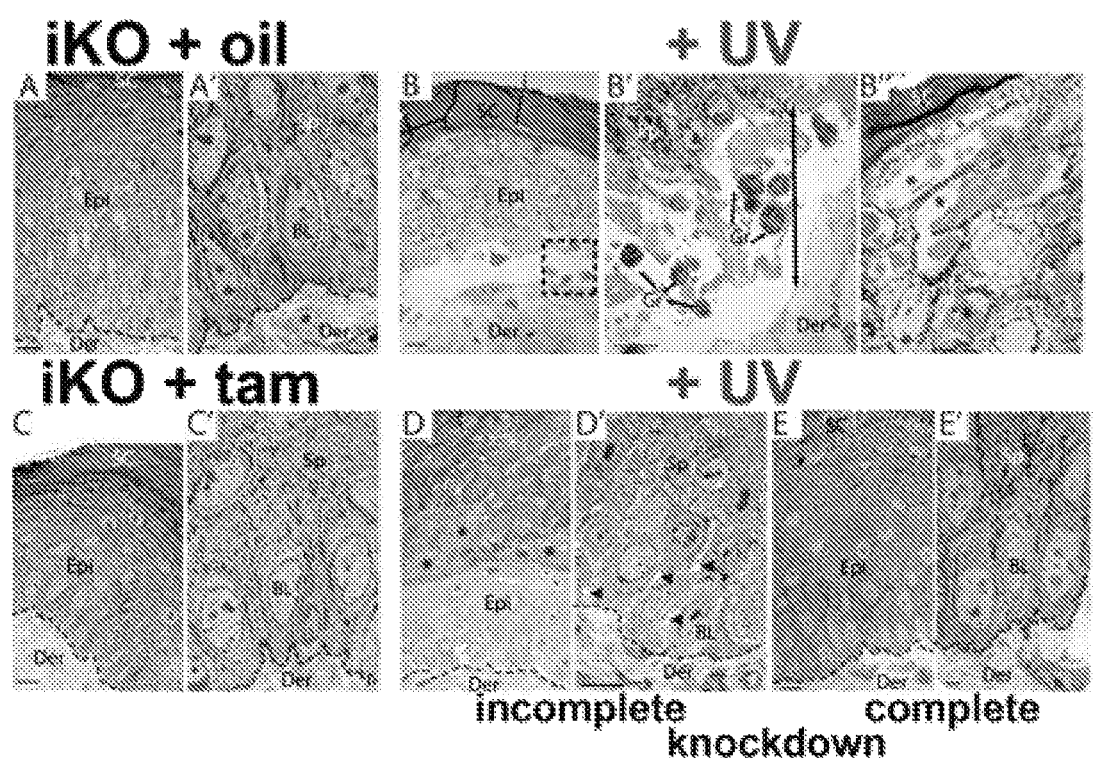
Figure 5B:
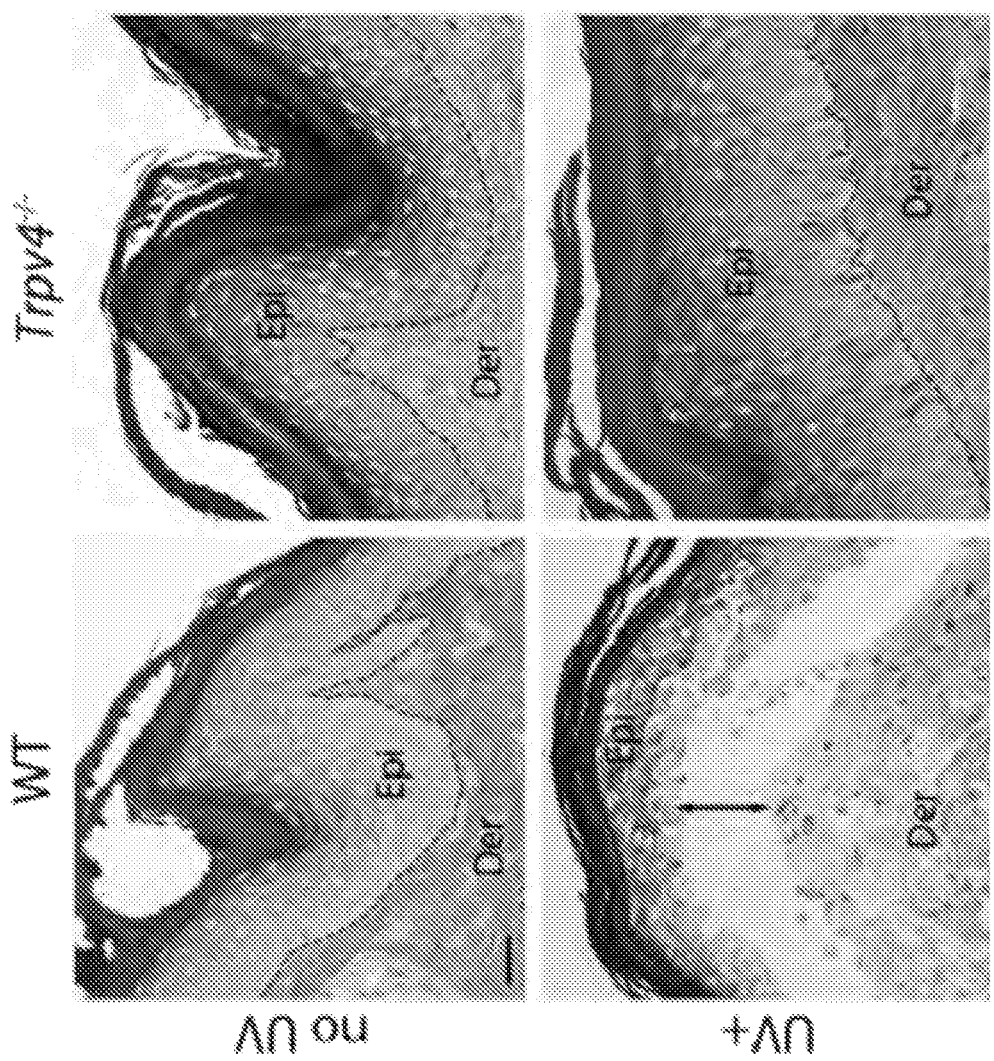
FIGS. 5A-5E: Histopathology in Trpv4−/− and control mice in response to UVB.
Figure 5A:
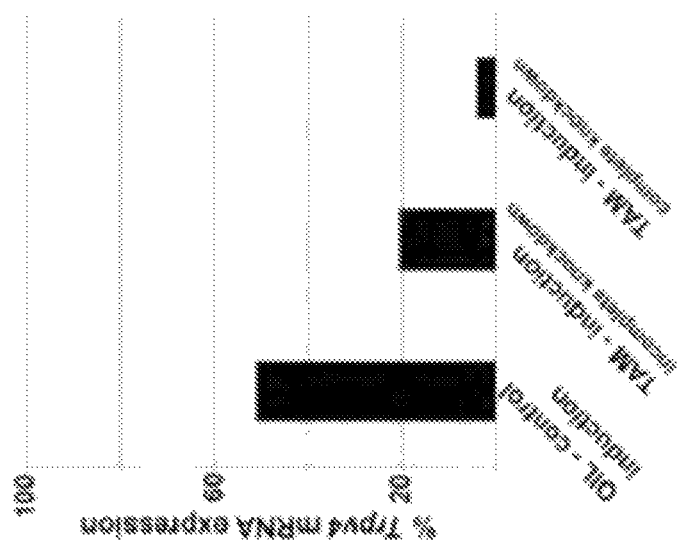
Figure 5C:
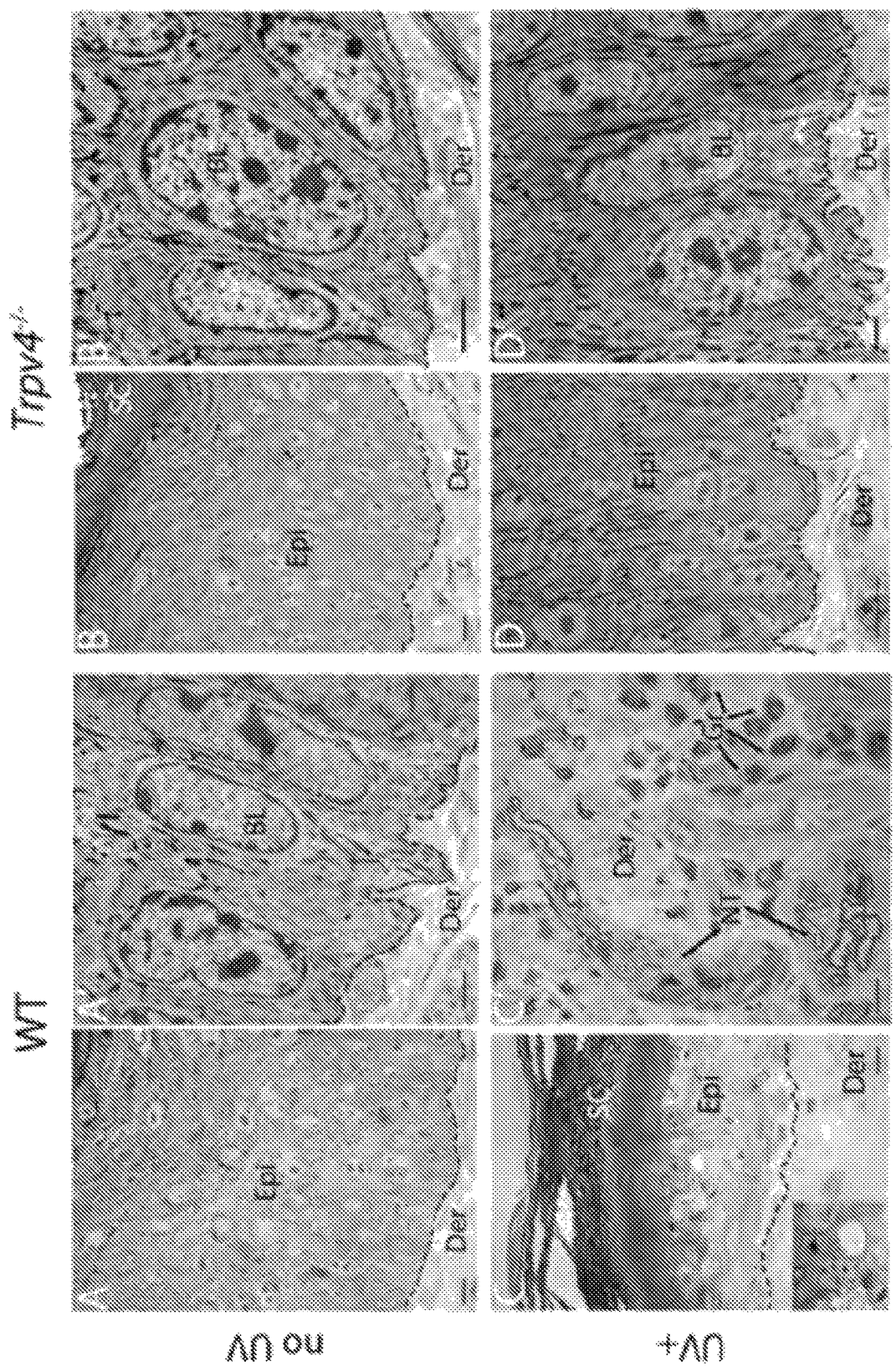
Figure 5D:
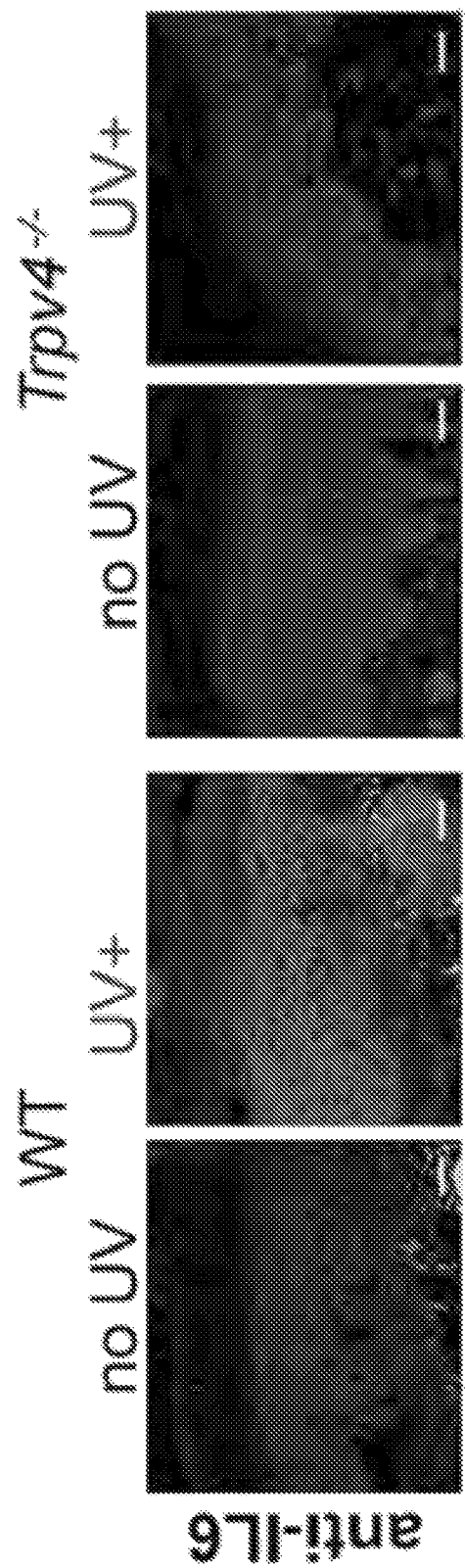

We next sought to identify the specific TRPV4-dependent epidermal signals that occur in WT mice exposed to UVB, and the immune cell populations that respond. IL-6 was a suitable candidate for the epidermal signal since it is an established marker of skin epidermal activation during UV dermatitis, and in addition, IL-6 is robustly algogenic. Indeed not only was IL-6 immunoreactivity observed in the UVB-exposed epidermis of control mice, but in addition, this robust IL-6 upregulation was virtually eliminated in conditionally targeted as well as pan-null Trpv4 knockout skin (FIG. 4B and FIG. 5D).

Figure 4C:
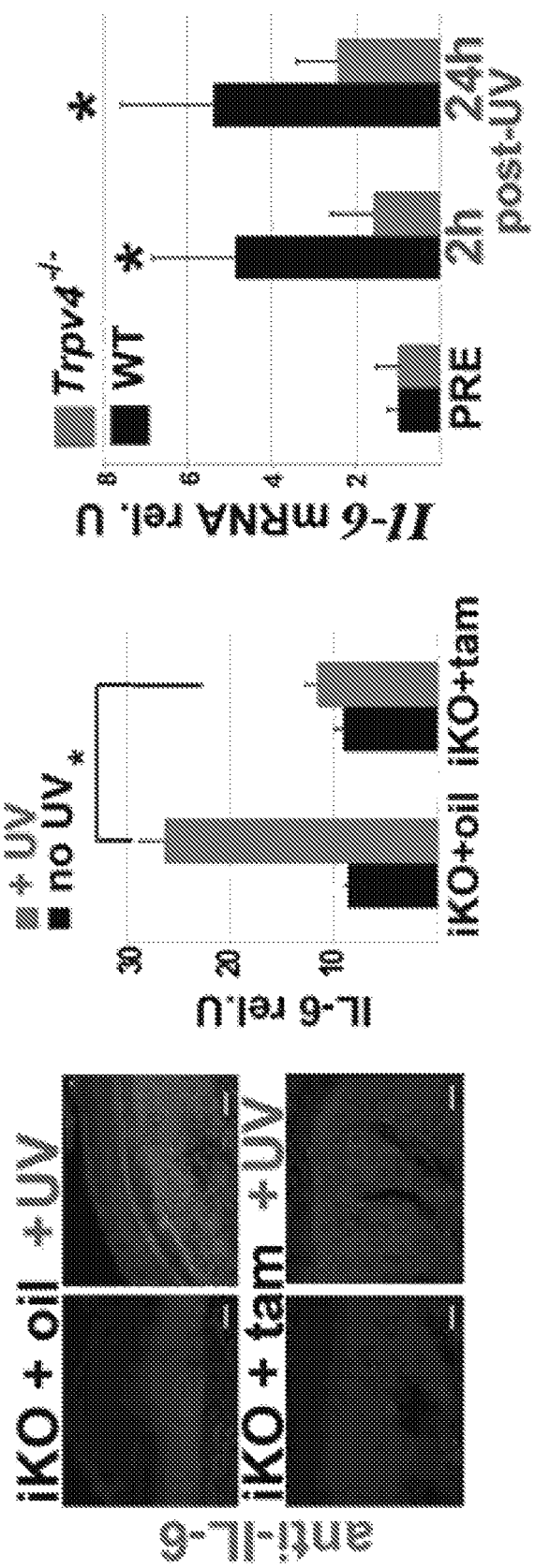
Figures 4D, 4E:
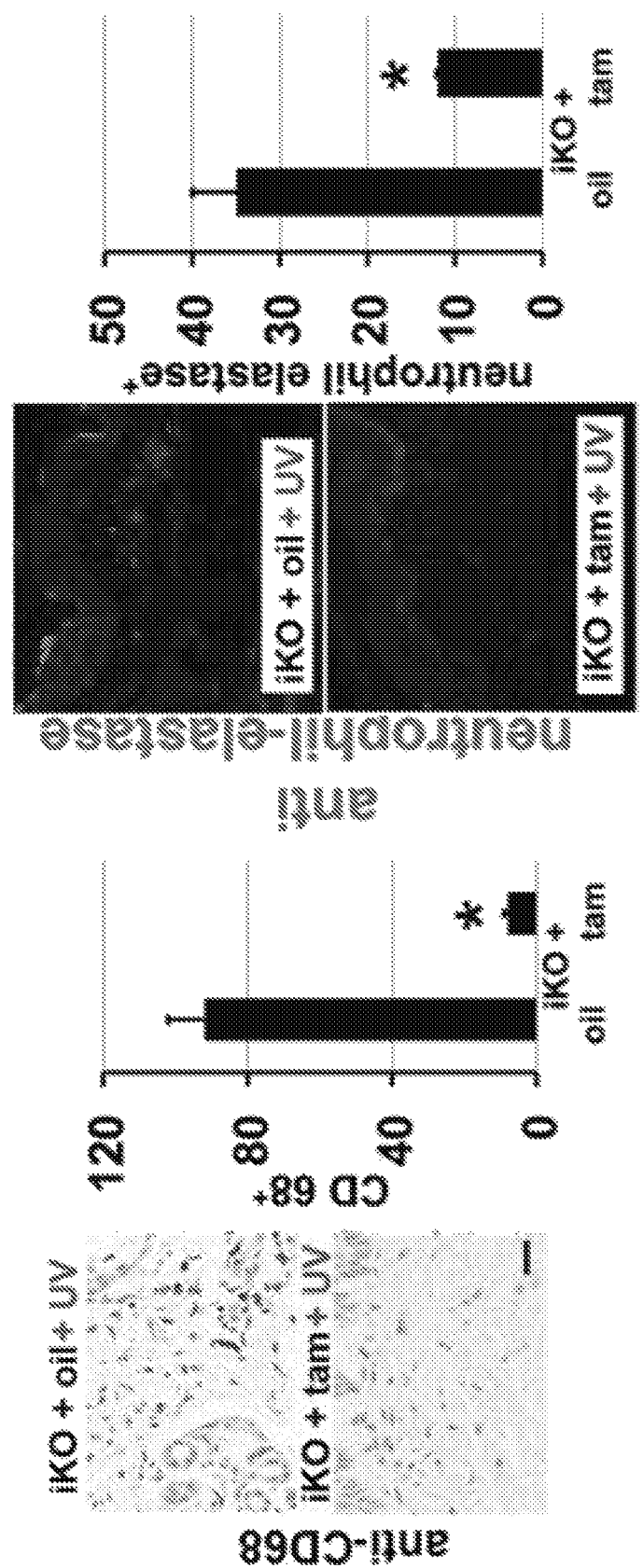
Figure 5E:
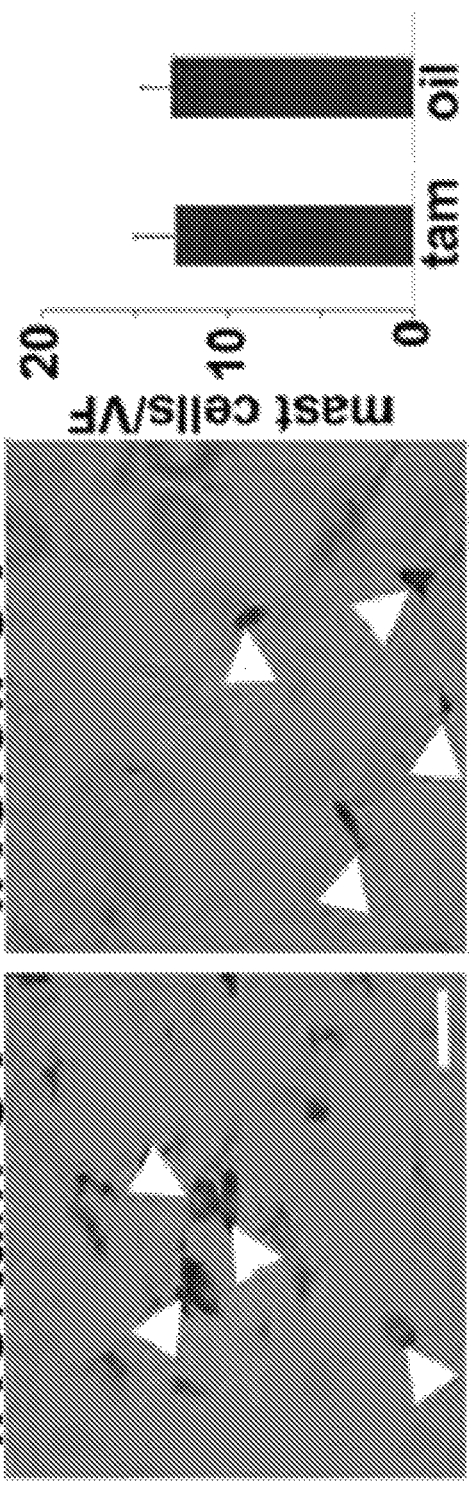

Both macrophages and neutrophils are known to contribute to the reduction of pain thresholds via their expression of a host of proalgesic/algogenic mediators such as TNFα, IL-6, IL-8, proteases, and chemokines. As judged by immunostaining for CD68 (macrophages) and a cell type-specific elastase (indicative of activated neutrophils, also known to enhance nociception), UVB-induced infiltration of both of these cell populations was markedly reduced in the skin of Trvp4-conditional knockout mice (FIG. 4C-D). By contrast, the mast cell infiltrate was unaffected (FIG. 5E), underscoring the specificity of macrophage and activated neutrophil findings; T-cell count was not changed between genotypes either. Taken together, these findings showed that TRPV4 expression by keratinocytes is critical for their ability to generate IL-6 and attract macrophages and activated neutrophils in response to UVB radiation.

Example 6: The UVB-Induced Ca++ Response in Primary Mouse Keratinocytes to UVB is Critically Dependent on Extracellular Ca++ Influx Through TRPV4

Figures 6C, 6D:
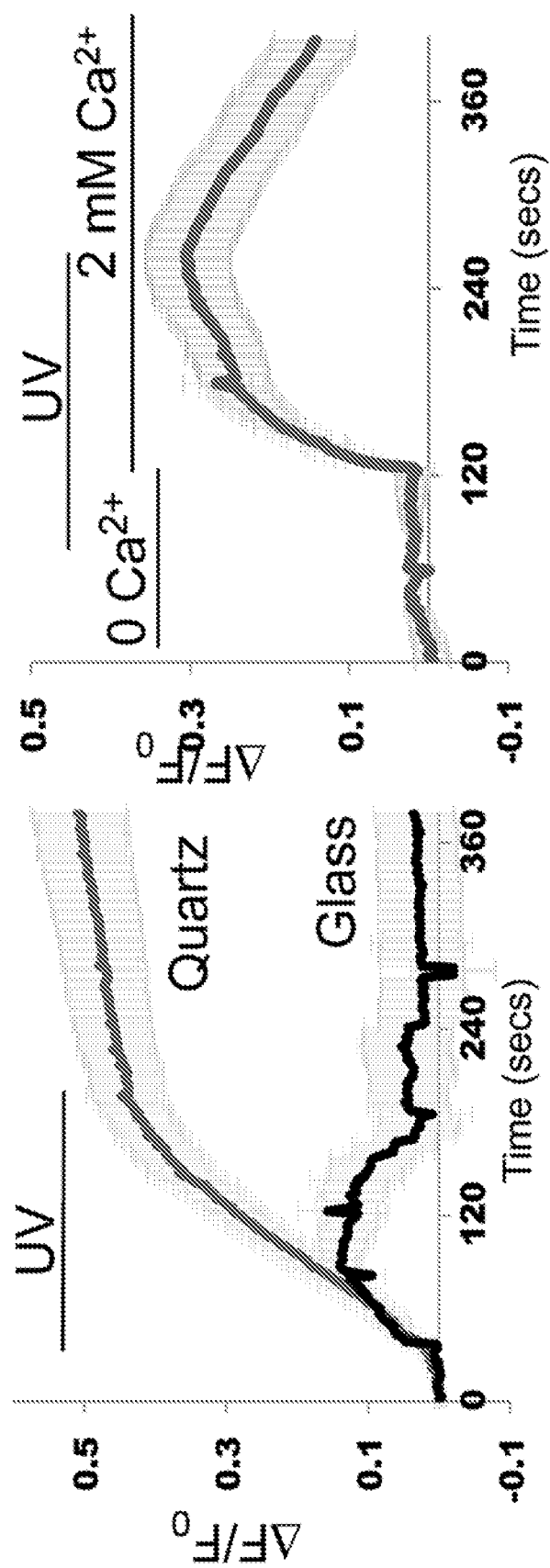

To further dissect the underlying mechanisms involved, we built a customized device for specific and narrow-band UVB stimulation of primary mouse epidermal keratinocytes (1° MK) cultured in vitro (FIG. 6A-B and FIG. 2A-D). This allowed use of the Ca++ sensitive dye, fluo-4, and assessment of 1° MK's Ca++ dynamics following UVB exposure (FIG. 6B). The elicited Ca++ signal was obliterated by a UV-refracting glass coverslip, underscoring the strict dependence of the calcium response on UVB (FIG. 6C and FIG. 2A).

Next, we asked whether the UVB-mediated Ca++ response is dependent on extracellular Ca++, and recorded affirmative findings by sequential exposure to first UVB, then Ca++ (FIG. 6D). This finding prompted us to directly query the role of TRPV4 in the UVB-mediated Ca++ response. Indeed, 1° MK from Trpv4−/− mice exhibited a greatly diminished response relative to their WT counterparts (FIG. 6E). Moreover, when a selective small molecule-compound, GSK205 (Vincent and Duncton. Current Topics in Medicinal Chemistry 2011, 11, 2216-2226), was used to block TRPV4 channel function, WT 1° MK showed a very similar response to that of Trpv4−/− 1° MK (FIG. 6F).

Figure 2E:
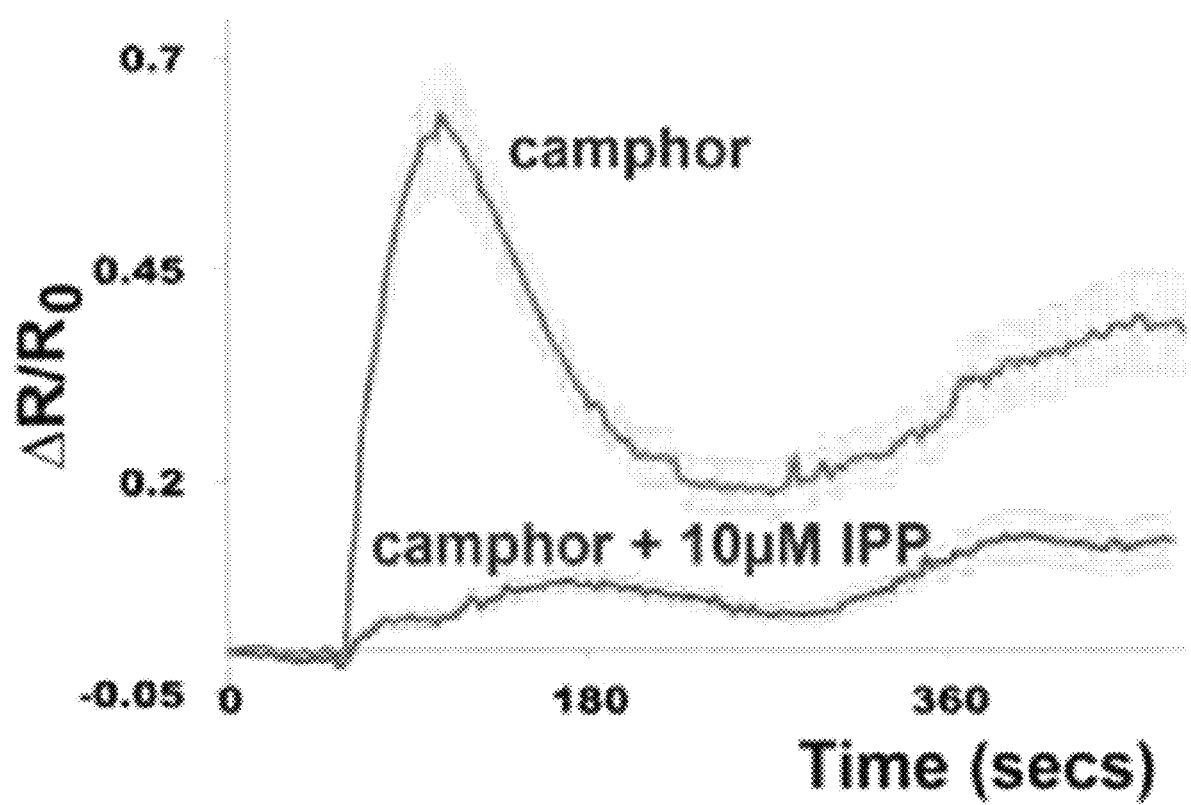

In view of the known robust expression of TRPV3 in keratinocytes (Moqrich et al., 2005; Peier et al., 2002), we also addressed TRPV3's role in UVB-mediated Ca++ increase, but observed no effect with the TRPV3-selective inhibitor, IPP (FIG. 6G). The same dose of IPP was effective in inhibiting camphor-evoked Ca++ transients (FIG. 2E), validating the negative result.

Figure 2F:
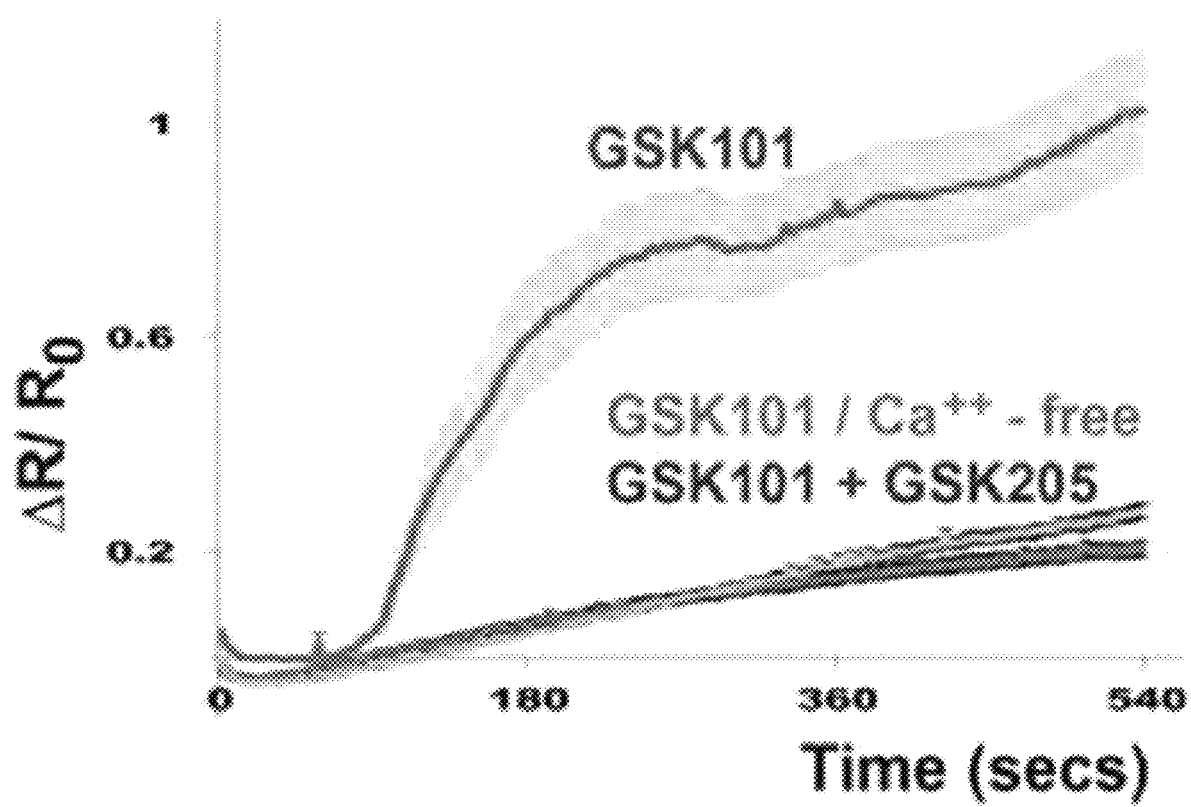

Together, our experiments indicated that UVB exposure to the epidermis elicits the influx of extracellular Ca++ through TRPV4 and not TRPV3 channels. Since both channels were present, the data further suggested that TRPV4 channels are selectively activated by UVB light. We obtained corroborating findings by chemically activating TRPV4 with GSK101, which can directly stimulate TRPV4 in WT 1° MK. The GSK101-mediated response was dependent upon external Ca++ and was eliminated by the TRPV4 inhibitor GSK205 (FIG. 2F). These findings showed that direct chemical channel activation of TRPV4 shares critical properties of UVB-evoked Ca++ dynamics.

Figure 2G:
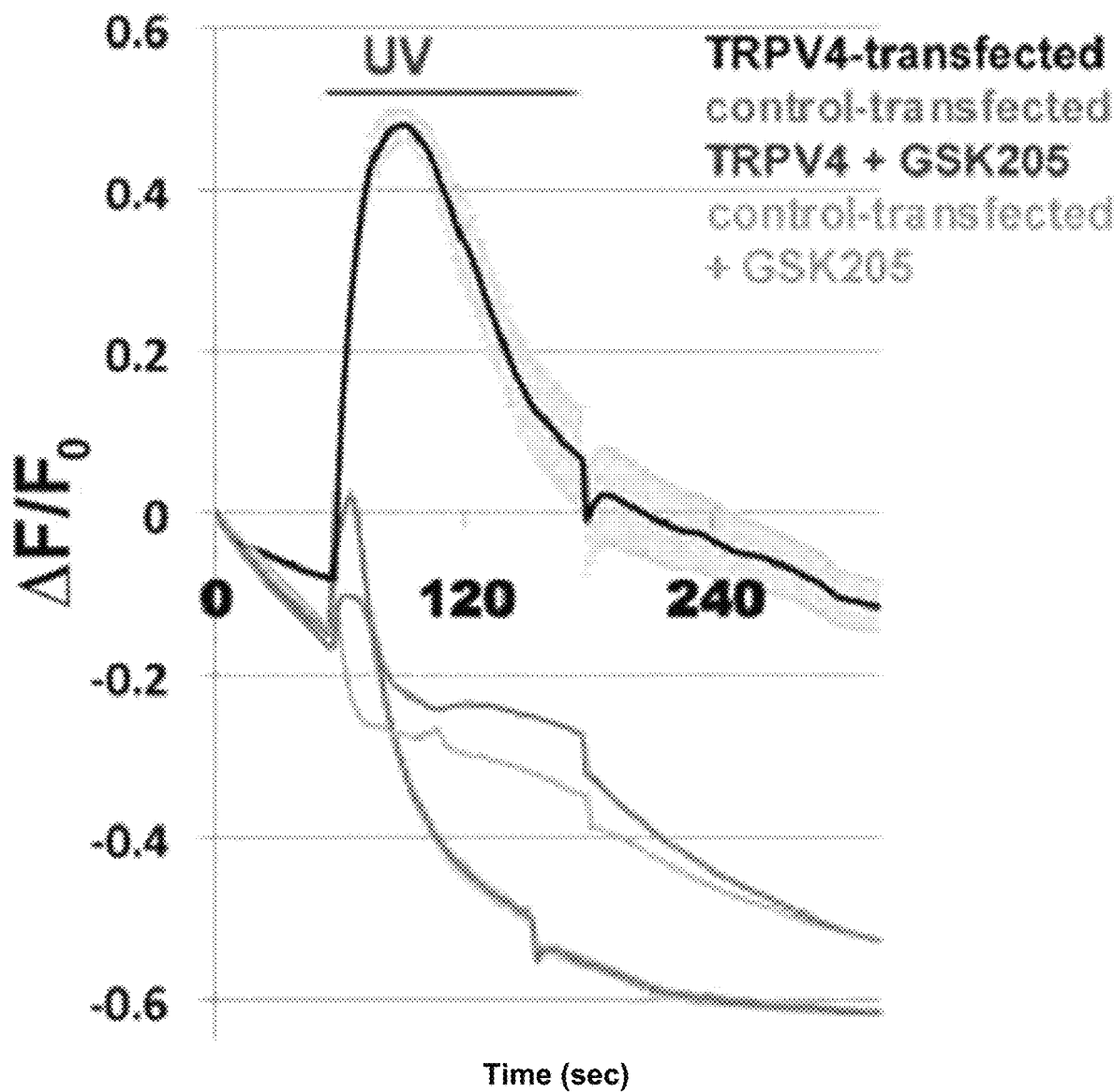

To assess whether TRPV4 is sufficient for the UVB-evoked Ca++ influx, we introduced high levels of TRPV4 into HEK293 epithelial cells. TRPV4 expression endowed these cells with the ability to generate robust Ca++ signaling in response to UVB (FIG. 2G). Moreover, if they were pre-exposed to GSK205, the response was blocked. Thus, heterologous TRPV4 expression is sufficient for UVB radiation to cause a cellular Ca++ transient.

Example 7: Elevated Endothelin-1 is a Critical Epidermal Effector of the UVB-TRPV4-Ca++ Response The UVB-TRPV4-Ca++ response depended on upon phospholipase-C (PLC), as it was virtually eliminated by the specific PLC inhibitor, U73122 (FIG. 6H). The reliance of TRPV4 activation upon PLC signaling suggested that PLC's respective lipid products, such as IP3, might be involved. It also hinted at possible involvement of G protein-coupled receptor signaling.

Using a candidate approach, we focused on endothelin receptors [ET(R)], which are known to be expressed in skin keratinocytes. ET(R)s were particularly good candidates since they function pro-algesic-/algogenically, and their cognate peptide ligand, endothelin-1 (ET1), is elevated when keratinocytes are exposed to UVB. When our 1° MK were exposed to ET1, they exhibited a significant increase in their UVB-induced Ca++ signaling (FIG. 7A(i)). This response was dependent upon TRPV4, as it was greatly diminished by GSK205. Consistent with this result, ET1 augmented GSK101-evoked Ca++ signaling (FIG. 8A).

We next blocked ET1 secretion by applying the proendothelin convertase-inhibitor, CGS35066. This inhibitor significantly diminished UVB-induced Ca++ signaling in 1° MK (FIG. 7A(i)). Since ET1's enhancing effect on Ca++ signaling was dependent upon TRPV4, and the UVB-Ca++ response was significantly sustained by ET1 secretion in vitro, we posited that autocrine/paracrine signaling involving ET1 may function to activate its cognate receptors, ET-R(A) and ET-R(B). In good agreement with this notion, ET-R inhibitors markedly attenuated the Ca++ signal in response to UVB and ET1 co-exposure. Interestingly, antagonism of ET-R(A) eliminated later phases of the Ca++ response, while leaving the initial rise unaffected; by contrast, antagonism of ET-R(B) converted the UVB-Ca++ response into a more protracted one (FIG. 7A(ii)). Co-application of both inhibitors completely eliminated the UVB-induced Ca++ response by 1° MKs (FIG. 7A(iii)).

Taken together, these findings indicate that UVB-mediated ET1 secretion is a significant contributor to the UVB-TRPV4-Ca++ response. The data further suggest that independently from UVB's other effects, ET1-ET(R) co-signaling can amplify a TRPV4-dependent Ca++ response. In support of this notion, the UVB-Ca++ response could be recapitulated by omitting UVB-exposure and instead co-treating 1° MKs with ET1 and the selective TRPV4 activator 4α-PDD. Moreover, this response was significantly attenuated by ET(R)-A inhibition, and greatly diminished by ET(R)-B inhibition (FIG. 7B). Selective antagonism of ET(R)s led to attenuation for both compounds, yet showed a slight difference to the pattern observed with UVB, namely co-dependency for both ET(R)s for UVB, and recruitment of ET(R)-B more than -A for 4α-PDD. Given the pleiotropic effects of UVB, these minor differences were not surprising, and overall, the results provided compelling support for the interdependence of TRPV4 and ET(R) signaling in the response.

Figure 8C:
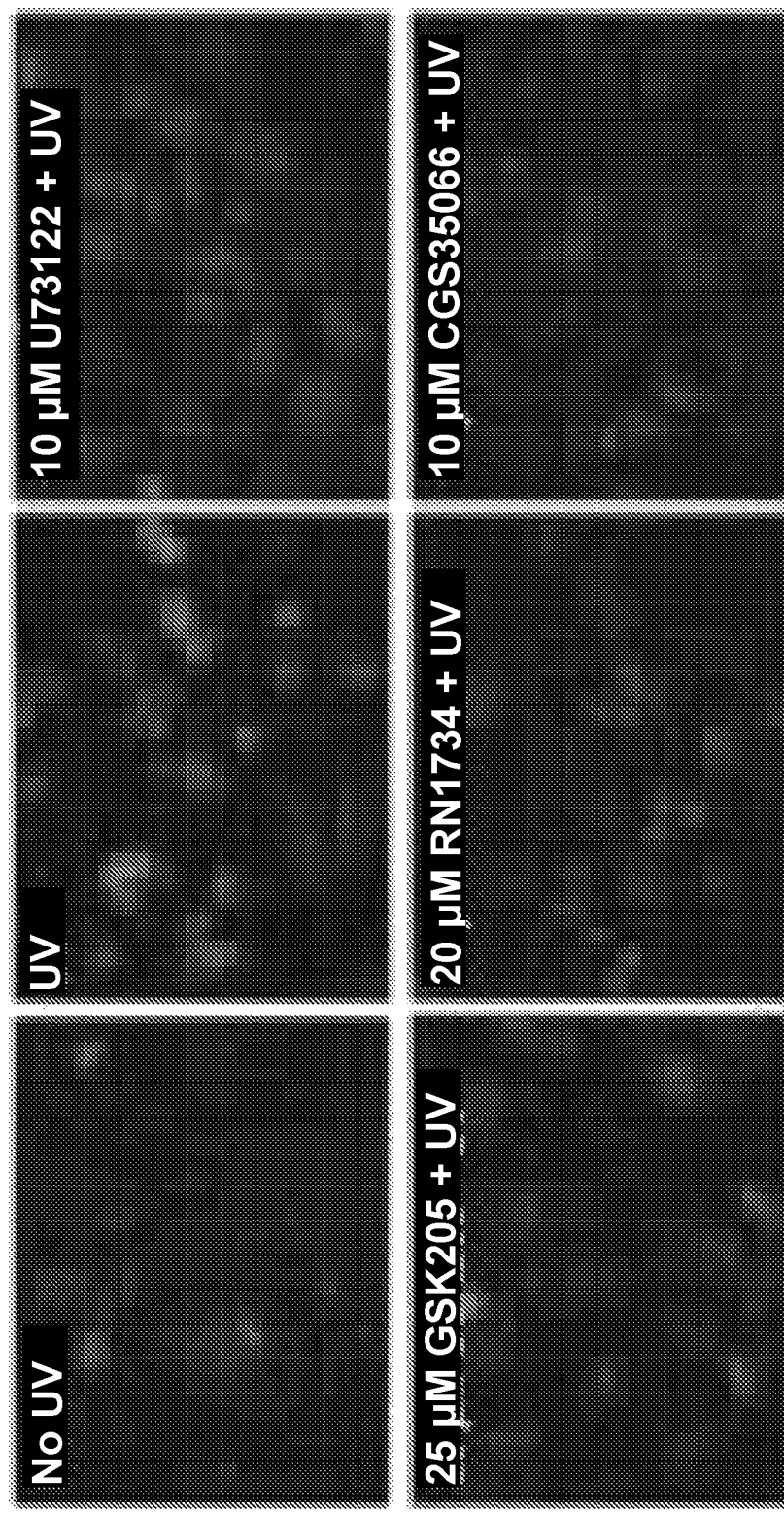
Figure 8D:
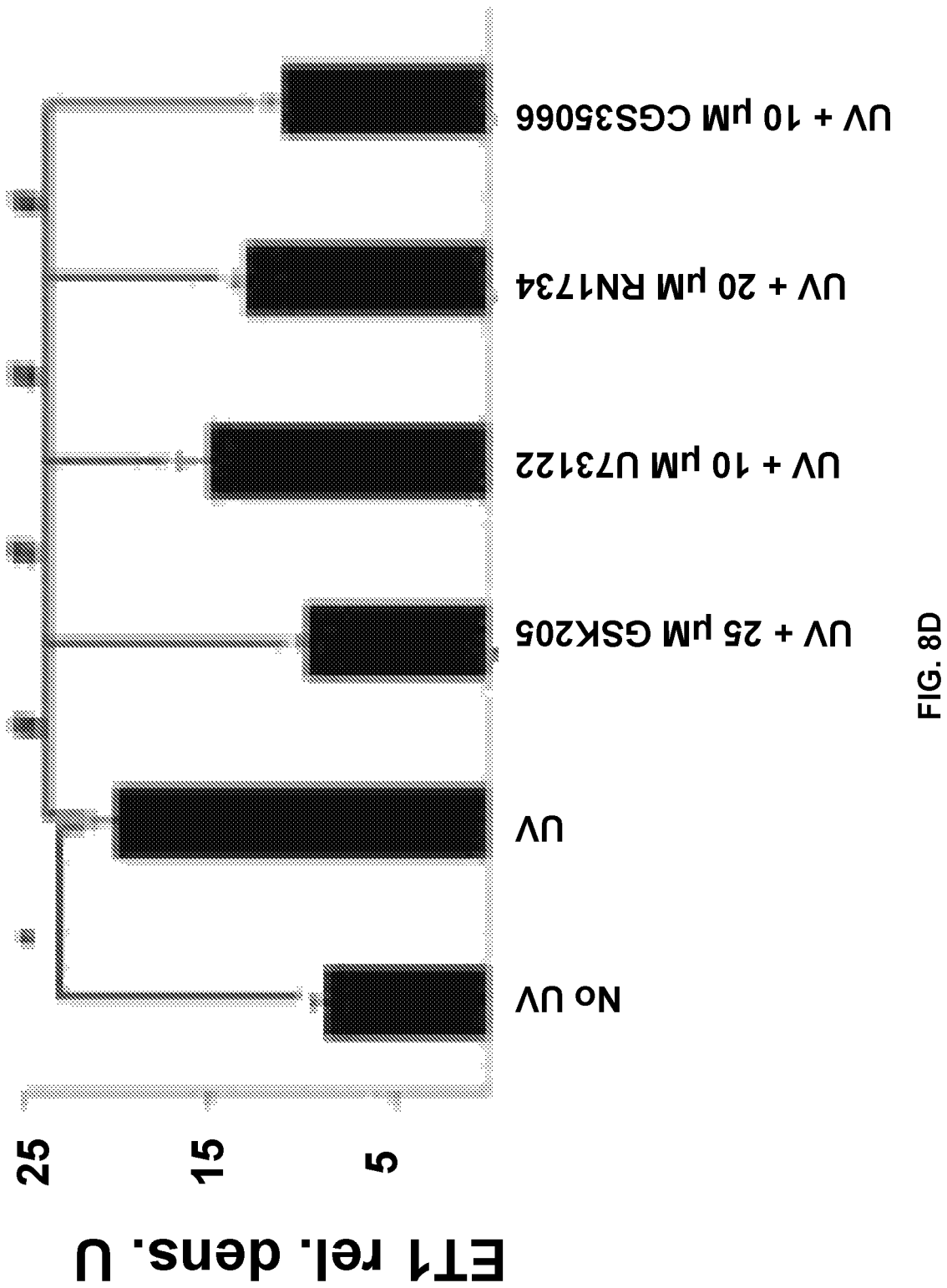

Interestingly, un-stimulated 1° MKs produced appreciable levels of ET1, secretory behavior which was dependent upon TRPV4 and PLC (FIG. 8B). We tested whether UVB causes ET1 upregulation in a TRPV4-dependent manner. Given the exquisite wave-length dependence of ET1 expression in 1° MKs, we resorted to the UVB-LED device as for Ca++ imaging (FIG. 6A and FIG. 2A-D). UVB-exposed 1° MKs showed increased ET1 immunolabeling, which was diminished when cells were preincubated with TRPV4-inhibitors, GSK205 and RN1734 (FIG. 8C-D). Consistent with its effects on UVB-evoked Ca++ transients, PLC-inhibitor U73122 also dampened ET1 expression. Together, these findings suggested a limited feed-forward mechanism that involves TRPV4-dependent increase of ET1 expression in response to UVB, and autocrine/paracrine signaling via ET(R)s. This leads to TRPV4-dependent Ca++ signaling, which in turn amplifies ET1 signaling in a paracrine/autocrine fashion.

Figure 7D:
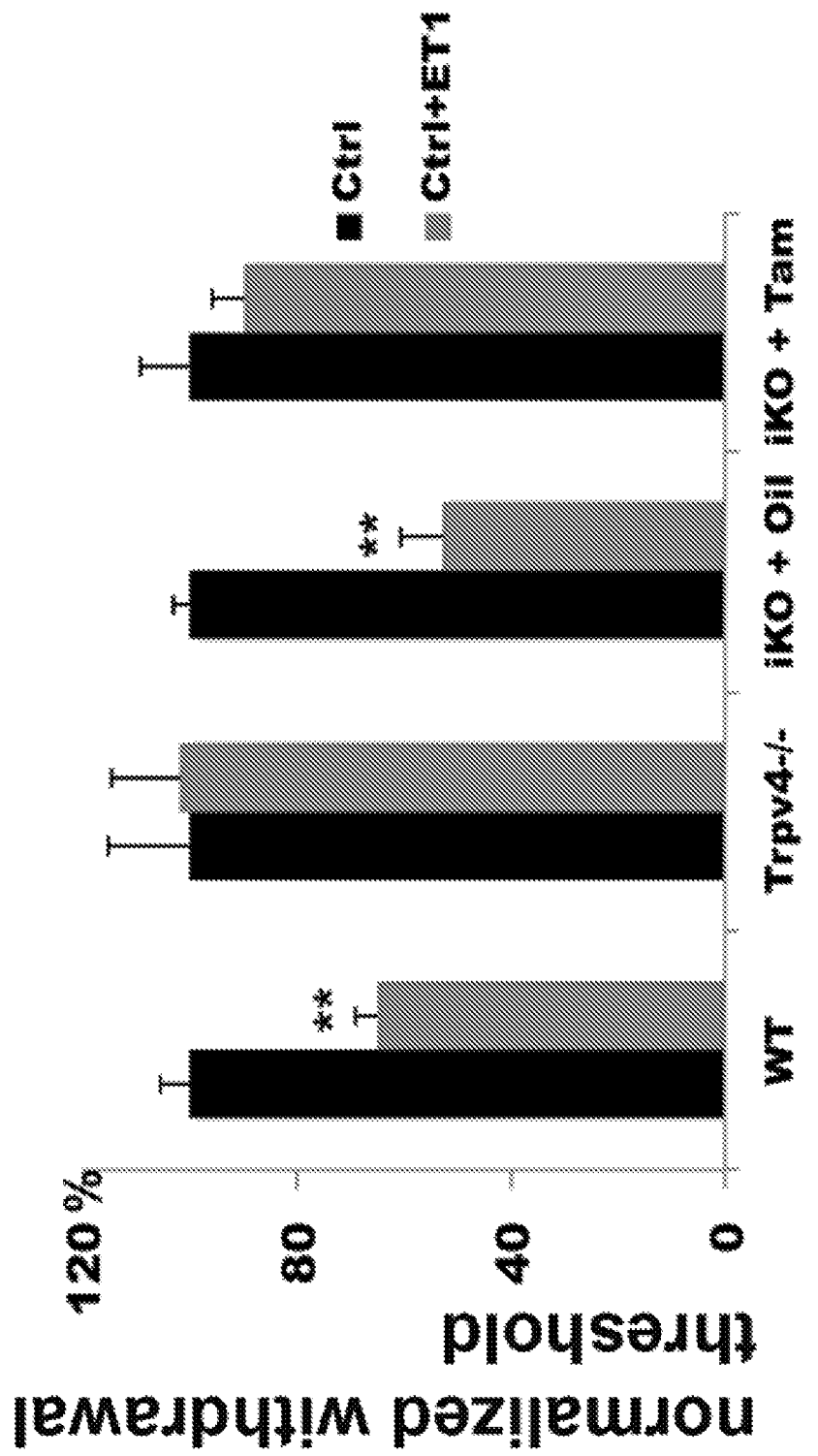

To assess the physiological relevance of our findings in vivo, we exposed paw-pads to UVB. An interesting time course of Edn1 mRNA expression was apparent in paw-pad skin of WT mice where it peaked after 120 min and relented at 24 hours, but remained significantly elevated. In contrast, there was no regulated expression of Edn1 in paw-pad skin of Trpv4−/− mice. These findings suggest a more direct regulation of Edn1 gene-expression by TRPV4 in response to UVB. ET1 was readily detected in control epidermis but reduced in TRPV4-deficient epidermis (FIG. 7C). TRPV4 was also critical for the facilitatory effect of ET1 on nocifensive behavior, as judged by the finding that the withdrawal thresholds in response to von Frey hair stimulation were significantly lowered in control but not Trpv4−/− mice, both pan- and conditional null, in response to subepidermal ET1 injections (FIG. 7D). This result suggested that ET1's pro-algesic/algogenic effect is fully dependent on TRPV4 in keratinocytes. Although previous studies had shown that ET1 is sufficient to elicit nocifensive behavior, the elimination of ET1's pro-algesic/algogenic effect in our Trpv4-conditional null mice was unexpected given that both ET(R)s and TRPV4 are expressed by sensory afferents, which were unaffected in our tam-treated iKO mice.

Example 8: UVB-Induced Activation of Inflammasomes by Keratinocytes Depends Upon TRPV4

Figure 9A:
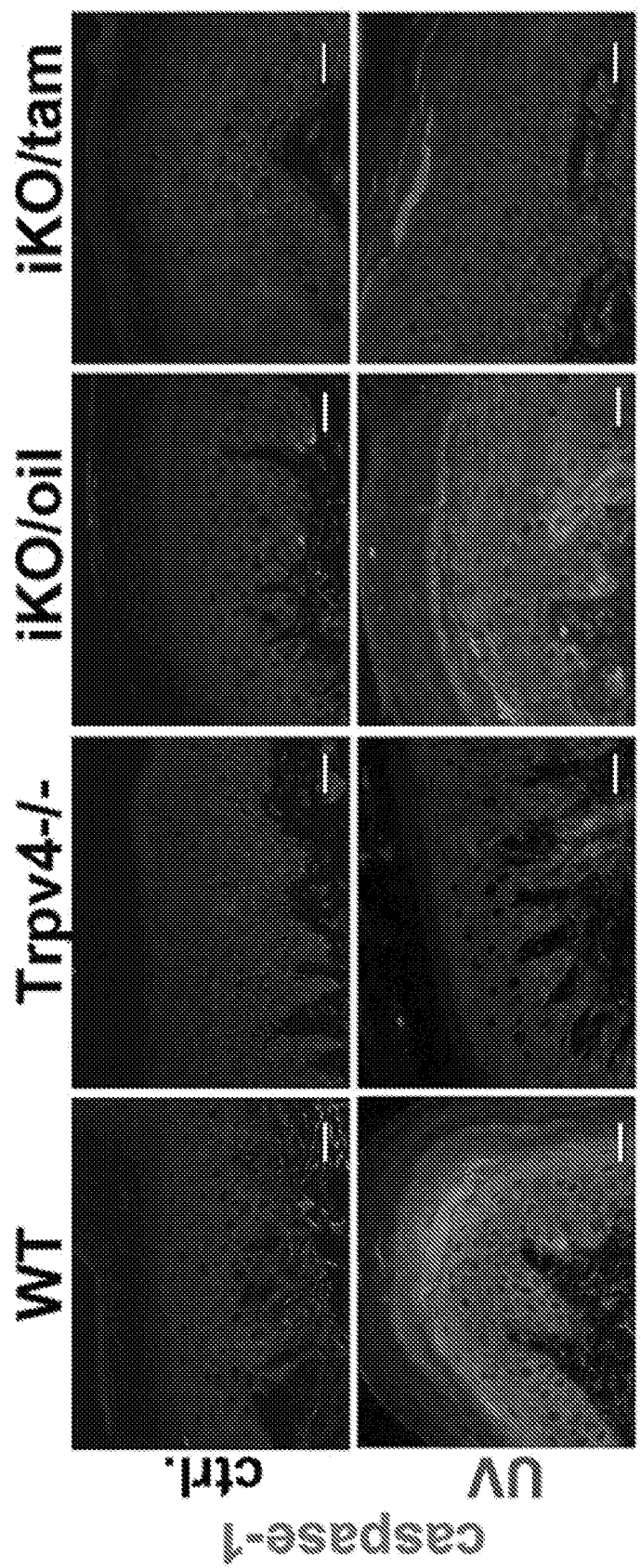

Another signaling mechanism linking UVB exposure to inflammation and nociception in keratinocytes is the inflammasome, a large multiprotein complex that assembles in response to infection and other cellular injury, and triggers an inflammatory cascade culminating in caspase-activation and production of cytokines IL-1 and IL-18. Previously, its formation was shown to depend upon Ca++ signaling, prompting us to query the dependence of inflammasome activation on TRPV4. Indeed, although caspase-1 was upregulated in UVB-treated control skin, this was largely eliminated in Trpv4−/− and greatly attenuated in tam-treated iKO skin (FIG. 9A-B). Moreover, even though caspase-1 cleavage (activation) was readily detected by Western blotting of lysates from WT 1° MK exposed to UVB, caspase-1 expression was lacking in Trpv4-null counterparts, even without UVB (FIG. 9C).

Figure 9F:
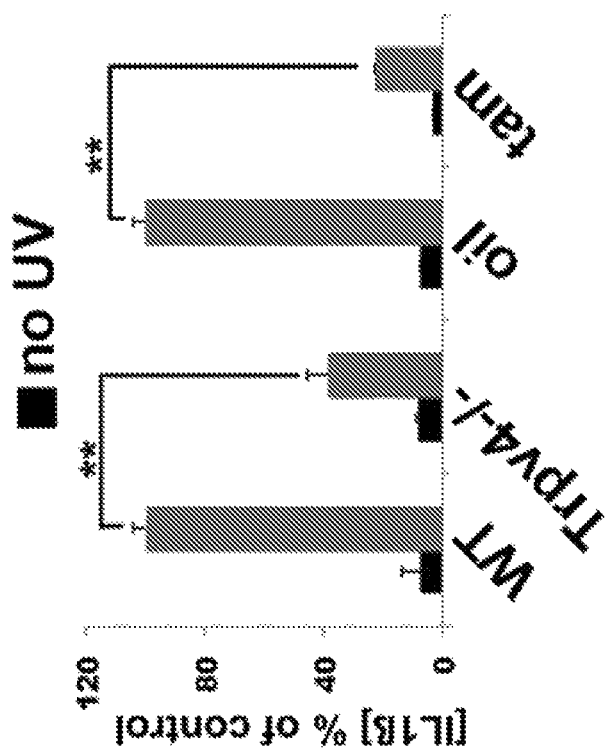
Figure 9E:
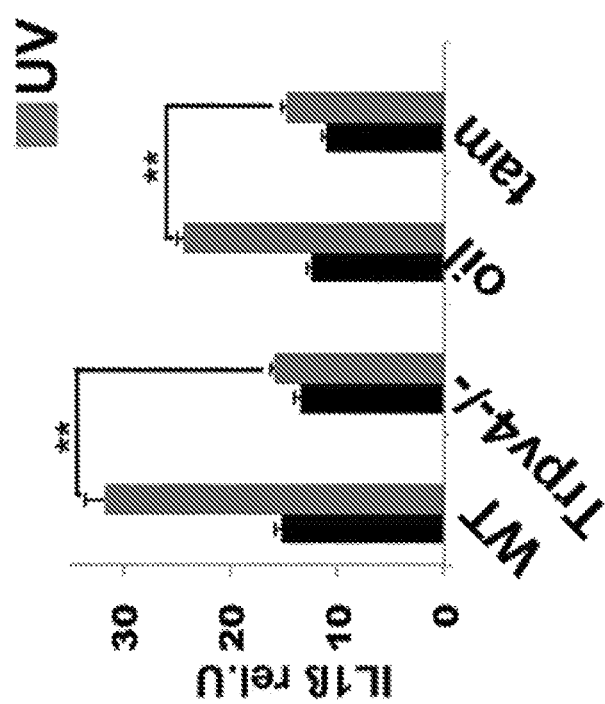

Similarly, upregulation of the pro-algesic inflammasome product IL-1β was readily detected in response to UVB treatment of control skin epidermis but not TRPV4-deficient epidermis. This was demonstrated not only by immunolabeling but also by measuring IL-1β levels in paw-pad edema interstitial fluid (FIG. 9D-F). Together, these results establish a fundamental importance of TRPV4 in keratinocyte-mediated activation of inflammasomes, which enhance caspase-1-mediated proteolytic cleavage of pro-IL-1β to form active IL-1β.

Figure 9G:
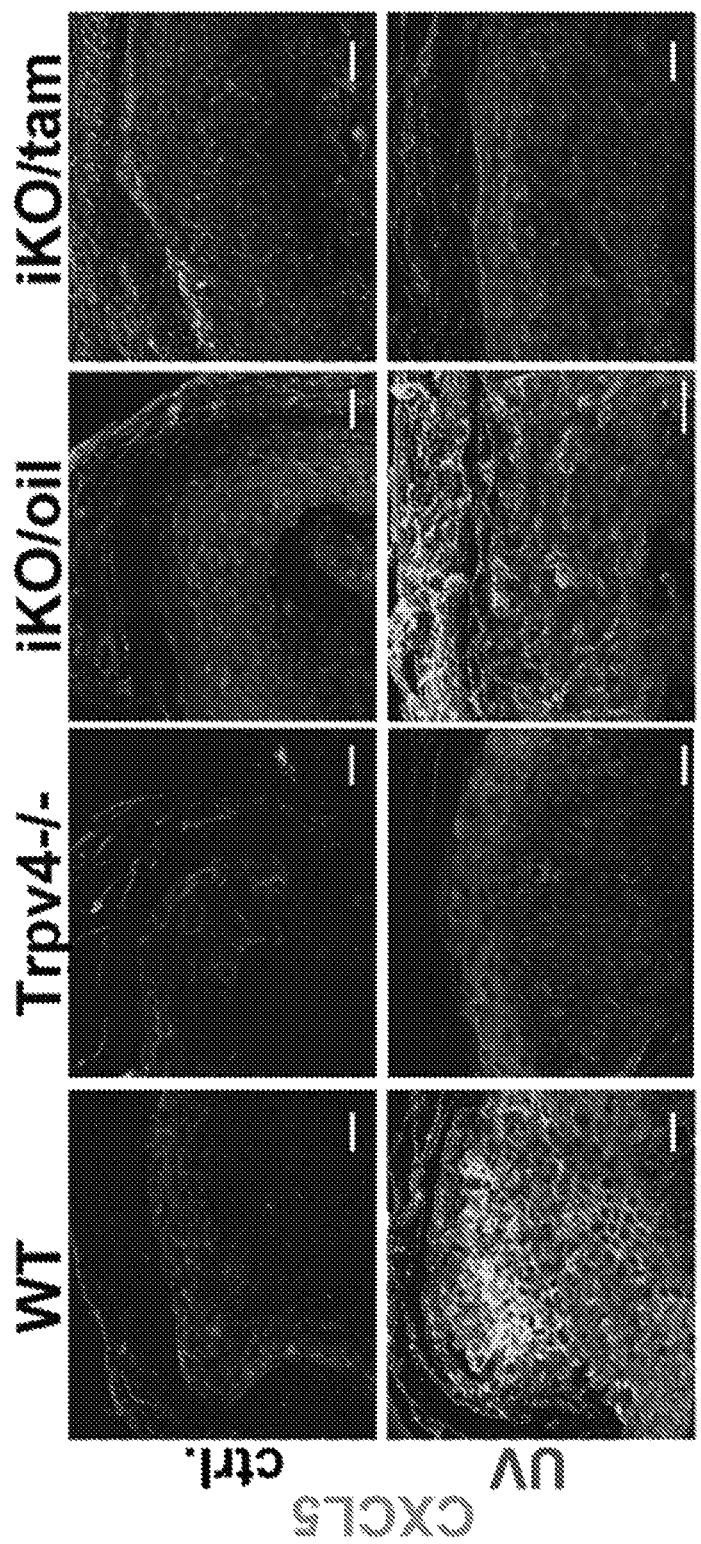
Figure 9H:
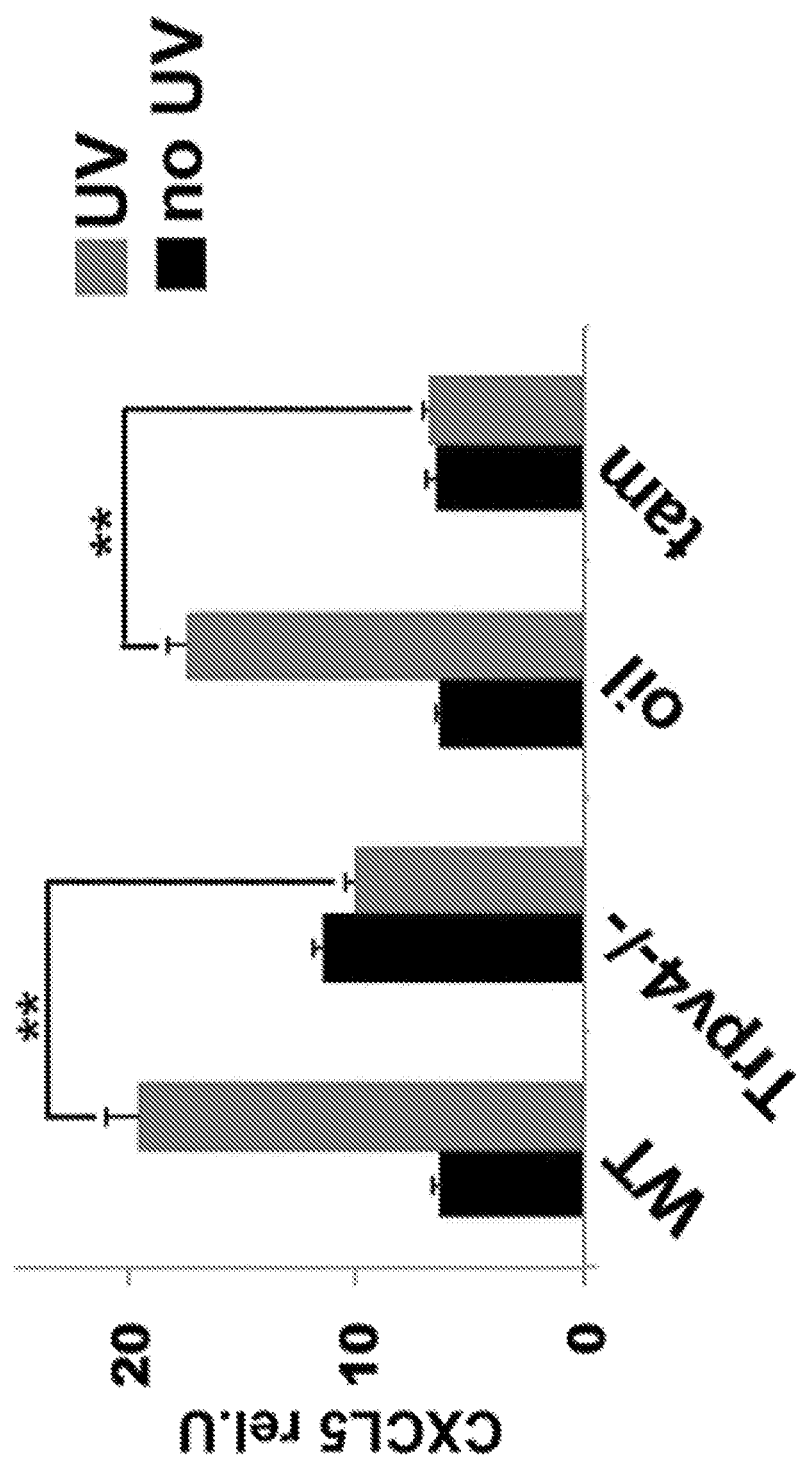

Related to IL-1β secretion by skin in response to UVB, we queried dependence of CXCL5 on Trpv4. CXCL5, whose expression is dependent upon IL1β/IL1R1 signaling, has recently been reported to function in a proalgesic/algogenic manner in keratinocytes in response to UVB in rodents and humans. Consistent with the reliance of inflammasome function and IL-1β expression on TRPV4, we found that similarly, UVB-induced proalgesic/algogenic CXCL5 upregulation is also dependent upon keratinocyte-derived TRPV4 (FIG. 9G-H).

Figure 10A:
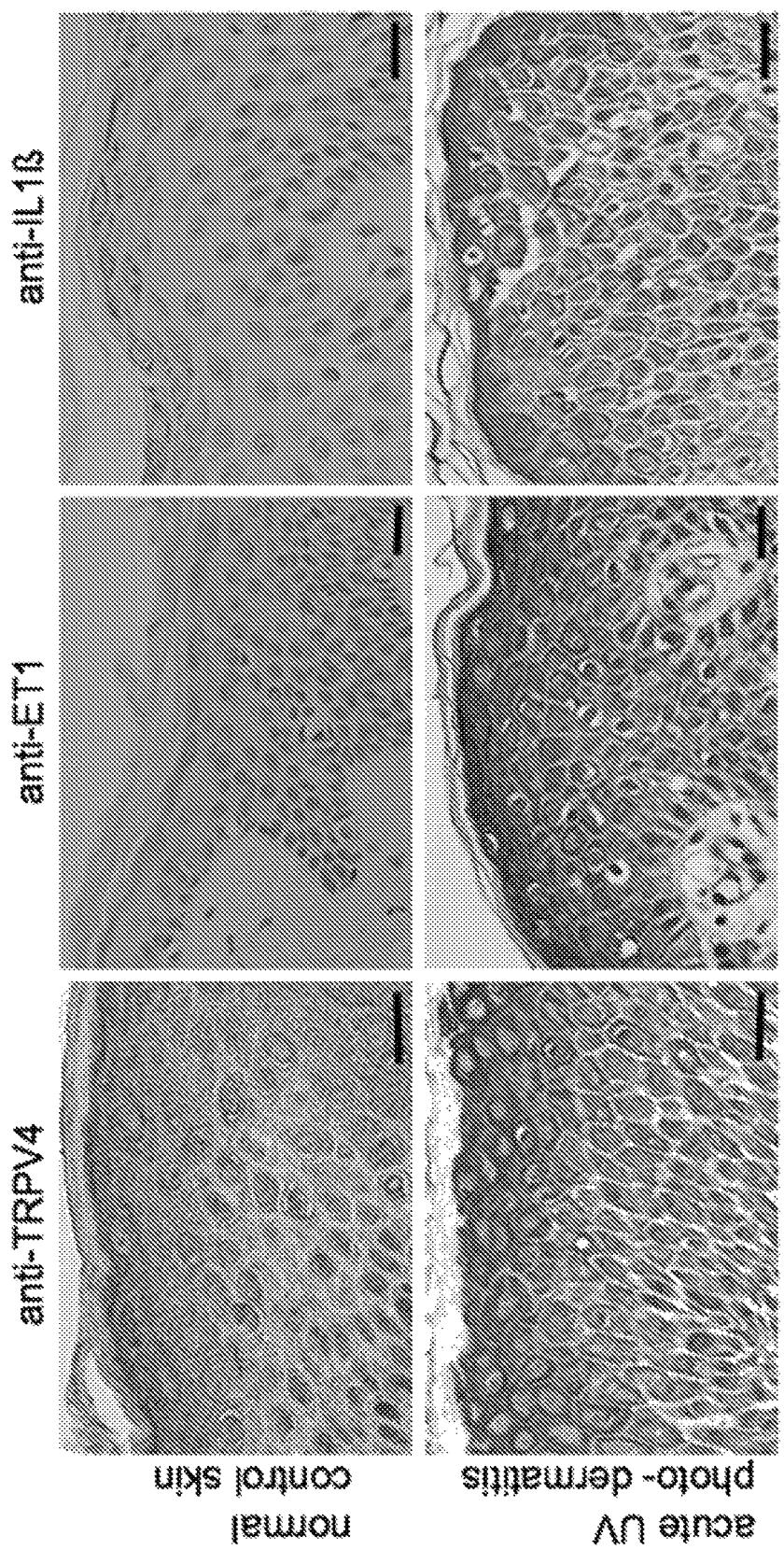
FIGS. 10A-10B: Epidermal TRPV4, ET1 and IL-1β are elevated in photodermatitis as compared to healthy human skin.
Figure 10B:
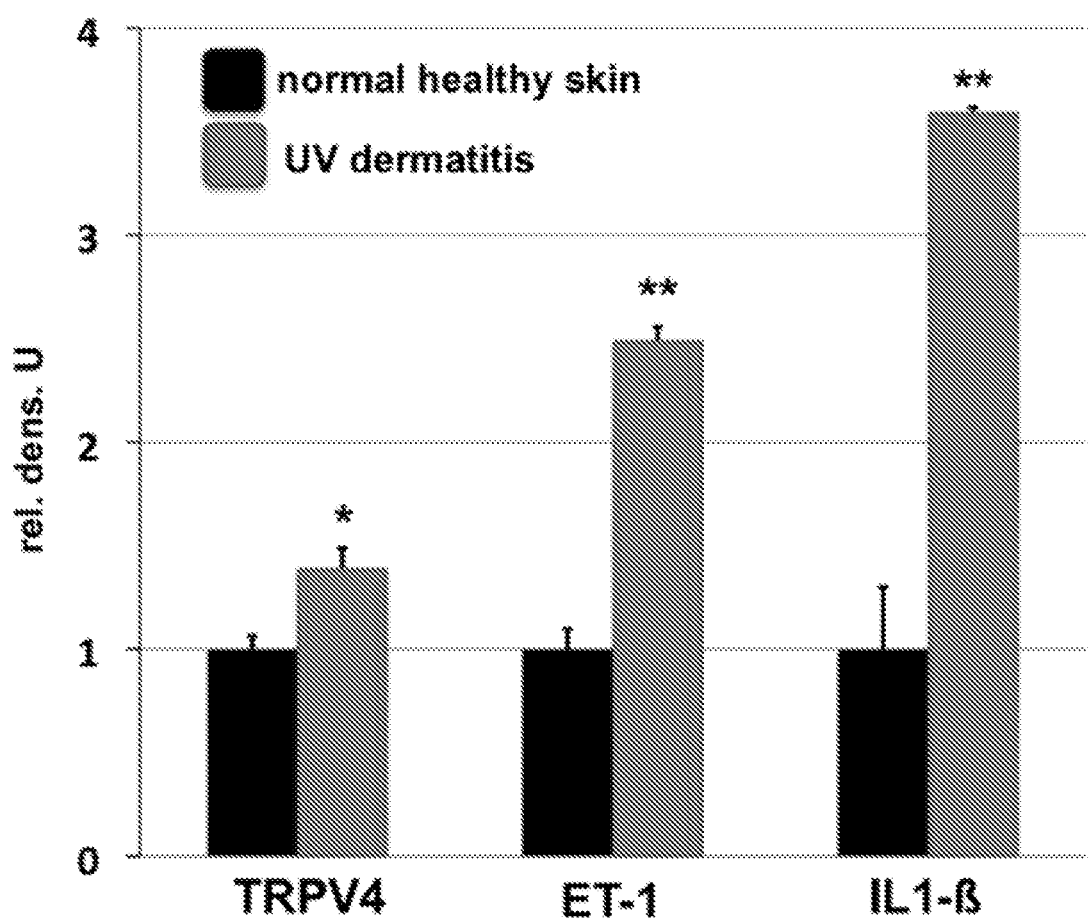
Figure 11:
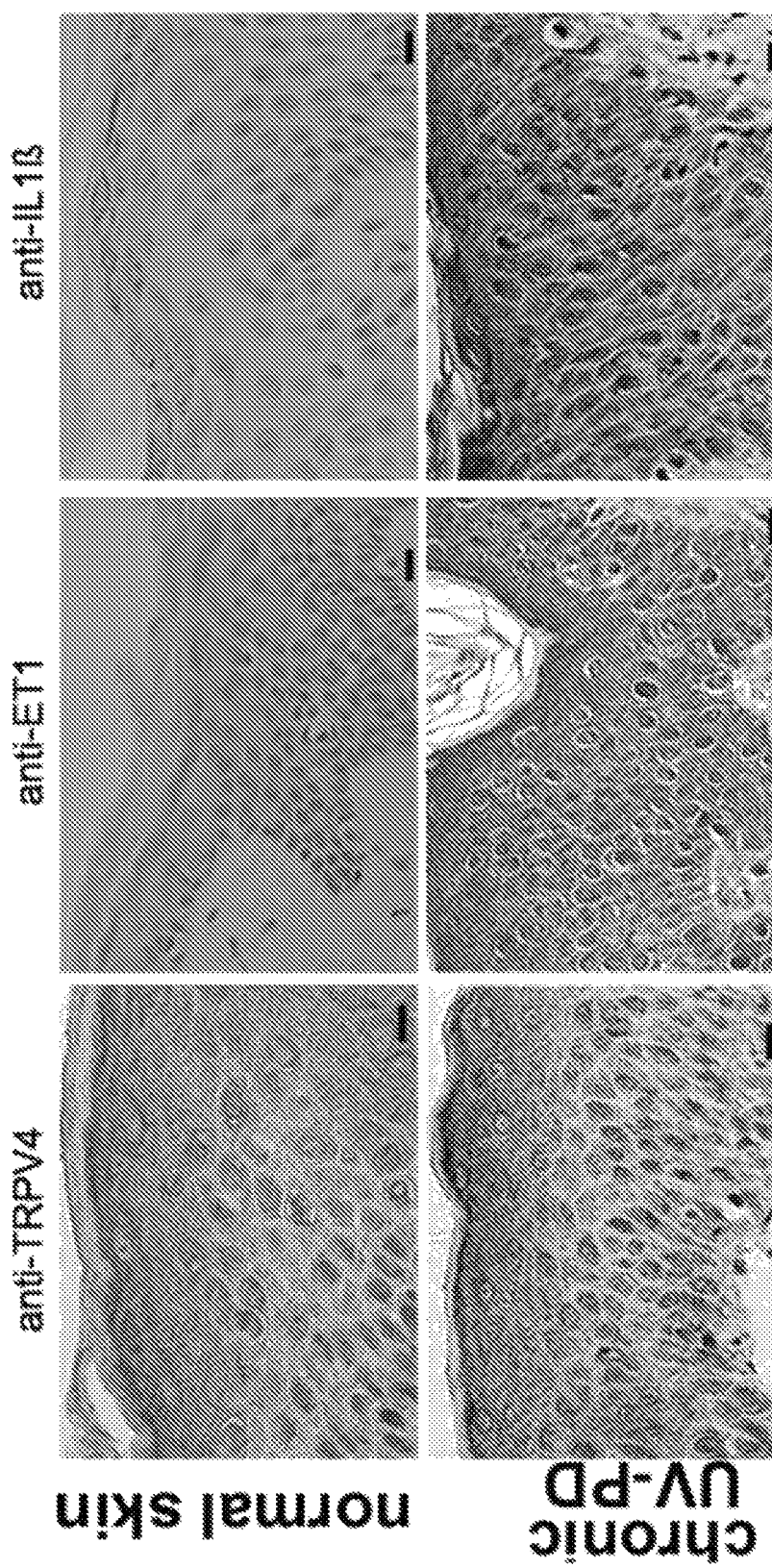
FIG. 11: Exemplars of human chronic photodermatitis. Upper panel shows normal healthy human skin, as displayed in FIG. 10A, for comparison. Lower panel shows examples of chronic photodermatitis with elevated expression of TRPV4, in spinous and basal layers, ET1 (throughout) and IL-1β (throughout). In comparison to acute photodermatitis, note reduced interstitial intraepidermal edema. Bar=50 μm.

Example 9: Clinical Relevance of Epidermally-Derived TRPV4 in Transmitting Nociceptive Responses to UVB Exposure Interestingly, TRPV4 was significantly increased in the epidermis of human patients with UV photodermatitis (FIG. 10A and FIG. 11). As compared to healthy skin controls, a robust increase was also seen for ET1 and IL-1β immunostaining in acute photodermatitis (FIG. 10A-B). These findings suggest that TRPV4 is also likely to be involved in UVB-induced photodermatitis, one of the various responses of human skin to damaging UV radiation.

Figure 12A:
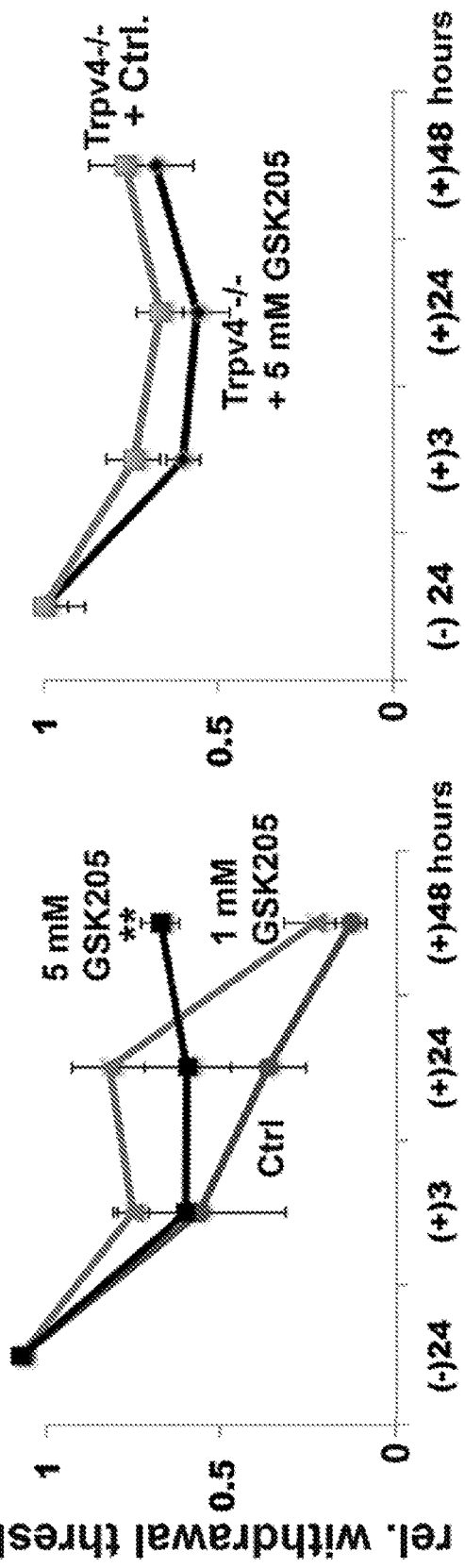
FIGS. 12A-12D: External-topical application of a selective TRPV4 inhibitor attenuates UVB-evoked nocifensive behavior and inflammation.

In view of the observed impact of epidermal-specific TRPV4-deficiency on mouse nociception in response to UVB, and because of the unambiguous effects of selective TRPV4 blockers on 1° MK in vitro, we tested the possible clinical relevance of our findings. For this purpose, we topically applied TRPV4 inhibitor GSK205 to WT mouse skin and subsequently exposed animals to UVB (FIG. 12A). While solvent-treated control mice displayed a normal thermal hypersensitivity response, mice treated with 1 mM GSK205 showed a ~24 hour delay in sensitivity, and increasing the dose to 5 mM GSK205 resulted in a sustained attenuation of thermally-evoked nocifensive behavior. Of note, this treatment also resulted in a significantly reduced sensitivity of mice to von Frey hair mechanical stimulation.

To assess specificity of the external-topical treatment, we applied 5 mM GSK205 to Trpv4−/− mice vs. vehicle control (FIG. 12A). Nocifensive behavior did not show any inter-group differences, yet was significantly different from pre-stimulation thresholds. Based upon these results, topical treatment with 5 mM GSK205 in vivo did not elicit off-target effects on other channels or signaling pathways that might measurably influence withdrawal behavior. Although GSK205-mediated antagonism of macrophage and neural TRPV4 cannot be excluded, the epidermis is the initial target of topically applied drugs, and the effects we measured with 5 mM GSK205 were consistent with those we observed in Trpv4 tam-induced iKO skin.

Figure 14A:
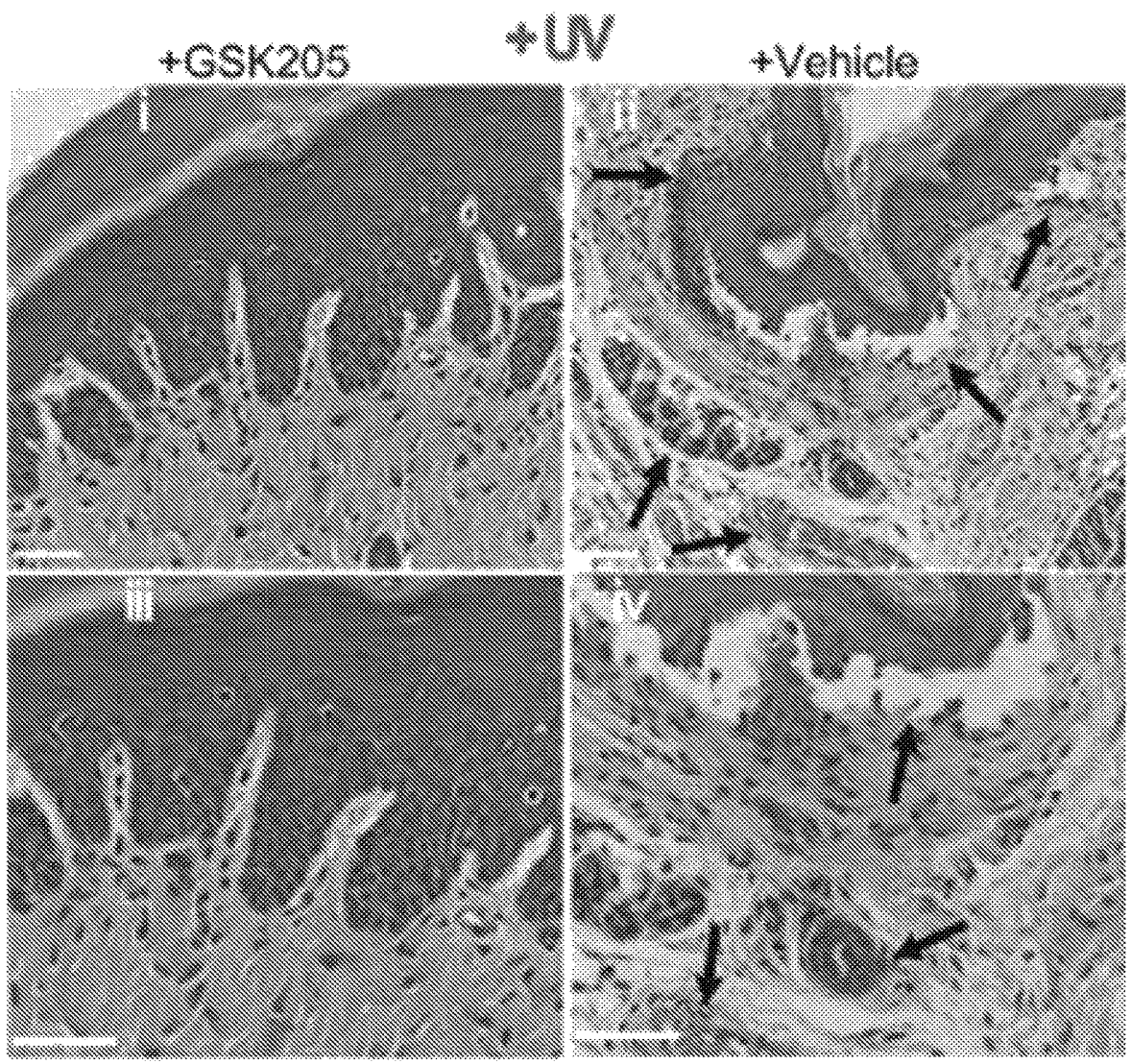
Figure 14B:
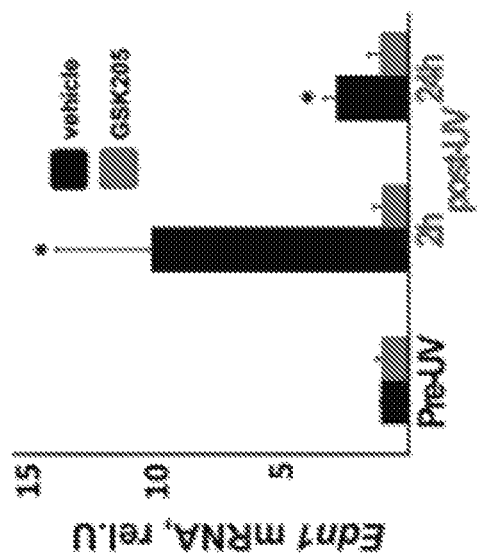
(FIG. 14B) Topical treatment with a TRPV4-specific inhibitor attenuates upregulation of algogenic ET1/Edn1. Edn1 mRNA was determined by qPCR after extraction of total RNA from paw-pad epidermis. In vehicletreated skin, note increase of Edn1 expression with early up-regulation at the 2 hour time-point, and sustained elevation up to the 24 hour time-point. This time-course resembles that seen in WT control mice, when comparing to Trpv4−/− (FIG. 15). Importantly, topical treatment with 5 mM GSK205 results in complete lack of this regulation; n=4 mice/group, *p<0.05 ANOVA.
Figure 15:
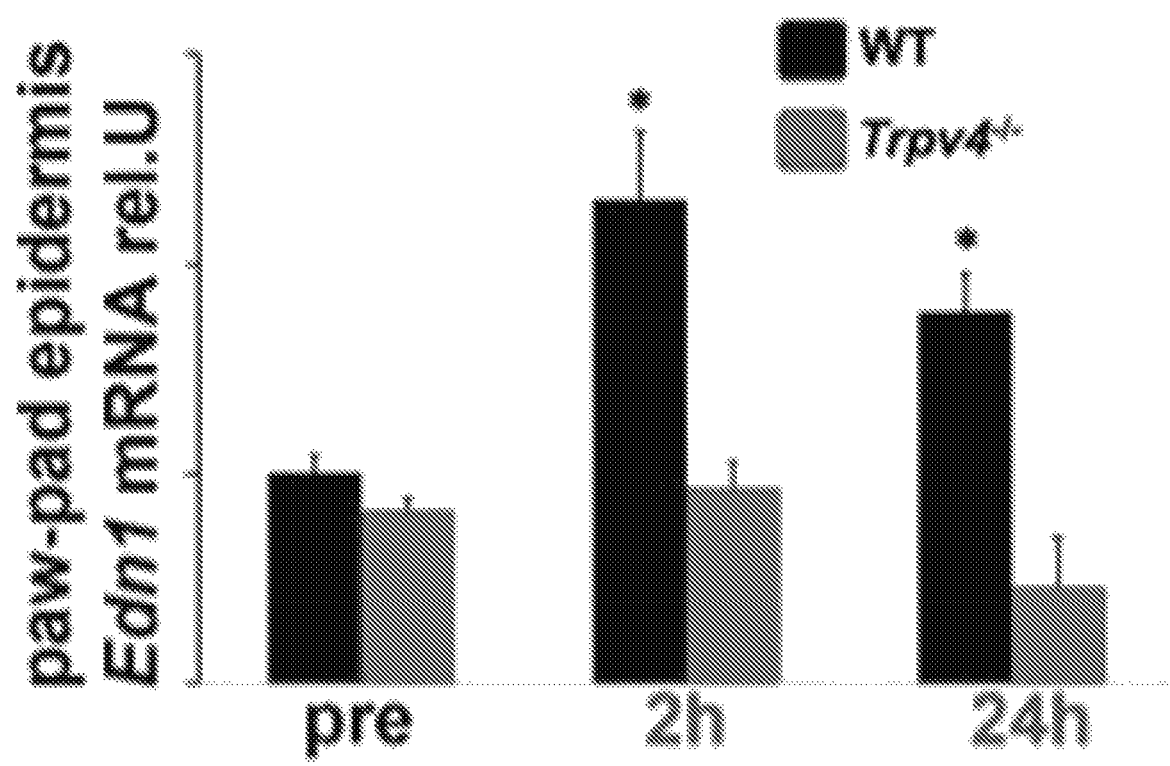
FIG. 15: Upregulation of ET1/End1 in mouse paw in response to UVB. Edn1 mRNA was determined by qPCR after isolation of total RNA from paw-pad epidermis. Note the early increase, at the 2 hour time-point, in WT control epidermis, and its complete lack in Trpv4−/−, and sustained upregulation at 24 hours, slightly reduced vs. 2 hour time-point, again complete lack of upregulation in Trpv4−/−. Quantifications are for n=4 mice/group. ** denotes statistically significant (p<0.01, t-test).

Histopathology of GSK205-topically-treated skin showed hallmarks of UVB-photodermatitis in vehicle-treated paws, strikingly contrasting to GSK205-treated animals (5 mM), whose paws showed virtual elimination of inflammation (FIG. 14A). In view of TRPV4-dependence of ET/Edn1 expression in skin, we measured Edn1 mRNA abundance in GSK205 vs. vehicle treated paw-pad skin. We detected an early upregulation in vehicle-treated mice at the 2 hour time-point which was still significantly elevated over preexposure animals at 24 hours, resembling Edn1 regulation and time-course in untreated WT mice (FIG. 14B, compare to FIG. 15). In striking contrast, and in keeping with histopathology, Edn1 mRNA-expression in GSK205 topically-treated skin was found unchanged.

Figure 14C:
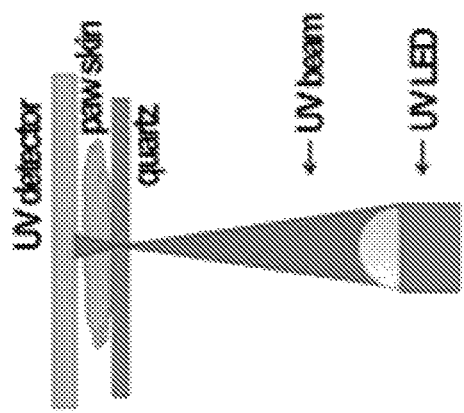
(FIG. 14C) GSK205 does not function as sunscreen. Schematic illustrates the experimental set-up.
Figure 14D:
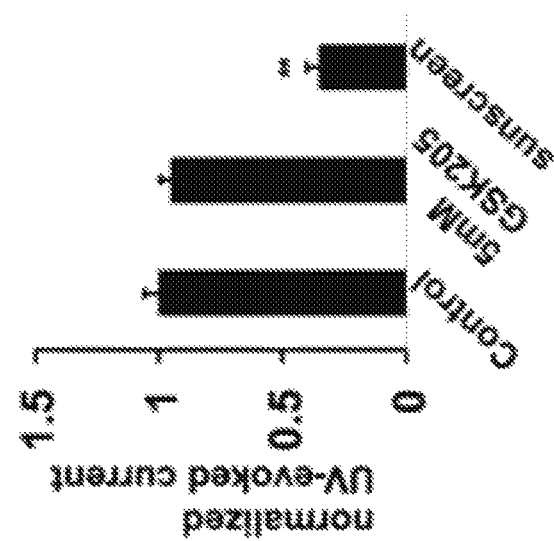
(FIG. 14D) GSK205 does not function as sunscreen. The bar diagram shows results from n=7-8 mice/group, note absence of a change in UVB permeation with 5 mM GSK205, topically applied as for (B), vs. vehiclecontrol, yet significantly reduced with sunscreen SPF100.

To validate these finding, we tested UVB absorption in GSK205-treated paw-pad skin, and whether GSK205 thus functions as sunscreen. Results were negative, as demonstrated by equal UVB permeation of GSK205-vs. vehicle-treated paw-pad skin, yet valid, as demonstrated by significant decrease of UVB permeation with SPF100 sunscreen (FIG. 14CD and FIG. 16AB). These results corroborate that effects of topically applied GSK205 are caused by TRPV4 antagonism, likely by affecting TRPV4 in epidermal keratinocytes.

Figure 12B:
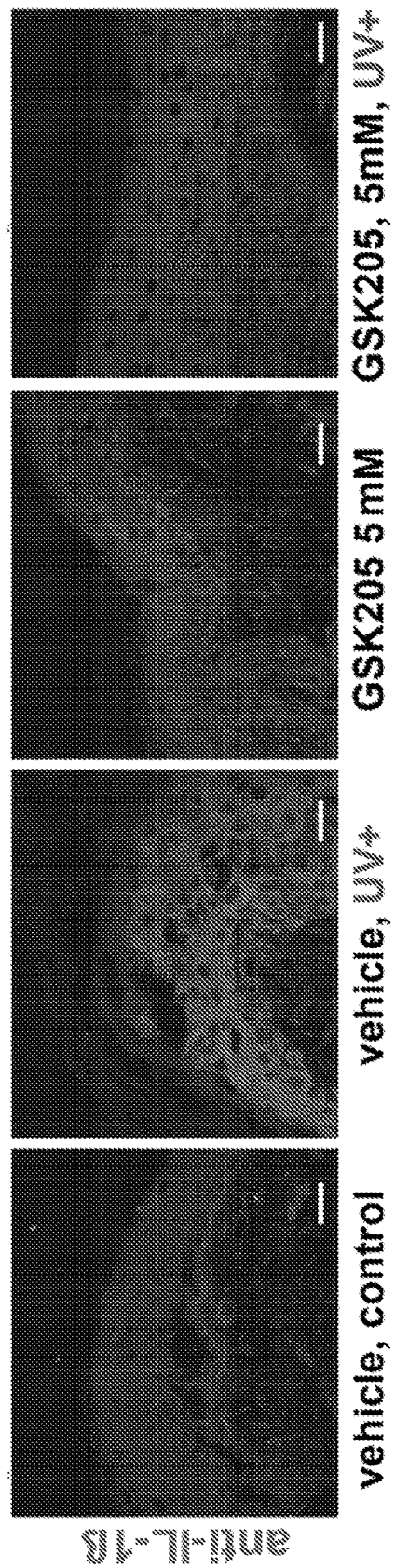
Figures 12C, 12D:
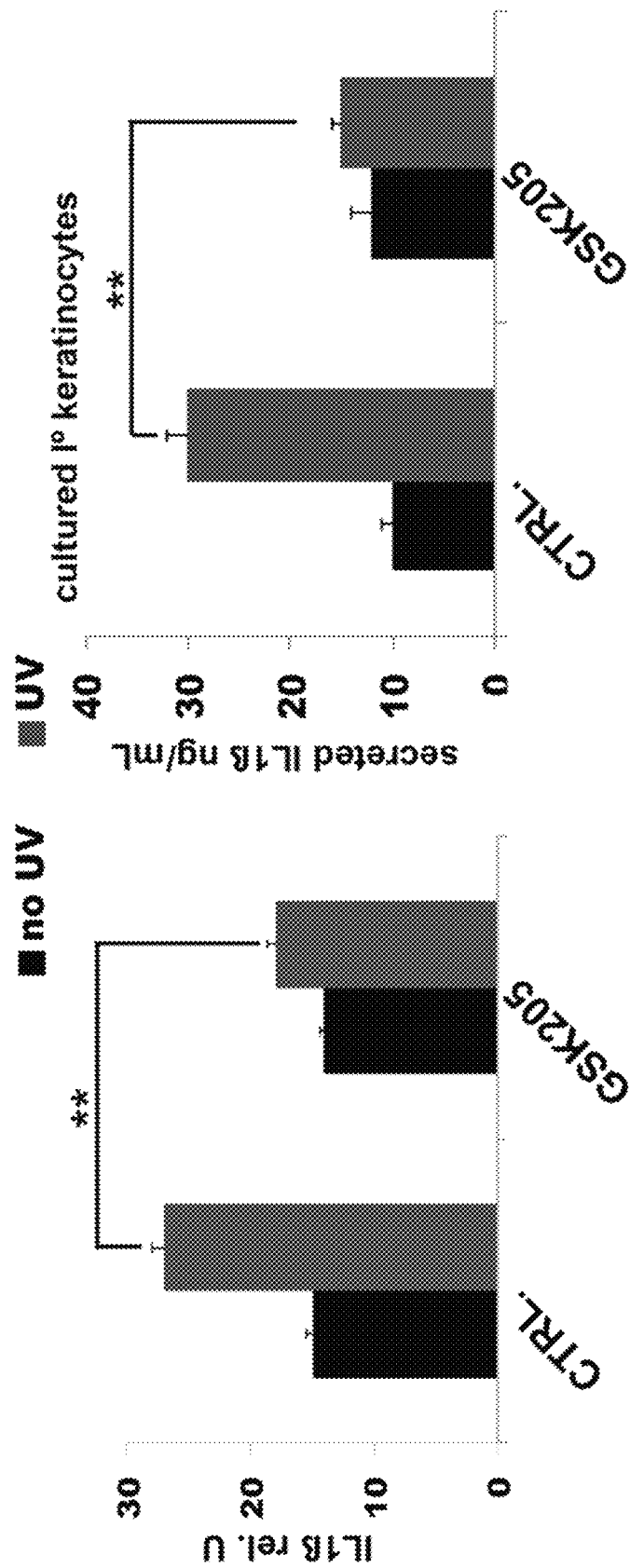
Figure 13A:
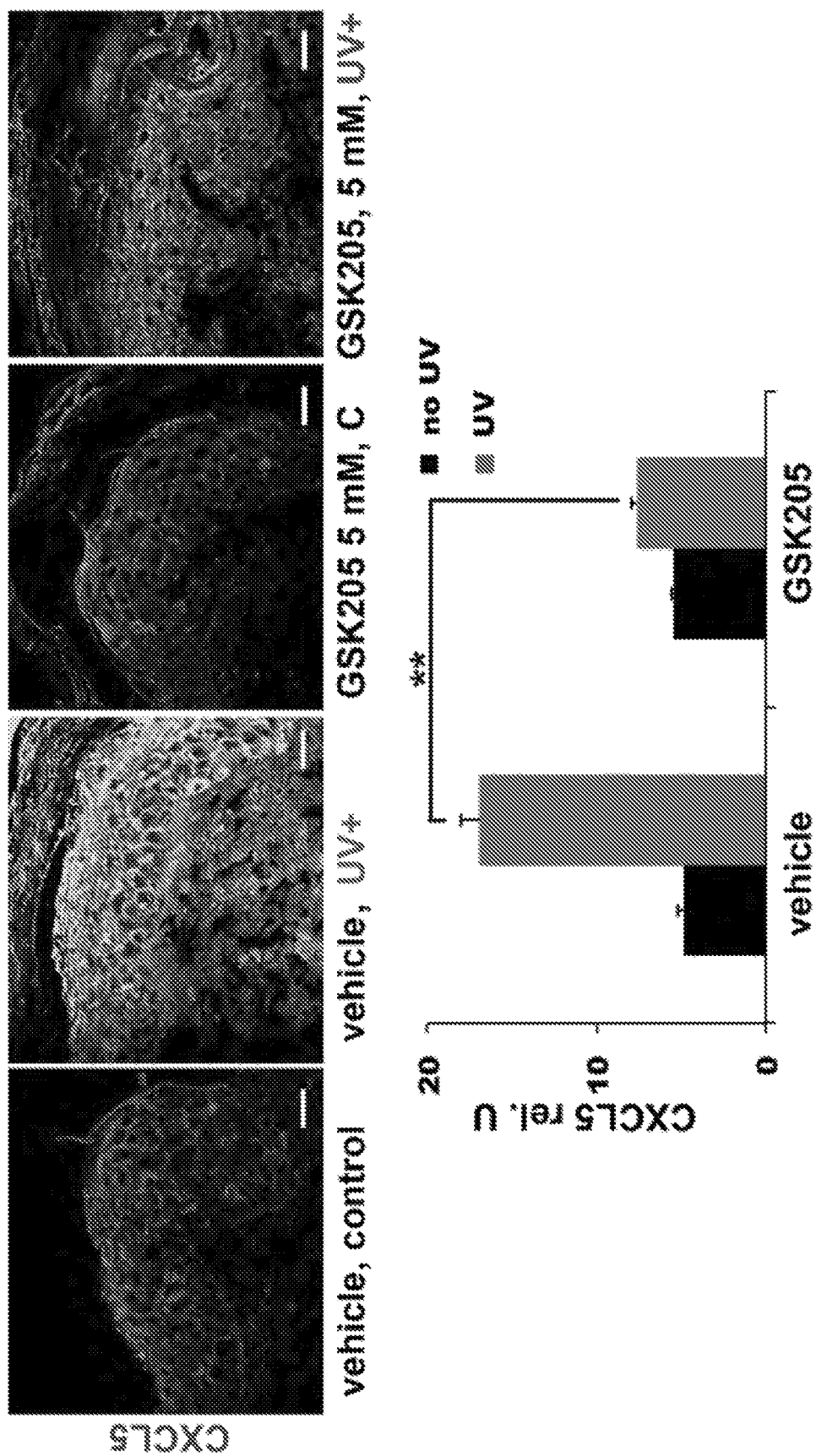
FIGS. 13A-13B: Topical application of a selective TRPV4 inhibitor attenuates UVB-evoked nocifensive behavior by suppressing upregulation of pro-algesic/algogenic mediators in murine keratinocytes—Findings for CXCL5 and IL6.
Figure 13B:
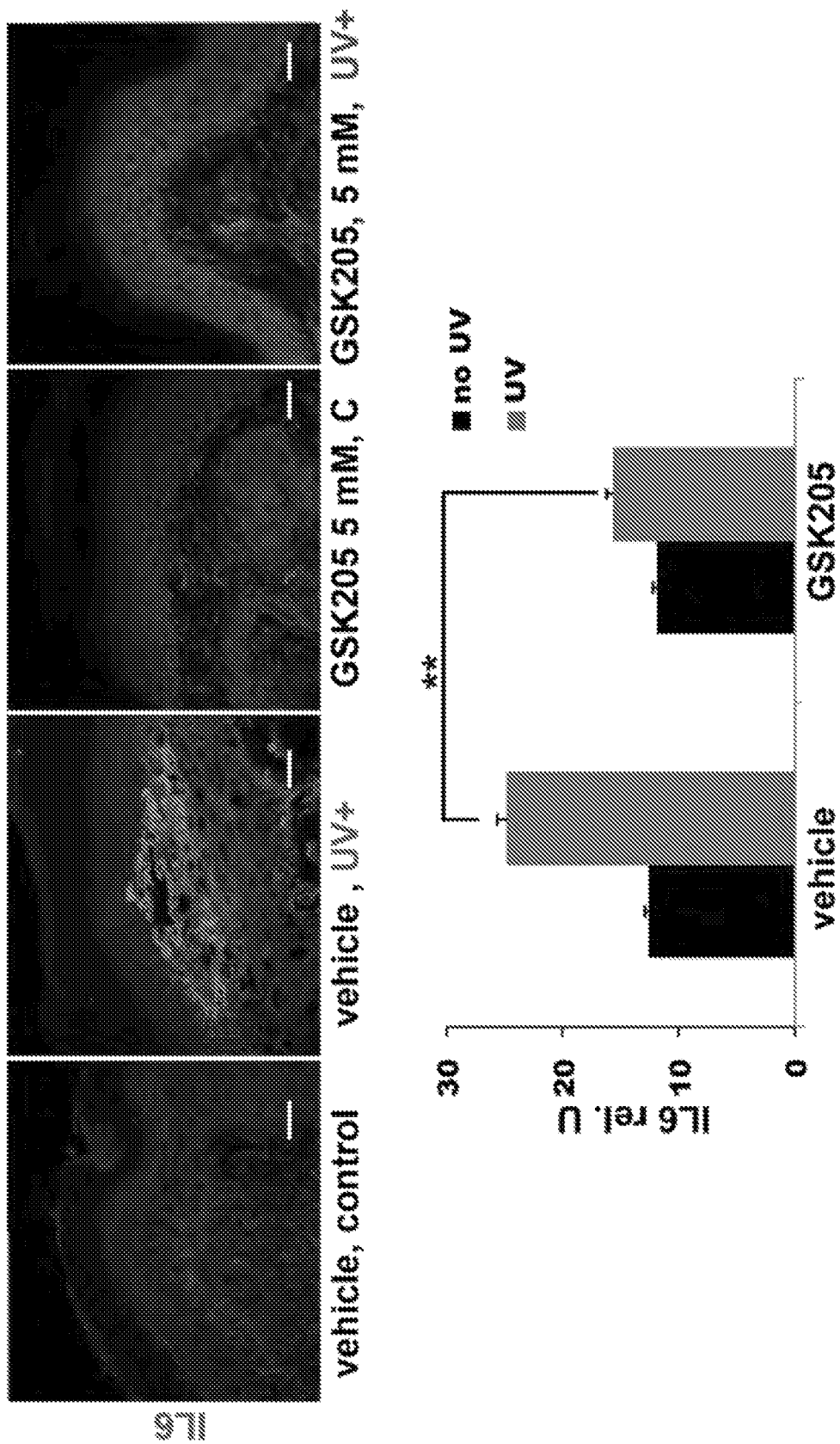

We also tested the response of down-stream UVB effector mechanisms to GSK205 treatment in vivo. In mouse skin, IL-1β was upregulated in response to UVB with vehicle treatment, yet failed to upregulate with 5 mM GSK205 (FIG. 12B-C). This in vivo finding was recapitulated in 1° MK whose UVB-induced increase in IL-1β secretion was completely eliminated in the presence of 5 μM GSK205 (FIG. 12D). Comparably significant blocks were observed on CXCL5 and IL-6 upregulation (FIG. 13A-B).

Thus, the UVB-evoked signaling in the epidermis was reduced both when TRPV4 was antagonized by topical application of specific small molecule inhibitors, and when Trpv4 was targeted genetically in our keratinocyte-specific and inducible Trpv4 conditional null mice. This suggests ion channel function of TRPV4 to be the critical factor common to both experimental approaches. Taken together, these findings render selective TRPV4 blockers, such as GSK205, excellent candidates for therapeutic approaches to reduce damaging inflammatory responses caused by UVB exposure in humans.

Example 10: Importance of TRPV4 for the Itch-Response

Figure 17:
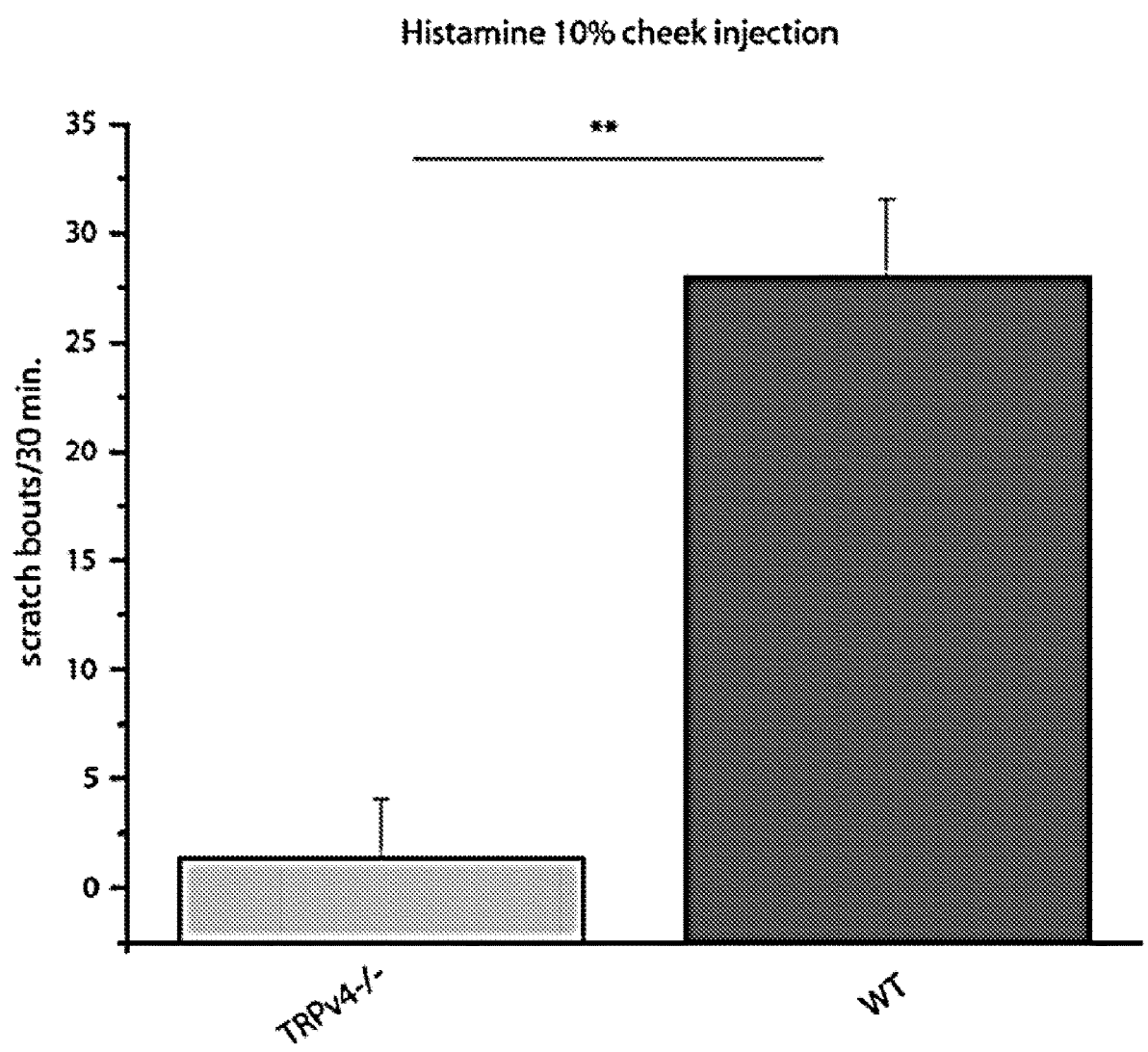
FIG. 17: Role of TRPV4 in itch transmission in mice in vivo. Histamine (10%) was injected intracutaneously into the cheek of C57bl/6 control (WT) or TRPV4 knockout mice (Trpv4 pan-knockout; n=6 per group). Over 30 min, TRPV4 null mice showed a significant reduction ((p<0.01) t-test)) of itch-behavior as compared to WT mice.

Behavioral studies show reduced scratching behavior in Trpv4 null mice compared to WT mice. Histamine (10%) was injected intracutaneously into the cheek of C57b/6 control (WT) or Trpv4 null mice (n=6 per group). Over 30 min, Trpv4 null mice showed a significant reduction ((p<0.01) t-test) as compared to WT mice (FIG. 17). The results demonstrated that similar to TRPV1 and TRPA1, TRPV4 is involved in itch, and that blockers of TRPV4 activation may be beneficial for the treatment of itch.

Example 11: Evidence for the Role of TRPV4 in Itch

It was further examined whether TRPV4 has a role in itch using mice with a selective TRPV4 deletion and Compound 48/80. Compound 48/80 (available from Sigma-Aldrich, St. Louis, Mo.) is a well-established pruritogen and elicits histamine-dependent itch by degranulating mast-cells. Mice were used in which TRPV4 channels had been selectively deleted in skin keratinoctyes by gene targeting, and the targeted allele was induced by feeding of tamoxifen, as detailed in Example 2. Wild-type mice were used as a control.

Figure 18:
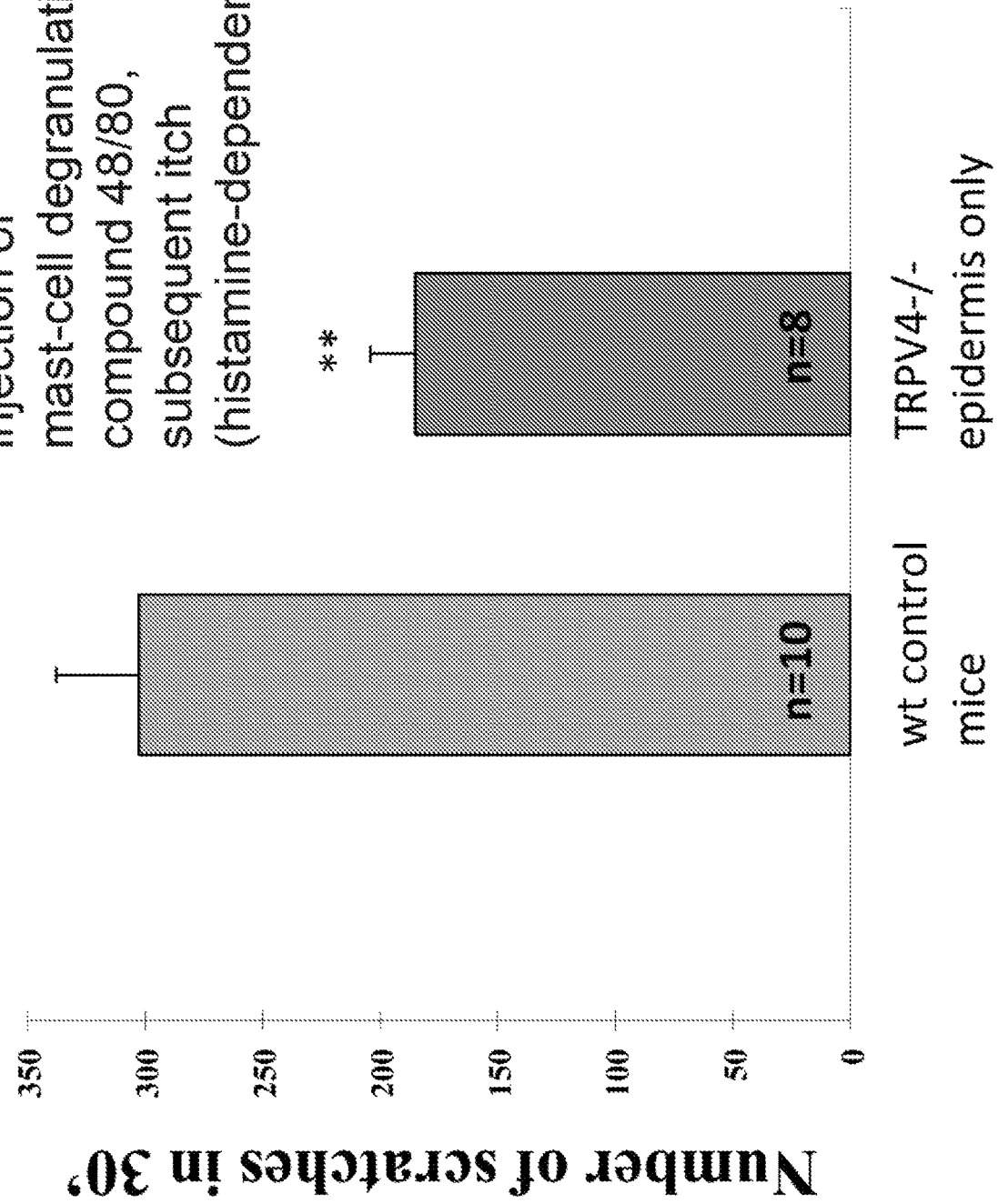
FIG. 18: The role of TRPV4 in itch. Shown is a graph of scratching behavior after administration of a pruritogen in mice with TRPV4 deletion in keratinocytes after induction of the TRPV4 knockout, as compared to mice without induction. Without induction, the mice function as wild-type control mice (Moore et al. *Proc. Natl. Acad. Sci. U.S.A.* 2013, 110, E3225-E3234). Compared to control mice, scratch behavior was significantly reduced for mice in which TRPV4 channels had been selectively deleted in skin keratinoctyes.

Compound 48/80 (100 micrograms in 50 μL) was injected retro-auricularly into the mice, and mouse scratch behavior in response thereto was monitored. Results are shown in FIG. 18. Compared to control mice, scratch behavior over 30 min was significantly reduced for mice in which TRPV4 channels had been selectively deleted in skin keratinoctyes.

The results provided additional evidence for the role of TRPV4 in itch, and in particular, dependence of itch on the TRPV4 ion channel expressed in keratinocytes of the skin. The results clearly indicated that TRPV4 in skin epithelial cells (keratinocytes), and not sensory neurons or immune-related or allergy-related cells, is the critical site of TRPV4 expression and function in histamine-dependent itch. These findings also suggested that topical targeting of TRPV4 channels may be successful in combating itch.

Example 12: Overall Preparation of Compounds

The general scheme for preparation of compounds 16-8, 16-12c, 16-13, 16-14, 16-16, 16-18, and 16-19 is below, with the following reagents and conditions for each step: (i) $K_2CO_3$, $CH_3CN$; (ii) Zn, MeOH, 12 M HCl; (iii) 1,1'-Thiocarbonyldiimidazole (iv) 7 M $NH_3$ in MeOH; (v) EtOH, reflux:

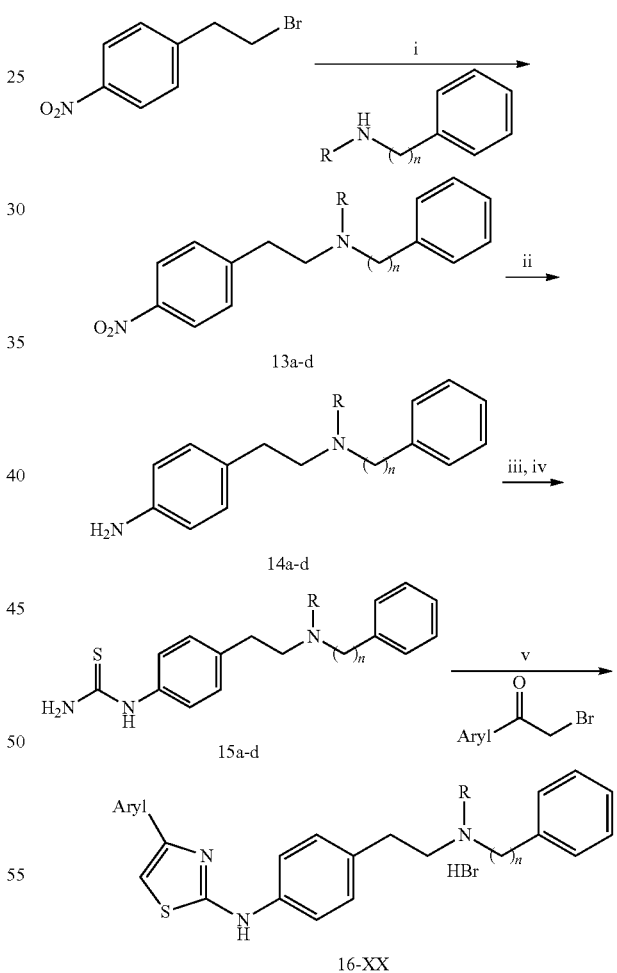

Step (i) General Procedure for the SN2 Displacement of 4-Nitrophenethyl Bromide.

Powdered, oven-dried $K_2CO_3$ (1.5 eq.) and the amine (1.5 eq.) were added sequentially to a room temperature solution of the bromide (0.33 M) in anhydrous $CH_3CN$. The reaction mixture was heated to 80° C. (oil bath temp) until analysis of the reaction mixture by LCMS indicated complete consumption of the bromide (~6-18 hours). The mixture was cooled to room temperature and diluted with brine (two volume equivalents). The resulting emulsion was extracted with EtOAc (2× one volume equivalent). The combined extracts were added to silica gel (mass of silica gel=2× mass of starting bromide) and the mixture was concentrated to dryness under reduced pressure. Flash column chromatography (RediSepRf $SiO_2$, 100% $CH_2Cl_2$→5% MeOH in $CH_2Cl_2$) gave the product as a brown to amber oil. The yield of the intermediates 13a-d (the tertiary amines formed in step (i)) are presented in Table 1.

TABLE 1

Yield of tertiary amines 13a-d formed in step (i)

| Intermediate No. | R | n | yield |
|---|---|---|---|
| 13a | Me | 0 | 17% |
| 13b | Me | 1 | 49% |
| 13c | Me | 2 | 42% |
| 13d | Et | 1 | 15% |

Step (ii) General Procedure for the Nitro to Aniline Reduction.

A solution of the nitro compound (0.5 M in MeOH) was cooled in an ice-NaCl bath. Zinc dust (4.5 eq.) was added in one portion followed by drop wise addition of 12 M HCl (4.5 eq.) over 2-3 minutes. After 1 hour, the cooling bath was removed, and the reaction mixture was allowed to stir over night at room temperature. The following morning, the mixture was cooled in an ice-NaCl bath once again and 30% aqueous NaOH was added drop wise until pH 14 (universal indicating pH paper) was reached. The mixture was diluted with $CH_2Cl_2$ (five volume equivalents) and stirred for 5 minutes. After this time, insolubles were removed at the vacuum, and the filter cake was washed with $CH_2Cl_2$ (2×25 mL). The organic phase of the filtrate was separated, washed with brine (100 mL), and dried ($MgSO_4$). The drying agent was removed by filtration. Silica gel (~5 g) was added, and the filtrate was concentrated to dryness under reduced pressure. Flash column chromatography (RediSepRf $SiO_2$, 100% $CH_2Cl_2$→5% MeOH in $CH_2Cl_2$) gave the product as a clear, amber oil. The yield of the intermediates 14a-d (the anilines formed in step (ii)) are presented in Table 2.

TABLE 2

Yield of anilines 14a-d formed in step (ii)

| Intermediate No. | R | n | yield |
|---|---|---|---|
| 14a | Me | 0 | 75% |
| 14b | Me | 1 | 84% |
| 14c | Me | 2 | 97% |
| 14d | Et | 1 | 85% |

Steps (iii) and (iv) General procedure for thiourea formation. A solution of the aniline (0.22 M) in anhydrous $CH_2Cl_2$ was added drop wise over 2-5 minutes to an ice-NaCl bath cooled solution of 1,1'-thiocarbonyldiimidazole (2 eq., 0.15 M) in anhydrous $CH_2Cl_2$. After 15 minutes, the cooling bath was removed and the reaction mixture was stirred at room temperature until analysis by TLC (5% MeOH in $CH_2Cl_2$) indicated complete consumption of the starting aniline. The mixture was cooled once again in an ice bath and 7 M $NH_3$ in MeOH (10.5 eq.) was added drop wise over 2-5 minutes. The bath was removed and the mixture was stirred over night at room temperature. Silica gel (mass of silica gel=2× mass of starting aniline) was added and the mixture was concentrated to dryness under reduce pressure. Flash column chromatography (RediSepRf $SiO_2$, 100% $CH_2Cl_2$→10% MeOH in $CH_2Cl_2$) gave the pure thiourea. The yield of the intermediates 15a-d (the thioureas formed in steps (iii)-(iv)) are presented in Table 3.

TABLE 3

Yield of thioureas 15a-d formed in steps (iii)-(iv)

| Intermediate No. | R | n | yield |
|---|---|---|---|
| 15a | Me | 0 | 99% |
| 15b | Me | 1 | 96% |
| 15c | Me | 2 | 88% |
| 15d | Et | 1 | 67% |

Step (v) General Procedure for Thiazole Formation.

A mixture of the thiourea (0.1 M) in EtOH and the α-bromoacetophenone derivative (1.1 eq.) was heated to 75° C. (oil bath temperature) until analysis by TLC (5% MeOH in $CH_2Cl_2$) indicated complete consumption of the thiourea. Silica gel (mass of silica gel=2× mass of starting thiourea) was added, and the mixture was concentrated to dryness under reduced pressure. Flash column chromatography (RediSepRf $SiO_2$, 100% $CH_2Cl_2$→10% MeOH in $CH_2Cl_2$) gave the pure thiazole hydrobromide. The yield of the final products 16-8 to 16-19 (the thiazole hydrobromides formed in step (v)) are presented in Table 4.

TABLE 4

Yield of thiazole hydrobromides 16-8 to 16-19 formed in step (v)

| Compound No. | R | n | aryl | yield |
|---|---|---|---|---|
| 16-8 | Me | 1 | phenyl | 56% |
| 16-12c | Me | 2 | 3-pyridyl | 82% |
| 16-13 | Me | 1 | 4-pyridyl | 83% |
| 16-14 | Me | 1 | 2-pyridyl | 94% |
| 16-16 | Me | 0 | 3-pyridyl | 98% |
| 16-18 | Et | 1 | 3-pyridyl | 31% |
| 16-19 | Et | 1 | phenyl | 93% |
| 16-43C | Me | 1 | 3-pyridyl | 52% |

Example 13: Preparation of Compounds 16-8 and 16-19

Compound 16-8. Compound 16-8 was prepared as detailed in Example 11. Briefly, a suspension of the bromide (5.01 g, 21.8 mmol), N-benzyl methylamine (4.2 mL, 33 mmol, 1.5 eq.) and $K_2CO_3$ (4.6 g, 33 mmol, 1.5 eq.) in anhydrous $CH_3CN$ (65 mL) was heated to 80° C. (oil bath temp) for 18 hours, after which time the starting material was nearly complete. The mixture was cooled to room temperature and diluted with brine (120 mL). The resulting emulsion was extracted with EtOAc (2×60 mL). The combined extracts were added to silica gel (~10 g) and the mixture was concentrated to dryness under reduced pressure. Flash column chromatography (RediSepRf $SiO_2$ (120 g), 100% $CH_2Cl_2$→5% MeOH in $CH_2Cl_2$) gave the product as a clear, dark orange oil (2.91 g, 49%). $^1$H NMR ($CDCl_3$, 400 MHz): 8.13 (d, J=8.4 Hz, 2H), 7.32 (d, J=8.4 Hz, 2H), 7.30-7.22 (m, 5H), 3.55 (s, 2H), 2.91 (t, J=6.8 Hz, 2H), 2.68 (t, J=6.8 Hz, 2H), 2.29 (s, 3H). ESIMS: m/z 271 [(M+H)+].

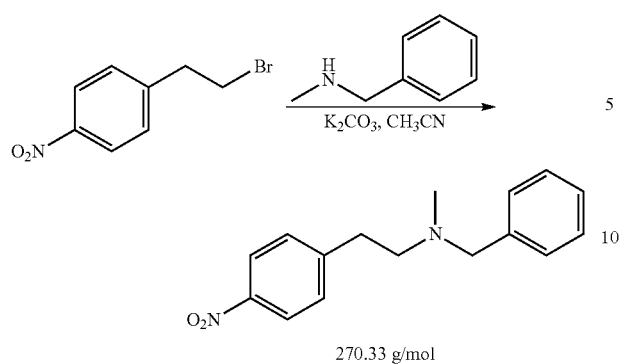

A solution of the nitro compound (2.8 g, 10.4 mmol) in MeOH (20 mL) was cooled in an ice-NaCl bath. Zinc dust (325 mesh, 3 g, 4.5 eq.) was added followed by drop wise addition of 12 M HCl (3.8 mL, 4.5 eq.) over 2-3 minutes. After 1 hour, the cooling bath was removed and the reaction mixture was allowed to stir over night at room temperature. The following morning, the mixture was cooled in an ice-NaCl bath once again and 30% aqueous NaOH was added drop wise until pH 14 (universal indicating pH paper) was reached. The mixture was diluted with $CH_2Cl_2$ (100 mL) and stirred for 5 minutes. After this time, insolubles were removed at the vacuum and the filter cake was washed with $CH_2Cl_2$ (2×25 mL). The organic phase of the filtrate was separated, washed with brine (100 mL) and dried ($MgSO_4$). The drying agent was removed by filtration. Silica gel (~5 g) was added and the filtrate was concentrated to dryness under reduced pressure. Flash column chromatography (RediSepRf $SiO_2$ (120 g), 100% $CH_2Cl_2$→5% MeOH in $CH_2Cl_2$) gave the product as a clear, amber oil (2.1 g, 84%). ESIMS: m/z 241 [(M+H)+]. This material was used in the next step without further analysis or purification.

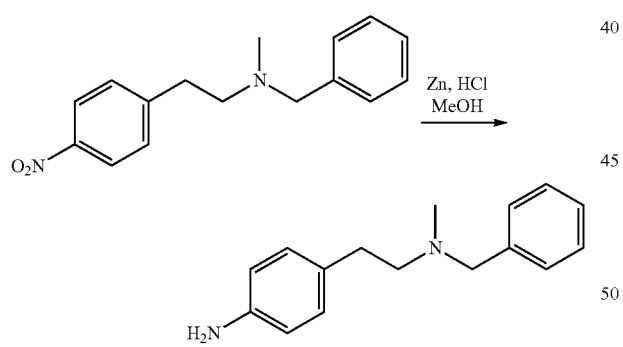

A solution of the amine (2.1 g, 8.7 mmol) in anhydrous $CH_2Cl_2$ (40 mL) was added dropwise over 2-5 minutes to an ice-NaCl bath cooled solution of 1,1'-thiocarbonyldiimidazole (95%, 3.1 g, 17.4 mmol, 2 eq.) in anhydrous $CH_2Cl_2$ (120 mL). After 15 minutes, the cooling bath was removed and the reaction mixture was stirred at room temperature for 1.5 hours after which time analysis by TLC (5% MeOH in $CH_2Cl_2$) indicated complete consumption of the starting aniline. The mixture was cooled once again in an ice bath and 7 M $NH_3$ in MeOH (13 mL, 91 mmol, 10.5 eq.) was added dropwise over 2-5 minutes. The bath was removed and the mixture was stirred over night at room temperature. Silica gel (~5 g) was added and the mixture was concentrated to dryness under reduce pressure. Flash column chromatography (RediSepRf $SiO_2$ (120 g), 100% $CH_2Cl_2$→10% MeOH in $CH_2Cl_2$) gave the thiourea as an amber oil that solidified to a tacky residue upon standing (2.5 g, 96%).

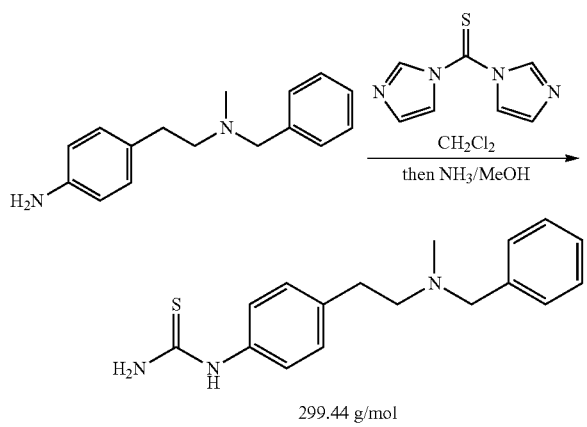

A mixture of the thiourea (2.5 g, 8.3 mmol) and 2-bromoacetophenone (1.8 g, 9.1 mmol, 1.1 eq.) in EtOH (80 mL) was heated to 75° C. (oil bath temperature) for 20 minutes after which time analysis by TLC (5% MeOH in $CH_2Cl_2$) indicated complete consumption of the thiourea. Silica gel (~5 g) was added and the mixture was concentrated to dryness under reduce pressure. Flash column chromatography (RediSepRf $SiO_2$ (120 g), 100% $CH_2Cl_2$→10% MeOH in $CH_2Cl_2$) gave the thiazole hydrobromide as a straw colored glass (3.73 g, 93%).

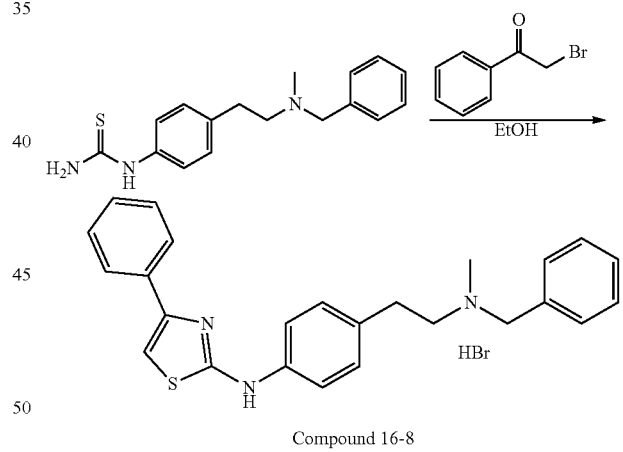

Compound 16-8

Figure 19:
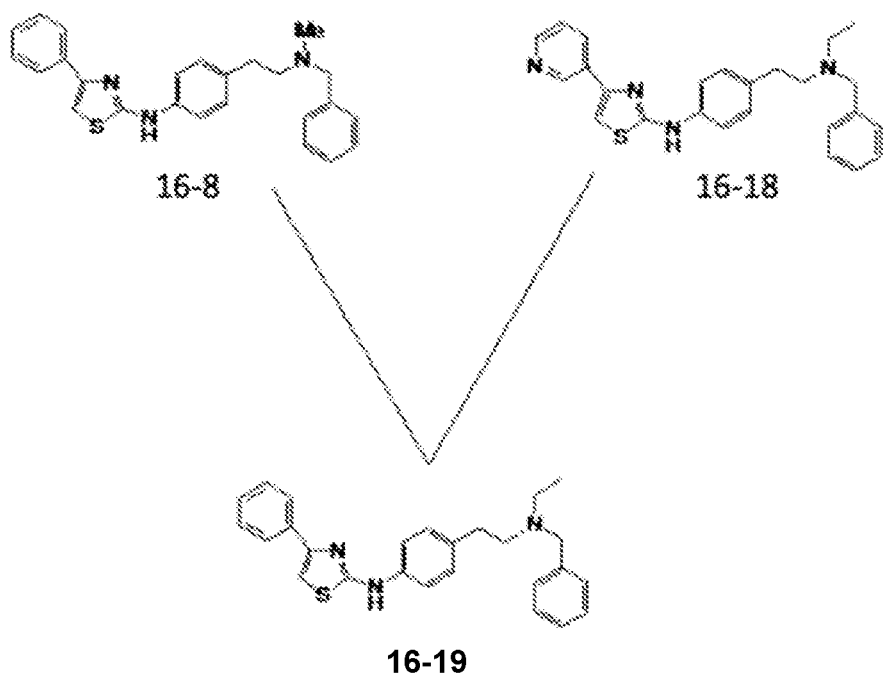
FIG. 19: Compound 16-19. Compound 16-8/18 h was designed as a hybrid of compounds 16-8 and 16-18. Compound 16-19 may also be referred to herein as 16-8/18hy.

Compound 16-19. Upon examination of the activity of GSK205 relative to compounds 16-8 and 16-18, it seemed that removal of a nitrogen from the pyridyl group increased the potency of the TRPV4 antagonist, and addition of an extra carbon to the nitrogen carbon side chain increased the potency of the TRPV4 antagonist. Compound 16-19 was formed and based on the structures of 16-8 and 16-18. See FIG. 19.

Compound 16-19 was prepared as detailed in Example 11. Briefly, a suspension of the bromide (5.01 g, 21.8 mmol), N-benzyl ethylamine (4.9 mL, 33 mmol, 1.5 eq.) and $K_2CO_3$ (4.6 g, 33 mmol, 1.5 eq.) in anhydrous $CH_3CN$ (65 mL) was heated to 80° C. (oil bath temp) for 18 hours, after which time the starting material was nearly complete. The mixture was cooled to room temperature and diluted with brine (120 mL). The resulting emulsion was extracted with EtOAc (2×60 mL). The combined extracts were added to silica gel (~10 g) and the mixture was concentrated to dryness under reduced pressure. Flash column chromatography (RediSepRf SiO$_2$ (120 g), 100% CH$_2$Cl$_2$→5% MeOH in CH$_2$Cl$_2$) gave the product as an orange oil that solidified upon standing at room temperature (3.3 g, 53%). $^1$H NMR (CDCl$_3$, 400 MHz): 8.13 (d, J=8.4 Hz, 2H), 7.32 (d, J=8.4 Hz, 2H), 7.30-7.22 (m, 5H), 3.55 (s, 2H), 2.91 (t, J=6.8 Hz, 2H), 2.68 (t, J=6.8 Hz, 2H), 2.87 (q, J=6.8 Hz, 2H), 1.20 (t, J=6.8 Hz, 3H). ESIMS: m/z 285 [(M+H)+].

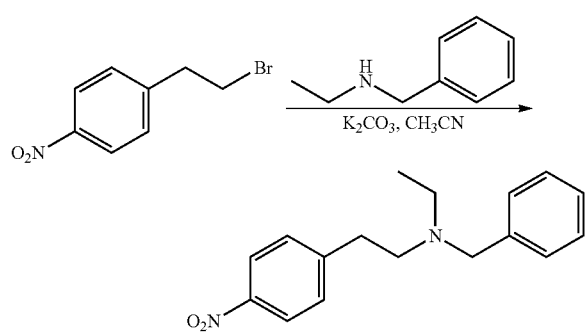

A solution of the nitro compound (3.0 g, 10.4 mmol) in MeOH (20 mL) was cooled in an ice-NaCl bath. Zinc dust (325 mesh, 3 g, 4.5 eq.) was added followed by drop wise addition of 12 M HCl (3.8 mL, 4.5 eq.) over 2-3 minutes. After 1 hour, the cooling bath was removed and the reaction mixture was allowed to stir over night at room temperature. The following morning, the mixture was cooled in an ice-NaCl bath once again and 30% aqueous NaOH was added drop wise until pH 14 (universal indicating pH paper) was reached. The mixture was diluted with CH$_2$Cl$_2$ (100 mL) and stirred for 5 minutes. After this time, insolubles were removed at the vacuum and the filter cake was washed with CH$_2$Cl$_2$ (2×25 mL). The organic phase of the filtrate was separated, washed with brine (100 mL) and dried (MgSO$_4$). The drying agent was removed by filtration. Silica gel (~5 g) was added and the filtrate was concentrated to dryness under reduced pressure. Flash column chromatography (RediSepRf SiO$_2$ (120 g), 100% CH$_2$Cl$_2$→5% MeOH in CH$_2$Cl$_2$) gave the product as a clear, amber oil (2.3 g, 87%). ESIMS: m/z 255 [(M+H)+]. This material was used in the next step without further analysis or purification.

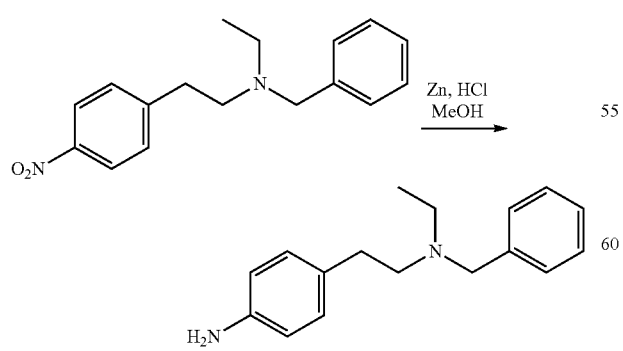

A solution of the amine (0.110 g, 0.43 mmol) in anhydrous CH$_2$Cl$_2$ (2 mL) was added dropwise over 2-5 minutes to an ice-salt bath cooled solution of 1,1'-thiocarbonyldiimidazole (95%, 0.162 g, 0.87 mmol, 2 eq.) in anhydrous CH$_2$Cl$_2$ (6 mL). After 15 minutes, the cooling bath was removed and the reaction mixture was stirred at room temperature for 1.5 hours after which time analysis by TLC (10% MeOH in CH$_2$Cl$_2$) indicated complete consumption of the starting aniline. The mixture was cooled once again in an ice bath and 7 M NH$_3$ in MeOH (620 μL, 4.3 mmol, 10 eq.) was added dropwise over 2-5 minutes. The bath was removed and the mixture was stirred over night at room temperature. Silica gel (~1 g) was added and the mixture was concentrated to dryness under reduce pressure. Flash column chromatography (RediSepRf SiO$_2$ (40 g), 100% CH$_2$Cl$_2$→10% MeOH in CH$_2$Cl$_2$) gave the thiourea as an amber oil that solidified upon standing (0.130 g, 97%).

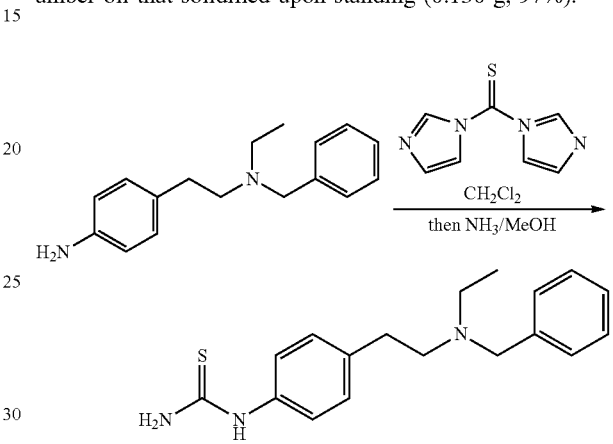

A mixture of the thiourea (159 mg, 0.51 mmol) and 2-bromoacetophenone (0.113 g, 0.56 mmol, 1.1 eq.) in EtOH (5 mL) was heated to 75° C. (oil bath temperature) for 1 hour, after which time analysis by TLC (10% MeOH in CH$_2$Cl$_2$) indicated complete consumption of the thiourea. Silica gel (~1 g) was added and the mixture was concentrated to dryness under reduce pressure. Flash column chromatography (RediSepRf SiO$_2$ (40 g), 100% CH$_2$Cl$_2$→10% MeOH in CH$_2$Cl$_2$) gave the thiazole hydrobromide as a straw colored glass (0.165 g, 78%).

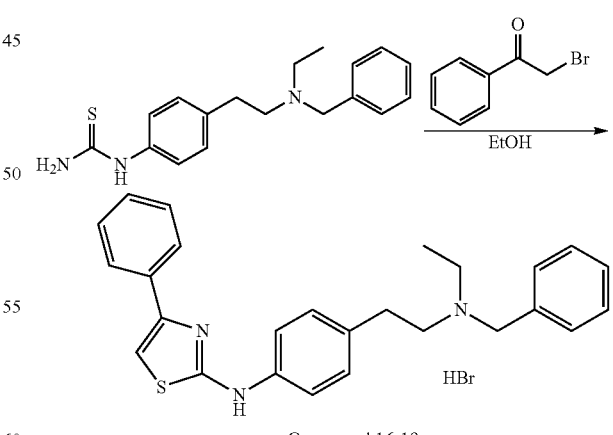

Compound 16-19

Example 14: Effect on TRPV4-Mediated Calcium Transport

Compounds (GSK205, 16-12, 16-13, 16-14, 16-18, 16-8, and 16-19) were tested for their effect on TRPV4-mediated calcium influx in N2a cultured cells with targeted expression of human TRPV4. Ca2+ imaging was performed according to Li et al. (*Environ. Health Perspect.* 2011, 119, 784-93) and Moore et al. (*Proc. Natl. Acad. Sci. U.S.A.* 2013, 110, E3225-E3234). Briefly, Ca2+ imaging of primary mouse epidermal keratinocytes (1° MK) in response to chemical activation of TRPV4 was conducted after loading with 2 µM fura2-AM, following a ratiometric Ca2+-imaging protocol with 340/380 nm blue light for dual excitation. Ratios of emissions were acquired at 0.5 Hz. ΔR/R0 was determined as the fraction of the increase of a given ratio over baseline ratio, divided by baseline ratio. For stimulation of cells with UVB, where fura-2 was not suitable because of the proximity of stimulation with 340/380 nm vs. 295 nm, 2 µM fluo4-AM was used instead. Ca2+ imaging was carried out at 488 nm excitation, acquisition of emissions at 0.5 Hz, expressed as ΔF/F0. TRPV4 was activated with 10 nM GSK101, a specific activator, which had no effect on RFP-transfected cells. Each of the six compounds were added to a concentration of 2.5 µM, and its effect was observed.

Figure 20:
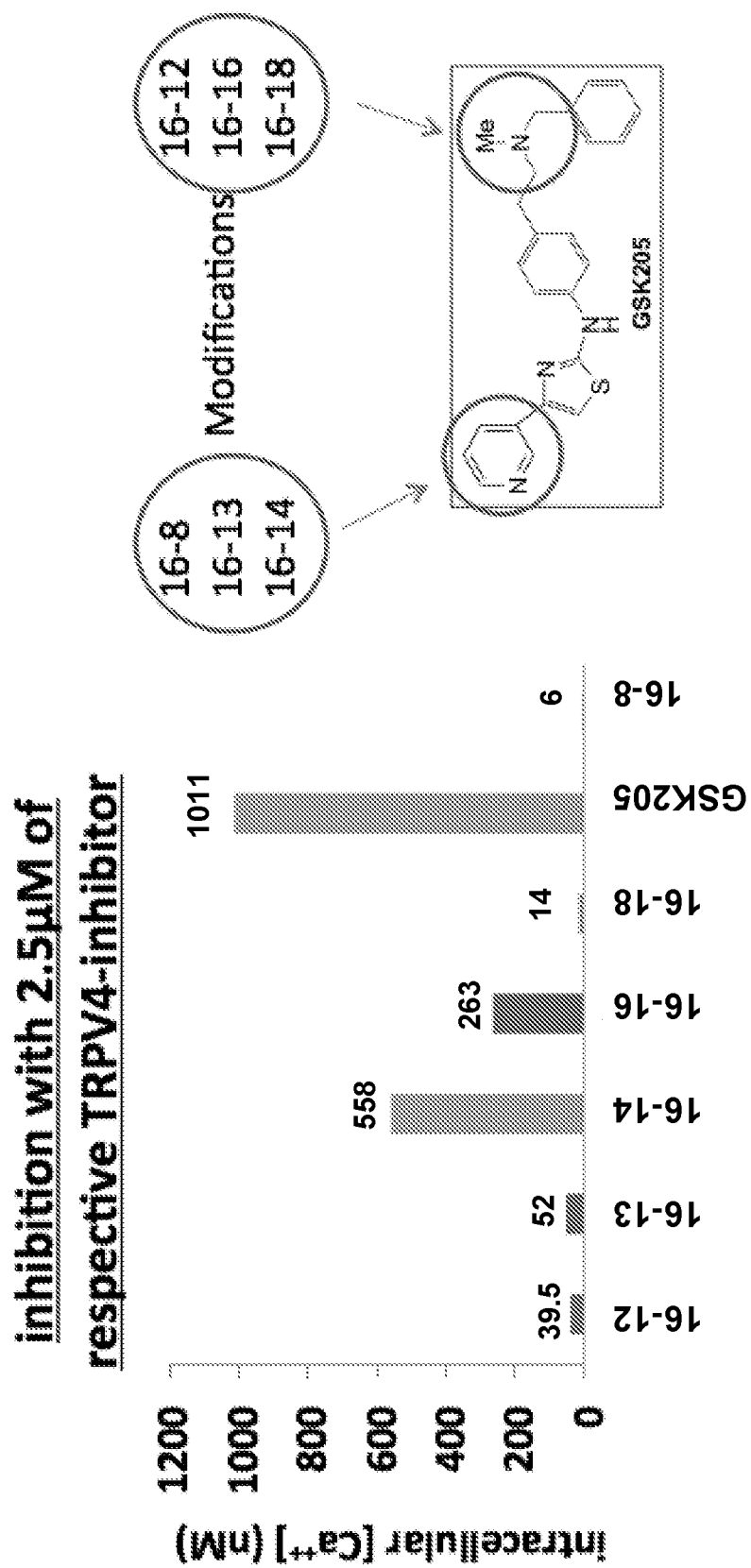
FIG. 20: Inhibition of calcium ion flux through TRPV4. Compounds of the present invention demonstrated inhibitory activity against TRPV4 and were stronger antagonists that GSK205.
Figure 21A:
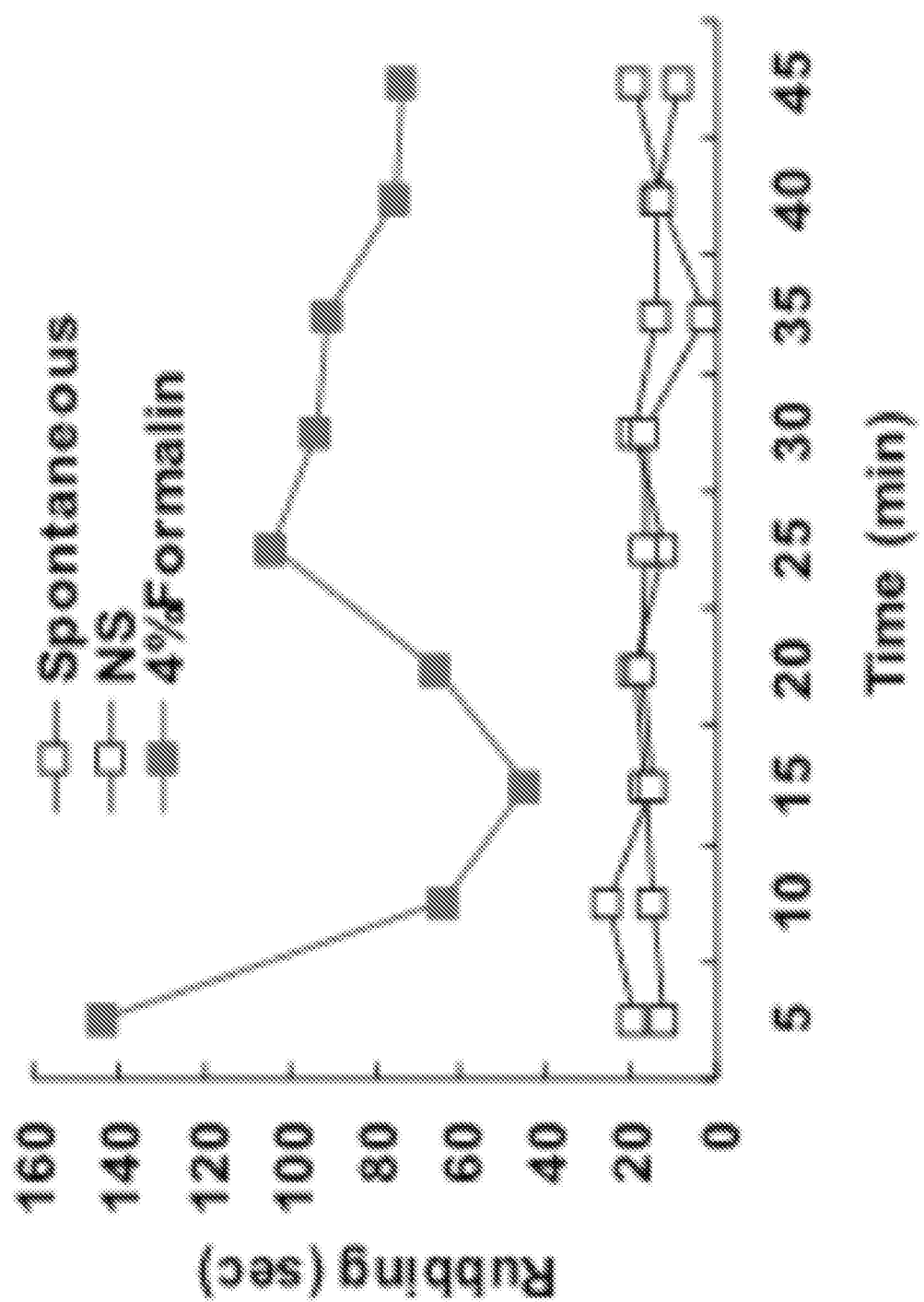
FIG. 21: Treatment of pain. Compounds as disclosed herein attenuated nocifensive behavior in mice.
Figure 21B:
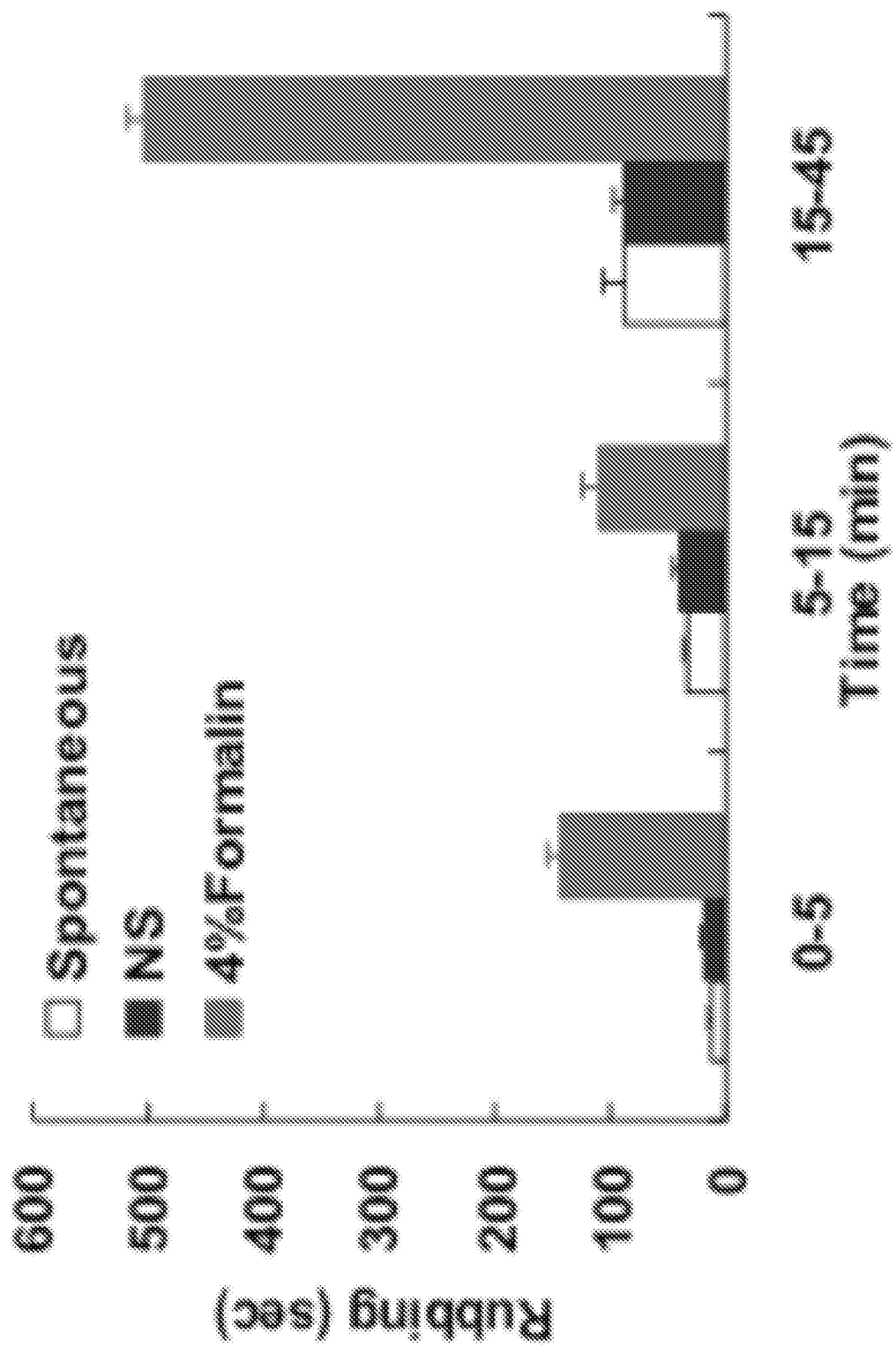
Figure 21C:
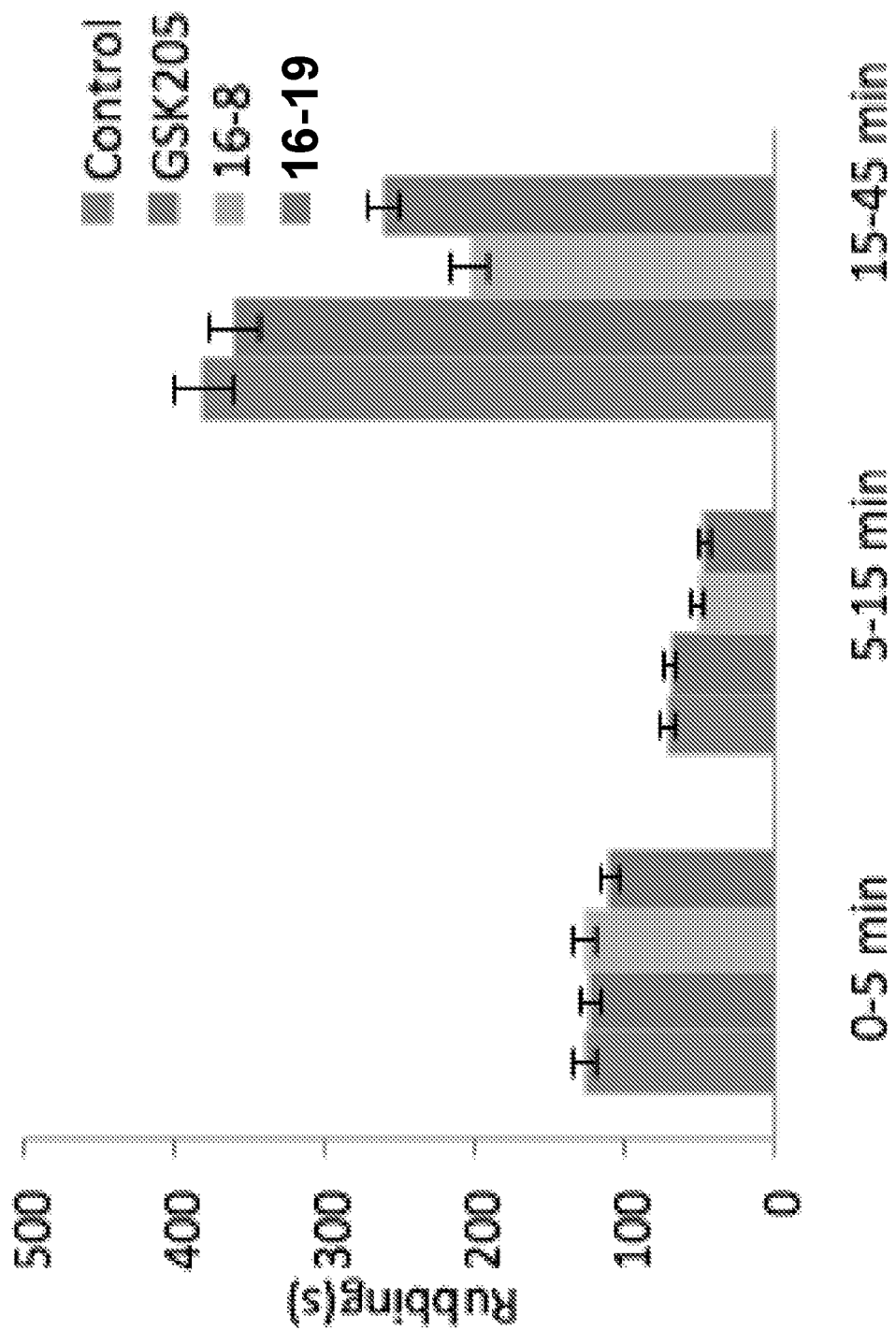
Figure 21D:
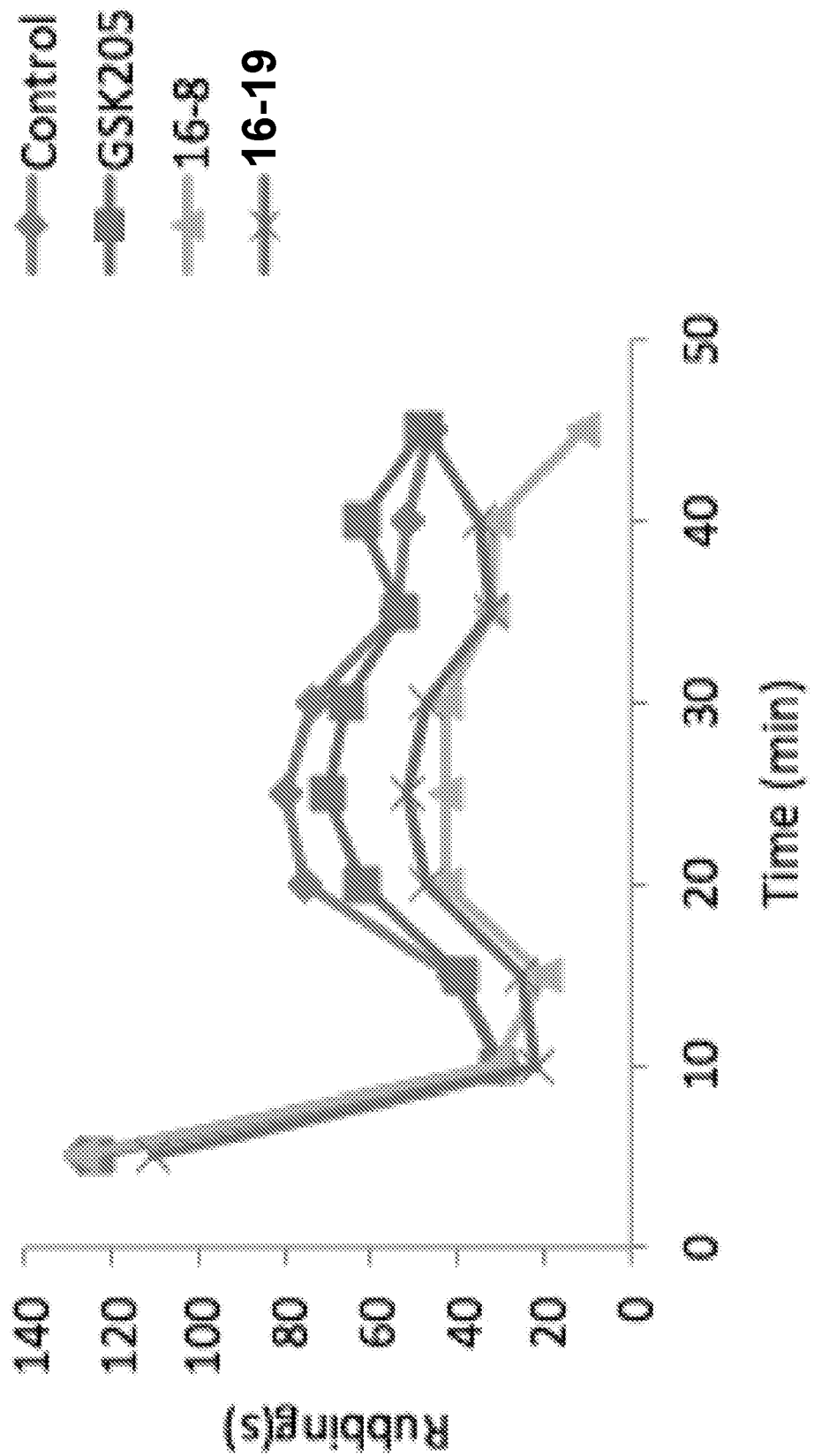

Results are shown in FIG. 20. The bar diagram to the left shows the effects of 2.5 µM of the respective inhibitor (pre-incubation for 10 min). The ordinate is the peak calcium concentration in the cells (average n>75 cells) in nM. All six compounds were effective in inhibiting TRPV4-mediated calcium influx, with 16-18 and 16-8 being the most potent. 16-19 did not show enhanced inhibition over 16-8 (data not shown). It was noted that GSK205 had a very low potency at this concentration in cultured cells with targeted over-expression.

Example 15: In Vivo Pain Model in Mice

Compounds were tested for their effect in reducing pain using an in vivo pain model in mice. For mouse formalin-evoked irritant behavior measurements, mice were well-fed, well-rested, and tested at the same time of day, at the same time-point of their circadian rhythm. They were allowed to acclimate to a plexiglas chamber for at least 30 min before testing, and received 10 µL subcutaneous injection of 4% of formalin (diluted from an aqueous solution of commercial 37% formaldehyde with normal saline (NS)) through a 30-gauge needle into the right whiskerpad, as further detailed in Luccarini et al. (*J. Pain*, 2006, 7, 908-914). Normal saline was used as control injection. After injection, mice were immediately placed back into the chamber and the rubbing behavior was recorded by a private consumer-type video-camera for a 45 min observation period. The recording time was divided into 9 blocks of 5 min, and a nociceptive score was determined per block by measuring the time that the animals spent rubbing the injected area predominantly with the ipsilateral fore-paw and rarely with hind-paw. This rubbing behavior with fore-paw is evoked by pain, which is distinct from itch behavior. Behavioral analysis was conducted by observers blinded to treatment.

To investigate the effects of the specific compounds GSK205, 16-8, and 16-19 on formalin-induced nociceptive behavior, mice received a single subcutaneous injection of the compounds into the whiskerpad (10 µL, dissolved in 4% DMSO) 15 min before formalin injection. Control animals received the same volume of NS, 4% DMSO.

Results are shown in FIG. 21. FIG. 21A shows the time-course of nocifensive behavior in response to whisker-pad injection of formalin to BL6 mice. Note the biphasic response and "clean" controls. FIG. 21B shows quantitation of FIG. 21A, with n=10 animals per group. Note the significant increase in response to formalin injection. FIG. 21C shows similar quantitation when compounds where pre-injected topically at 0.5 mM/10 µL. This concentration had no effect on residual nocifensive behavior in Trpv4−/− mice. Note the lack of effect of GSK205 at this concentration, yet a significant attenuation of nocifensive behavior, in particular of the centrally caused second phase, in response to 16-8 and 16-19. FIG. 21D shows the time course for the three compounds. GSK205, at this concentration, was not different from control, whereas 16-19 and 16-8 significantly attenuated nocifensive behavior. Note the reduction to control levels with the less lipophilic 16-8 at the 45-min time-point, and the reversal to control levels with the more lipophilic 16-19 at this time-point. Also note that none of the compounds influenced the first phase, which was caused by the direct irritation that formalin causes on peripheral whisker-pad nerve endings.

Example 16: UVB-Exposure Evoked Nocifensive Behavior

Compounds were tested for their effect on nocifensive behavior (response to pain) following UVB overexposure. Behavioral tests were performed to evaluate the decrease in withdrawal thresholds in response to mechanical von Frey hair or thermal stimuli applied to hind paws. The Von-Frey apparatus (Ugo Basile) applied a mechanical stimulus with a flexible steel wire from underneath the hind paw. The force leading to withdrawal was determined. For the thermal stimuli test, paws were stimulated with heat from underneath applied by an infrared beam (Hargreave's test apparatus; Ugo Basile), and withdrawal latencies were recorded. The withdrawal thresholds were ascertained before and after UV exposure. Mice were exposed to UVB 3-5 days after the last application of tam/oil, using a Bio-Rad Gel Doc 2000 UV transilluminator (302 nm) for 5 min with an exposure of 600 mJ/cm$^2$. This represents 5-10 times the minimal erythema-inducing dose, in keeping with the rationale of inducing sunburn and studying sunburn-evoked pain.

Figure 22:
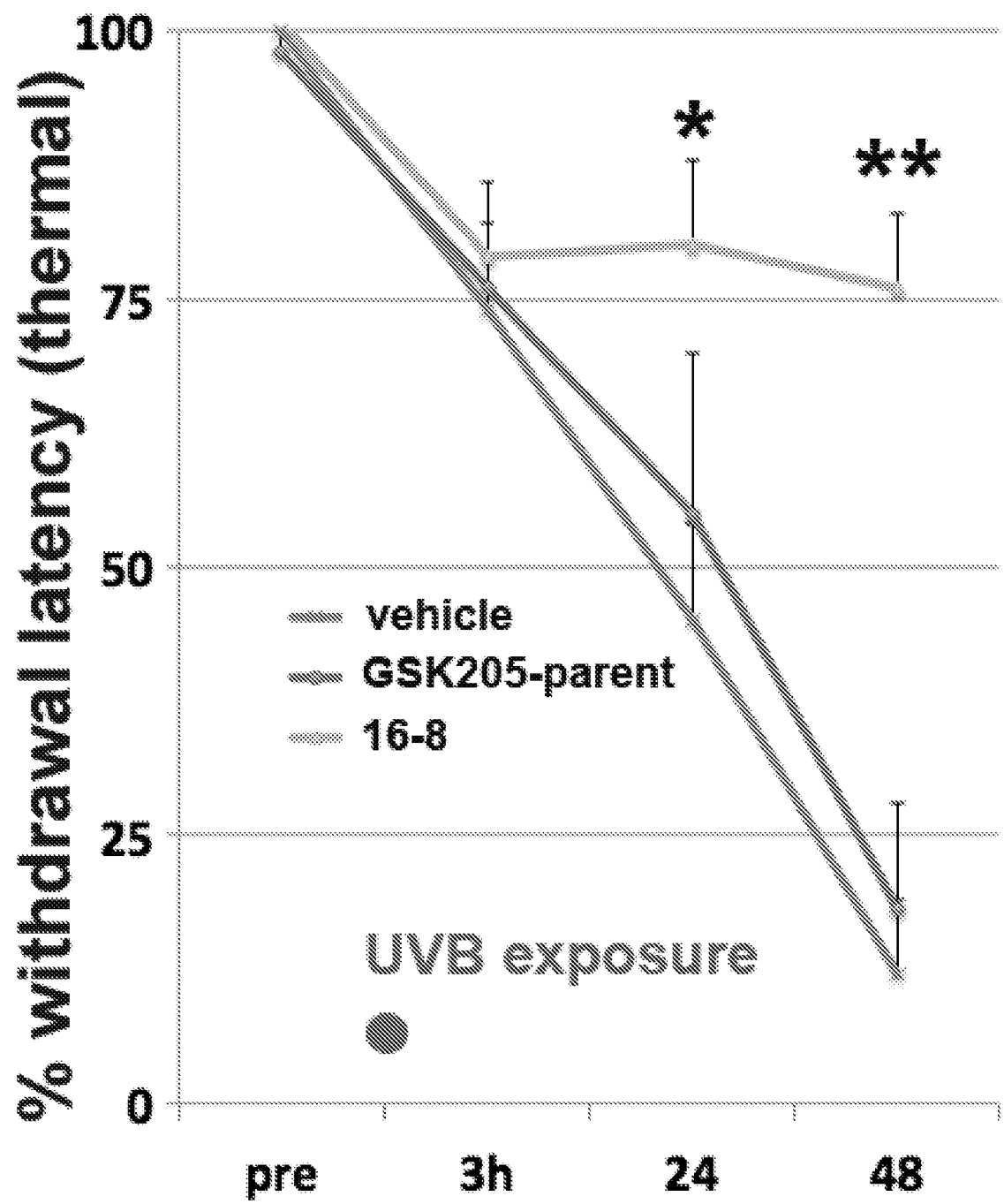
FIG. 22: Treatment of pain after UVB exposure. Compounds as disclosed herein attenuated nocifensive behavior in a mouse model for sunburn.

Results are shown in FIG. 22, demonstrating the effective topical treatment of UVB-overexposure evoked nocifensive behavior by compound 16-8. Topically applied 16-8 was especially effective in reducing the response to pain following UVB exposure, whereas GSK205 at this concentration (0.5 mM in 40 µL), was as effective as vehicle (n=4/group).

Example 17: Effect on TRPA1

Compounds were tested for their effect on TRPA1. N2a permanent cells were transfected with human TRPA1 cDNA, using a pcDNA3.1 expression plasmid. They were co-transfected with eGFP-expressing plasmid, or, for control, with eGFP plasmid only.

Vehicle-treated TRPA1-expressing cells showed a robust Ca2+ transience in response to 60 µM AITC and also to 1 mM mustard oil, which are both known electrophilic TRPA1-activators. However, eGFP-expressing control-transfected cells (no TRPA1) did not respond to the TRPA1-activator AITC. Cells were then pre-exposed to 5 µM of compounds 16-8 and 16-19 for 10 min.

Figure 23:
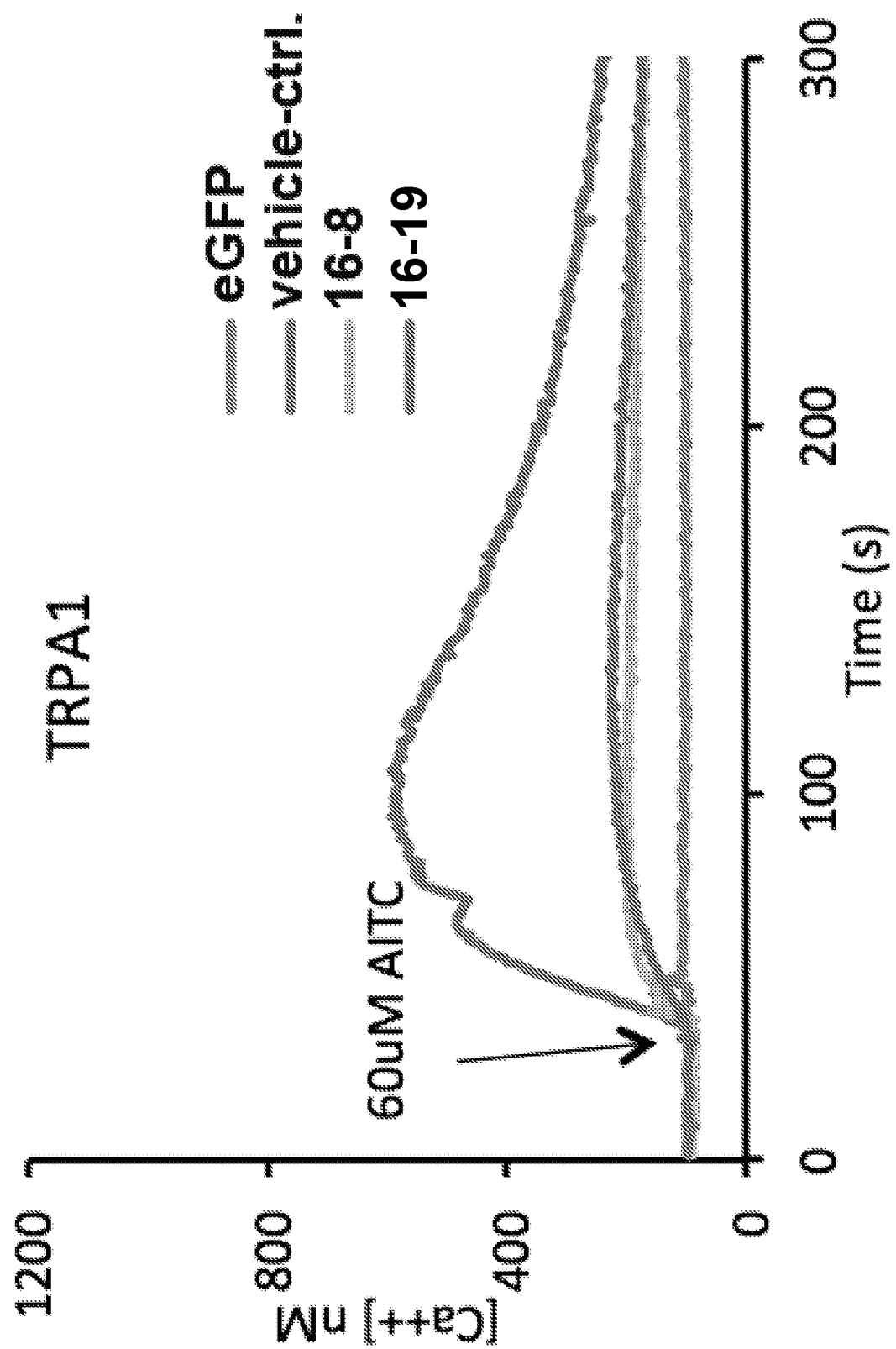
FIG. 23: Effect on TRPA1. Compounds as disclosed herein inhibited TRPA1, as indicated by measuring calcium transience.

Results are shown in FIG. 23. Averaged Ca2+ signal is shown from >75 cells. The resulting Ca2+ transient evoked by 60 µM AITC was reduced by >80% upon administration of compound 16-8 or 16-19 at 5 µM, indicating appreciable TRPA1-inhibitory effects of both compounds. Therefore, compounds 16-8 and 16/8-18hy showed inhibitory activity against human TRPA1. For doses below or equaling 25 µM, GSK205 did not inhibit TRPA1 activity.

Example 18: Effect on TRPV1, TRPV2, and TRPV3

Compounds were tested for their effect on TRPV1, TRPV2, and TRPV3. Methods were similar to those described in Example 15. Briefly, N2a cells were transfected with human TRPV1, TRPV2, or TRPV3. eGFP-transfection was used as control. For specific stimulation of TRPV1, 5 µM capsaicin was used. For stimulation of TRPV2, hypotonicity (260 mosmol/L) was used, based on previous reports of TRPV2 being osmotically responsive. N2a cells were not responsive to hypotonicity, and neither were control-transfected cells. For TRPV3-expressing cells, camphor (20% of a commercially available stock solution) was used. Camphor by itself did not stimulate eGFP-expressing control N2a cells or native N2a cells. Stimulation and control protocols were applied as for TRPA1-expressing N2a cells as detailed above in Example 15.

Figure 24A:
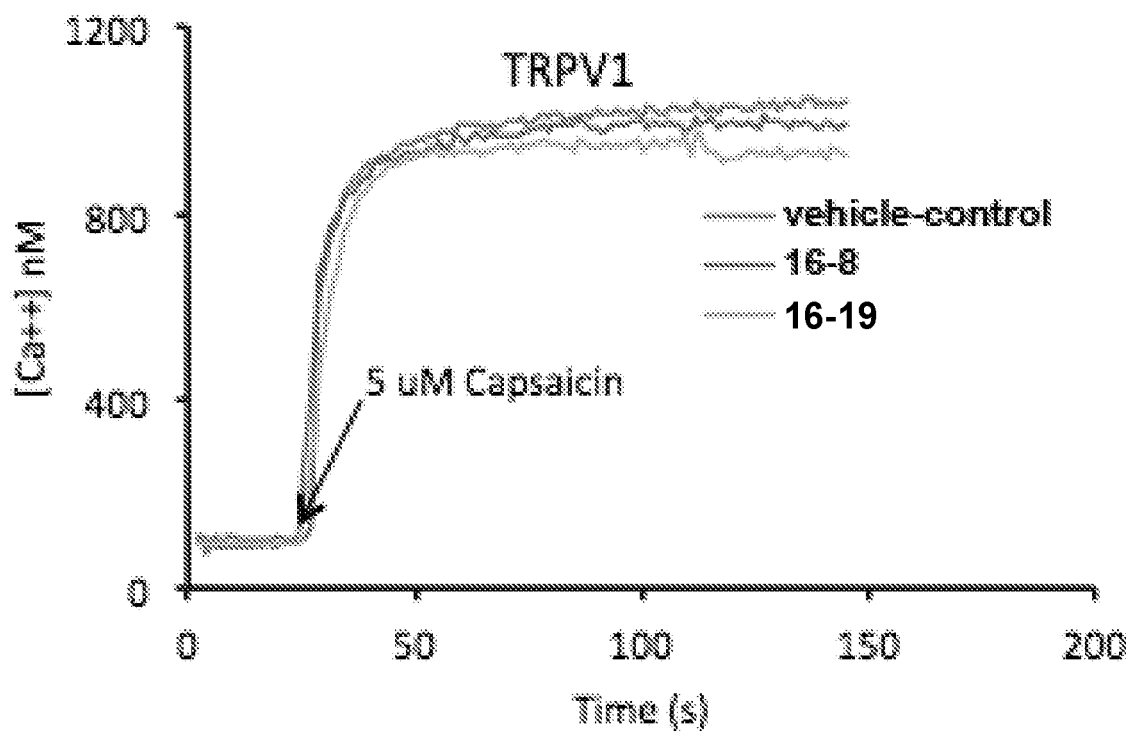
FIG. 24: Effect on TRPV1, TRPV2, and TRPV3. Compounds as disclosed herein did not inhibit TRPV1, TRPV2, or TRPV3, as indicated by measuring calcium transience.
Figure 24B:
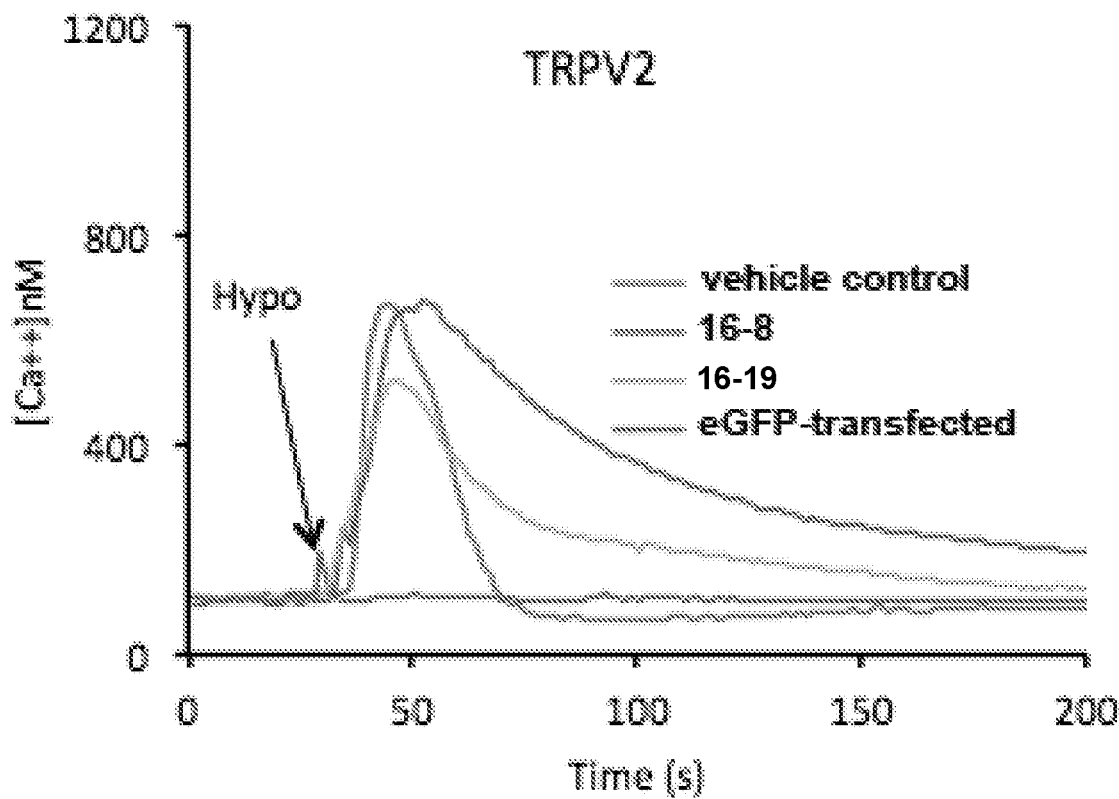
Figure 24C:
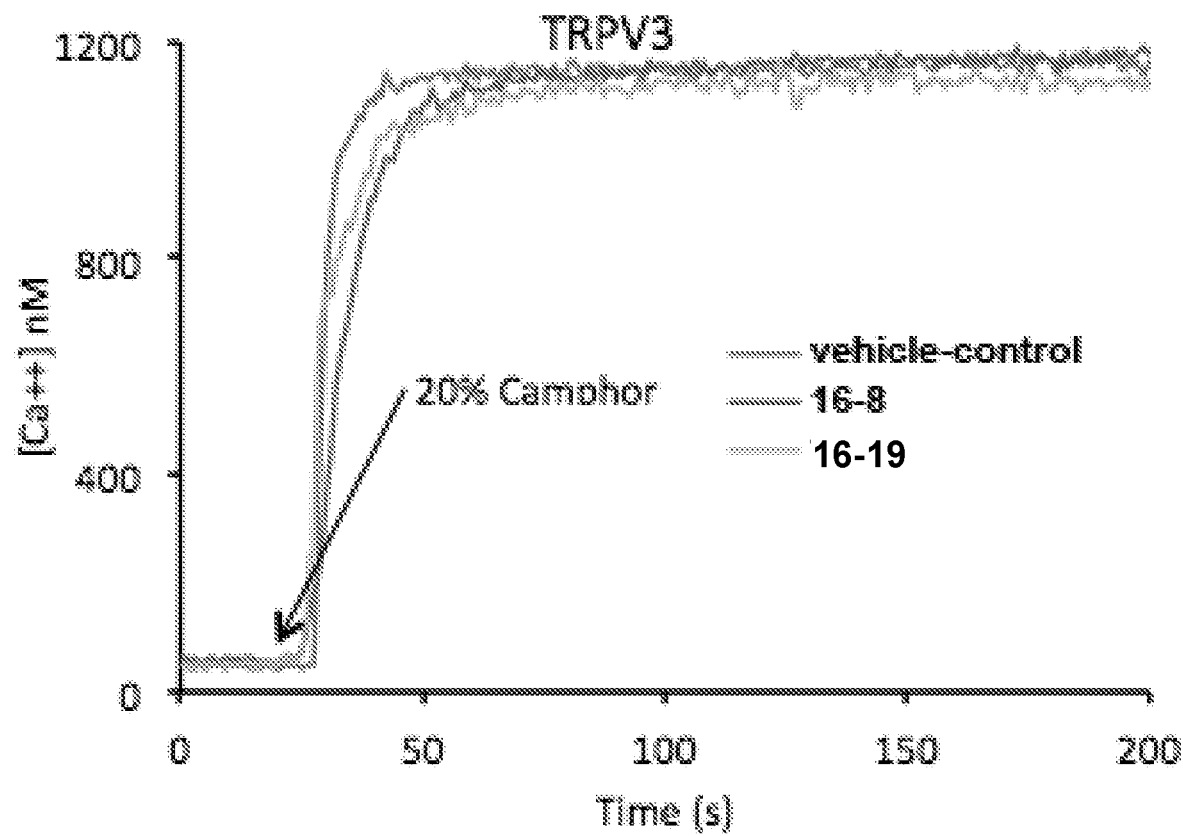

Results are shown in FIG. 24, which shows the Ca2+ signals for specific stimulation of TRPV1, TRPV2, and TRPV3. Control-transfected N2a cells did not respond to capsaicin (TRPV1 activation) or camphor (TRPV3 activation). For TRPV1, TRPV2, and TRPV3, Ca2+ transience was not affected by administration of 16-8 or 16-19. Therefore, compounds 16-8 and 16-19 did not affect TRPV1, TRPV2, and TRPV3.

Figure 25:
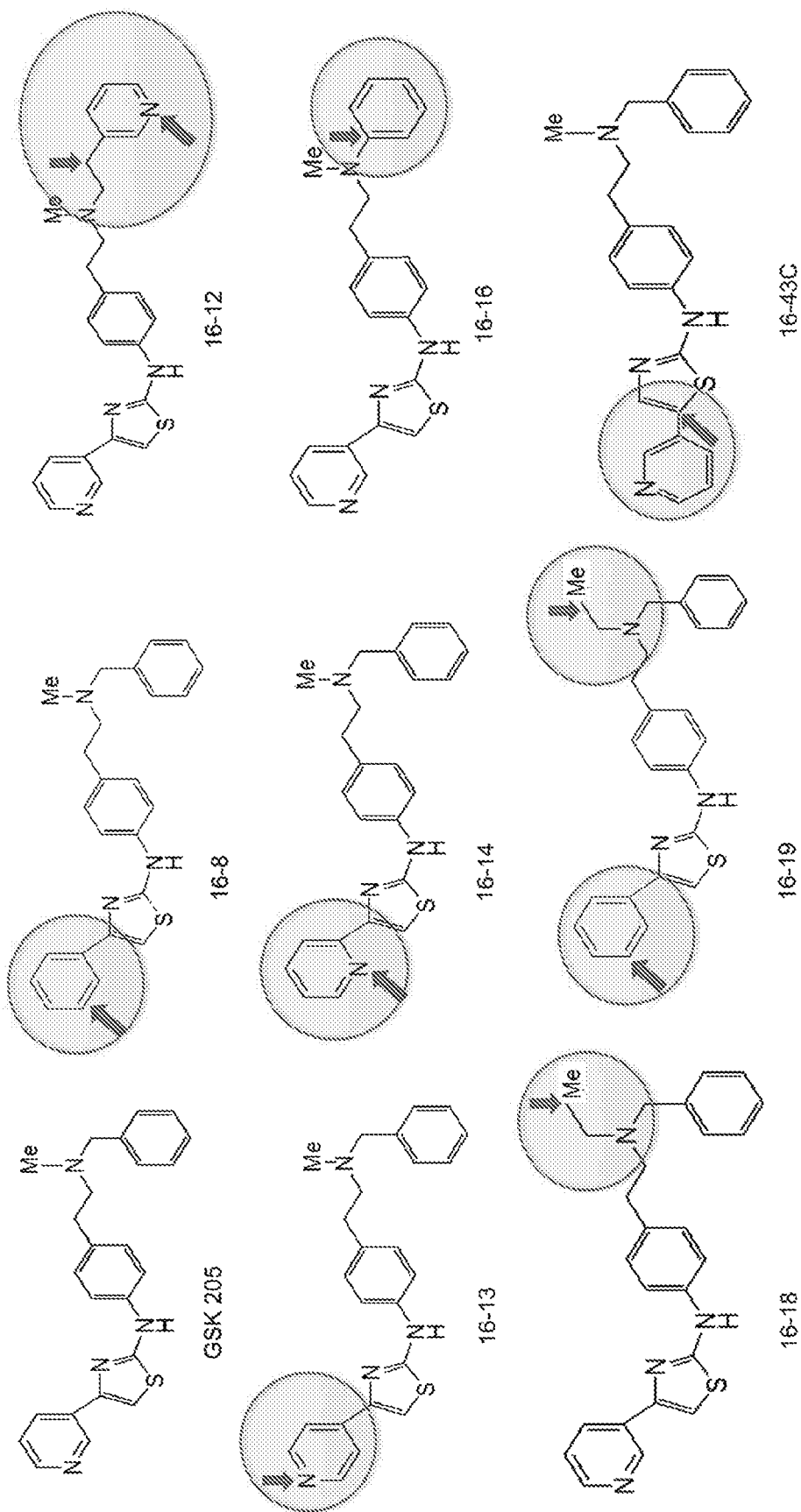
FIG. 25: Modifications of tool compound GSK205 for improved targeting of TRPV4. The synthesized compounds differed in the highlighted part of the molecule, changed residue indicated with arrow. Compound 16-19 compound was synthesized to incorporate two modifications from two compounds, 16-8 and 16-18, found most potent in anti-TRPV4 screening assays (see FIG. 26).
Figures 26A, 26B:
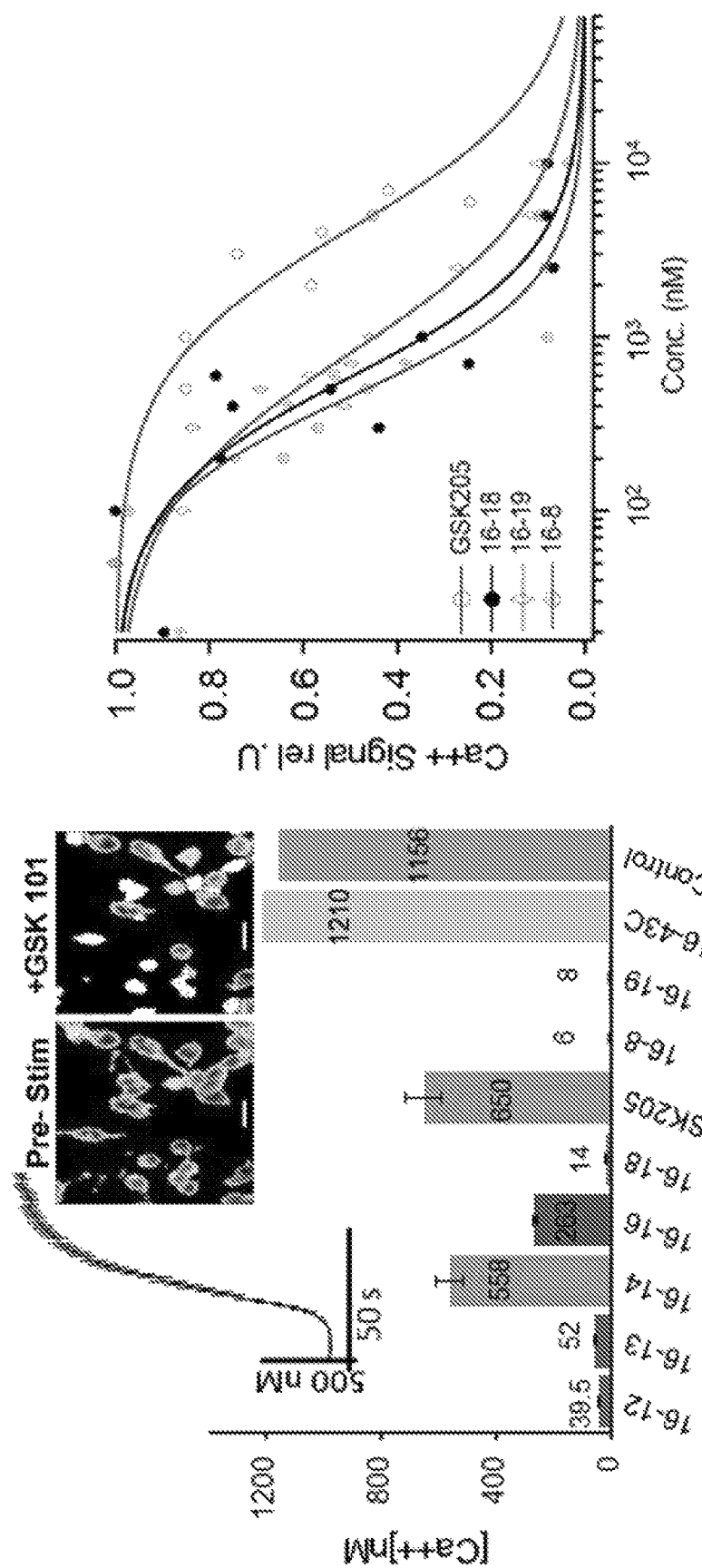
FIGS. 26A-26B: Assessment of compounds in N2a cells with directed expression of TRPV4.

Example 19: Chemical Synthesis of GSK205 Derivatives and Assessment of their TRPV4-Inhibitory Potency in Cell-Based Assays We modified compound GSK205 by generating 7 primary modifications, as shown in FIG. 25. One additional compound (16-19) that had the combined respective modifications of the two most potent compounds, as defined in primary screens, was also synthesized. We assessed TRPV4-inhibitory potency of these synthetic compounds in a Ca++ imaging assay in neuronal 2a (N2a) permanent tissue culture cells with directed expression of mammalian (rat) TRPV4. TRPV4 channels were stimulated with a selective activator compound, GSK1016790A (GSK101), used at 5 nM. For first round assessment, all TRPV4-inhibitory compounds were used at 5 µM (FIG. 26A). Compound 16-43C did not inhibit Ca++ influx, and its effect was similar to vehicle control. All other compounds inhibited TRPV4-mediated Ca++ influx, with compounds 16-8 and 16-18 emerging as the two most potent. Compound 16-19 which incorporated the modifications of both 16-8 and 16-18, was also effective in inhibiting TRPV4-mediated currents. However, we did not find a significant difference between com-pound 16-19 and 16-8, both of which virtually eliminated Ca++ influx.

Figure 27B:
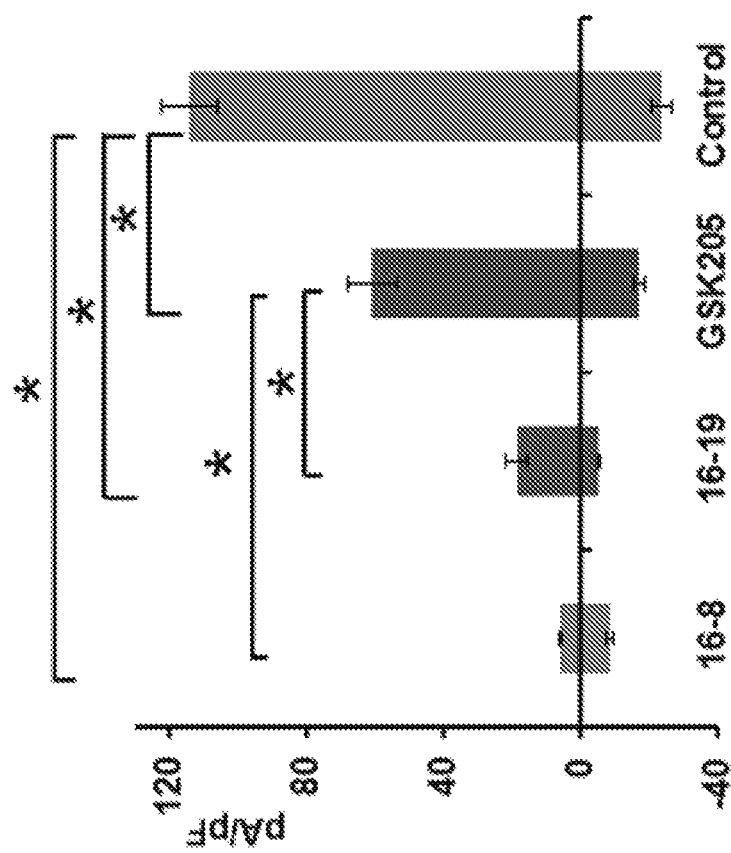
FIGS. 27A-27B: TRPV4 channel inhibition by compounds 16-8 and 16-19-patch-clamp e-phys.
Figure 27A:
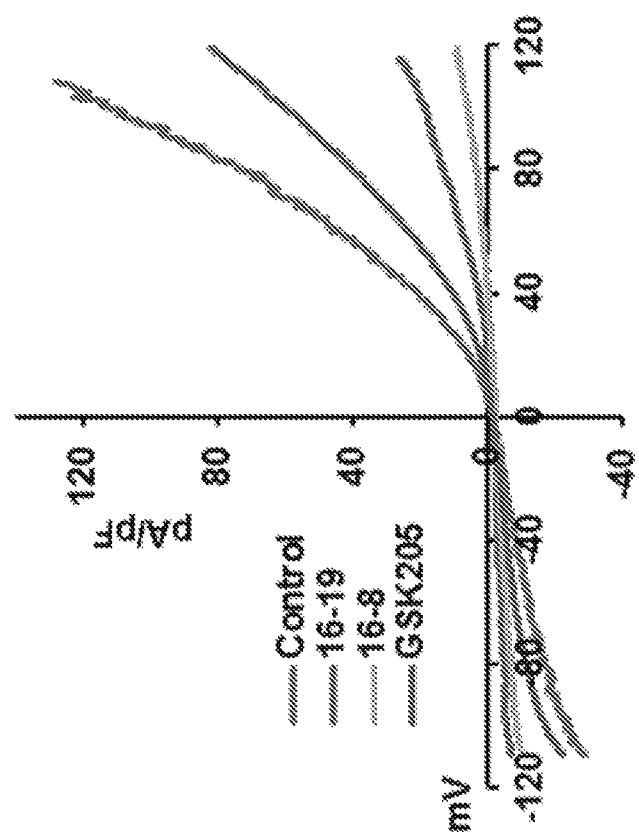

We then conducted more detailed dose-response assessments for compounds 16-8, 16-18 and 16-19, which showed an $IC_{50}$ of 0.45, 0.81 and 0.59 µM, respectively, vs. an $IC_{50}$ of 4.19 µM for parental compound GSK205. These findings represent an increased potency of the GSK205-derivative compounds by approximately 10-fold for 16-8, 8-fold for 16-19 and 5-fold for 16-18. Surprisingly, compound 16-19 was not significantly more potent than 16-8, whereas 16-8 was more potent than 16-18. Based on these results, we tested 16-8 and 16-19 vs GSK205 (as a control) in patch-clamp studies (FIG. 27). Our results indicate significantly increased potency of compounds 16-8 and 16-19 as compared to the parental molecule, GSK205 (all applied at 5 µM) in attenuating TRPV4-mediated currents.

We next decided to assess potency of the most potent compound 16-8 vs. parental compound GKS205 in two types of primary cells that are known to express TRPV4 and in which TRPV4 function has been demon-strated in a relevant biological context. We examined articular chondrocytes, which have prominent TRPV4 expression, where TRPV4 serves as the mechanotransducer of physiologic mechanical loads to regulate the cells' anabolic response, and thus tissue homeostasis, in cartilage[19]. In addition, we studied brain astrocytes, where TRPV4 expression and relevant function has been previously demonstrated in regulating astrocyte cellular edema, in the coupling of neuronal activity to cerebral blood flow, and in mediating CNS traumatic injury[35-37]. Fulfilling our main objective, in both cell types we observed significantly increased potency of com-pound 16-8 as compared to the parental molecule, GSK205 (FIG. 28). Evaluation of the inhibitory potency of GSK205 derivatives in these primary cells, which express functional and biologically-relevant TRPV4 without directed over-expression of the channel (FIG. 28), directly corroborate the findings of more basic studies using heterologously TRPV4-overexpressing immortalized cell lines (FIG. 26), strongly supporting our conclusions on the increased potency of the newly derived compounds. Taken together, we identified compound 16-8 as a TRPV4-inhibitory compound with sub-micromolar potency in heterologous systems, with approximately a 10× increase in potency as compared to its parental molecule, GSK205. Moreover, 16-8 proved more effective in TRPV4-expressing primary skeletal and CNS-derived cells. However, the rational modification to compound 16-19, intended to further enhance potency, did not yield the intended effect.

Before testing these compounds in relevant in-vivo animal models, we next tested the cellular toxicity as well as the specificity of these compounds against other selected TRP ion channels.

Example 20: Novel TRPV4 Inhibitors are Selective, with Benign Toxicity Profile, Yet Display Potent Inhibi-tion of TRPA1

Figure 29B:
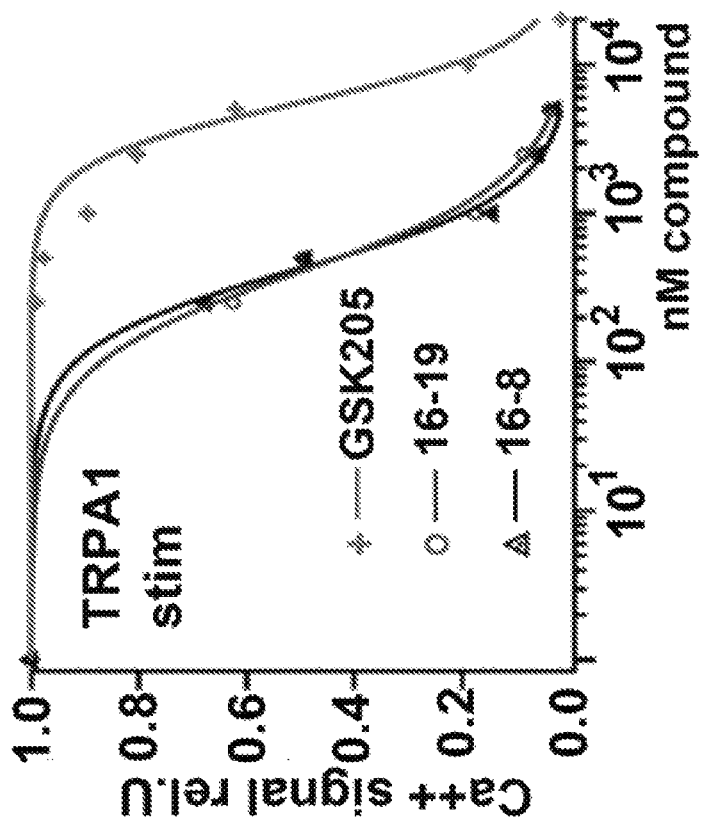
FIGS. 29A-29B: Compounds 16-8 and 16-19 also potently inhibit TRPA1, not TRPV1-3.
Figure 29A:
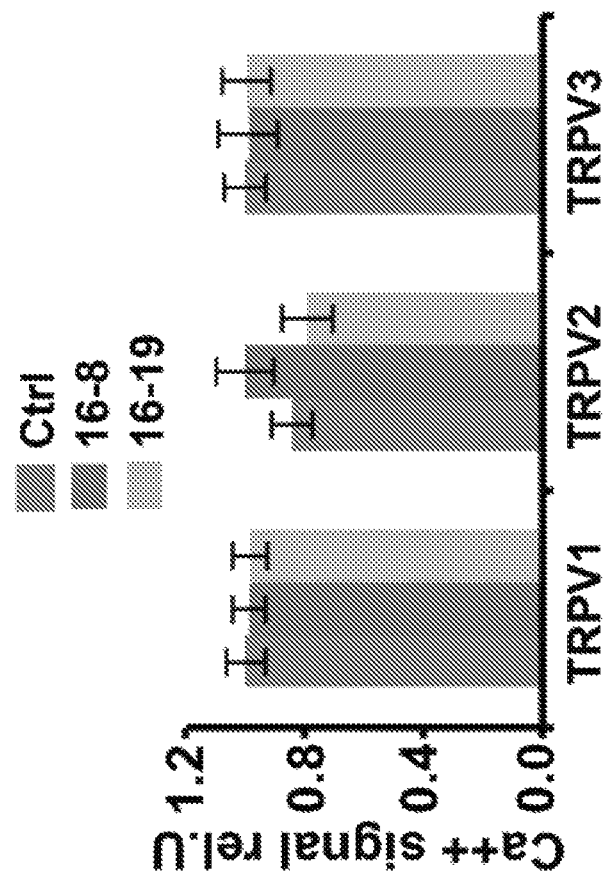

In heterologously transfected permanent N2a cells, we did not observe inhibitory potency of compounds 16-8 or 16-19 toward TRPV1, TRPV2 and TRPV3 (FIG. 29A). However, we made the unexpected discovery of sub-micromolar inhibitory potency vs TRPA1 for compounds 16-8 and 16-19, micromolar potency for GSK205, and, remarkably, no significant activity for compound 16-18 (FIG. 29B). We recorded $IC_{50}$ of 0.41, 0.43, 5.56 µM and >25 µM for compounds 16-8, 16-19, GSK205 and 16-18, respectively.

Figures 30A, 30B:
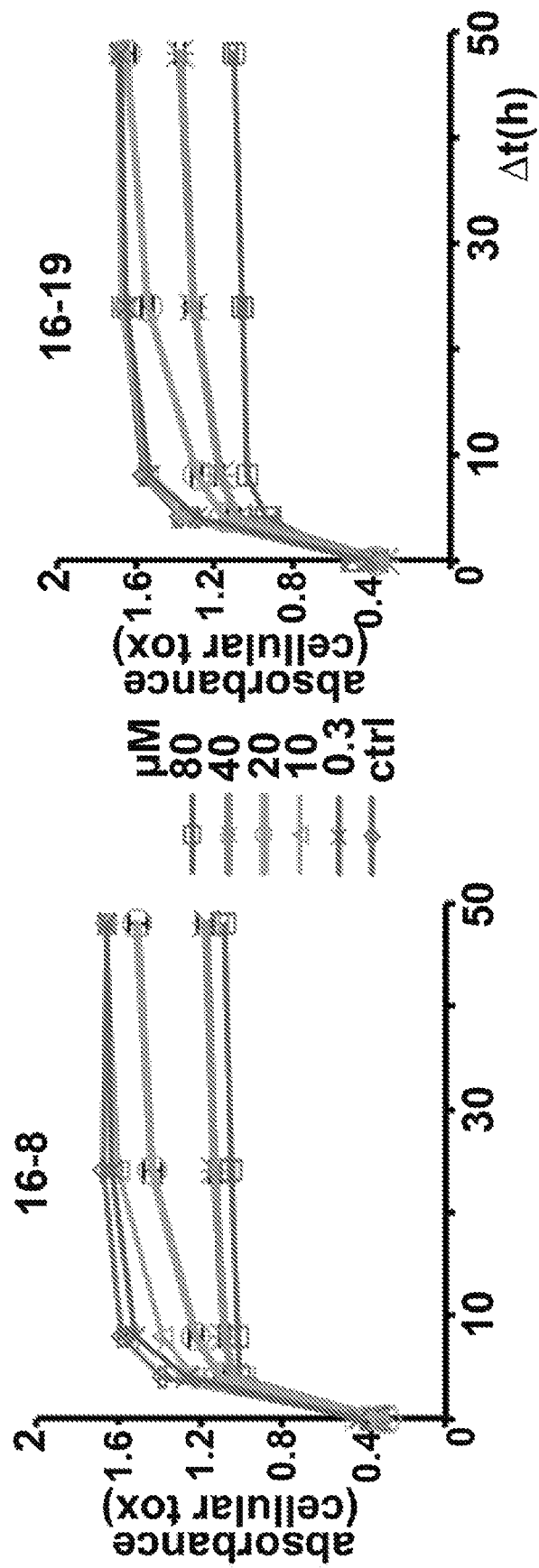
FIGS. 30A-30B: Cellular toxicity studies of compounds 16-8 and 16-19. N2a cells were subjected to increasing concentrations of compounds 16-8 and 16-19, resulting cell viability was analyzed for the next 48 h.

In terms of cellular toxicity, we found first evidence of toxicity using a sensitive cell viability assay over a time-course of 2 days, at 20 µM, and more pronounced effects at 40 µM (FIG. 30).

Taken together, our results indicate that compounds 16-8 and 16-19 also inhibit TRPA1 at sub-micromolar potency, and their cellular toxicity vs their inhibitory potency against TRPV4/TRPA1 ranges at a factor of 50-100.

Assessment of specificity of 16-8, 16-18 and 16-19 against a wider spectrum of receptors and ion channels will be the subject of dedicated future studies directed toward translation of these compounds to the clinic.

We next evaluated these compounds to an in-vivo model of irritant pain known to rely on both, TRPV4 and TRPA1.

Example 21: TRPV4/TRPA1 Dual-Inhibitors are Effective in Containing Trigeminal Irritant Pain We have previously described TRPV4 as a cellular receptor for formalin[13], and demonstrated its involvement in forma-lin irritant-evoked pain behavior, with a focus on trigeminally-mediated irritant pain behavior. In this recent study, we also demonstrate the co-contribution of TRPV4 together with TRPA1 in trigeminal formalin-evoked pain. We also showed the effective attenuation of trigeminal formalin-evoked pain behavior using GSK205 in a dose-dependent manner. Moreover, we found irritant pain behavior in response to selective activation of TRPV4 in the trigeminal territory, which was blocked by GSK205, and the absence of such an effect in Trpv4$^{-/-}$ pan-null mice.

Figure 31B:
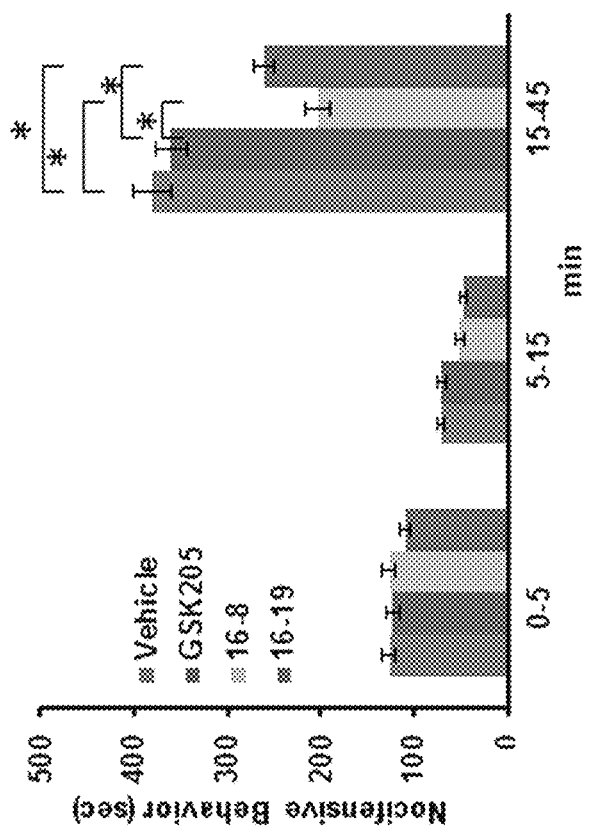
FIGS. 31A-31D: 16-8 and 16-19 effectively attenuate formalin-evoked trigeminal irritant pain.
Figure 31A:
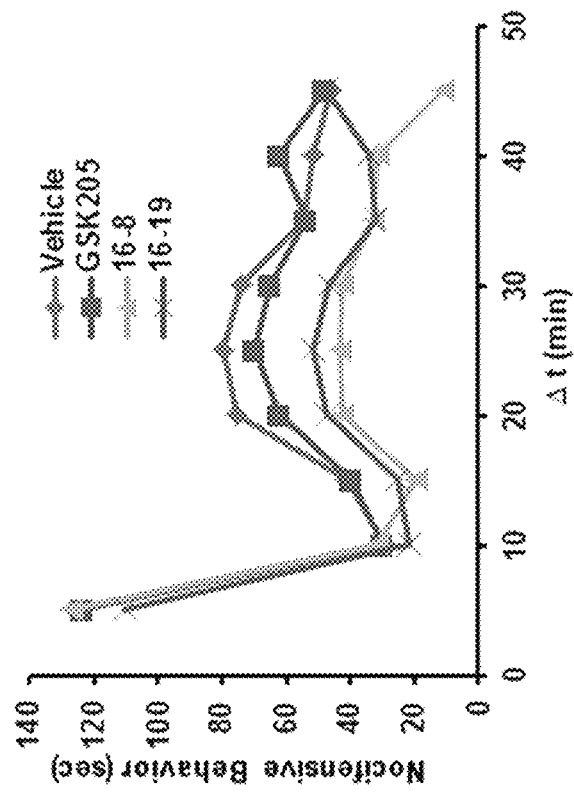

With this pertinent background as a rationale, we applied TRPV4/TRPA1 dual-inhibitory compounds 16-8 and 16-19 systemically, using GSK205 as control, at 10 mg/kg dosage. We prioritized the dual-inhibitors over testing of compound 16-18 (TRPV4-only inhibitor) because (i) the trigeminal formalin pain model relies on both TRPV4 and TRPA1, (ii) we intended to develop TRPV4/TRPA1 dual-inhibitory molecules toward translational use in the first place. None of the compounds were effective at significantly diminishing pain behavior in the early phase after formalin whisker-pad injection, which represents an acute chemical tissue injury pain. In the delayed phase, which is understood as neurally-mediated pain indicative of early maladaptive neural plasticity, there was a significant attenuation of formalin-evoked pain behavior in response to compound 16-8 and 16-19, with compound 16-8 diminishing pain behavior at a remarkable >50%[13], and compound 16-19 also showing a robust effect (FIG. 31A,B). Of note, at 10 mg/kg systemic application, there was no significant effect of GSK205, which was effective previously in a dose-dependent manner when applied by intradermal injection[13]. Thus, compounds 16-8 and 16-19, upon systemic application, effectively attenuate the late, neurally-mediated phase of trigeminal formalin pain, and these compounds are more potent in-vivo than their parental compound, GSK205.

Figures 31C, 31D:
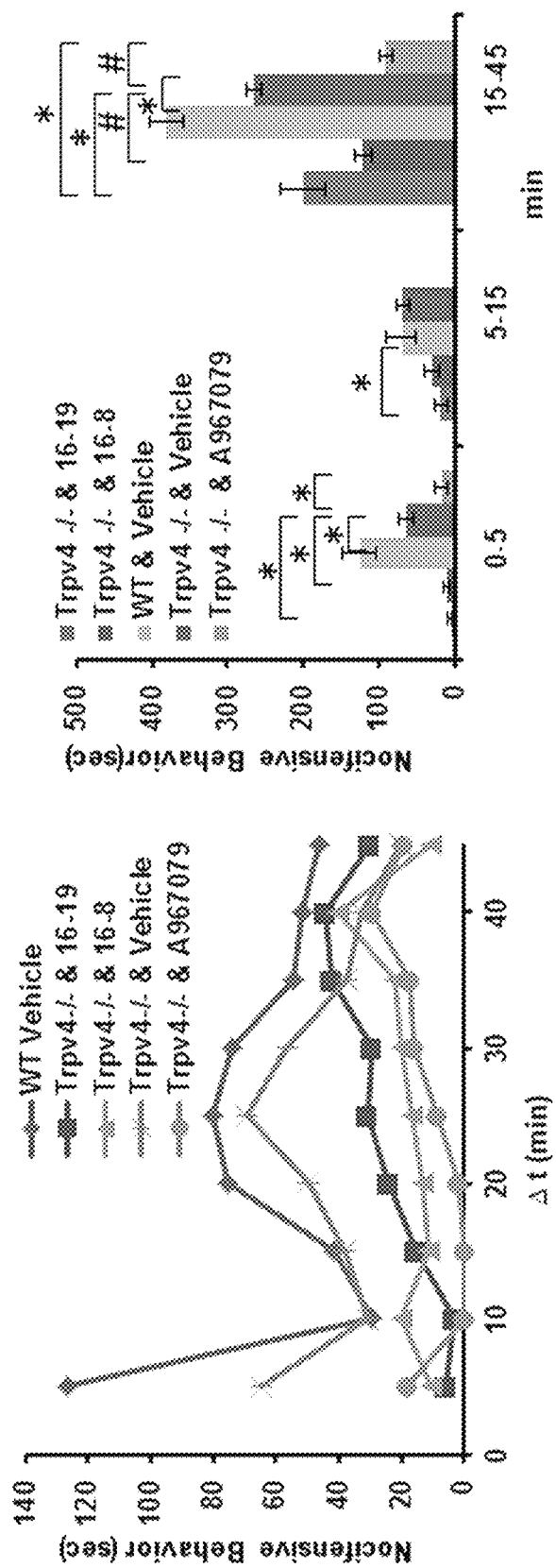
Figures 32D, 32E, 32F:
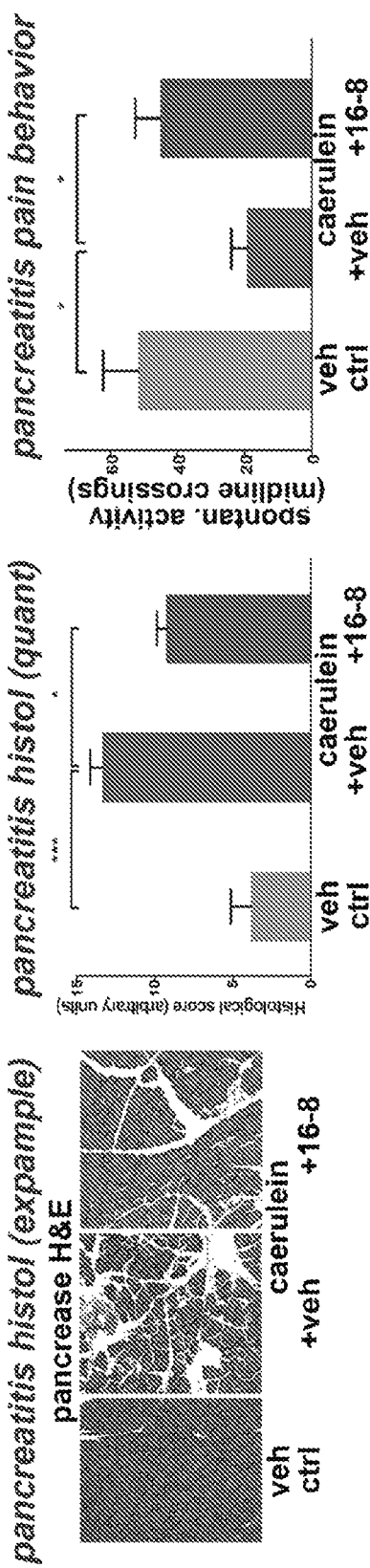

In view of these in-vivo findings, taken together with the results from heterologous cellular expression sys-tems that indicate an additional TRPA1-inhibitory effect of compounds 16-8 and 16-19, we decided to assess effectiveness of these compounds in a setting of genetically-encoded absence of Trpv4 (Trpv4$^{-/-}$ mouse), in order to better define their TRPA1-inhibitory potency in-vivo. We observed significant residual irritant-pain behavior in all phases of the formalin model in Trpv4$^{-/-}$ mice, consistent with our previous report[13] (FIG. 31C,D). Immediate-phase pain behavior was virtually eliminated with compounds 16-8 and 16-19, both applied again at 10 mg/kg body-weight. Late-phase pain behavior was strikingly reduced when applying compound 16-8, and still significantly reduced vs vehicle-treated Trpv4$^{-/-}$ when applying compound 16-19, although not as potently as 16-8. A reference TRPA1-inhibitory compound, A967079, was used at 25 mg/kg body weight as a positive control to inhibit TRPA1, based on a previous report[38]. Reduction of pain behavior in Trpv4$^{-/-}$ mice was striking, more than 50% in the late neural phase. We noted equal potency of compound 16-8 at 10 mg/kg body weight vs. refer-ence TRPA1-inhibitory compound A967079 at 25 mg/kg body weight, both reducing formalin-evoked trigeminal pain behavior to similarly robust degree (FIG. 31C,D).

We conclude that compound 16-8 also functions as a potent TRPA1-inhibitor in an in-vivo irritant pain model specifically designed to assess the contribution of TRPA1 to trigeminal irritant pain, and at least as potent as an established reference TRPA1-antagonistic compound.

Example 22: Potent TRPV4/TRPA1 Dual-Inhibitor, 16-8, is Effective at Controlling Inflammation and Pain in Acute Pancreatitis These findings define compound 16-8 as a potent TRPV4/TRPA1 dual-inhibitor molecule, based on cell-based and live-animal results. We therefore decided to test it in a more specific preclinical pain model that relies on both, TRPV4 and TRPA1, in order to establish proof-of-principle that a dual-inhibitor can effectively treat pain and inflammation in pancreatitis. We used a pancreatitis model because it provides high translation potential due to unmet clinical need for new effective treatments in this condition[39], as well as the known role of both TRPV4 and TRPA1 in pancreatitis pain and inflammation[8,25,40].

Pancreatitis was induced with caerulein, a well-characterized model for acute pancreatitis[41]. Animals were treated with 10 mg/kg bw 16-8 by intraperitoneal injection, 30 min before induction of inflammation. We found significant attenuation of inflammatory parameters, namely edema, which was virtually eliminated in 16-8 treated animals. Furthermore, serum amylase, a marker of inflammatory injury of the pancreas, was significantly reduced by 16-8 treatment, as was myelo-peroxidase content of the pancreas, as a marker of inflammatory cell infiltration of the pancreas. The histopathological score for pancreas inflammation was also significantly reduced (FIG. 32A-E). Of note, pain behavior, similar to the effect of 16-8 on pancreas edema, was virtually eliminated upon treatment with compound 16-8. Thus, compound 16-8 was found to be highly effective in attenuating pain and inflammation of acute chemically-evoked pancreatitis.

Figure 33B:
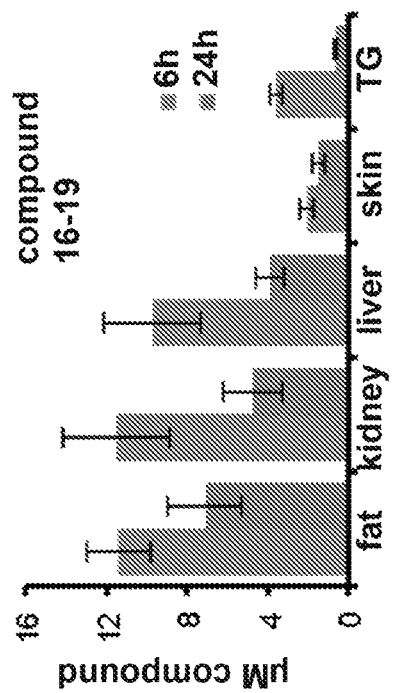
FIGS. 33A-33E: Pharmaco-kinetics/pharmaco-tox of compounds 16-8, 16-19 and GSK205 in-vivo.
Figure 33A:
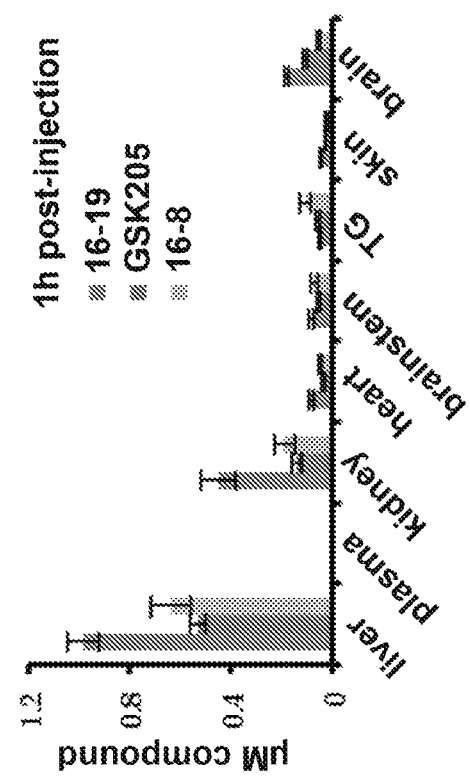
Figure 33E:
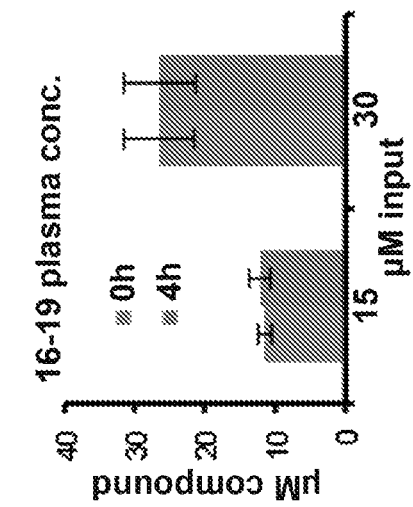
Figure 33D:
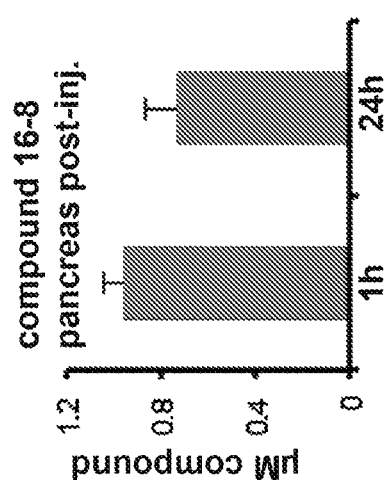
Figure 33C:
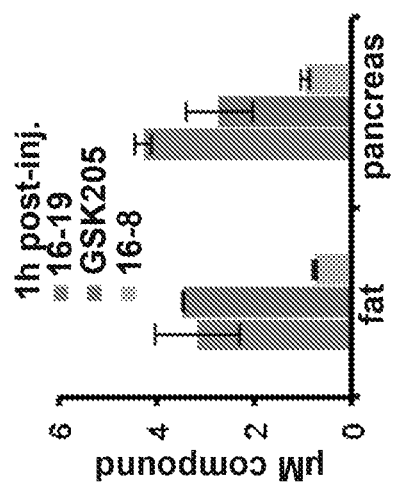

Example 23: Benign Preliminary Toxicity and Pharmacokinetics of Novel TPRV4/TRPA1 Inhibitors Promising properties of potent 16- . . . compounds prompted us to attempt to define their initial preliminary features in terms of in-vivo toxicity and pharmacokinetics, which will be followed by more extensive and in-depth investigations in future studies. For this, we chose compound 16-8 as the all-around most potent dual TRPV4/TRPA1 inhibitor, and also compound 16-19 with its potentially increased lipophilicity (TABLE 5). We measured compound concentration in several organs and plasma, and detected micromolar/submicromolar concentrations in liver and kidney, less than 100 nM concentrations in heart, brain, brainstem, trigeminal ganglion and skin. Of note, compounds were virtually undetectable in plasma (FIG. 33A). We detected higher concentrations of 16-19 in non-nervous tissue, especially liver and kidney, a pattern perhaps related to compound 16-19's increased lipo-philicity. Based on this finding, we next examined 6 and 24 h time-points and detected 10-20 fold higher concen-trations of 16-19 at the 6 h time-point, compared to the 1 h time-point, indicative of compound sequestration into solid organs (FIG. 33B-D). Values at the 24 h time-point were lower than at the 6 h but higher than at the 1 h time-point, indicating ongoing protracted compound clearance. We next confirmed that low/non-detectable concentrations in plasma were not caused by compound denaturation/degradation in plasma, as indicated in FIG. 33E, which shows no loss of detectable compound after 4 h incubation in plasma at 37° C., conducted using compound 16-19.

TABLE 5

Properties of GSK205, 16-8, and 16-19.

| Compound | MW | PSA | c-logP(oct/H2O) |
|---|---|---|---|
| GSK205 | 400 | 37.53 | 5.35 |
| 16-8 | 399.6 | 24.4 | 6.33 |
| 16-19 | 413.6 | 24.2 | 6.58 |

MW = Molecular weight.
PSA = Polar surface area.
C-logP(oct/H2O) indicates calculated logP(octanol solubility/H2O solubility).

Figure 34C:
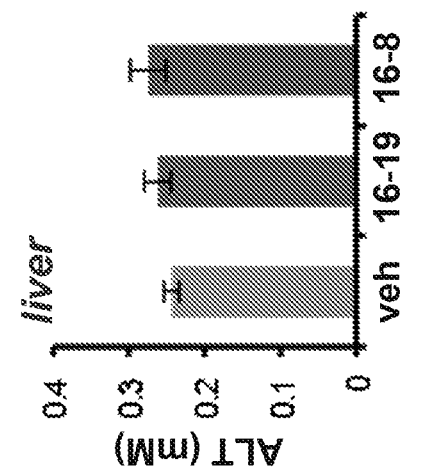
FIGS. 34A-34C: Absence of cardiac, renal and hepatic toxicty of compounds 16-8, 16-19.
Figure 34B:
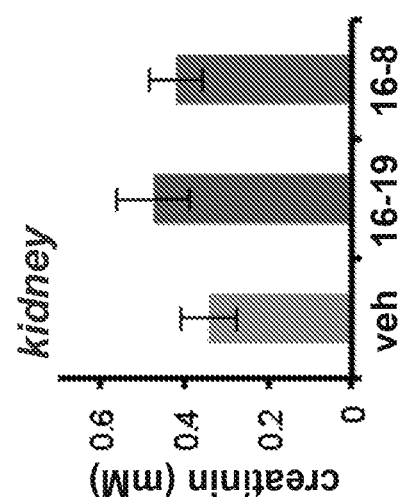
Figure 34A:
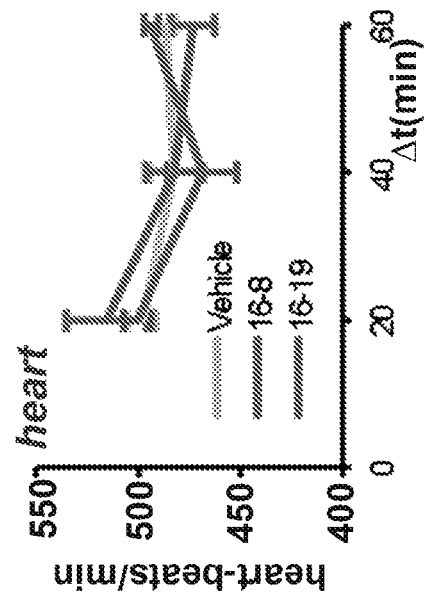

We next performed basic preliminary in-vivo toxicity studies for compounds 16-8 and 16-19, both at 10 mg/kg bw, which was the effective concentration in both in-vivo pain models. We did not detect first evidence of cardiac, hepatic and renal toxicity, when comparing compounds 16-8 and 16-19 with vehicle (FIG. 34). For cardiac assessment, we did not detect differences and changes in heart rate over 1 h, conducted by EKG at the 6 h time-point. Serum creatinin as marker of renal function and alanine-amino-transferase (ALT) as marker of hepato-cellular integrity were not significantly elevated in animals treated with compounds 16-8 or 16-19. Thus, initial evidence for potent 16- . . . compounds highlights their acceptable preliminary pharmacokinetics proper-ties as well as lack of gross systemic toxicity. Future studies will be necessary for more detailed assessment of the pharmacokinetics and toxicity of these compounds.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A composition comprising an inhibitor and iodine, wherein the inhibitor inhibits TRPV4, TRPA1, or a combination thereof.

Clause 2. A composition comprising an inhibitor and an anesthetic, wherein the inhibitor inhibits TRPV4, TRPA1, or a combination thereof.

Clause 3. The composition of clause 1 or 2 wherein the inhibitor does not inhibit TRPV1, TRPV2, or TRPV3.

Clause 4. The composition of any one of the above clauses, wherein the inhibitor comprises a compound according to Formula I:

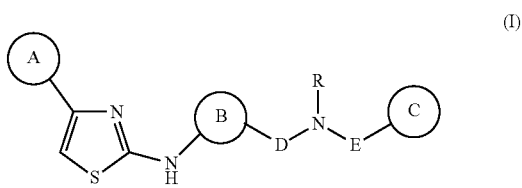

wherein A, B, and C are independently selected from the group consisting of aromatic, heteroaromatic, cycloalkenyl, and heterocycloalkenyl groups; D is $C_1$-$C_3$ alkylene; E is a bond, or $C_1$-$C_2$ alkylene; and R is selected from the group consisting of hydrogen, hydroxyl, amino, alkyl, alkenyl, heteroalkyl, aromatic ring, or heteroaromatic ring.

Clause 5. The composition of clause 4, wherein the inhibitor comprises a compound selected from the following:

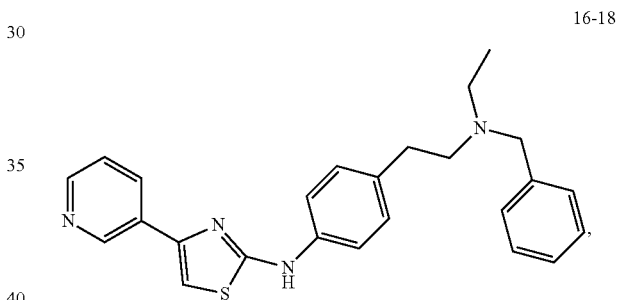

16-18

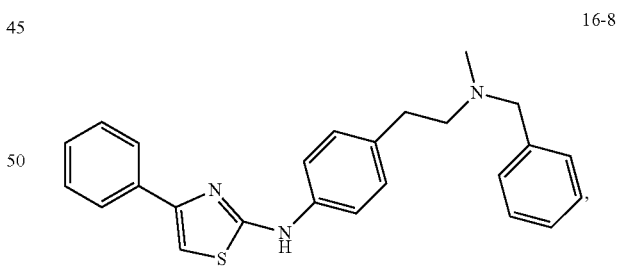

16-8

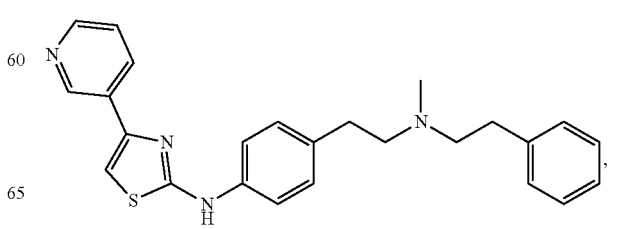

16-12c

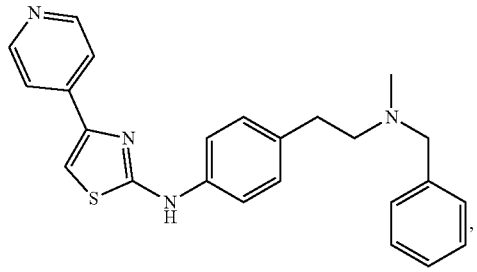
16-13,

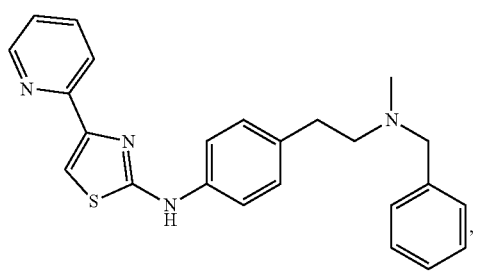
16-14,

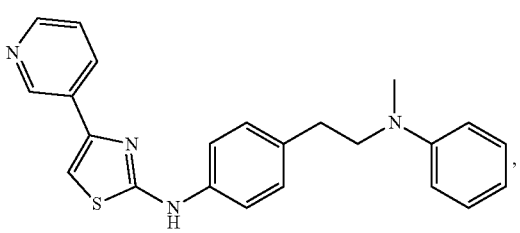
16-16,

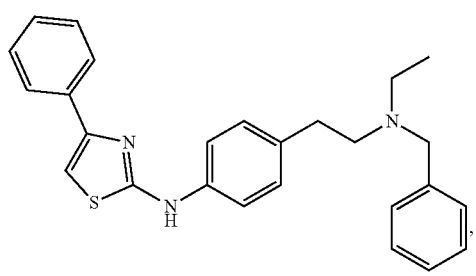
16-19 (16-8/18hy),

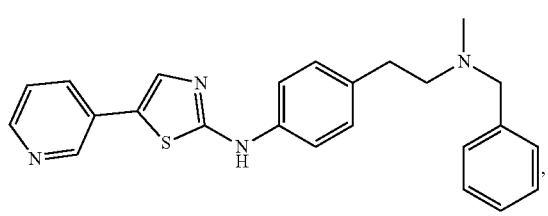
15-43,

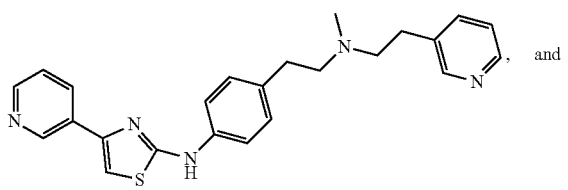
16-12, and

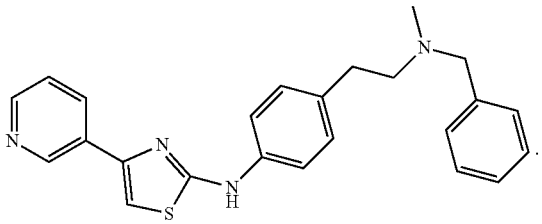
GSK-205.

Clause 6. A method of sanitizing a subject, the method comprising contacting the subject with the composition of any one of clauses 1 and 3-5.

Clause 7. The method of clause 6, wherein the subject is contacted with the composition for a period of time sufficient to cause a reduction in the population of microorganisms on the subject.

Clause 8. The method of clause 6 or 7, wherein the composition is administered to a surface of the subject, wherein the surface is selected from the group consisting of a skin area, a wound, and an ulcer.

Clause 9. The method of any one of clauses 6-8, wherein the composition disinfects the subject.

Clause 10. The method of any one of clauses 6-8, wherein the composition sterilizes the subject.

Clause 11. The method of any one of clauses 6-8, wherein the composition has antibacterial activity.

Clause 12. A method of anesthetizing a subject, the method comprising administering to the subject the composition of any one of clauses 2-5.

Clause 13. A method of anesthetizing a subject, the method comprising co-administering an anesthetic and an inhibitor to the subject, wherein the inhibitor inhibits TRPV4, TRPA1, or a combination thereof.

Clause 14. The method of clause 13, wherein the composition sanitizes and reduces pain.

Clause 15. A method of treating and/or preventing a dermatological disorder in a subject in need thereof, the method comprising administering to the subject an effective amount of a TRPV4 and/or TRPA1 inhibitor.

Clause 16. The method of clause 15, wherein the dermatological disorder is selected from the group consisting of pancreatitis, epilepsy, arthritis, osteoarthritis, multiple sclerosis, stroke, CNS autoimmune condition, traumatic brain injury, spinal cord injury, brain edema, CNS infection, neuro-psychiatric disorder, skeletal degenerative-inflammatory disorder, trigeminal pain, colitis, and sclerosis.

Clause 17. The method of clause 16 wherein the trigeminal pain comprises headache.

Clause 18. The method of any one of clauses 15-17, wherein the TRPV4 and/or TRPV4 inhibitor comprises a compound according to Formula I:

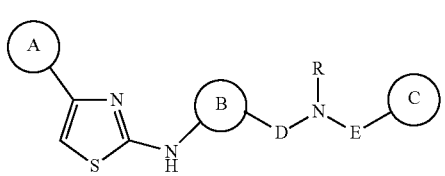
(I)

wherein A, B, and C are independently selected from the group consisting of aromatic, heteroaromatic, cycloalkenyl, and heterocycloalkenyl groups; D is $C_1$-$C_3$ alkylene; E is a bond, or $C_1$-$C_2$ alkylene; and R is selected from the group consisting of hydrogen, hydroxyl, amino, alkyl, alkenyl, heteroalkyl, aromatic ring, or heteroaromatic ring.

Clause 19. The method of clause 18, wherein the TRPV4 and/or TRPA1 inhibitor comprises a compound selected from the following:

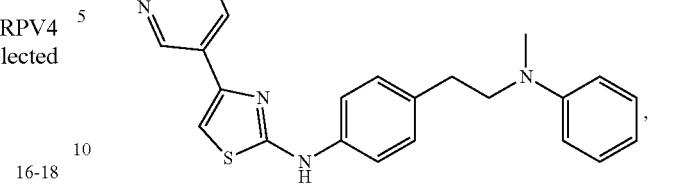
16-16

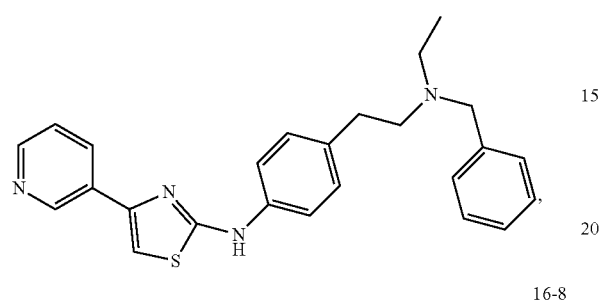
16-18

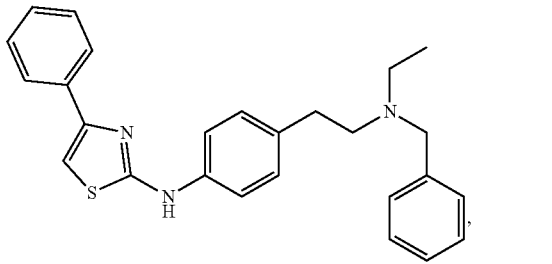
16-19

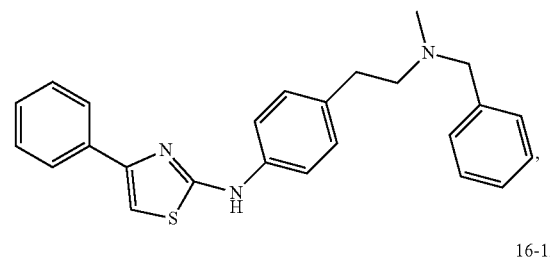
16-8

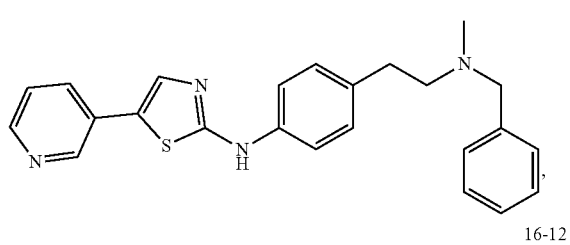
15-43

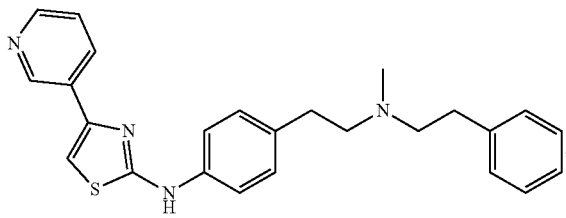
16-12c

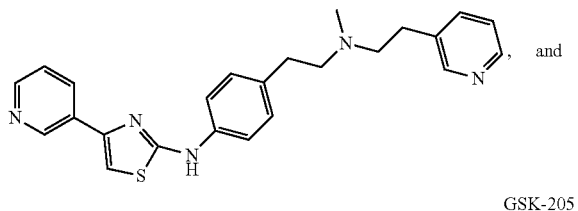
16-12

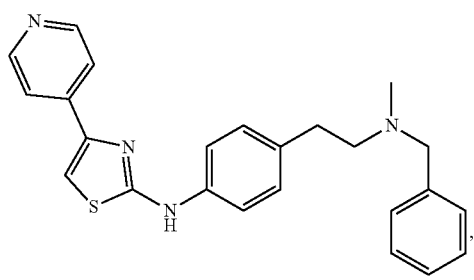
16-13

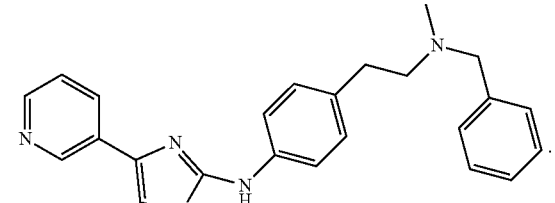
and
GSK-205

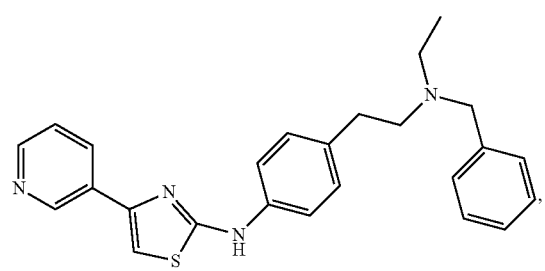
16-14

Clause 20. The method of clause 18 or 19, wherein the compound inhibits TRPV4 and TRPA1.

Clause 21. The method of clause 18 or 19, wherein the compound does not inhibit TRPV1, TRPV2, or TRPV3.

SEQUENCES

```
                                              (SEQ ID NO: 1)
5'-CCTGCTGGTCACCTACATCA (SEQ ID NO: 2)
5'-CTCAGGAACACAGGGAAGGA
```

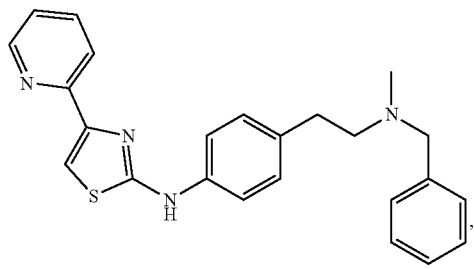

The invention claimed is:

1. A composition comprising an inhibitor and iodine, wherein the inhibitor inhibits TRPV4, TRPA1, or a combination thereof, wherein the inhibitor comprises a compound according to Formula I:

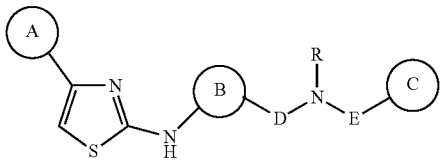
(I)

wherein A, B, and C are independently selected from the group consisting of aromatic, heteroaromatic, cycloalkenyl, and heterocycloalkenyl groups;
D is $C_1$-$C_3$ alkylene;
E is a bond, or $C_1$-$C_2$ alkylene; and
R is selected from the group consisting of hydrogen, hydroxyl, amino, alkyl, alkenyl, heteroalkyl, aromatic ring, or heteroaromatic ring.

2. A composition comprising an inhibitor and an anesthetic, wherein the inhibitor inhibits TRPV4, TRPA1, or a combination thereof, wherein the inhibitor comprises a compound according to Formula I:

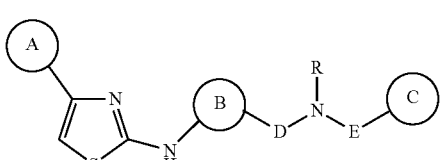
(I)

wherein A, B, and C are independently selected from the group consisting of aromatic, heteroaromatic, cycloalkenyl, and heterocycloalkenyl groups;
D is $C_1$-$C_3$ alkylene;
E is a bond, or $C_1$-$C_2$ alkylene; and
R is selected from the group consisting of hydrogen, hydroxyl, amino, alkyl, alkenyl, heteroalkyl, aromatic ring, or heteroaromatic ring.

3. The composition of claim 1, wherein the inhibitor does not inhibit TRPV1, TRPV2, or TRPV3.

4. The composition of claim 2, wherein the inhibitor does not inhibit TRPV1, TRPV2, or TRPV3.

5. A method of sanitizing a portion of the skin of a subject and reducing associated pain, the method comprising contacting the portion of the skin of the subject with a composition comprising iodine and a pain inhibitor, wherein the pain inhibitor inhibits TRPV4 and TRPA1 and comprises a compound according to Formula I:

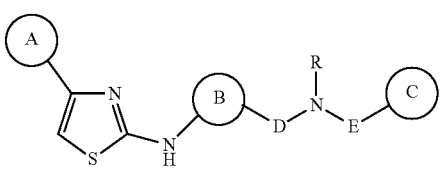
(I)

wherein A, B, and C are independently selected from the group consisting of aromatic, heteroaromatic, cycloalkenyl, and heterocycloalkenyl groups;
D is $C_1$-$C_3$ alkylene;
E is a bond, or $C_1$-$C_2$ alkylene; and
R is selected from the group consisting of hydrogen, hydroxyl, amino, alkyl, alkenyl, heteroalkyl, aromatic ring, or heteroaromatic ring.

6. The method of claim 5, wherein the compound is selected from the following:

16-18
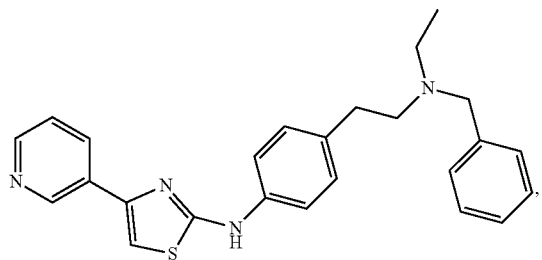

16-8
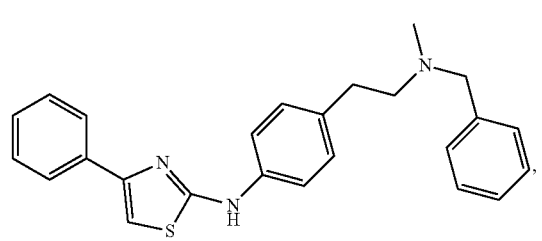

16-12c
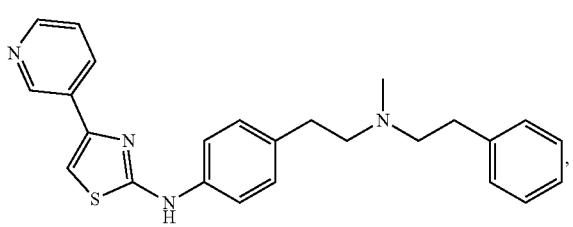

16-13
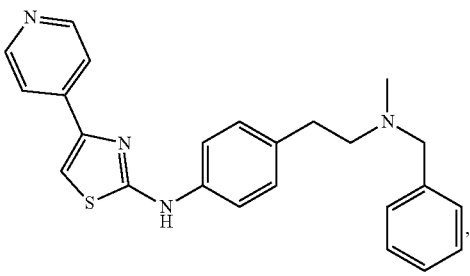

16-14
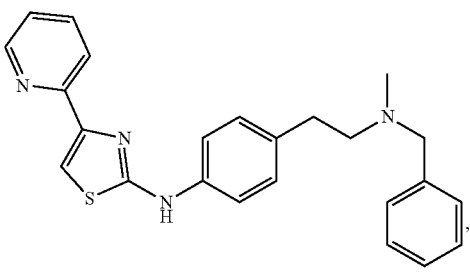

16-16
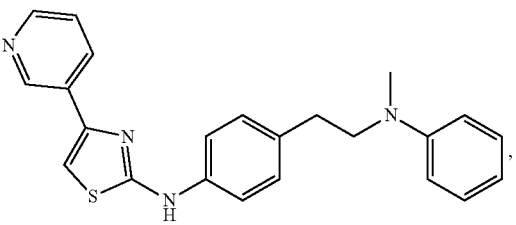

16-19 (16-8/18hy)
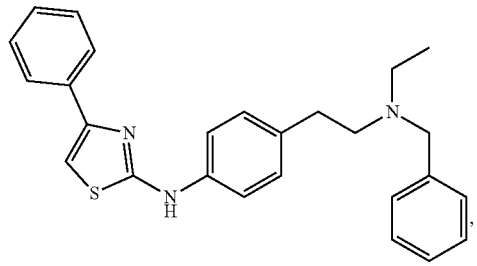

15-43
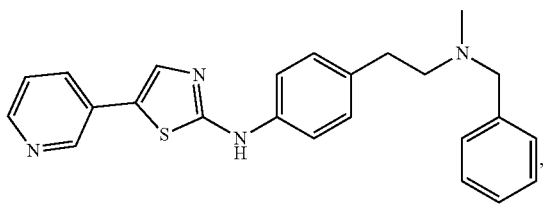

16-12
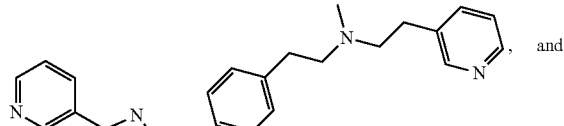

and

GSK-205
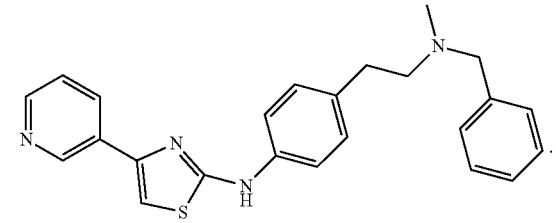

7. The method of claim 5, wherein the portion of the skin of the subject is contacted with the composition for a period of time sufficient to cause a reduction in the population of microorganisms on the portion of the skin of the subject.

8. The method of claim 5, wherein the portion of the skin of the subject comprises a wound or an ulcer.

9. The method of claim 5, wherein the composition disinfects the portion of the skin of the subject.

10. The method of claim 5, wherein the composition sterilizes the portion of the skin of the subject.

11. The method of claim 5, wherein the composition has antibacterial activity.

12. A method of anesthetizing a subject, the method comprising administering to the subject the composition of claim 2.

13. A method of anesthetizing a subject, the method comprising co-administering an anesthetic and an inhibitor to the subject, wherein the inhibitor inhibits TRPV4, TRPA1, or a combination thereof, wherein the TRPV4 and/or TRPV4 inhibitor comprises a compound according to Formula I:

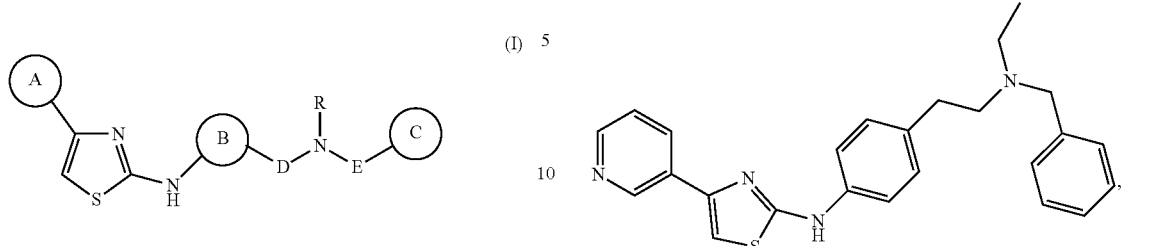

wherein A, B, and C are independently selected from the group consisting of aromatic, heteroaromatic, cycloalkenyl, and heterocycloalkenyl groups;

D is $C_1$-$C_3$ alkylene;

E is a bond, or $C_1$-$C_2$ alkylene; and

R is selected from the group consisting of hydrogen, hydroxyl, amino, alkyl, alkenyl, heteroalkyl, aromatic ring, or heteroaromatic ring.

14. The method of claim 13, wherein the composition sanitizes and reduces pain.

15. A method of treating and/or preventing a dermatological disorder in a subject in need thereof, the method comprising administering to the subject an effective amount of a TRPV4 and/or TRPA1 inhibitor, wherein the TRPV4 and/or TRPV4 inhibitor comprises a compound according to Formula I:

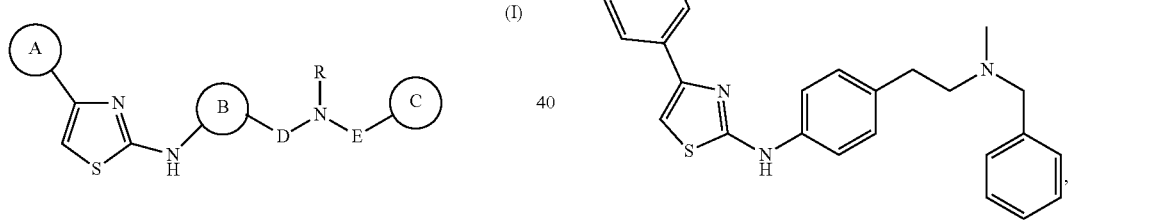

wherein A, B, and C are independently selected from the group consisting of aromatic, heteroaromatic, cycloalkenyl, and heterocycloalkenyl groups;

D is $C_1$-$C_3$ alkylene;

E is a bond, or $C_1$-$C_2$ alkylene; and

R is selected from the group consisting of hydrogen, hydroxyl, amino, alkyl, alkenyl, heteroalkyl, aromatic ring, or heteroaromatic ring.

16. The method of claim 15, wherein the dermatological disorder is selected from the group consisting of pancreatitis, epilepsy, arthritis, osteoarthritis, multiple sclerosis, stroke, CNS autoimmune condition, traumatic brain injury, spinal cord injury, brain edema, CNS infection, neuropsychiatric disorder, skeletal degenerative-inflammatory disorder, trigeminal pain, colitis, and sclerosis.

17. The method of claim 16 wherein the trigeminal pain comprises headache.

18. The method of claim 15, wherein the TRPV4 and/or TRPA1 inhibitor comprises a compound selected from the following:

16-18

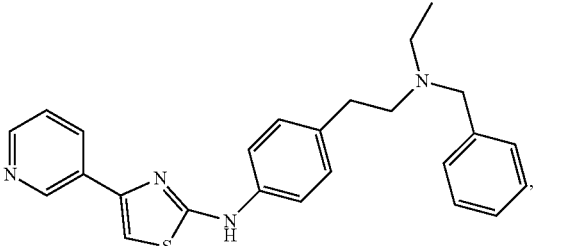

16-8

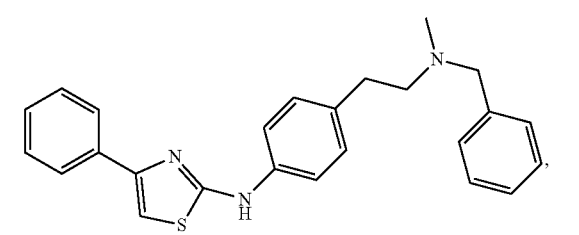

16-12c

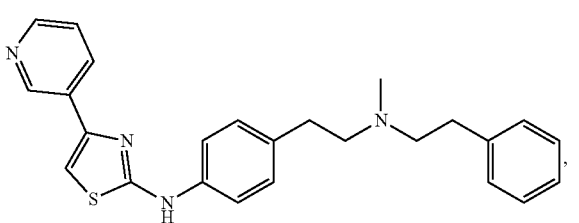

16-13

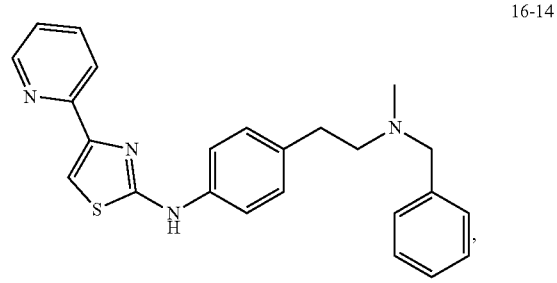 [SMILES: CN(CCc1ccc(Nc2nc(-c3ccccn3)cs2)cc1)Cc1ccccc1]

16-14

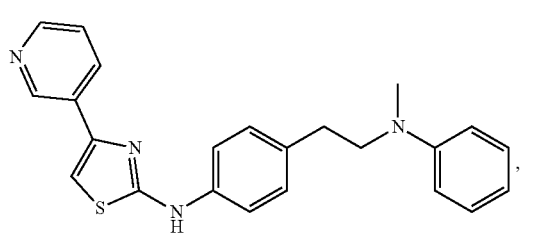

16-16

16-19

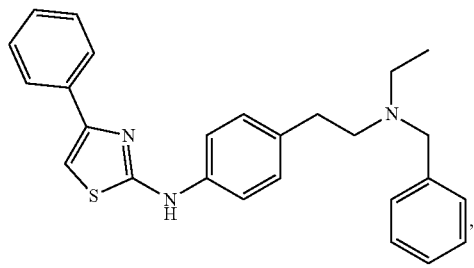

15-43

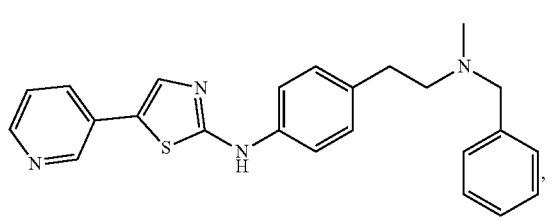

16-12

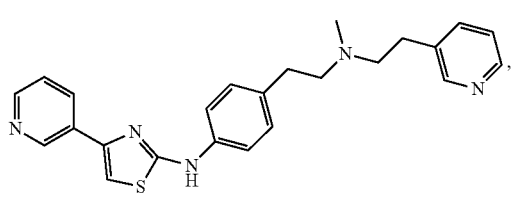, and

GSK-205

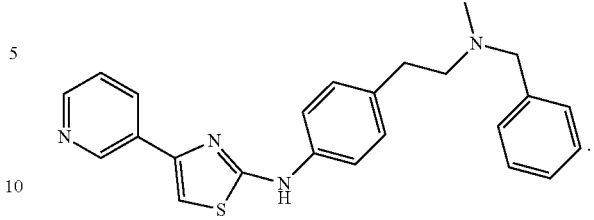.

19. The method of claim 15, wherein the compound inhibits TRPV4 and TRPA1.

20. The method of claim 5, wherein the compound does not inhibit TRPV1, TRPV2, or TRPV3.

21. The method of claim 5, wherein the iodine is administered to the subject in a dose of about 0.1 mg to about 2000 mg.

22. The method of claim 5, wherein the iodine is administered to the subject in a dose of about 0.5 to about 60 mg.

23. The method of claim 5, wherein the iodine is present in the composition as elemental iodine.

24. The method of claim 5, wherein the iodine is present in the composition as an iodine salt.

25. The method of claim 24, wherein the iodine is present in the composition as potassium iodide and/or sodium iodide.

* * * * *